(12) United States Patent
Armour et al.

(10) Patent No.: US 7,217,714 B1
(45) Date of Patent: May 15, 2007

(54) CCR5 MODULATORS

(75) Inventors: Duncan Robert Armour, Ramsgate (GB); David Anthony Price, Ringwould Deal (GB); Blanda Luzia Christa Stammen, Sandwich (GB); Anthony Wood, Margate (GB); Manoussos Perros, Ramsgate (GB); Martin Paul Edwards, Ringwould Deal (GB)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/451,826

(22) Filed: Nov. 30, 1999

(30) Foreign Application Priority Data

Dec. 23, 1998 (GB) ................................. 9828420.1
Sep. 18, 1999 (GB) ................................. 9922009.7

(51) Int. Cl.
*A61K 31/535* (2006.01)
*C07D 401/00* (2006.01)
*C07D 215/16* (2006.01)
*C07D 217/00* (2006.01)

(52) U.S. Cl. .............. 514/236.2; 514/252; 514/255; 514/256; 514/318; 514/326; 514/336; 514/359; 514/361; 514/363; 514/364; 546/139; 546/146; 546/147; 546/148; 546/152; 546/156; 546/161; 546/211; 546/218; 546/268.4; 546/268.7; 546/269.1; 546/192; 546/193; 546/194; 546/206; 546/209; 546/210; 546/216; 544/111; 544/112; 544/113; 544/114; 544/115; 544/224; 544/238; 544/242; 544/333; 544/336; 544/359; 544/361; 544/367

(58) Field of Classification Search ................ 546/192, 546/193, 194, 206, 209, 210, 216, 211, 218, 546/152, 156, 161, 139, 146, 147, 148, 266.4, 546/268.7, 269.1; 514/318, 326, 885, 336, 514/236.2, 252, 255, 256, 363, 359, 361, 514/364, 307, 314, 231.5; 544/111, 112, 544/113, 114, 115, 224, 238, 242, 333, 336, 544/359, 366, 367; 548/127, 131, 134, 136, 548/262.2, 266.2, 250

See application file for complete search history.

(56) References Cited

U.S. PATENT DOCUMENTS

| 5,444,074 | A | * | 8/1995 | Baker et al. ................. 548/192 |
| 5,489,599 | A | * | 2/1996 | Carter et al. ................. 546/192 |
| 5,824,650 | A |   | 10/1998 | De Lacharriere et al. |
| 5,972,892 | A |   | 10/1999 | De Lacharriere et al. |
| 6,511,994 | B2 | * | 1/2003 | Kim et al. ................... 514/319 |
| 6,586,430 | B1 | * | 7/2003 | Armour et al. .......... 514/235.2 |

FOREIGN PATENT DOCUMENTS

| WO | 9311122 | 6/1993 |
| WO | 9831364 | 7/1996 |
| WO | 9825604 | 6/1998 |
| WO | 9825605 | 6/1998 |
| WO | 9825617 | 6/1998 |
| WO | 9904794 | 2/1999 |
| WO | 9909984 | 3/1999 |

OTHER PUBLICATIONS

Brown et al, Chem. Abs. vol. 68. No. 105162, "Triazoles" (1968).*
Lipinski et al, Chem Abs. vol. 103 No. 160451, "Pseudosymmetry omlbioisasteris in bidryl pydridyl competitive histamine H2-receptor antagonists".*

* cited by examiner

*Primary Examiner*—Thomas McKenzie
*Assistant Examiner*—Raymond Covington
(74) *Attorney, Agent, or Firm*—Keith D. Hutchinson; Bryan C. Zielinski

(57) ABSTRACT

Compounds of Formula 1

$$[R_{egion}\ \alpha]-[R_{egion}\ \beta]-[R_{egion}\ \gamma]-[R_{egion}\ \delta] \qquad (I)$$

which are useful as modulators of chemokine activity. The invention also provides pharmaceutical formulations and methods of treatment using these compounds.

13 Claims, No Drawings

CCR5 MODULATORS

This application claims priority under 35 U.S.C. §119 of Great Britain applications 9828420.1 and 9922009.7, filed respectively on Dec. 23, 1998 and Sep. 18, 1999, the texts of which are hereby incorporated by reference herein in their entireties.

This invention relates to new chemical compounds. These compounds find particular but not exclusive use as pharmaceuticals, especially as CCR5 modulators.

This invention also relates to formulations or dosage forms including these compounds, to use of these compounds in manufacture of pharmaceutical formulations or dosage forms and methods of treatment, especially treatment of anti-inflammatory diseases and conditions and in the treatment and prevention of HIV-1 and genetically related retroviral infections.

The compounds of the present invention are modulators, especially antagonists, of the activity of chemokine CCR5 receptors, particularly those which occur on the surfaces of certain cells within the human body. Modulators of CCR5 receptor may be useful in the treatment and prevention of various inflammatory diseases and conditions, and in the treatment and prevention of infection by HIV-1 and genetically related retroviruses.

The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonizing, the activity of chemokines and their receptors, are useful in the therapeutic treatment of such inflammatory and infectious diseases.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES). The relationship between modulators, especially antagonists of CCR5 activity and therapeutic usefulness in treating inflammation and HIV infection, and the manner in which such a relationship may be demonstrated, is explained in more detail further below.

There is ongoing in the art a substantial investigation of different classes of modulators of chemokine receptor activity, especially that of the CCR5 chemokine receptor. A representative disclosure is Mills et al WO 98/25617 relating to substituted aryl piperazines as modulators of chemokine receptor activity. However, the compositions described therein are not the same as, nor suggestive of those of the present invention. Further disclosures are: WO 98/025605; WO 98/025604; WO 98/002151; WO 98/004554; and WO 97/024325.

The present invention relates to compounds which may be conveniently considered to have four independently variable regions, reading from the left-hand side to right-hand side of said compound: $R_{region}$ α, $R_{region}$ β, $R_{region}$ γ, and $R_{region}$ δ, of Formula (I):

$$[R_{egion}\ \alpha]\text{-}[R_{egion}\ \beta]\text{-}[R_{egion}\ \gamma]\text{-}[R_{egion}\ \delta] \qquad (I)$$

and pharmaceutically acceptable salts and prodrug derivatives thereof. The compounds of the present invention may be selective CCR5 receptor antagonists and are non-peptidyl in structure.

The compounds as exemplified by Formula (I) may contain one or more stereogenic centers and the present invention includes the recited compounds in both their separated and their unseparated forms. The separated forms can be obtained by conventional means, e.g., by asymmetric synthesis, by using high performance liquid chromatography employing a chiral stationary phase, or by chemical resolution via the formation of suitable salts or derivatives. It will be understood that the separate optically active forms of the compositions of the present invention, as well as reacemic mixtures thereof, will usually vary with respect to their biological properties because of the chirality-dependent conformation of the active site of an enzyme, receptor, etc.

The description which follows provides details of the particular moieties which comprise each of said $R_{egions}$. In order to present said details in an orderly and space-saving fashion, each major group in each Region is set out with a single dash ("-"), and each successive subdivision within each said group is set out in turn with two, three, etc. dashes as required.

In this specification and claims a reference to a range or class of groups for example $(C_1-C_3)$alkyl is to be understood as an express disclosure and reference of each member of the range or class, including isomers.

According to the present invention there is provided a compound of Formula (I);

$$[R_{egion}\ \alpha]\text{-}[R_{egion}\ \beta]\text{-}[R_{egion}\ \gamma]\text{-}[R_{egion}\ \delta] \qquad (I)$$

wherein $[R_{egion}\ \alpha]$ is selected from the group consisting of:

A. Aryl heterocyclyl substituent components comprising:
  1. hetero-phenylmethylene moieties of partial Formula (1.0.0):

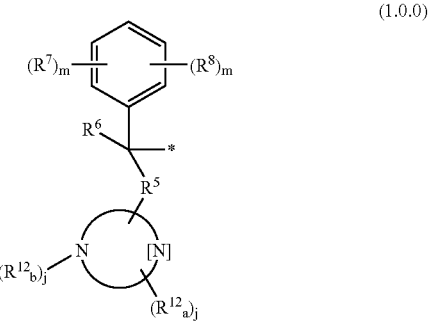

wherein: the symbol "*" indicates the point of attachment of the moiety of partial Formula (1.0.0) to $R_{region}$ β, as hereinafter defined;

$R^5$ is a member selected from the group consisting of a direct bond; —O—; —C(=O)—; —NR$^4$—; and —S(=O)$_p$—; where:

$R^4$ is hydrogen or $(C_1-C_2)$alkyl;

$R^6$ is a member selected from the group consisting of hydrogen; $(C_1-C_2)$alkyl; $(C_1-C_2)$alkoxy; —CN; —OH; and —C(=O)NH$_2$;

j is an integer selected from 0, 1, and 2;

m is an integer selected from 0, 1, and 2;

$R^7$ and $R^8$ are each a member selected from the group consisting of —F; —Cl; —CO$_2$R$^4$; —OH; —CN; —CON R$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl, and (C$_1$-C$_4$)alkoxy wherein said alkyl and alkoxy are each substituted with 0 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy; where:

p is an integer selected from 0, 1, and 2;

$R^4_a$ and $R^4_b$ are each independently selected from hydrogen and (C$_1$-C$_2$)alkyl;

the moiety represented by partial Formula (1.0.1):

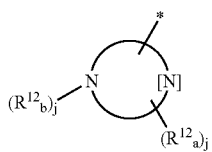

(1.0.1)

in partial Formula (1.0.0) represents a monocyclic heterocyclic group, or a bicyclic benzo-fused ring system containing said heterocyclic group wherein said heterocyclic group contains a total of 5 or 6 members of which one or two of said members is nitrogen, the presence of the optional second nitrogen atom being represented by: "[N]"; wherein said heterocyclic group or ring system are selected from the group consisting of pyrrolyl; pyrazolyl; imidazolyl; pyridinyl; pyrazinyl; pyrimidinyl; pyridazinyl; piperazinyl; indolyl; indazolinyl; benzimidazolyl; quinolinyl; iso-quinolinyl; and quinazolinyl; wherein:

$R^{12}_a$ is a member selected from the group consisting of hydrogen; F; Cl; —CO$_2$R$^4$; oxo; —OH; CN; NH$_2$; NH(C$_1$-C$_2$)alkyl; N(C$_1$-C$_2$)$_2$dialkyl; —CF$_3$; (C$_1$-C$_4$)alkyl; (C$_2$-C$_4$)alkenyl; (C$_1$-C$_4$)alkoxy; (C$_3$-C$_7$)cycloalkyl; and phenyl; wherein said alkyl, alkenyl, alkoxy, cycloalkyl and phenyl are substituted with 0 to 2 substituents R$^9$ where:

$R^9$ is a member independently selected from the group consisting of F; Cl; —CO$_2$R$^4$; —OH; cyano; —CONR$^4_a$R$^4_b$; —NR$^4_a$R$^4_b$—; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$) alkoxy wherein said alkyl and alkoxy are each independently substituted with 0 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy; and $R^{12}_b$ is absent or is a member selected from the group consisting of hydrogen; (C$_1$-C$_4$)alkyl; (C$_2$-C$_4$)alkenyl; (C$_1$-C$_2$)alkoxy; (C$_3$-C$_7$)cycloalkyl; and phenyl; wherein said alkyl, alkenyl, alkoxy, cycloalkyl and phenyl are substituted with 0 to 2 substituents R$^9$ wherein R$^9$ has the same meaning as above, except that it is selected independently selected therefrom; and 2. hetero-phenylmethylene moieties of partial Formula (1.1.0):

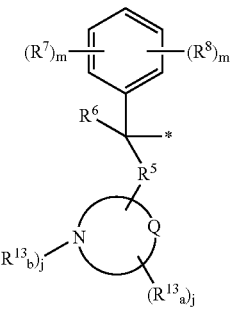

(1.1.0)

wherein: the symbol "*"; R$^5$; R$^6$; R$^7$; R$^8$; j and m are as defined further above, except that all of the above-recited substituents are selected independently of their selection above;

the moiety represented by partial Formula (1.1.1):

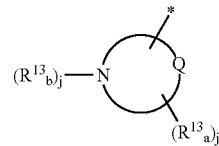

(1.1.1)

in partial Formula (1.1.0) represents:

a. a monocyclic heterocyclic group containing a total of 5 or 6 members of which one said member is nitrogen and Q is selected from O and S where said S may optionally be in the sulfonate form, —S(=O)$_2$; wherein said heterocyclic group is selected from the group consisting of oxazolyl; oxazolidinyl; isoxazolyl; thiazolyl; thiazolidinyl; isothiazolyl; morpholinyl; and thiomorpholinyl; or b. a monocyclic heterocyclic group containing a total of 5- or 6-member s of which two said members are nitrogen and a third or fourth said member is independently selected from N, O, and S where said S may optionally be in the sulfonate form, —S(=O)$_2$; wherein said heterocyclic group is selected from the group consisting of triazolyl; triazinyl; tetrazolyl; oxadiazolyl; thiadiazolyl; and $R^{13}_a$ is selected from the group consisting of hydrogen; F; Cl; —CO$_2$R$^4$; oxo; —OH; CN; NH$_2$; NH(C$_1$-C$_2$)alkyl; N(C$_1$-C$_2$)$_2$dialkyl; —CF$_3$; (C$_1$-C$_4$)alkyl; (C$_2$-C$_4$)alkenyl; (C$_1$-C$_2$)alkoxy; (C$_3$-C$_7$)cycloalkyl; and phenyl; wherein said alkyl, alkenyl, alkoxy, cycloalkyl and phenyl are substituted with 0 to 2 substituents R$^{11}$ where:

$R^{11}$ is a member selected from the group consisting of F; Cl; —CO$_2$R$^4$; —OH; —CN; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$)alkoxy wherein said alkyl and alkoxy are each independently substituted with 0 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy; and $R^{13}_b$ is a member selected from the group consisting of hydrogen; (C$_1$-C$_4$)alkyl; (C$_2$-C$_4$)alkenyl; (C$_1$-C$_2$)alkoxy; (C$_3$-C$_7$)cycloalkyl; C(=O)(C$_1$-C$_4$)alkyl;

$S(=O)_2(C_1-C_4)$alkyl; and phenyl; wherein said alkyl, alkenyl, alkoxy, cycloalkyl and phenyl are substituted with 0 to 2 substituents $R^{11}$ wherein $R^{11}$ has the same meaning as in above, except that it is selected independently;

B. a (substituted)-amido-aryl or -heterocyclyl moiety selected from the group consisting of
1. alkyl-, alkenyl-, and alkynyl-substituted-amido-aryl moieties of partial Formula (2.0.0):

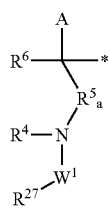
(2.0.0)

wherein: the symbol "*"; $R^4$ and $R^6$; are as defined above, except that all of the above-recited substituents are selected independently of their selection above;

A is a member selected from the group consisting of:
1. the moiety of partial Formula (2.0.3)

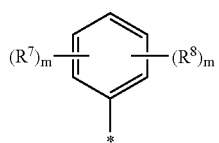
(2.0.3)

wherein: the symbol $R^7$; $R^8$ and m are as defined above, except that all of the above-recited substituents are selected independently of their selection above; and the symbol: "*" indicates the point of attachment of the moiety A to the, remaining portions of partial Formula (2.0.0);
2. the moiety of partial Formula (2.0.4)

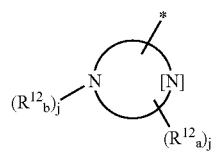
(2.0.4)

which represents a monocyclic heterocyclic group, selected from the group consisting of pyrrolyl; pyrazolyl; imidazolyl; pyridinyl; pyrazinyl; pyrimidinyl; wherein: the symbol $R^{12}_a$ and $R^{12}_b$ are as defined above, except that all of the above-recited substituents are selected independently of their selection above; and the symbol: "*" indicates the point of attachment of the moiety A to the other, remaining portions of partial Formula (2.0.0);

3. the moiety of partial Formula (2.0.5)

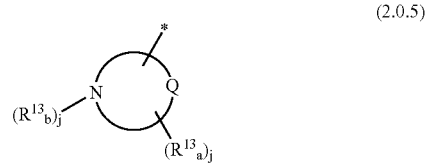
(2.0.5)

which represents
a. a monocyclic heteroaromatic group containing a total of 5-members of which one said member is nitrogen and Q is selected from O and S where said S may optionally be in the sulfonate form, $-S(=O)_2$; selected from the group consisting of oxazolyl; isoxazolyl; thiazoyl; and iso-thiazolyl; or
b. a monocyclic heterocyclic group containing a total of 5- or 6-members of which two said members are nitrogen and a third or fourth said member is independently selected from N, O, and S where said S may optionally be in the sulfonate form, $-S(=O)_2$; selected from the group consisting of triazolyl; triazinyl; tetrazolyl; oxadiazolyl; and thiadiazolyl; and
wherein: the $R^{13}_a$, $R^{13}_b$ and j are as defined above, except that all of the above-recited substituents are selected independently of their selection above; and the symbol: "*" indicates the point of attachment of the moiety A to the other, remaining portions of partial Formula (2.0.2);

$R^5_a$ is a member selected from the group consisting of a direct bond; $-C(=O)-$; and $-S(=O)_2-$;

$W^1$ is (1.) a direct bond; (2.) in the case where $R^5_a$ is $-C(=O)-$ or $-S(=O)_2$, $W^1$ is a direct bond or $-(C_1-C_3)$alkylene- wherein any single carbon atom thereof is substituted by 0 to 2 substituents $R^{23}$ where $R^{23}$ is a member selected from the group consisting of $-F$; $-Cl$; $-CO_2R^4$; $-OH$; CN; $(C_1-C_4)$alkoxy; $(C_3-C_7)$cycloalkyl; and phenyl; wherein said alkoxy, cycloalkyl, and phenyl are substituted with 0 to 2 substituents $R^{11}$, wherein said $R^{11}$ is as defined above, except that all of the above-recited substituents are selected independently of their selection above; or (3.) is a member independently selected from the group consisting of the moieties of partial Formulas (2.0.6) through (2.0.16), inclusive:

(2.0.6)

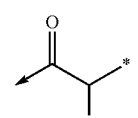
(2.0.7)

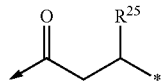
(2.0.8)

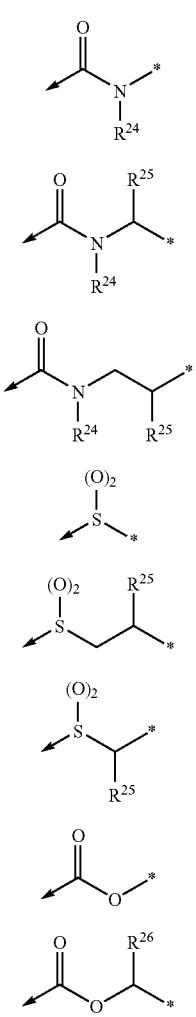

(2.0.9)
(2.0.10)
(2.0.11)
(2.0.12)
(2.0.13)
(2.0.14)
(2.0.15)
(2.0.16)

wherein: the symbol: "→" indicates the point of attachment of the moiety $W^1$ to the nitrogen atom in partial Formula (2.0.0), and the symbol: "*" indicates the point of attachment of the moiety $W^1$ to the other, remaining portions of partial Formula (2.0.0); and $R^4$ is as defined further above, but selected on an independent basis;

$R^{24}$ is selected from the group consisting of hydrogen and $(C_1-C_4)$alkyl; and $R^{25}$ and $R^{25}$ are each selected from the group consisting of —OH; $(C_1-C_2)$alkyl substituted by 0 to 3 substituents selected from F; and OH; and $(C_1-C_2)$alkoxy; and $R^{27}$ is selected from the group consisting of $(C_1-C_6)$alkyl; $(C_2-C_6)$alkenyl; and $(C_2-C_6)$alkynyl; wherein said alkyl, alkenyl, and alkynyl groups comprising $R^{27}$ are substituted with 0 to 3 substituents $R^{28}$ where:

$R^{28}$ is selected from the group consisting of phenyl; F or Cl; oxo; hydroxy; $(C_1-C_2)$alkyl; $(C_1-C_3)$alkoxy; —C(=O)OR$^{29}$; —C(=O)(C$_1$-C$_4$)alkyl; —S(=O)$_2$(C$_1$-C$_4$)alkyl; —C(=O)NR$^{29}$R$^{30}$; —NR$^{29}$R$^{30}$; —NR$^{29}$C(=O)R$^{30}$; —NR$^{29}$C(=O)OR$^{30}$; —NR$^{29}$S(=O)$_p$R$^{30}$; and —S(=O)$_2$NR$^{29}$R$^{30}$, where:

$R^{29}$ and $R^{30}$ are each a member independently selected from the group consisting of hydrogen and $(C_1-C_4)$ alkyl substituted by 0 to 3 substituents selected from the group consisting of F and Cl;

2. cycloalkyl-substituted-amido-aryl moieties of partial Formula (2.1.0):

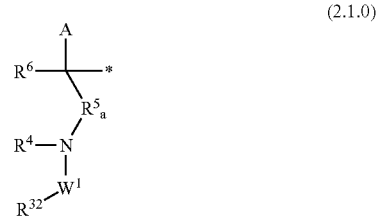

(2.1.0)

wherein: A; $W^1$; the symbol "*"; $R^4$; $R^5_a$; and $R^6$ have the same meaning as set out above, except that all of the above-recited substituents are selected independently of their selection above; and $R^{32}$ is a member selected from the group consisting of —(CH$_2$)$_n$-(C$_3$-C$_7$)cycloalkyl, where n is an integer selected from 0, 1, and 2; in the event n is 0, then the α-carbon atom of said (C$_3$-C$_7$)cycloalkyl is substituted by 0 or 1 (C$_1$-C$_4$)alkyl or phenyl, where said alkyl or phenyl are substituted by 0, 1, or 2 of CH$_3$, OCH$_3$, OH or NH$_2$; and in the event that n is 1 or 2, the resulting methylene or ethylene is substituted by 0 or 1 of F; NH$_2$; N(CH$_3$)$_2$; OH; OCH$_3$; (C$_1$-C$_4$)alkyl; or phenyl; where said alkyl and phenyl are substituted by 0, 1, or 2 of CH$_3$, OCH$_3$, OH, and NH$_2$; and further wherein said (C$_3$-C$_7$)cycloalkyl is substituted by 0 to 3 substituents $R^{28}$ where $R^{28}$ is as defined further above, but selected independently 3. aryl and heterocyclic-substituted-amido-aryl moieties of partial Formula (2.2.0):

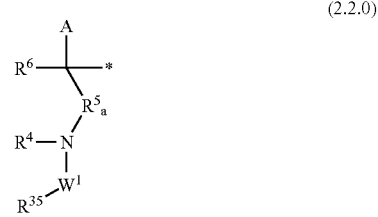

(2.2.0)

wherein: A; $W^1$; the symbol: "*"; $R^4$; $R^5_a$; and $R^6$ have the same meaning as set out above, except that all of the above-recited substituents are selected independently of their selection above; and $R^{35}$ is selected from the group consisting of phenyl; furyl; tetrahydrofuranyl; tetrahydropyranyl; oxetanyl; thienyl; pyrrolyl; pyrrolidinyl; oxazolyl; isoxazolyl; thiazolyl; isothiazolyl; imidazolyl; pyrazolyl; oxadiazolyl; thiadiazolyl; triazolyl; pyridyl; pyrazinyl; pyridazinyl; piperazinyl; pyrimidinyl; pyranyl; azetidinyl; morpholinyl; parathiazinyl; indolyl; indolinyl; benzo[b]furanyl; 2;3-dihydrobenzofuranyl; benzothienyl; 1H-indazolyl; benzimidazolyl; benzoxazolyl; benzisoxazolyl; benzthiazolyl; quinolinyl; isoquinolinyl; phthalazinyl; quinazolinyl; and quinoxalinyl; wherein (1.) said group $R^{35}$ may be substituted upon any one or more carbon atoms thereof by 0 to 3 substituents $R^{28}$ where $R^{28}$ is as defined above, except that it is selected independently; (2.) said group $R^{35}$ is substituted with respect to any one or more nitrogen atoms thereof that is not a point of attachment of said aryl or heterocyclic moiety, by 0 to 3 substituents $R^{13}{}_b$ where $R^{13}{}_b$ is as defined above, except that it is selected independently; and (3.) said group $R^{35}$ with respect to any sulfur atom thereof that is not a point of attachment of said heterocyclic moiety, is substituted by 0 or 2 oxygen atoms;

[$R_{egion}$ β] is an alkyl bridging element of partial Formula (3.0.0):

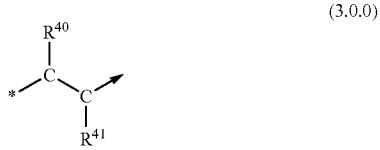

wherein:
"*" is a symbol which represents the point of attachment of the moiety of partial Formula (3.0.0) to $R_{egion}$ α;
"→" is a symbol which represents the point of attachment of the moiety of partial Formula (3.0.0) to $R_{egion}$ γ;
$R^{40}$ and $R^{41}$ are both selected from the group consisting of hydrogen; $(C_1-C_2)$ alkyl including dimethyl; hydroxy; and $(C_1-C_3)$ alkoxy;

[$R_{egion}$ γ] is an aza-monocyclic moiety of partial Formula (4.0.0):

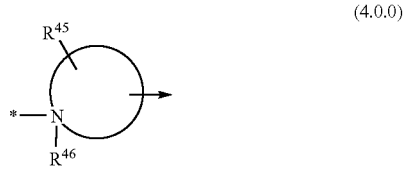

wherein:
"*" is a symbol which represents the point of attachment of the moiety of partial Formula (4.0.0) to $R_{egion}$ β of the compound of Formula (I);
"*→*" is a symbol representing a covalent bond attaching any carbon atom of said aza-monocyclic moiety of partial Formula (4.0.0) to $R_{egion}$ δ;
the moiety of partial Formula (4.0.1):

in partial Formula (4.0.0) represents a monocyclic heterocyclic group containing a total of from 4- to 7-members of which one said member is nitrogen, wherein said heterocyclic group is a member independently selected from the group consisting essentially of azetidinyl; pyrrolidinyl; piperidinyl; and azepinyl;
$R^{45}$ is absent or is a member independently selected from the group consisting essentially of $(C_1-C_4)$alkyl including dimethyl; $(C_3-C_6)$cycloalkyl; $(C_1-C_4)$alkoxy; $(C_1-C_2)$alkoxy(C1–C2)alkyl; $CF_3$; —$CO_2R^4$ where $R^4$ is as defined further above; oxo; —OH; cyano; —C(=O)$NR^4{}_aR^4{}_b$; —$NR^4{}_aR^4{}_b$; —$NR^4{}_aC(=O)R^4{}_b$; —$NR^4{}_aC(=O)OR^4{}_b$; —$NR^4{}_aS(=O)_pR^4{}_b$; —$S(=O)_p NR^4{}_aR^4{}_b$; $(C_1-C_2)$alkoxycarbonyl; $(C_1-C_2)$alkylcarbonyl; $(C_1-C_2)$alkylcarbonyloxy; and $(C_1-C_2)$alkoxy$(C_1-C_2)$alkyl; it being understood that in the moiety of partial Formula (4.0.0) $R^{45}$ is a substituent attached to a single carbon atom thereof; where:
$R^4{}_a$ and $R^4{}_b$ are each independently selected from hydrogen and $(C_1-C_2)$alkyl;
$R^{46}$ is absent or is a member independently selected from the group consisting essentially of hydrogen; and $(C_1-C_4)$alkyl substituted by 0 or 1 substituent independently selected from $(C_1-C_2)$alkoxy and —$CO_2R^4$ where $R^4$ is as defined further above; and ⊙⊙; it being understood that in the case where substituent $R^{46}$ is chosen to be other than absent, that it results in said nitrogen atom and said moiety of partial Formula (4.0.0) being in quaternary form;

[$R_{egion}$ δ] is a (substituted)-heterocyclyl moiety selected from the group consisting of:
1. a heterocyclyl moiety of partial Formula (5.3.0):

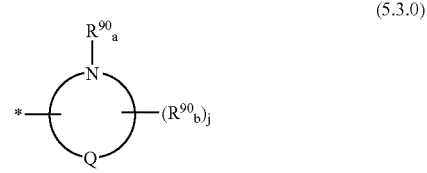

wherein: the symbol: "*" indicates the point of attachment of partial Formula (5.3.0) to $R_{egion}$ γ; Q is N, O or S and partial Formula (5.3.0) represents:
a. a monocyclic heterocyclic group containing a total of 5-members of which one said member is nitrogen and a second said member is selected from O and S where said S may optionally be in the sulfonate form, wherein said heterocyclic group is selected from the group consisting of oxazolyl; isoxazolyl; thiazolyl; and isothiazolyl; or
b. a monocyclic heterocyclic group containing a total of 5-members of which two said members are nitrogen and a third or fourth said member is independently selected from N, O, and S where said S may optionally be in the sulfonate form, —$S(=O)_2$; wherein said heterocyclic group is independently selected from the group consisting of triazolyl; triazinyl; tetrazolyl; oxadiazolyl; and thiadiazolyl; and
$R^{90}{}_a$ and $R^{90}{}_b$ are each a member independently selected from the group consisting of hydrogen, —$(C_1-C_2)$alkylcarbonyl; —$(C_1-C_4)$alkyl; —$(CH_2)_n$-$(C_3-C_7)$cycloalkyl; —$(C_2-C_3)$alkenyl; —$(CH_2)_n$-(phenyl); and —$(CH_2)_n$-(HET$_1$), where n is an integer independently selected from 0, 1, and 2; wherein said $(C_1-C_4)$alkyl, alkenyl, cycloalkyl, phenyl, and HET$_1$ groups are independently substituted with 0 to 3 substituents $R^{91}$, where:
j has the same meaning as set forth above, but is selected on an independent basis therefrom;
HET$_1$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; and morpholinyl; where:
$R^{91}$ is selected from the group consisting of —F; —Cl; —$CO_2R^4$; -oxo; —OH; —CN; —$CONR^{93}R^{94}$;

—NR$^{93}$R$^{94}$; C(=O)(C$_1$-C$_4$)alkyl; —NR$^{93}$C(=O)R$^{94}$; —NR$^{93}$C(=O)OR$^{94}$; —NR$^{93}$S(=O)R$^{94}$; —S(=O) NR$^{93}$R$^{94}$; (C$_1$-C$_4$)alkyl, and (C$_1$-C$_4$)alkoxy wherein said alkyl and alkoxy are each independently substituted with 0 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy; wherein:

R$^{93}$ and R$^{94}$ are each a member independently selected from the group consisting of hydrogen; and (C$_1$-C$_2$) alkyl; and 2. a heterocyclyl moiety of partial Formula (5.4.0):

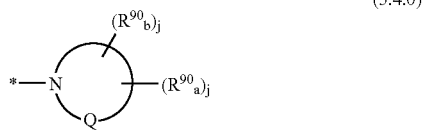

(5.4.0)

wherein: R$^{90}_a$; R$^{90}_b$; and j have the same meanings as set out above, but are selected independently.

Attention is drawn to our copending applications nos P60162WO and P60191WO.

An important aspect of the present invention is the limitation to R$_{egion}$ δ. The copending cases relate to alternative limitations of Formula (I).

This invention also provides pharmaceutical formulations and dosage forms including as an active ingredient a compound of Formula I. Use of a compound of Formula I in manufacture of a formulation or dosage form and methods of treatment are also provided.

[R$_{egion}$ α] is at the left-hand end of the CCR5 receptor modulator of the present invention. The region designated as R$_{egion}$ α may comprise a moiety selected from several different classes of substituent components, all of which, however, are contemplated to be, and are preferably isosteres of each other.

The first class of R$_{egion}$ α substituent components (under A.) are heterocyclyl phenylmethylene moieties as described further below. A preferred group of heterocyclyl phenylmethylene moiety embodiments (under A.1.) comprises the group consisting of hetero-phenylmethylene moieties of partial Formula (1.0.0),

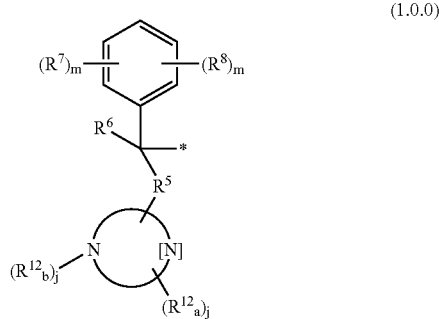

(1.0.0)

The substituent R$^5$ is a member independently selected from the group consisting of a direct bond; —O—; —C(=O)—; —NR$^4$—; and —S(=O)$_p$—; where R$^4$ is hydrogen or (C$_1$-C$_2$)alkyl.

The substituent R$^6$ is a member independently selected from the group consisting of hydrogen; (C$_1$-C$_2$)alkyl; (C$_1$-C$_2$)alkoxy; —C(=O)NH$_2$; —CN; and —OH. Most preferably R$^6$ is hydrogen and there is no substituent at this position.

Included within the partial Formula (1.0.0) are position isomer variations thereof that are not shown, but that arise where the optional substituents R$^7$ and R$^8$ are different. Substituents R$^7$ and R$^8$ are present once or twice or not at all, as indicated by their representation as: "(R$^7$)$_m$" and "(R$^8$)$_m$", where m is defined as being an integer selected from 0, 1, and 2. In the most preferred embodiments of the present invention, m is 0, although in alternative embodiments m is 1.

The substituents R$^7$ and R$^8$ comprise —F; —Cl; —CO$_2$R$^4$; —OH; —CN; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$)alkoxy wherein said alkyl and alkoxy are each independently substituted with 0 to 3 substituents independently selected from —F and —Cl; (C$_1$-C$_2$)alkoxycarbonyl; (C$_1$-C$_2$)alkylcarbonyl; and (C$_1$-C$_2$)alkylcarbonyloxy. The substituents R$^4_a$ and R$^4_b$, in turn, are selected from hydrogen and (C$_1$-C$_2$)alkyl. With regard to the R$^7$ and R$^8$ substituent groups, it is preferred that they are absent (m=0); or that if they are present, that they be methyl; cyclopropyl, cyclobutyl; methoxy; —COOH; —OH; —F; —Cl; —COO(C$_1$-C$_2$) alkyl; or —CF$_3$. Of these choices, the more preferred substituent choices for R$^7$ and R$^8$ are that they are absent or that they are —F or Cl.

R$^5$ as defined by Formula (1.0.0) is preferably a direct bond. The moiety R$^5$ may alternatively be selected from —O—; —C(=O)—; —NR$^4$— where R$^4$ is hydrogen or (C$_1$-C$_2$)alkyl; and —S(=O)$_p$—.

In partial Formula (1.0.0), the presence of substituent R$^{12}_a$ is determined by the subscript "j", which is an integer independently selected from 0, 1, and 2. Where j is 0, accordingly, the substituent R$^{12}_a$ will be absent Where j is 1 or 2, there may be one or two substituents R$^{12}_a$ present, and these may be attached to any available carbon atom in partial Formula (1.0.0).

R$^{12}_a$ is a member independently selected from the group consisting of hydrogen; —F; —Cl; —CO$_2$R$^4$ where R$^4$ is hydrogen or (C$_1$-C$_2$)alkyl as already defined above; -oxo; —OH; —CN; —NH$_2$; —NH(C$_1$-C$_2$)alkyl; —N(C$_1$-C$_2$)$_2$dialkyl; —CF$_3$; (C$_1$-C$_4$)alkyl; (C$_2$-C$_4$)alkenyl; (C$_1$-C$_4$)alkoxy; (C$_3$-C$_7$)cycloalkyl; and phenyl; wherein said alkyl, alkenyl, alkoxy, cycloalkyl and phenyl groups are substituted with 0 to 2 substituents R$^9$ wherein R$^9$ is a member independently selected from the group consisting of —F; —Cl; —CO$_2$R$^4$ where R$^4$ is hydrogen or (C$_1$-C$_2$)alkyl; —OH; cyano; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$)alkoxy wherein said alkyl and alkoxy are each independently substituted with 0 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy.

Where a R$^{12}_a$ substituent is present and consists of an alkyl, alkenyl, alkoxy, cycloalkyl or phenyl group, it may optionally be mono- or di-substituted in turn by a further substituent R$^9$, which is independently selected from the above-recited groups. This includes in particular (C$_1$-C$_4$) alkyl substituted with 1 to 3 substituents independently selected from F and Cl. Accordingly, the substituent —CF$_3$ is a preferred definition of R$^9$ in the compounds of partial Formula (1.0.0).

The R$^{12}_b$ substituent is attached directly to the nitrogen atom of the heterocyclic group depicted in partial Formula (1.0.0), and its presence is determined by the subscript "j", which is an integer independently selected from 0, 1, and 2. Where j is 0, accordingly, the substituent $R^{12}{}_b$ is absent. In that case that the nitrogen atom is attached by a covalent double bond to an adjacent atom in the heterocyclic group depicted in partial Formula (1.0.0). Where j is 1 or 2, there will be one or two substituents $R^{12}{}_b$ attached to the nitrogen atom of the heterocyclic group depicted in partial Formula (1.0.0). Where two such $R^{12}{}_b$ substituents are attached, the nitrogen atom is in quaternary form. The substituent $R^{12}{}_b$ is independently selected from the group consisting of hydrogen; $(C_1\text{-}C_4)$alkyl; $(C_2\text{-}C_4)$alkenyl; $(C_1\text{-}C_2)$alkoxy; $(C_3\text{-}C_7)$cycloalkyl; and phenyl; wherein said alkyl, alkenyl, alkoxy, cycloalkyl and phenyl are substituted with 0 to 2 substituents $R^9$ wherein $R^9$ has the same meaning as in $R^9$ defined above, except that it is selected independently therefrom.

The group represented by partial Formula (1.0.1):

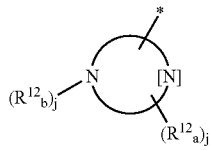

(1.0.1)

represents a monocyclic heterocyclic group, or a bicyclic benzo-fused ring system containing said heterocyclic group wherein said heterocyclic group contains a total of 5- or 6-members of which one or two of said members is nitrogen, the presence of the optional second nitrogen atom being represented by: "[N]"; wherein said heterocyclic group or ring system is selected from the group consisting of pyrrolyl; pyrazolyl; imidazolyl; pyridinyl; pyrazinyl; pyrimidinyl; pyridazinyl; piperazinyl; indolyl; indazolinyl; benzimidazolyl; quinolinyl; iso-quinolinyl; and quinazolinyl.

N-containing heterocyclic moieties of partial Formula (1.0.0) result in some of the following preferred embodiments of $R_{egion}$ α, represented by partial Formulas (1.0.4) through (1.0.10), inclusive:

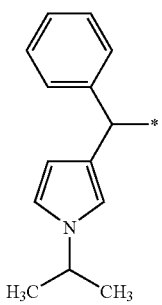

(1.0.4)

-continued

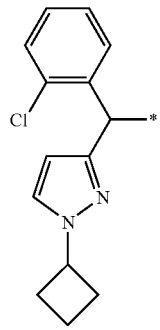

(1.0.5)

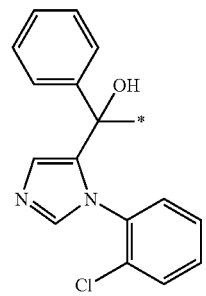

(1.0.6)

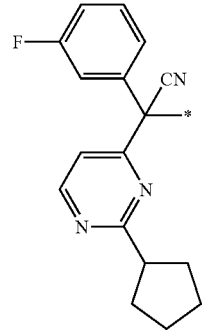

(1.0.7)

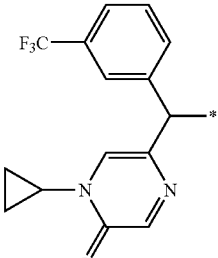

(1.0.8)

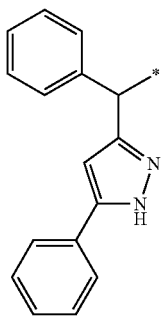

(1.0.9)

-continued

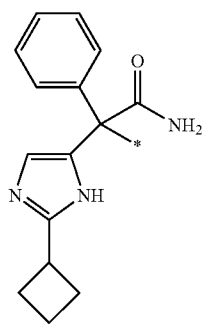

(1.0.10)

A further group of N-containing heterocyclic phenylmethylene moieties (under A.2 comprises several subgeneric groups within partial Formula (1.1.0):

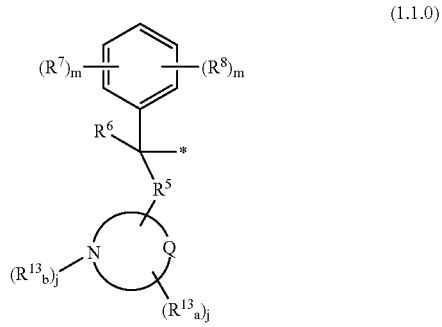

(1.1.0)

where the symbol "*" and $R^5$; $R^6$; $R^7$; $R^8$; j and m are as defined above;

and $R^{13}_a$ is a member selected from the group consisting of hydrogen; F; Cl; —CO$_2$R$^4$; oxo; —OH; CN; NH$_2$; NH(C$_1$–C$_2$)alkyl; N(C$_1$–C$_2$)$_2$dialkyl; —CF$_3$; (C$_1$–C$_4$)alkyl; (C$_2$–C$_4$)alkenyl; (C$_1$–C$_2$)alkoxy; (C$_3$–C$_7$)cycloalkyl; and phenyl; wherein said alkyl, alkenyl, alkoxy, cycloalkyl and phenyl are substituted with 0 to 2 substituents $R^{11}$ wherein $R^{11}$ is a member independently selected from the group consisting of F; Cl; —CO$_2$R$^4$; —OH; —CN; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$–C$_4$)alkyl including dimethyl, and (C$_1$–C$_4$)alkoxy wherein said alkyl and alkoxy are each independently substituted with 0, to 3 substituents independently selected from F and Cl; (C$_1$–C$_2$)alkoxycarbonyl; (C$_1$–C$_2$)alkylcarbonyl; and (C$_1$–C$_2$)alkylcarbonyloxy; and $R^{13}_b$ is selected from the group consisting of hydrogen; (C$_1$–C$_4$)alkyl; (C$_2$–C$_4$)alkenyl; (C$_1$–C$_2$)alkoxy; (C$_3$–C$_7$)cycloalkyl; C(=O)(C$_1$–C$_4$)alkyl; S(=O)$_2$(C$_1$–C$_4$)alkyl; and phenyl; wherein said alkyl, alkenyl, alkoxy, cycloalkyl and phenyl are substituted with 0 to 2 substituents $R^{11}$ wherein $R^{11}$ has the same meaning as in above, except that it is independently selected therefrom.

The moiety of partial Formula (1.1.1):

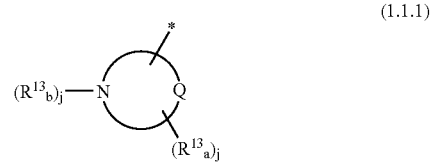

(1.1.1)

represents, inter alia, a monocyclic heterocyclic group containing a total of 5-members of which one said member is nitrogen and Q is selected from O and S The heterocyclic group may be selected from the group consisting of oxazolyl; oxazolidinyl; isoxazolyl; thiazolyl; thiazolidinyl; isothiazolyl: morpholinyl and thiamorpholinyl.

Moieties of partial Formula (1.1.0) containing the group of partial Formula (1.1.1) result in the following preferred embodiments of $R_{egion}$ α, represented by partial Formulas (1.1.3) through (1.1.9):

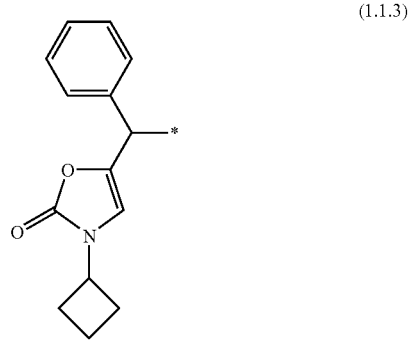

(1.1.3)

(1.1.4)

(1.1.5) 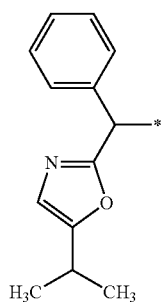
(1.1.6) 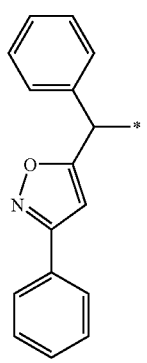
(1.1.7) 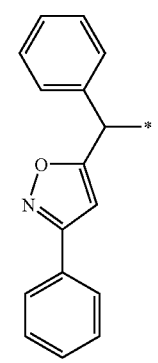
(1.1.8) 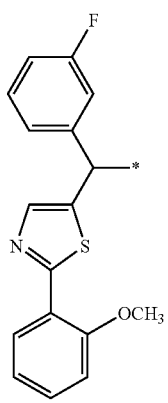
(1.1.9) 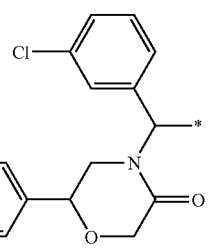
In alternative preferred embodiments the heterocyclic group may selected from the group consisting of triazolyl; triazinyl; tetrazolyl; oxadiazolyl; and thiadiazolyl.
Further preferred embodiments of $R_{egion}$ α, are represented by partial Formulas (1.1.20) through (1.1.24), inclusive:
(1.1.20) 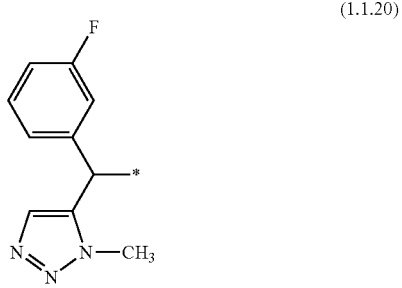
(1.1.21) 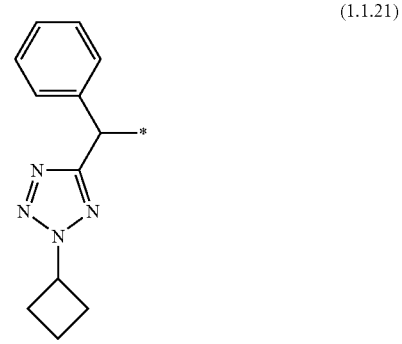
(1.1.22) 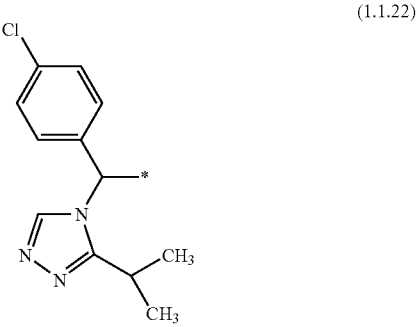

-continued (1.1.23)

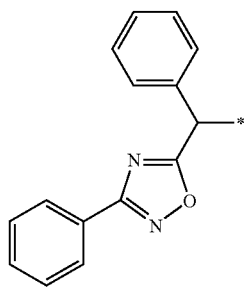

(1.1.24)

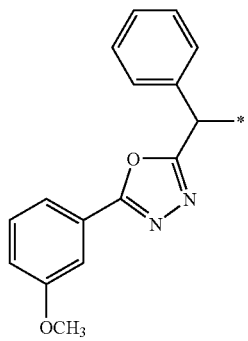

Another class of which R$_{egion}$ α moeities (under B) are (substituted)-amido-aryl or -heterocyclyl moieties which may be independently selected from several groups, as described in more detail below.

The first such class of (substituted)-amido-aryl or -heterocyclyl moieties of R$_{egion}$ α are those in which the amido-aryl or -heterocyclyl portion of the group is substituted by alkyl-, alkenyl-, or alkynyl, as represented by partial Formula (2.0.0)

(2.0.0)

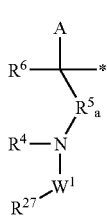

where the symbol "*" and R$^4$ and R$^6$; and m, R$^7$ and R$^8$ in the further definition of A; are as defined in the partial formulas above, except that all of the above-recited substituents are selected independently.

The moiety A in partial Formula (2.0.0) is a member independently selected from the group consisting of several different classes of moieties, as discussed below. The first class represented by partial Formula (2.0.3) is a preferred embodiment of this invention (2.0.3)

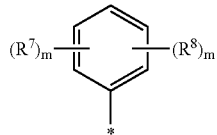

wherein the symbols R$^7$; R$^8$ and m are as defined in the partial formulas further above, except that all of the above-recited substituents are selected independently of their selection in said partial formulas further above; and the symbol: "*" indicates the point of attachment of the moiety A to the other, remaining portions of partial Formula (2.0.0).

Further embodiments of moiety A are depicted by partial Formulas (2.0.4) and (2.0.5). Partial Formula (2.0.4) is:

(2.0.4)

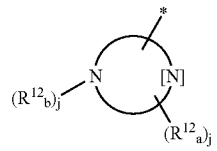

which represents a monocyclic heterocyclic group, selected from the group consisting of pyrrolyl; pyrazolyl; imidazolyl; pyridinyl; pyrazinyl; and pyrimidinyl. It is noted that in the moiety of partial Formula (2.0.3), the symbols R$^{12}_a$ and R$^{12}_b$, and the subscript "j" which determines their presence, are as defined in the partial formulas further above, except that "j" is 0 or 1 and all of the above-recited substituents are selected independently of their selection further above; and the symbol: "*" indicates the point of attachment of the moiety A to the other, remaining portions of partial Formula (2.0.0).

Further embodiments of moiety A are depicted by partial Formula (2.0.5)

(2.0.5)

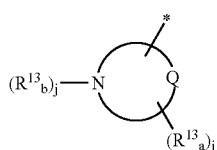

which represents a monocyclic heteroaromatic group containing a total of 5-members of which one said member is nitrogen and Q is selected from O and S where said S may optionally be in the sulfonate form, —S(=O)$_2$. Said heterocyclic group may be selected from the group consisting of oxazolyl; isoxazolyl; thiazolyl; and isothiazolyl; triazolyl; triazinyl; tetrazolyl; oxadiazolyl; and thiadiazolyl. It is noted that the symbols R$^{13}_a$ and R$^{13}_b$, and the subscript "j" which determines their presence, are as defined in the partial formulas further above, except that "j" is 0 or 1 and all of the above-recited substituents are selected independently of their selection in said partial formulas further above; and the symbol: "*" indicates the point of attachment of the moiety A to the other, remaining portions of partial Formula (2.0.0).

The group $R^5_a$ is selected from a direct bond; C(=O)—; and —S(=O)$_2$—. In preferred embodiments of the present invention $R^5_a$ is a direct bond. It is provided, however, that where $R^5_a$ is —CO— or —SO$_2$—, the divalent moiety $W^1$ is defined to additionally include the meaning of being a direct bond.

In partial Formula (2.0.0), $R^{27}$ is a member selected from the group consisting of (C$_1$-C$_6$)alkyl; (C$_2$-C$_6$)alkenyl; and (C$_2$-C$_6$)alkynyl; wherein said alkyl, alkenyl, and alkynyl groups comprising $R^{27}$ may be substituted with 0 to 3 substituents $R^{28}$ where $R^{28}$ is selected from the group consisting of F; Cl; oxo; hydroxy; (C$_1$-C$_2$)alkyl; (C$_1$-C$_3$)alkoxy; —C(=O)OR$^{29}$; C(=O)(C$_1$-C$_4$)alkyl; —S(=O)$_2$(C$_1$-C$_4$)alkyl; —C(=O)NR$^{29}$R$^{30}$; —NR$^{29}$R$^{30}$; —NR$^{29}$C(=O)R$^{30}$; —NR$^{29}$C(=O)OR$^{30}$; —NR$^{29}$S(=O)$_2$R$^{30}$; and —S(=O)$_2$NR$^{29}$R$^{30}$, where $R^{29}$ and $R^{30}$ are independently selected from hydrogen and (C$_1$-C$_4$)alkyl.

The moiety $W^1$ is a member independently selected from the group consisting of divalent moieties of partial Formulas (2.0.6) through (2.0.16), inclusive:

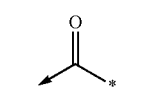
(2.0.6)

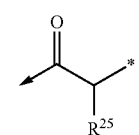
(2.0.7)

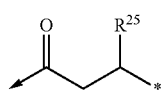
(2.0.8)

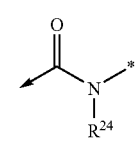
(2.0.9)

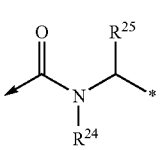
(2.0.10)

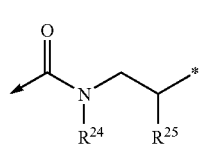
(2.0.11)

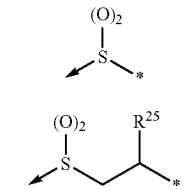
(2.0.12)

(2.0.13)

-continued

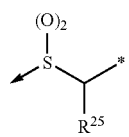
(2.0.14)

(2.0.15)

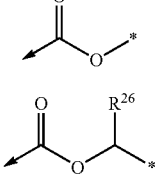
(2.0.16)

where the symbol: "→" indicates the point of attachment of the moiety $W^1$ to the nitrogen atom in partial Formula (2.0.0), and the symbol: "*" indicates the point of attachment of the moiety $W^1$ to the moiety $R^{27}$ which represents the remaining portions of partial Formula (2.0.0); and $R^{25}$ and $R^{26}$ are each independently a member selected from the group consisting of hydrogen; (C$_1$-C$_2$)alkyl substituted by 0 or 1 substituent independently selected from F and OH; and (C$_1$-C$_2$)alkoxy.

The bridging element —N(R$^4$)—W$^1$— may alternatively constitute or contain several different functionalities. The first and most preferred of these is an amide functionality, which may be represented as: —NR$^4$—C(=O)—. Other functionality types include sulfonamido and ureido moieties within the scope of partial Formulas (2.0.6) through (2.0.16).

Preferred alkyl and alkenyl groups $R^{27}$ include: methyl; ethyl; isopropyl; t-butyl; and propenyl (allyl). These alkyl and alkenyl groups may be substituted by 0 to 3 substituents $R^{28}$. It is preferred that where a substituent is present that it be a single substituent independently selected from F; Cl; OH; CF$_3$; CH$_3$; OCH$_3$; CN; NHCH$_3$; N(CH$_3$)$_2$; NHCOCH$_3$; NCH$_3$(COCH$_3$) and NH$_2$. Consequently, groups of partial Formula (2.0.0) which are preferred embodiments of the present invention constituting $R_{egion}$ α include the following moieties of partial Formulas (2.0.30) through (2.0.36), inclusive:

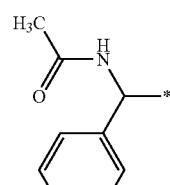
(2.0.30)

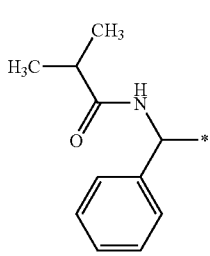
(2.0.31)

-continued (2.0.32) 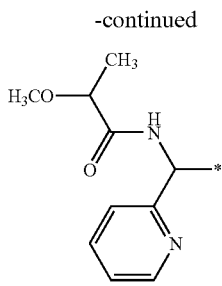

(2.0.33) 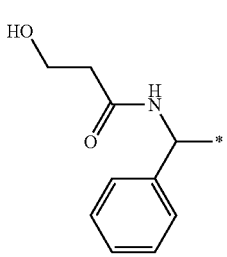

(2.0.34) 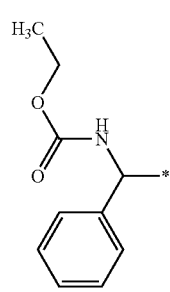

(2.0.35) 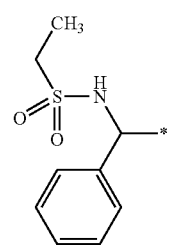

(2.0.36) 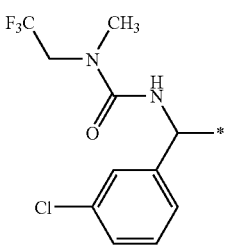

The second class of (substituted)-amido-aryl moieties comprising $R_{egion}$ α are those in which the amido-aryl portion of the group is substituted by -(cycloalkyl) or -alkyl(cycloalkyl), as represented by partial Formula (2.1.0).

(2.1.0) 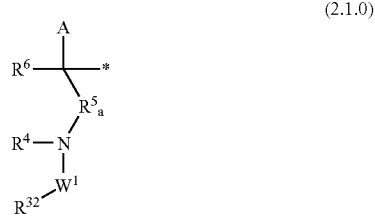

where; A; $W^1$; the symbol "*" and $R^4$; $R^5_a$; $R^6$; and m, $R^7$ and $R^8$ in the further definition of A; have the same meaning as set out in the partial formulas further above, except that all of the above-recited substituents are selected independently of their selection further above. $R^{32}$ is a member independently selected from the group consisting of —$(CH_2)_n$-$(C_3$-$C_7)$cycloalkyl, where n is an integer selected from 0, 1, and 2; in the event n is 0, then the α-carbon atom of said $(C_3$-$C_7)$cycloalkyl may be substituted by $(C_1$-$C_4)$alkyl or phenyl, where said alkyl or phenyl may be substituted by 1, or 2 of $CH_3$, $OCH_3$, OH or $NH_2$; and in the event that n is 1 or 2, the resulting methylene or ethylene group may be substituted by of F; Cl; CN; $NH_2$; $N(CH_3)_2$; OH; $OCH_3$; $(C_1$-$C_4)$alkyl; or phenyl. It will also be further noted that the basic $(C_3$-$C_7)$cycloalkyl group comprising $R^{32}$ may also be substituted by 0 to 3 substituents $R^{28}$ where $R^{28}$ has the same meaning as defined further above with respect to substituents for group $R^{27}$ under partial Formula (2.0.0), but independently selected therefrom.

Representative cycloalkyl and alkylcycloalkyl groups within the scope of $R^{32}$ include cyclopropyl, cyclobutyl, cyclopentyl, cyclohexyl; cyclopropylmethyl; cyclobutylethyl; cyclopentylpropmethyl; and cyclopentylmethyl. More preferred single substituents for these cycloalkyl and alkylcycloalkyl groups include F, Cl, and CN, especially OH; $OCH_3$; and $NH_2$. Accordingly, groups of partial Formula (2.1.0) which are preferred embodiments of $R_{egion}$ α include partial Formulas (2.1.3) through (2.1.10).

(2.1.3) 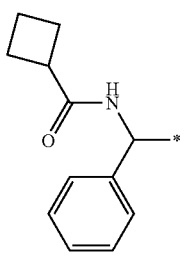

(2.1.4) 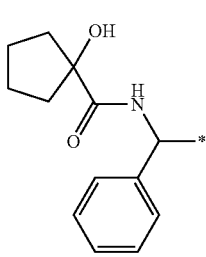

(2.1.5) 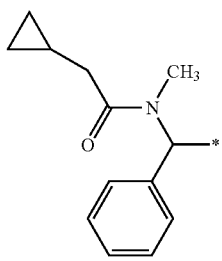

(2.1.6) 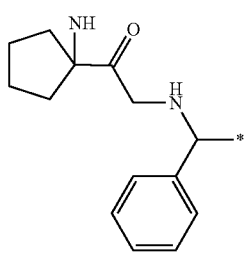

(2.1.7) 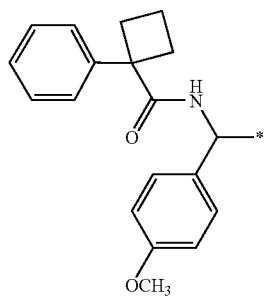

(2.1.8) 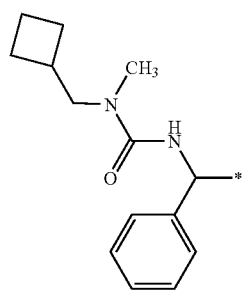

(2.1.9) 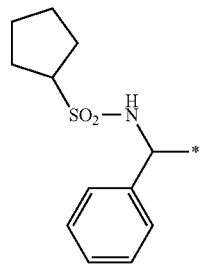

(2.1.10) 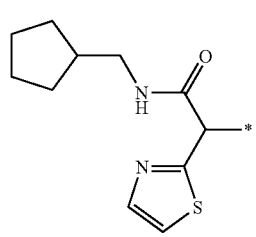

The third class of (substituted)-amido-aryl moieties of $R_{egion}\ \alpha$ are those in which the amido-aryl portion of the group is substituted by aryl- and heterocyclyl-substituted-amido-aryl moieties of partial Formula (2.2.0).

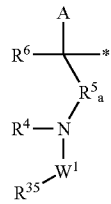

(2.2.0)

where A; $W^1$; the symbol "*" and $R^4$; $R^5_a$; $R^6$; and m, $R^7$ and $R^8$ in the definition of A; have the same meaning as set out above, except that all of the above-recited substituents are selected independently.

The moiety $R^{35}$ may be selected from the group consisting of phenyl; furyl; tetrahydropyranyl; tetrahydrofuranyl; oxetanyl; thienyl; pyrrolyl; pyrrolidinyl; oxazolyl; isoxazolyl; thiazolyl; isothiazolyl; imidazolyl; imidazolinyl; pyrazolyl; pyrazolinyl; oxadiazolyl; thiadiazolyl; G: triazolyl; pyridyl; pyrazinyl; pyridazinyl; piperazinyl; pyrimidinyl; pyranyl; azetidinyl; morpholinyl; parathiazinyl; indolyl; isoindolyl; 3H-indolyl; indolinyl; benzo[b]furanyl; 2;3-dihydrobenzofuranyl; benzothienyl; 1H-indazolyl; benzimidazolyl; benzoxazolyl; benzisoxazolyl; benzthiazolyl; benzoxdiazolyl; quinolinyl; isoquinolinyl; phthalazinyl; quinazolinyl; and quinoxalinyl.

Preferred meanings of $R^{35}$ are phenyl; pyrrolyl; oxazolyl; imidazolyl; pyridinyl; pyrimidinyl; triazolyl; indolyl; benzimidazolyl; benzotriazolyl; quinolinyl; thienyl; furfuryl; benzofuranyl; thiazolyl; oxazolyl; isoxazolyl; oxadiazolyl; and benzoxazolyl; and benzoxadiazolyl. Most preferred are tetrahydropyranyl; oxetanyl; azetidinyl and tetrahydrofuranyl. Group $R^{35}$ may be substituted by 3 substituents $R^{28}$ where $R^{28}$ has the same meaning as defined above but selected independently.

Alternative aryl and heterocyclyl groups falling within the scope of $R^{35}$ include phenyl; pyrrolyl; imidazolyl; pyridyl; oxazolyl; furyl; and benzofuranyl. Preferred single or double substituents for these groups include —CN; —F; Cl; —CONH₂; —CH₃; —CF₃; and —OCH₃.

Accordingly, groups of partial Formula (2.2.0) which are preferred embodiments of $R_{egion}\ \alpha$ include partial Formulas (2.2.3) through (2.2.14)

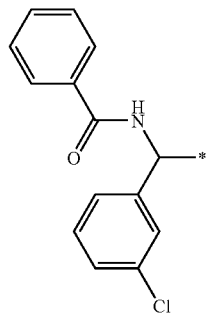

(2.2.3)

-continued
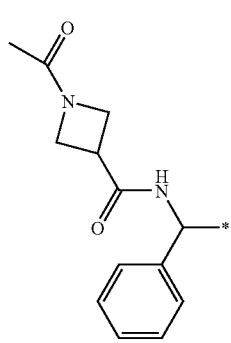 (2.2.4)
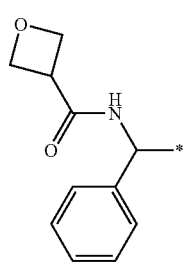 (2.2.5)
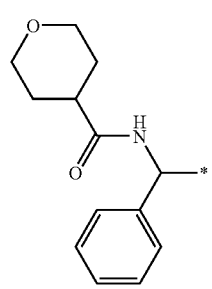 (2.2.6)
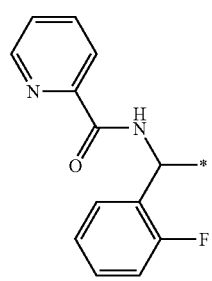 (2.2.7)
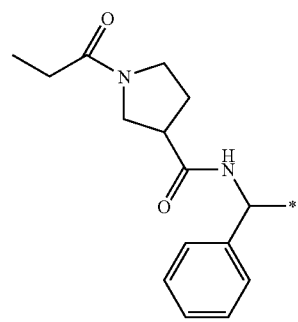 (2.2.8)
-continued
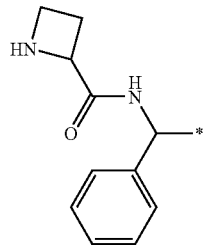 (2.2.9)
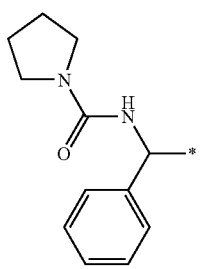 (2.2.10)
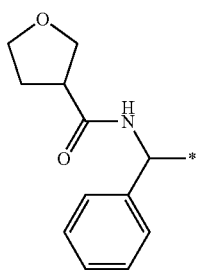 (2.2.11)
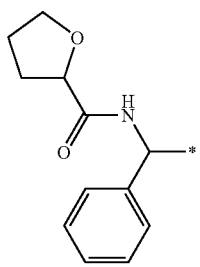 (2.2.12)
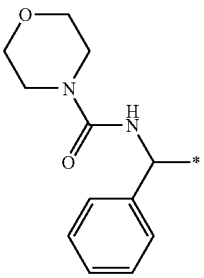 (2.2.13)

(2.2.14)

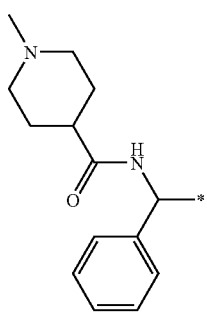

[R$_{egion}$ β] comprises a bridging element between R$_{egion}$ α described above and R$_{egion}$ γ described below.

The alkyl bridging element of R$_{egion}$ β comprises a moiety of partial Formula (3.0.0):

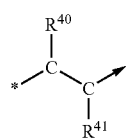

(3.0.0)

where the symbol "*" represents the point of attachment of the alkyl bridging element moiety of partial Formula (3.0.0) to R$_{egion}$ α of the modulator compound of Formula (I); and the symbol "→" represents the point of attachment of the alkyl bridging element moiety of partial Formula (3.0.0) to R$_{egion}$ γ of the modulator compound of Formula (I). Substituents R$^{40}$ and R$^{41}$ are both independently selected from the group consisting of hydrogen; ($C_1$–$C_2$) alkyl including dimethyl; hydroxy; and ($C_1$–$C_3$) alkoxy; provided that only one of R$^{40}$ and R$^{41}$ may be ($C_1$–$C_3$) alkoxy or hydroxy, the other one of R$^{40}$ or R$^{41}$ being selected from hydrogen and ($C_1$–$C_2$) alkyl including dimethyl.

Accordingly, R$^{40}$ and R$^{41}$ may be hydrogen; methyl; ethyl; dimethyl, i.e., two methyl groups joined to the single carbon atom to which R$^{40}$ or R$^{41}$ is attached; hydroxy; methoxy; ethoxy; or propoxy.

Some representative embodiments of the alkyl bridging element of partial Formula (3.0.0) include the following moieties of partial Formulas (3.0.1) through (3.0.7), inclusive:

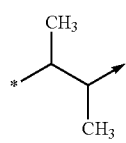

(3.0.1)

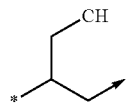

(3.0.2)

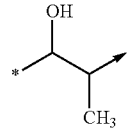

(3.0.3)

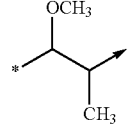

(3.0.4)

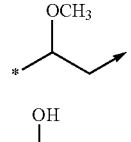

(3.0.5)

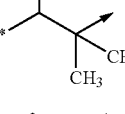

(3.0.6)

(3.0.7)

In the most preferred embodiments of the modulator compounds of the present invention, both R$^{40}$ and R$^{41}$ are hydrogen, and the alkyl bridging element of partial Formula (3.0.0) is unsubstituted ethylene. In preferred embodiments a single methyl, hydroxy, or methoxy substituent may be present, resulting in alkyl bridging elements such as those of partial Formulas (3.0.8) through (3.0.10):

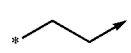

(3.0.8)

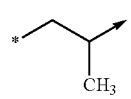

(3.0.9)

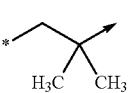

(3.0.10)

[R$_{egion}$ γ] comprises a member selected from the group consisting of a moiety of partial Formula (4.0.0):

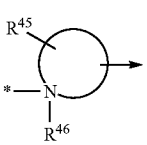

(4.0.0)

where "*" is a symbol representing the point of attachment of the aza-monocyclic moiety of partial Formula (4.0.0) to R$_{egion}$ β; and "→" is a symbol representing the point of attachment to R$_{egion}$ δ. It will be noted that in the moieties of partial Formula (4.0.0) the nitrogen atom covalently bonds said heterocyclic moieties to R$_{egion}$ β.

The heterocyclic moiety of partial Formula (4.0.1):

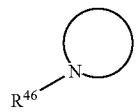

(4.0.1)

constituting a part of partial Formula (4.0.0) represents a monocyclic heterocyclic group containing a total of from 4- to 7-members of which one said member is nitrogen, wherein said heterocyclic group is a member independently selected from the group consisting essentially of azetidinyl; pyrrolidinyl; piperidinyl; and azepinyl, which may also be referred to as homopiperidinyl. With respect to the moieties of partial Formula (4.0.0) which define $R_{egion\ \chi}$ then, there is included the following groups represented by partial Formulas (4.0.2) through (4.0.5):

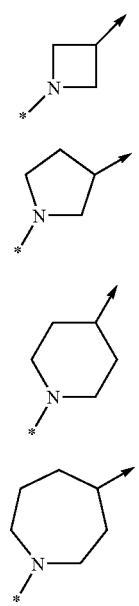

(4.0.2)

(4.0.3)

(4.0.4)

(4.0.5)

The above-defined moieties of partial Formula (4.0.0) are optionally mono-substituted by $R^{45}$ where $R^{45}$ is absent or is a member independently selected from the group consisting essentially of $(C_1-C_4)$alkyl including dimethyl; $(C_3-C_6)$cycloalkyl; $(C_1-C_4)$alkoxy; $(C_1-C_2)$alkoxy$(C_1-C_2)$alkyl; —$CF_3$; —$CO_2R^4$ where $R^4$ is as defined further above; oxo; —OH; —CN; —C(=O)$NR^4{}_aR^4{}_b$; —$NR^4{}_aR^4{}_b$; —$NR^4{}_aC(=O)R^4{}_b$; —$NR^4{}_aC(=O)OR^4{}_b$; —$NR^4{}_aS(=O)_pR^4{}_b$; —$S(=O)_pNR^4{}_aR^4{}_b$ where $R^4{}_a$ and $R^4{}_b$ are are each independently selected from hydrogen; $(C_1-C_2)$alkyl; $(C_1-C_2)$alkoxycarbonyl; $(C_1-C_2)$alkylcarbonyl; $(C_1-C_2)$alkylcarbonyloxy; and $(C_1-C_2)$alkoxy$(C_1-C_2)$alkyl. It will be understood that in the moieties of partial Formula (4.0.0), the substituent $R^{45}$ is attached to a single carbon atom of the above-above-described heterocyclic group. It will be further understood that where $R^{45}$ is defined as $(C_1)$alkyl, the methyl substituent may occur twice on a single carbon atom of the heterocyclic group, i.e., be a dimethyl substituent.

The substituent group $R^{46}$ is absent or is a member independently selected from the group consisting essentially of hydrogen; $(C_1-C_4)$alkyl substituted by 0 or 1 substituent independently selected from $(C_1-C_2)$alkoxy and —$CO_2R^4$ where $R^4$ is as defined further above; and →O. It will be appreciated that in the case where substituent $R^{46}$ is selected to be other than absent, that it will result in said nitrogen atom and said moiety of partial Formula (4.0.0) being in quaternary form. However, generally the quaternary forms of the compounds of the present invention are less preferred than their non-quaternary counterparts, although the skilled artisan can readily foresee that some particular embodiment may have more advantageous properties in its quaternary form than in its non-quaternary form.

Although it is preferred that the moieties of partial Formula (4.0.0) remain unsubstituted, i.e., that $R^{45}$ be absent, some examples of substituted moieties which are included within the scope of preferred embodiments of the present invention are those depicted in partial Formulas (4.0.6) through (4.0.13), inclusive:

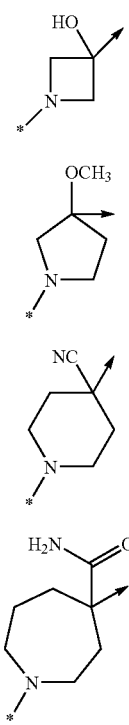

(4.0.6)

(4.0.7)

(4.0.8)

(4.0.9)

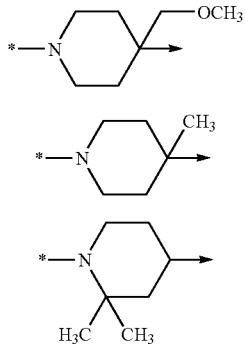

(4.0.10)

(4.0.11)

(4.0.12)

-continued (4.0.13)

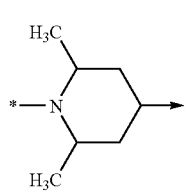

[R$_{egion}$ δ] constitutes the right-hand end of the compounds of Formula (I) and is attached directly to R$_{egion}$ γ described above. R$_{egion}$ δ of the compounds of Formula (I) comprises two subclasses of (substituted)-heterocyclyl moieties.

The first subclass of such heterocyclyl moieties is selected from those of partial Formula (5.3.0):

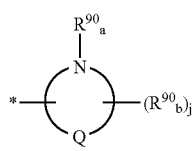

(5.3.0)

where the symbol: "*" indicates the point of attachment of partial Formula (5.3.0) to R$_{egion}$ γ; Q is N, O or S; and R$^{90}_a$ and R$^{90}_b$, are independently selected from the group consisting of hydrogen, —(C$_1$-C$_2$)alkylcarbonyl; —(C$_1$-C$_4$) alkyl; —(CH$_2$)$_n$-(C$_3$-C$_7$)cycloalkyl; —(C$_2$-C$_3$)alkenyl; —(CH$_2$)$_n$-(phenyl); and —(CH$_2$)$_n$-(HET$_1$), where n is an integer selected from 0, 1, and 2. Further, j has the same meaning as above, but is selected independently. It is more preferred that j is 0, in which case the R$^{90}_b$ substituent is absent. However, preferred embodiments of the present invention also include those wherein j is 1 and R$^{90}_b$ is methyl.

The heterocyclyl group HET$_1$ may be selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; morpholinyl.

The above-mentioned alkyl, alkenyl, cycloalkyl, phenyl, and heterocyclyl groups are optionally substituted with up to 3 substituents R$^{91}$ independently selected from the group consisting of F; Cl; —C(=O)OR$^{93}$; -oxo; —H; —CN; C(=O)(C$_1$-C$_4$)alkyl; S(=O)$_2$(C$_1$-C$_4$)alkyl; —CONR$^{93}$R$^{94}$; —NR$^{93}$R$^{94}$—; —NR$^{93}$C(=O)R$^{94}$; —NR$^{93}$C(=O)OR$^{94}$; —NR$^{93}$S(=O)$_2$R$^{94}$; —S(=O)$_2$NR$^{93}$R$^{94}$; (C$_1$-C$_4$)alkyl including dimethyl, and (C$_1$-C$_4$) alkoxy each substituted with 1 to 3 substituents independently selected from F and Cl; (C$_1$-C$_2$)alkoxycarbonyl; (C$_1$-C$_2$)alkylcarbonyl; and (C$_1$-C$_2$)alkylcarbonyloxy, where R$^{93}$ and R$^{94}$ are each a member independently selected from the group consisting of hydrogen; and (C$_1$-C$_2$)alkyl.

The heterocyclyic group which constitutes a part of the moiety of partial Formula (5.3.0), may be a five membered monocyclic group containing two or more of N, O or S, for example oxazolyl; isoxazolyl; thiazolyl; isothiazolyl; triazolyl; triazinyl; tetrazolyl; oxadiazolyl; and thiadiazolyl.

Preferred embodiments include Formulas (5.3.5) through (5.3.9):

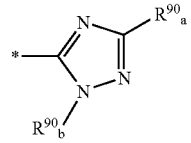

(5.3.5)

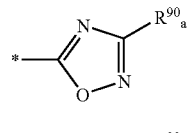

(5.3.6)

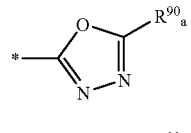

(5.3.7)

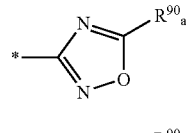

(5.3.8)

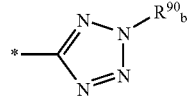

(5.3.9)

Accordingly, the following are preferred embodiments of the compounds of the present invention comprising moieties defining R$_{egion}$ δ in accordance with partial Formula (5.3.0), as represented by partial Formulas (5.3.15) through (5.3.26):

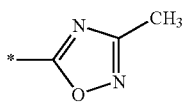

(5.3.15)

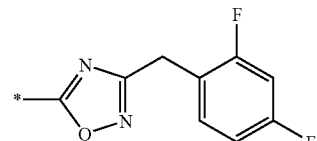

(5.3.16)

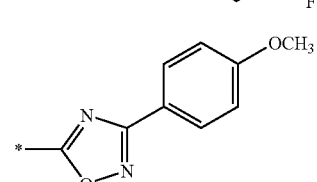

(5.3.17)

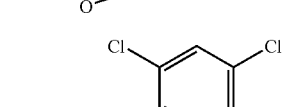

(5.3.18)

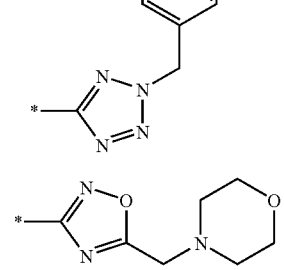

(5.3.19)

-continued (5.3.20)
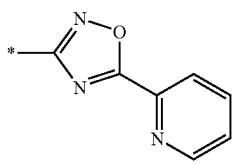

(5.3.21)
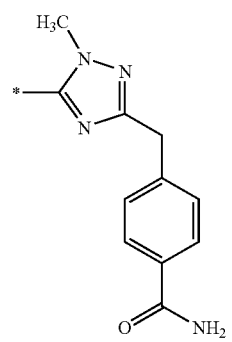

(5.3.22)
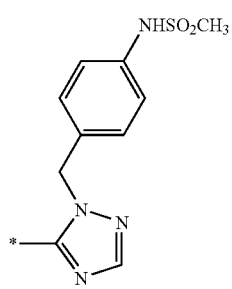

(5.3.23)
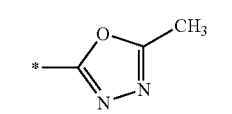

(5.3.24)
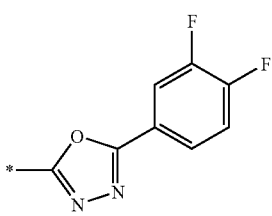

(5.3.25)
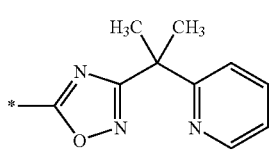

(5.3.26)
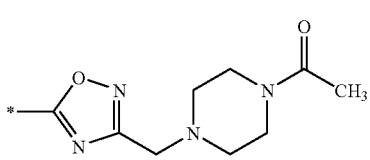

The second subclass of moieties (under C.2.) defining $R_{egion}$ δ may be selected from those of partial Formula (5.4.0):

(5.4.0)
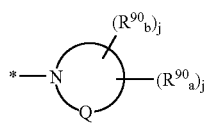

where Q, $R^{90}{}_a$ and $R^{90}{}_b$ have the same meaning as defined above, but are selected independently.

The heterocyclic group may be the same as in Formula 5.3.0 except that the nitrogen atom is the point of attachment Accordingly, Formulas (5.4.5) through (5.4.8) result:

(5.4.5)
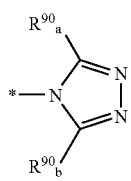

(5.4.6)
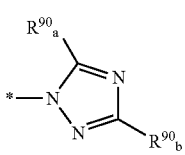

(5.4.7)
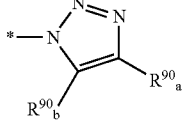

(5.4.8)
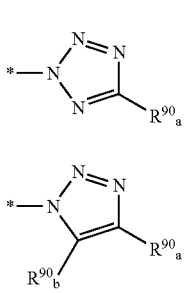

The following preferred embodiments of $R_{egion}$ δ are represented by partial Formulas (5.4.10) through (5.4.17):

(5.4.10)
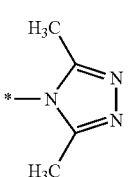

(5.4.11)
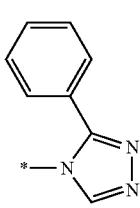

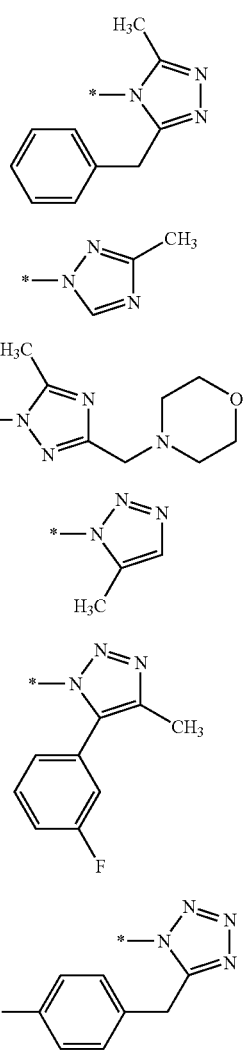

The compounds of the present invention may be utilized in the form of acids, esters, or other chemical derivatives. It is also within the scope of the present invention to utilize those compounds in the form of pharmaceutically acceptable salts derived from various organic and inorganic acids and bases in accordance with procedures well known in the art. The expression "pharmaceutically acceptable salt" as used herein is intended to mean an active ingredient comprising a compound of Formula (I) utilized in the form of a salt thereof, especially where said salt form confers on said active ingredient improved pharmacokinetic properties as compared to the free form of said active ingredient or other previously disclosed salt form.

A pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation or excretion of said active ingredient. While the route of administration of the pharmaceutical composition is important and various anatomical, physiological and pathological factors can critically affect bioavailability, the solubility of said active ingredient is usually dependent upon the character of the particular salt form thereof which it utilized. Further, an aqueous solution may provide the most rapid absorption of an active ingredient into the body of a patient being treated, while lipid solutions and suspensions, as well as solid dosage forms, may result in less rapid absorption. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

Well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such agents as ($C_1$–$C_4$) alkyl halides, e.g., methyl, ethyl, iso-propyl and tert-butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and stearyl chlorides, bromides and iodides; and aryl-($C_1$–$C_4$) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The compounds of this invention can be administered alone but will generally be administered in admixture with one or more suitable pharmaceutical excipients, diluents or carriers selected with regard to the intended route of administration and standard pharmaceutical practice.

For example, the compounds of the formula (I) can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art For oral and parenteral administration to human patients, the daily dosage level of the compounds of the formula (I) will usually be from 1 microgram/kg to 25 mg/kg (in single or divided doses).

Thus tablets or capsules of the compound of the formula (I) may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, eg dichlorodifluoromethane, trichlorofluoromethane, dichlorotetrafluoroethane, a hydrofluoroalkane such as 1,1,1,2-tetrafluorethane (HFA 134a), carbon dioxide or other suitable gas. In the case of a pressurised aerosol, the dosage unit may be determined by providing a valve to deliver a metered amount. The pressurised container or nebuliser may contain a solution or suspension of the active compound, eg using a mixture of ethanol and the propellant as the solvent, which may additional contain a lubricant, eg sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 µg to 20 mg of a compound of the formula (I) for delivery to the patient. The overall daily dose with an aerosol will be in the range of from 20 µg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benyl alcohol and water.

The compounds of Formula (I) are described herein as possessing biological activity such that they are able to modulate CCR5 chemokine receptor activity and consequent or associated pathogenic processes subsequently mediated by the CCR5 receptor and its ligands. The expression "modulate CCR5 chemokine receptor activity" as used herein is intended to refer to manipulation of the basic physiological processes and agencies which involve CCR5 chemokine receptors and their ligands. Included within the scope of this intended meaning are all types and subtypes of CCR5 receptors, in whatever tissues of a particular patient they are found, and in or on whatever components of the cells comprising those tissues they may be located. Most commonly, CCR5 receptors are situated on the cell membranes of particular cell types such as monocytes. CCR5 receptors participate in and define, along with various endogenous ligands to which they are naturally bound, signaling pathways which control important cellular and tissue functions by means of the influence which they exert on the movement of agents such as the chemokines, into and out of those cells and tissues.

The basic functioning of the CCR5 receptors and their ligands may be modulated in a number of ways, and the scope of the present invention is not limited in that regard to any particular existing or hypothesized pathway or process.

Thus, included within the intended meaning of modulation of CCR5 chemokine receptor activity, is the use of synthetically derived modulators introduced into a patient being treated, such as the compounds of Formula (I) described herein. These exogenous agents may modulate CCR5 receptor activity by such well known mechanisms as competitive binding in which the natural ligands are displaced and their inherent functions disrupted. However, the present invention is not limited to any such specific mechanism or mode of action. Thus, "modulation" as used herein is intended to encompass preferably antagonism, but also agonism, partial antagonism and/or partial agonism. Correspondingly, the term "therapeutically effective amount" means the amount of the subject compound that will elicit the biological or medical response of a tissue, system, animal or human that is being sought.

The term "patient" in this specification refers particularly to humans. However the compounds, methods and pharmaceutical compositions of the present invention may be used in the treatment of animals.

Further included within the scope of the present invention are metabolites or residues of the compounds of Formula (I) which possess biological activity such that they are able to modulate CCR5 chemokine receptor activity and consequent or associated pathogenic processes subsequently mediated by the CCR5 receptor and its ligands. Once synthesized, the CCR5 chemokine receptor modulating activities and specificities of the compounds of Formula (I) according to the present invention may be determined using in vitro and in vivo assays which are described in detail further below.

The desirable biological activity of the compounds of Formula (I) may also be improved by appending thereto appropriate functionalities which enhance existing biological properties of the compound, improve the selectivity of the compound for the existing biological activities, or add to the existing biological activities further desirable biological activities. Such modifications are known in the art and include those which increase biological penetration into a given biological system, e.g., blood, the lymphatic system, and central nervous system; increase oral availability; increase solubility to allow administration by injection; alter metabolism; and alter the rate of excretion of the compound of Formula (I).

The dosage and dose rate of the compounds of Formula (I) effective for treating or preventing diseases and conditions in a patient which are mediated by or associated with modulation of CCR5 chemokine receptor activity as described herein, as well as for favorably affecting the outcome thereof in said patient, in accordance with the methods of treatment of the present invention comprising administering to said patient a therapeutically effective amount of a compound of Formula (I), will depend on a variety of factors such as the nature of the active ingredient, the size of the patient, the goal of the treatment, the nature of the pathology being treated, the specific pharmaceutical composition used, the concurrent treatments that the patient may be subject to, and the observations and conclusions of the treating physician.

Generally, however, the effective therapeutic dose of a compound of Formula (I) which will be administered to a patient will be between about 10 µg (0.01 mg)/kg and about 60.0 mg/kg of body weight per day, preferably between about 100 µg (0.1 mg)/kg and about 10 mg/kg of body weight per day, more preferably between about 1.0 mg/kg and about 6.0 mg/kg of body weight per day, and most preferably between about 2.0 mg/kg and about 4.0 mg/kg of body weight per day of the active ingredient of Formula (I).

Included within the scope of the present invention are embodiments comprising coadministration of, and compositions which contain, in addition to a compound of the present invention as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combinations of therapeutic agents is especially pertinent with respect to the treatment and prevention of infection and multiplication within a patient in need of treatment or one at risk of becoming such a patient, of the human immunodeficiency virus, HIV, and related pathogenic retroviruses. The ability of such retroviral pathogens to evolve within a relatively short period of time into strains resistant to any monotherapy which has been administered to said patent is well known in the technical literature.

In addition to the requirement of therapeutic efficacy which may necessitate the use of active agents in addition to the CCR5 chemokine receptor modulating compounds of Formula (I), there may be additional rationales which compel or highly recommend the use of combinations of drugs involving active ingredients which represent adjunct therapy, i.e., which complement and supplement the function performed by the CCR5 chemokine receptor modulating compounds of the present invention. Such supplementary therapeutic agents used for the purpose of auxiliary treatment include drugs which, instead of directly treating or preventing a disease or condition mediated by or associated with CCR5 chemokine receptor modulation, treat diseases or conditions which directly result from or indirectly accompany the basic or underlying CCR5 chemokine receptor modulated disease or condition. For example, where the basic CCR5 chemokine receptor modulated disease or condition is HIV infection and multiplication, it may be necessary or at least desirable to treat opportunistic infections, neoplasms, and other conditions which occur as the result of the immune-compromised state of the patient being treated. Other active agents may be used with the compounds of Formula (I), e.g., in order to provide immune simulation or to treat pain and inflammation which accompany the initial and fundamental HIV infection.

Thus, the methods of treatment and pharmaceutical compositions of the present invention may employ the compounds of Formula (I) in the form of monotherapy, but said methods and compositions may also be used in the form of multiple therapy in which one or more compounds of Formula (I) are coadministered in combination with one or more known therapeutic agents such as those described in detail further herein.

The present invention also provides methods of treatment in which said pharmaceutical compositions are administered to a patient. Such methods relate to treating or preventing a disease or condition by modulating CCR5 chemokine receptor activity and consequent or associated pathogenic processes subsequently mediated by the CCR5 receptor and the active ligands with which it interacts or is bound. CCR5 and the other chemotactic cytokine, i.e., chemokine, receptors, play a key role in the control of a number of processes which take place in the bodies of animals. Chemokine receptors, of which more than forty different species divided into four families are presently known to exist, are proteins having a number of structural features in common, which act through chemical signaling. In the α family of chemokines, one amino acid (X) separates the first two cysteine residues, while in the β-chemokines the first two cysteine residues are adjacent to each other (C-C). Accordingly, these two families are identified as CXC and CC chemokines, respectively. The chemokines bind specific cell-surface receptors belonging to the family of G-protein-coupled seven-transmembrane-domain proteins called "chemokine receptors", named in accordance with the class of chemokines which they bind, followed by "R" and a number. Thus, "CCR5" is a C-C chemokine receptor. See Horuk, *Trends Pharm. Sci.,* 15,159–165 (1994) for further details. CCR5 thus belongs to the β-chemokine receptor family, which is currently known to contain eight members, CCR1 through CCR8.

The CC type of chemokine receptor interacts with various signaling proteins, including the monocyte chemoattractant proteins, MCP-1, -2, -3, 4, and -5; eotaxin-1; macrophage inflammatory proteins MIP-1α, and MIP-1β; and those regulated upon activation which are normal T-cell expressed and secreted, RANTES. The CCR5 type of chemokine receptor in particular is known to interact with MIP-1α, MIP-1β; and RANTES in monocytes, activated T cells, dendritic cells, and natural killer cells. These β-chemokines do not act on neutrophils but rather attract monocytes, eosinophils, basophils, and lymphocytes with varying degrees of selectivity.

The present invention relates to compounds of Formula (I) which are useful in treating or preventing HIV infection, and to methods of treatment and pharmaceutical compositions containing such compounds as the active ingredient. It will be understood that the term 'HIV' as used herein refers to human immunodeficiency virus (HIV), which is the etiological agent of AIDS (acquired immune deficiency syndrome), a disease that results in progressive destruction of the immune system and degeneration of the central and peripheral nervous system. Several HIV replication inhibitors are currently used as therapeutic or prophylactic agents against AIDS, and numerous others are presently under investigation.

In addition to cell-surface CD4, it has recently been shown that for entry into target cells, human immunodeficiency viruses require a chemokine receptor, CCR5 and CXCR-4 among others, as well as the virus's primary receptor CD4. The principal cofactor for entry mediated by the envelope glycoproteins of primary macrophage-tropic strains of HIV-1 is CCR5, which as already mentioned, is a receptor for the β-chemokines RANTES, MIP-1α and MIP-1β. See Deng, et al., *Nature,* 381, 661–666 (1996) for a further description of CCR5 mediated HIV entry.

HIV attaches to the CD4 molecule on cells through a region of its envelope protein, gp120, and gp120 is part of a multi-subunit complex, most likely a trimer of gp160, i.e., gp120+gp41. It is believed that the CD4 binding site on the gp120 of HIV interacts with the CD4 molecule on the cell surface, triggering conformational changes across the trimer, which allow it to bind to another cell-surface receptor, such as CCR5. This in turn enables gp41 to induce fusion with the cell membrane, and entry of the viral core into the cell. In addition, macrophage-tropic HIV and SIV envelope proteins have been shown to induce a signal through CCR5 on CD4+ cells, which may enhance the replication of the virus. See Weissman, et al., *Nature,* 389, 981–985 (1997) for a description of this phenomenon. Further, it has been shown that a complex of gp120 and soluble CD4 interacts specifically with CCR5 and inhibits the binding of the natural CCR5 ligands, as described in Wu, et al., *Nature,* 384, 179–183 (1996); and Trkola, et al., *Nature,* 384, 184–187 (1996). It has further been demonstrated that β-chemokines and related molecules, e.g., (AOP)—RANTES, prevent HIV fusion to the cell membrane and subsequent infection, both in vitro, as described in Dragic, et al., *Nature,* 381, 667–673 (1996), and in animal models. Finally, absence of CCR5 appears to confer protection from HIV-1 infection, as described in *Nature,* 382, 668–669 (1996). In particular, an inherited frame-shifting mutation in the CCR5 gene, Δ32, has been shown to abolish functional expression of the gene in vitro, and individuals homozygous for the mutation are apparently not susceptible to HIV infection, while at the same time they do not seem to be immunocompromised by this variant Furthermore, those heterozygote individuals that have been infected by HIV progress more slowly to full-blown clinical AIDS. In addition to validating the role of CCR5 in the infectious cycle of HIV, the above observations suggest that CCR5 is dispensable in the adult organism.

Although most HIV-1 isolates studied to date utilize CCR5 or CXCR-4, at least nine other chemokine receptors, or structurally related molecules, have also been described as supporting HIV-1 env-mediated membrane fusion or viral entry in vitro. These include CCR2b, CCR3, BOB/GPR15, Bonzo/STRL33/TYMSTR, GPR1, CCR8, US28, V28/CX3CR1, LTB-4, and APJ. There is good evidence that CCR3 can be used efficiently by a significant fraction of HIV-1 isolates in vitro, provided that this protein is over-expressed in transfected cells. Nevertheless, consistent evidence indicates that anti-HIV drugs targeted to chemokine receptors may not be compromised by this variability. Indeed, the chemokines RANTES, MIP-1α, MIP-1β, SDF-1 have been shown to suppress replication of primary HIV isolates. A derivative of RANTES, (AOP)-RANTES, is a sub-nanomolar antagonist of CCR5 function in monocytes. Monoclonal antibodies to CCR5 have been reported to block infection of cells by HIV in vitro. A small molecule antagonist of CXCR4, identified as AMD3100, has been reported to inhibit infection of susceptible cultures by CXCR4 dependent primary and lab-adapted HIV viruses while another small molecule called TAK 779 blocks entry of CCR5-tropic strains (Baba, et al. *PNAS,* 96 (10), 5698–5703 (1999); In addition, the majority of primary strains from early and late disease stages utilize CCR5 exclusively or in addition to other chemokine receptors, indicating that CCR5 dependent infection may play an essential role in the initiation and maintenance of productive HIV infection in a host. Accordingly, an agent which blocks CCR5 in patients including mammals, and especially humans who possess normal chemokine receptors, can reasonably be expected to prevent infection in healthy individuals and slow or halt viral progression in infected patients.

Accordingly, the present invention is directed to the compounds of Formula (I) which inhibit the entry of human immunodeficiency virus into target cells and are therefore of value in the prevention and/or treatment of infection by HIV, as well as the prevention and/or treatment of the resulting acquired immune deficiency syndrome (AIDS). Evidence can be produced which is probative of the fact that the compounds of Formula (I) described herein inhibit viral entry through selective blockade of CCR5 dependent fusion. Consequently, the present invention also relates to pharmaceutical compositions containing the compounds of Formula (I) as an active ingredient, as well as to the corresponding method of use of the compounds of Formula (I) as stand-alone agents, or in conjunction with other agents for the prevention and treatment of infection by HIV and resulting AIDS.

The utility of the compounds of Formula (I) of the present invention as inhibitors of HIV infection may be demonstrated by any one or more methodologies known in the art, such as the HIV microculture assays described in Dimitrov et al., *J. Clin. Microbiol.* 28, 734–737 (1990)), and the pseudotyped HIV reporter assay described in Connor et al., *Virology* 206 (2) 935–44 (1995). In particular, specific compounds of Formula (I) disclosed herein as preferred embodiments are shown to inhibit p24 production following replication of laboratory-adapted and primary HIV strains in primary blood lymphocytes (PBLs) and clonal cell-lines known to support replication of both CCR5 and CXCR4 tropic viruses, e.g., PM-1 and MOLT4-clone 8. It is also noted that only those viral strains known to use CCR5 are shown to be inhibited, whereas replication of CXCR4 tropic viruses is shown to be unaffected, indicating that compounds of Formula (I) disclosed herein are able to prevent viral entry through selective blockade of CCR5 dependent fusion. Furthermore, compounds of Formula (I) are shown to inhibit entry of chimeric HIV reporter viruses pseudotyped with envelope from a CCR5 dependent strain (ADA). Finally, compounds of Formula (I) are shown to inhibit infection of primary cells by HIV isolated from infected patient blood. Further confirmation of this anti-HIV mechanism is provided by experiments outlined below.

The ability of the compounds of Formula (I) to modulate chemokine receptor activity is demonstrated by methodology known in the art, such as the assay for CCR5 binding following procedures disclosed in Combadiere et al., *J. Leukoc. Biol.* 60, 147–52 (1996); and/or intracellular calcium mobilisation assays as described by the same authors. Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293. In particular, the compounds of Formula (I) disclosed herein are shown to have activity in preventing binding of all known chemokine ligands to CCR5 in the above-mentioned binding assays. In addition, the compounds of Formula (I) disclosed herein are shown to prevent intracellular calcium mobilization in response to endogenous agonists, which is consistent with their functioning as CCR5 antagonists. For the treatment of infection by HIV and the prevention and/or treatment of the resulting acquired immune deficiency syndrome (AIDS), compounds of Formula (I) which are shown to be antagonists are preferred to compounds of Formula (I) which are shown to be agonists.

The present invention in one of its preferred embodiments is directed to the use of the compounds of Formula (I) disclosed herein for the prevention or treatment of infection by a retrovirus, in particular, the human immunodeficiency virus (HIV) and the treatment and/or delaying of the onset of consequent pathological conditions, including but no limited to AIDS. The expressions "treating or preventing AIDS", and "preventing or treating infection by HIV" as used herein are intended to mean the treatment of a wide range of states of HIV infection: AIDS, ARC (AIDS related complex), both symptomatic and asymptomatic, and actual or potential exposure to HIV. The quoted expressions are not intended, however, to be limited to the recited treatments, but rather are contemplated to include all beneficial uses relating to conditions attributable to an AIDS causative agent For example, the compounds of Formula (I) are useful in treating infection by HIV after suspected past exposure to HIV by, e.g., blood transfusion, organ transplant, exchange of body fluids, sexual intercourse, bites, needle stick, or exposure to patient blood. In addition, a compound of Formula (I) may be used for the prevention of infection by HIV and the prevention of AIDS, such as in pre-or post-coital prophylaxis or in the prevention of maternal transmission of the HIV virus to a fetus or a child, whether at the time of birth, during the period of nursing, or in any other manner as above-described.

In a preferred embodiment of the present invention, a compound of Formula (I) may be used in a method of inhibiting the binding of human immunodeficiency virus to a chemokine receptor such as CCR5, which comprises contacting the target cell with a therapeutically effective amount of a compound of Formula (I) which is effective to inhibit the binding of the virus to the chemokine receptor. The subject treated by these preferred methods of the present invention is a mammal, preferably a human, male or female, in whom modulation of chemokine receptor activity is desired and contemplated to be efficacious. As already pointed out, the term "modulation" as used herein is intended to encompass preferably antagonism, but also agonism, partial antagonism and/or partial agonism. Also, the expression "therapeutically effective amount" as used herein is intended to mean the amount of a compound of Formula (I) as disclosed herein that will elicit the biological or medical response of a tissue, system, or animal, especially human that is being sought.

In another preferred embodiment of the present invention, a compound of Formula (I) may be used to evaluate putative retrovirus, especially HIV, mutants considered to be resistant to anti-HIV therapeutic agents, including the compounds of Formula (I) disclosed herein. Mutant viruses may be isolated from in vitro cultures by methods known in the art, but may also be isolated from in vivo animal infection models which have been disclosed in the art. More significantly, mutant viruses may be isolated from samples of patients undergoing treatment, whether optimal or sub-optimal, comprising administration of a compound of Formula (I), or any combination thereof with other known or to-be-discovered therapeutic agents. Such mutant viruses or their components, particularly their envelope proteins, may be used for several advantageous purposes, including but not limited to the following: (1) the evaluation and/or development of novel chemokine modulators or other agents having improved activity against such mutant viruses; and (ii) the development of diagnostics capable of assisting physicians or other clinicians in the choice of a therapeutic regimen and/or outcome prediction for a patient.

In a further preferred embodiment of the present invention, compounds of Formula (I) disclosed herein are used as tools for determining the co-receptor affinity of retroviruses including HIV and SIV, or their components, especially their envelope proteins. This affinity data can be used for several advantageous purposes, including but not limited to phenotyping a given viral population, e.g. prior to administration of anti-retroviral therapy. The affinity data may also be used to predict the progression and outcome of the infection by the virus population involved.

In another preferred embodiment of the present invention, a compound of Formula (I) is used in the preparation and execution of screening assays for compounds which modulate the activity of chemokine, especially CCR5 receptors. For example, compounds of Formula (I) as disclosed herein are useful for isolating receptor mutants, which can then be made into screening tools for the discovery of even more potent compounds, following procedures well known in the art. Furthermore, the compounds of Formula (I) are useful in establishing or characterizing the binding sites of other ligands, including compounds other than those of Formula (I) and viral envelope proteins, to chemokine receptors, e.g., by competitive inhibition. The compounds of Formula (I) are also useful for the evaluation of putative specific modulators of various chemokine receptors. As will be appreciated by the artisan, thorough evaluation of specific agonists and antagonists of the above-described chemokine receptors has been hampered by the lack of non-peptidyl, i.e., metabolically resistant compounds with high binding affinity for these receptors. Thus, the compounds of Formula (I) are useful as products which may be commercially exploited for these and other beneficial purposes.

Included within the scope of the present invention are combinations of the compounds of Formula (I) with one or more therapeutic agents useful in the prevention or treatment of AIDS. For example, the compounds of the present invention may be effectively administered, whether at periods of pre-exposure and/or post-exposure to HIV, in combination with therapeutically effective amounts of known AIDS antivirals, immunomodulators, anti-infectives, or vaccines familiar to those skilled in the art It will be understood that the scope of such combinations which include the compounds of Formula (I) is not limited to the above-recited list, but includes as well any combination with another pharmaceutically active agent which is useful for the prevention or treatment of HIV and AIDS.

Preferred combinations of the present invention include simultaneous, or sequential treatments with a compound of Formula (I) and one or more inhibitors of HIV protease and/or inhibitors of HIV reverse transcriptase, preferably selected from the class of non-nucleoside reverse transcriptase inhibitors (NNRTI), including but not limited to nevirapine, delavirdine, and efavirenz; from among the nucleoside/nucleotide inhibitors, including but not limited to zidovudine, didanosine, zalcitabine, stavudine, lamivudine, abacavir, and adefovir dipivoxil; and from among the protease inhibitors, including but not limited to indinavir, ritonavir, saquinavir, nelfinavir, and amprenavir. Other agents useful in the above-described preferred embodiment combinations of the present invention include current and to-be-discovered investigational drugs from any of the above classes of inhibitors, including but not limited to FTC, PMPA, fozivudine tidoxil, talviraline, S-1153, MKC-442, MSC-204, MSH-372, DMP450, PNU-140690, ABT-378, and KNI-764. There is also included within the scope of the preferred embodiments of the present invention, combinations of a compound of Formula (I) together with a supplementary therapeutic agent used for the purpose of auxiliary treatment, wherein said supplementary therapeutic agent comprises one or more members independently selected from the group consisting of proliferation inhibitors, e.g., hydroxyurea; immunomodulators, e.g., sargramostim, and various forms of interferon or interferon derivatives; fusion inhibitors, e.g., AMD3100, T-20, PRO-542, AD-349, BB-10010 and other chemokine receptor agonists/antagonists; integrase inhibitors, e.g., AR177; RNaseH inhibitors; inhibitors of viral transcription and RNA replication; and other agents that inhibit viral infection or improve the condition or outcome of HIV-infected individuals through different mechanisms.

Preferred methods of treatment of the present invention for the prevention of HIV infection, or treatment of aviremic and asymptomatic subjects potentially or effectively infected with HIV, include but are not limited to administration of a member independently selected from the group consisting of: (i) a compound within the scope of Formula (I) as disclosed herein; (ii) one NNRTI in addition to a compound of (i); (iii) two NRTI in addition to a compound of (i); (iv) one NRTI in addition to the combination of (ii); and (v) a compound selected from the class of protease inhibitors used in place of an NRTI in combinations (iii) and (iv).

The preferred methods of the present invention for therapy of HIV-infected individuals with detectable viremia or abnormally low CD4 counts further include as a member to be selected: (vi) treatment according to (i) above in addition to the standard recommended initial regimens for the therapy of established HIV infections, e.g., as described in Bartlett, J. G., "1998 Medical management of HIV infection", Johns Hopkins University publishers, ISBN 0-9244-2809-0. Such standard regimens include but are not limited to an agent from the class of protease inhibitors in combination with two NRTIs; and (vii) a standard recommended initial regimens for the therapy of established HIV infections, e.g., as described in Bartlett, J. G., "1998 Medical management of HIV infection", Johns Hopkins University publishers, ISBN 0-9244-2809-0), where either the protease inhibitor component, or one or both of the NRTIs is/are replaced by a compound within the scope of Formula (I) as disclosed herein. The preferred methods of the present invention for therapy of HIV-infected individuals that have failed antiviral therapy further include as a member to be selected: (viii) treatment according to (i) above, in addition to the standard recommended regimens for the therapy of such patients, e.g., as described in Bartlett, J. G., "1998 Medical management of HIV infection", Johns Hopkins University publishers, ISBN 0-9244-2809-0); and (ix) a standard recommended initial regimens for the therapy of patients who have failed antiretroviral therapy, e.g., as described in Bartlett, J. G., "1998 Medical management of HIV infection", Johns Hopkins University publishers, ISBN 0-9244-2809-0), where either one of the protease inhibitor components, or one or both of the NRTIs is/are replaced by a compound within the scope of Formula (I) as disclosed herein. In the above-described preferred embodiment combinations of the present invention, the compound of Formula (I) and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s). The compounds of Formula (I) may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In particular, however, the treatment of retroviral infections, and more particularly HIV, may be guided by genotyping and phenotyping the virus in the course of or prior to the initiation of administration of the therapeutic agent. In this way, it is possible to optimise dosing regimens and efficacy when administering a compound of Formula (I) for the prevention or treatment of infection by a retrovirus, in particular, the human immunodeficiency virus (HIV).

The compounds of this invention may be used for treatment of respiratory disorders, including: adult respiratory distress syndrome (ARDS), bronchitis, chronic bronchitis, chronic obstructive pulmonary disease, cystic fibrosis, asthma, emphysema, rhinitis and chronic sinusitis.

The invention is further described by means of examples, but not in any limitative sense. The following general synthetic routes were employed.

Methods of Preparing Compounds of the Present Invention

Synthesis I base such as sodium hydroxide, in an alcoholic solvent, typically methanol or ethanol, at room temperature.

Compounds of the general formula VII may be prepared by the reductive alkylation of an appropriate amine of formula V, with an aldehyde, of formula IV. The reaction may be carried out in the presence of an excess of suitable reducing agent (e.g. sodium triacetoxyborohydride) in a protic solvent system (acetic acid in dichloromethane or 1,1,1-trichloroethane), at room temperature, for between 30 minutes and 18 hours.

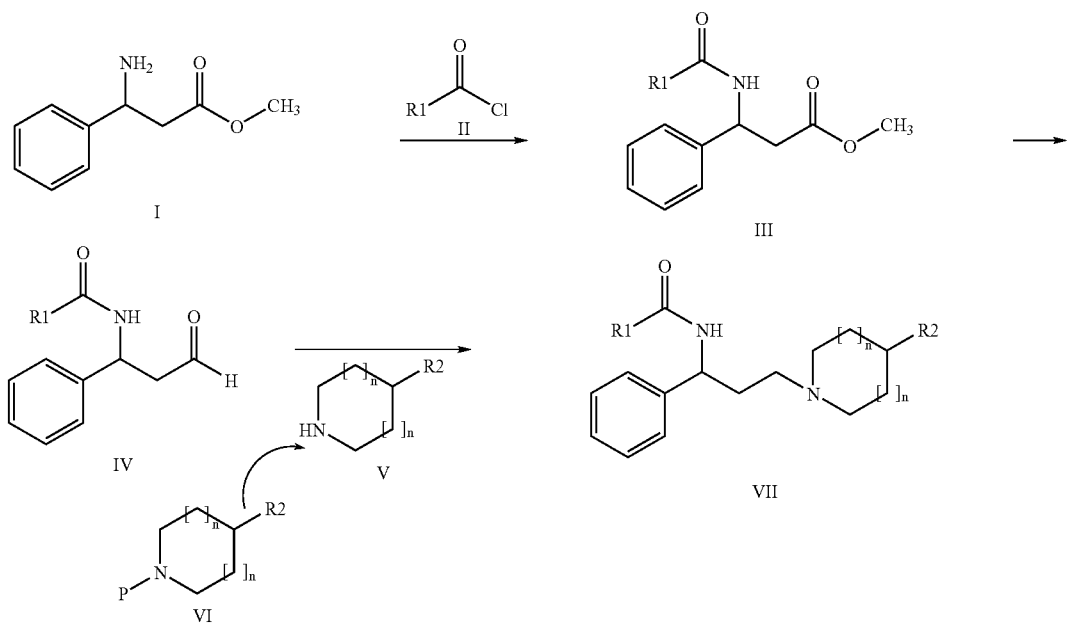

n=0 or 1

Compounds of formula III may be prepared by coupling the amino acid derivative of formula I with an acid chloride of formula II in the presence of a tertiary amine, such as triethylamine, in a suitable solvent, such as dichloromethane at between 0° C. and room temperature. Compounds of formula IV may be prepared by reduction of compounds of formula III, using a suitable reducing agent, preferably diisobutylaluminium hydride in dichloromethane at −78° C.

Removal of the nitrogen protecting group (where P is a protecting group, is typically, benzyl, Boc, CBz or trifluoroacetate), from the amine of formula VI, may be achieved using standard methodology, to provide the amine of formula V. For example, Boc may be removed under conditions of protonolysis using hydrochloric acid or trifluoroacetic acid in a suitable solvent such as dichloromethane, methanol or tetrahydrofuran, at room temperature for between 2 and 15 hours. Removal of a benzyl or CBz group may be achieved under conditions of transfer catalytic hydrogenation, using a catalyst such as Pearlman's catalyst, in the presence of excess ammonium formate, in a suitable solvent such as ethanol under reflux conditions. Alternatively, a benzyl group may be removed by treatment with 1-chloroethyl chloroformate in a suitable solvent such as dichloromethane at between 0° C. and room temperature.

A trifluoroacetate protecting group may be removed under conditions of basic hydrolysis, using an excess of a suitable Alternatively, a compound of formula VIII may be prepared in a "one-pot" procedure, by deprotection of the nitrogen protecting group from the compound of formula VI, and reacting the intermediate amine V, with the aldehyde of formula IV, under conditions of reductive alkylation, using the methods described above.

When a compound of formula I, is required as a single enantiomer, it may be obtained according to the method of Davies et al. (J. Chem. Soc. Perk. Trans. I; 9; 1994; 1129).

Synthesis II

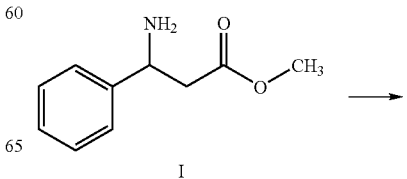

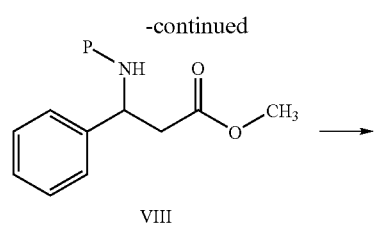

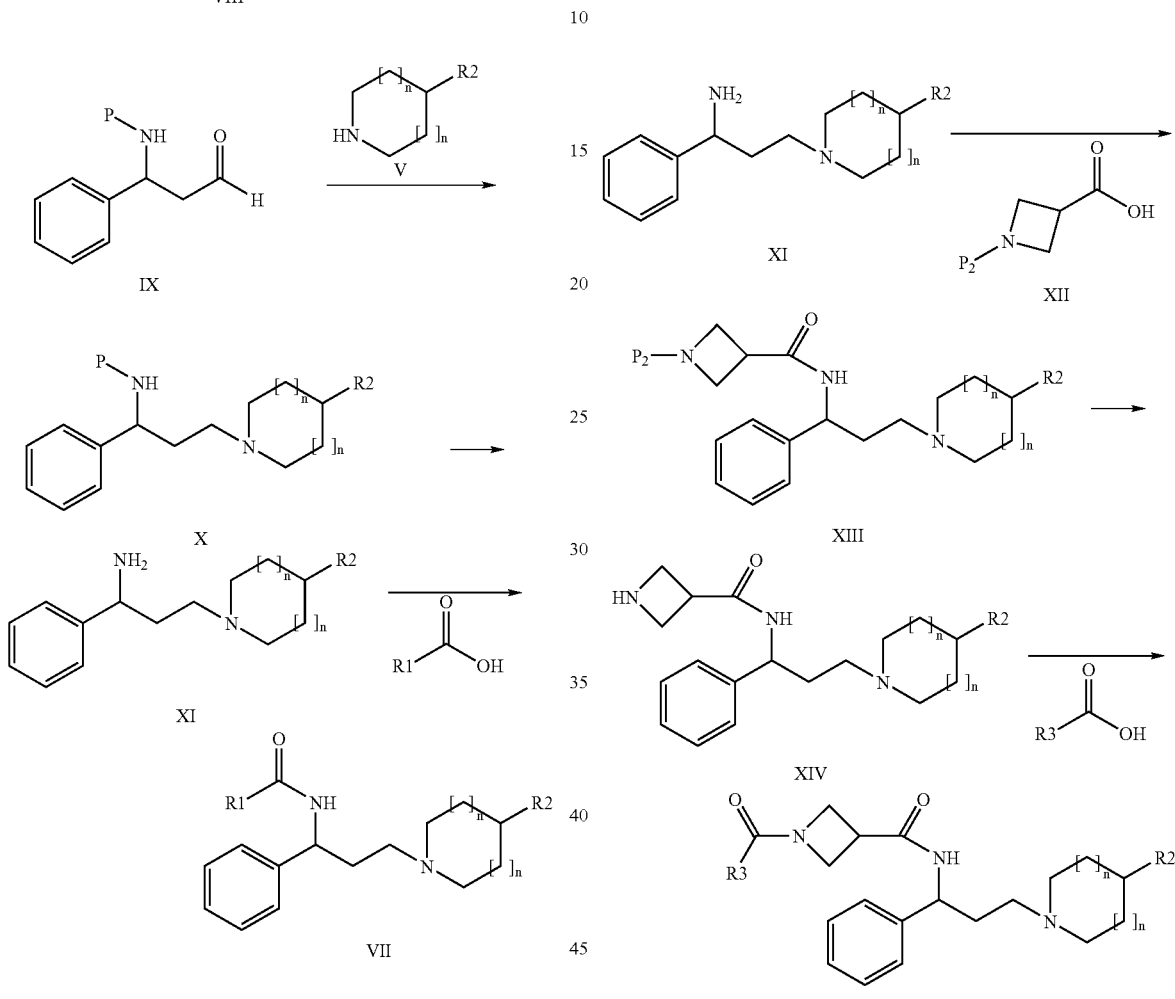

Preparation of the compounds of formula VIII from the amino acid derivative I where P is a suitable protecting group (preferably BOC), may be achieved for example, by reaction with di-tert-butyl dicarbonate in the presence of a base such as aqueous sodium hydroxide in a suitable solvent such as tetrahydrofuran. Compounds of formula IX may be prepared by reduction of compounds of formula VIII, according to the method described in synthesis 1. Reductive alkylation of the amine of formula V, with the aldehyde of formula IX, according to the method described in synthesis I, may provide the compounds of formula X.

Subsequent removal of the nitrogen protecting group may be achieved, for example using trifluoroacetic acid or hydrochloric acid in a solvent such as methanol or dichloromethane at room temperature for from 1 to 60 hours to provide the compound of formula XI. Compounds of general formula VII may be prepared by coupling the amine of formula XI with an acid ($R1CO_2H$) using conventional amide bond forming techniques. For example, the acid may be activated using a carbodiimide such as 3(3-dimethylamino-1-propyl)-1-ethylcarbodiimide, optionally in the presence of 1-hydroxybenzotriazole hydrate. These reactions may be performed in a suitable solvent such as dichloromethane, optionally in the presence of a tertiary amine, such as triethylamine or N-ethyldiisopropylamine at about room temperature.

Synthesis III

Compounds of the general formula XIII may be prepared by coupling the amine of formula XI with the protected amino acid of formula XII (P is a protecting group, typically BOC) using methods previously described in synthesis II. Removal of the nitrogen protecting group, using standard methodology such as protonolysis using trifluoroacetic acid, according to the methods previously described, provides the compound of formula XIV.

Alternatively, the amine of general formula XIV may be formed in a "one-pot" procedure, by coupling the amine of formula XI with the acid of formula XII, followed by deprotection of the resultant intermediate, using the methods previously described.

Compounds of formula XV may be prepared by coupling the amine of formula XIV with an acid ($R3CO_2H$), according to the methods described in synthesis II.

Synthesis IV

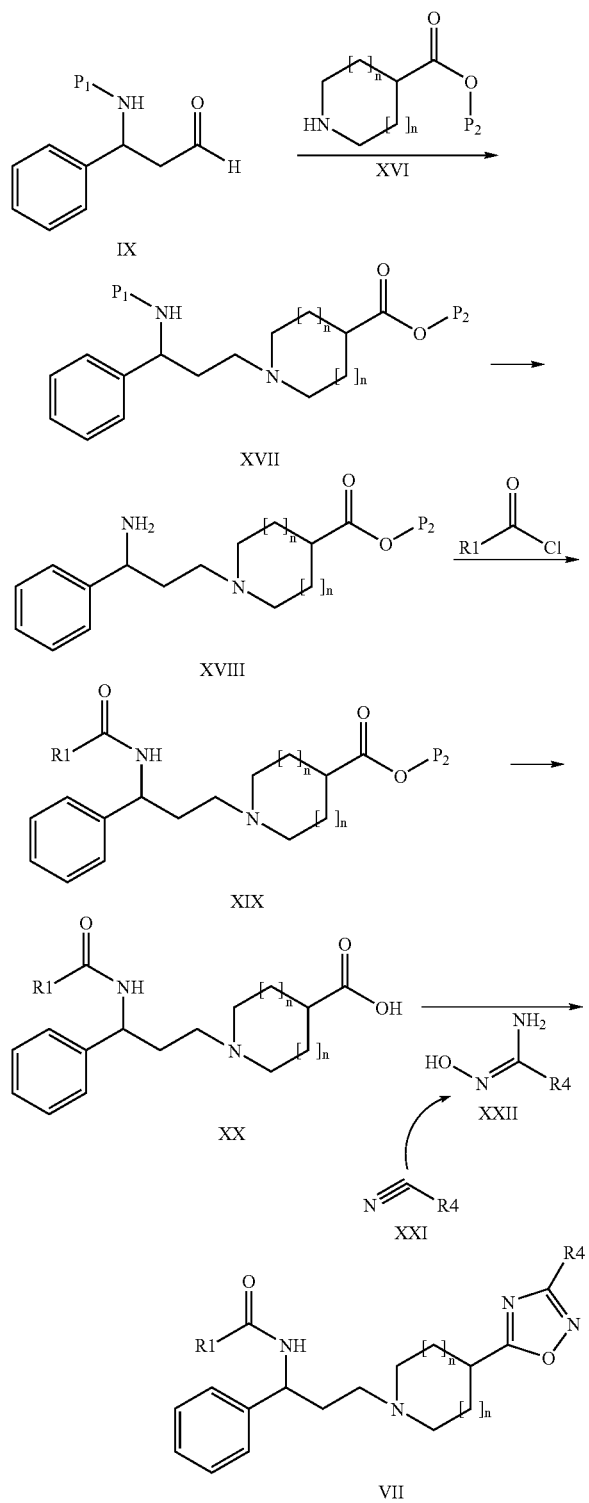

Compounds of general formula XVII may be prepared by reductive alkylation of the protected amine XVI (where P2 is preferably benzyl), with the aldehyde of general formula IX (where P1 is preferably Boc), according to the methods previously described. Removal of the nitrogen protecting group, P1, using conditions previously described, provides the amine of general formula XVIII. Compounds of formula XIX may be prepared by coupling the amine of formula XVIII with an acid chloride (R1COCl), in the presence of a tertiary amine, such as N-ethyldiisopropylamine, in a suitable solvent, such as dichloromethane at room temperature. Removal of the oxygen protecting group, from the compound of formula XIX using standard methodology provides the acid of formula XX. Typically removal of the benzyl group may be achieved under catalytic hydrogenation conditions using a catalyst such as palladium on charcoal, in an alcoholic solvent, preferably ethanol, at a hydrogen pressure of about 1 atm, and room temperature.

Compounds of formula XXII may be prepared from compounds of formula XXI using conventional techniques. For example, treatment of the nitrile of formula XXI, with a 5-fold excess of hydroxylamine hydrochloride, in the presence of a 5-fold excess of base, typically sodium carbonate or sodium methoxide, in a suitable solvent such as aqueous methanol, at room temperature, may provide compounds of formula XXII.

Compounds of formula VII may be prepared by coupling the acid of formula XX with an appropriate amidoxime of formula XXII, using conventional amide bond forming techniques, followed by in-situ cyclocondensation of the intermediate product.

For example, the acid may be activated using a carbodiimide such as 3-(3-dimethylamino-1-propyl)-1-ethylcarbodiimide, optionally in the presence of N-dimethylaminopyridine. These reactions may be performed in a solvent such as dichloromethane, optionally in the presence of a tertiary amine, such as N-methylmorpholine or N-ethyldiisopropylamine at about room temperature. Alternatively, the acid may be activated using a fluorinating agent, such as N,N,N',N'-bis(tetramethylene)fluoroformamidinium hexafluorophosphate (J.A.C.S. 1995; 117(19); 5401) in the presence of a base such as N-ethyldiisopropylamine in a suitable solvent such as dichloromethane at room temperature. Cyclocondensation of the resultant intermediate may subsequently be achieved by heating in an appropriate solvent such as dioxane or toluene at elevated temperature (e.g. 130° C.) for between 4 and 15 hours.

Alternatively, a compound of formula VII may be formed in a "one-pot procedure", by preparing the amidoxime of formula XXII from the nitrile of formula XXI, then coupling and cyclising the resultant intermediate with the acid of formula XX according to the methods described above.

Synthesis V

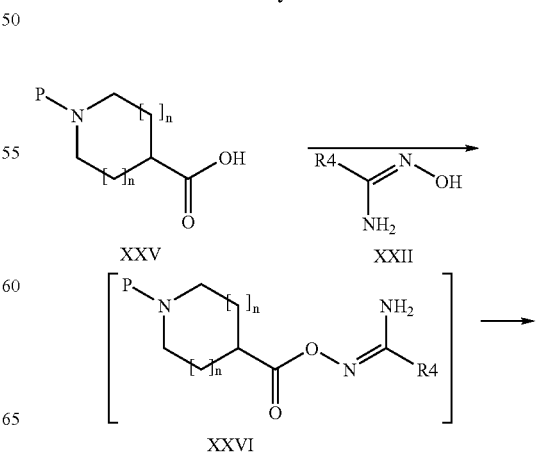

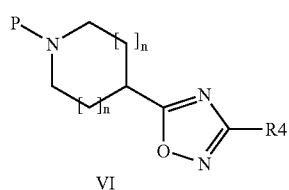

n is independently 0 or 1.

Compounds of formula VI may be prepared by coupling the protected amino acid of formula XXV (where P is a protecting group, preferably trifluoroacetate) with an amidoxime of formula XXII, followed by cyclisation of the resultant intermediate. The acid amine coupling may be achieved using methods previously described in synthesis IV, Cyclisation of the resultant O-acylamidoxime intermediate, of formula XXVI to afford the compound of formula VI, may be achieved by heating in an appropriate solvent such as dioxane or toluene at elevated temperature (110° C.) for about 18 hours.

Alternatively, in a variation of this "one-pot" procedure, the O-acylamidoxime may be isolated, and then cyclised using the methods described above.

Synthesis VI

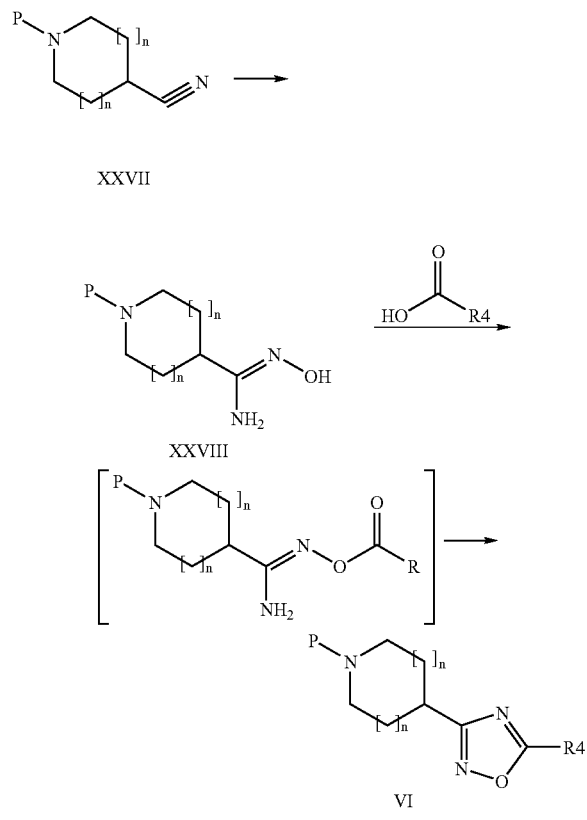

n=independently 0 or 1

The compound of formula XXVIII may be prepared from the protected nitrile of formula XXVII (where P is typically Boc), using standard methodology. Typically, the nitrile is treated with an excess of hydroxylamine hydrochloride in the presence of an excess of suitable base, such as sodium bicarbonate, in an appropriate solvent, (for example aqueous methanol) at reflux temperature for about 5 hours. The compounds of formula VI may be prepared by coupling the amid oxime of formula XXVIII with the acid ($R_4CO_2H$), and cyclisation of the resultant intermediate, according to the methods described in synthesis V.

Synthesis VII

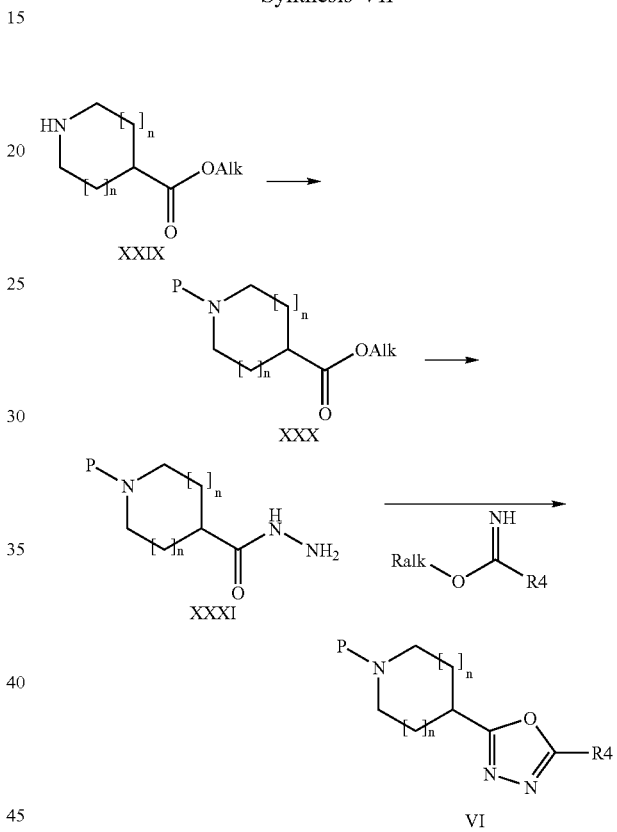

Ralk=C1–C6 alkyl, preferably, C1–C2.
N=independently, 0 or 1

Preparation of the compounds of formula XXX from the amine XXIX, where P is a suitable protecting group (preferably BOC), may be achieved for example, by reaction with di-tert-butyl dicarbonate in the presence of a base such as aqueous sodium hydroxide in a suitable solvent such as dioxane or tetrahydrofuran. The hydrazide of formula XXXI may be prepared from the compound of formula XXX, using standard methodology. For example, the alkyl ester of formula XXIX may be treated with excess hydroxylamine, in an alcoholic solvent such as methanol, at the reflux temperature of the mixture. The compound of formula VI may be prepared by condensation of this hydrazide of formula XXXI with an excess of iminoether (RalkOC(NH)R4), in a suitable solvent such as ethanol, at reflux temperature for about 18 hours.

Synthesis VIII

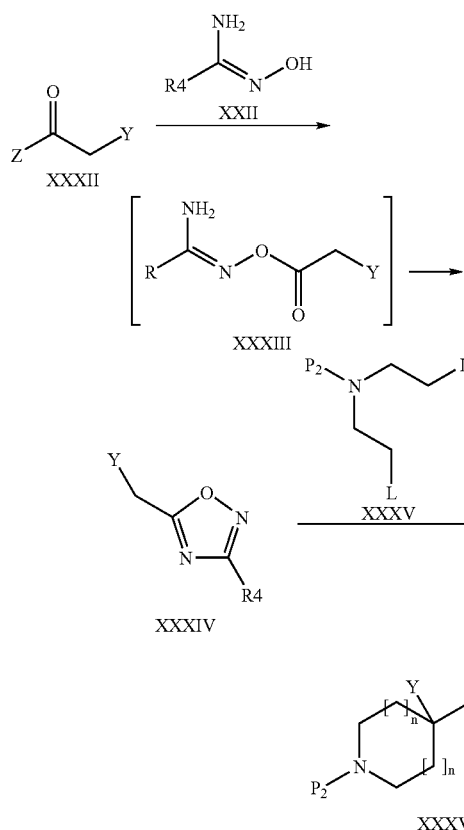

Compounds of general formula XXXIII may be prepared by coupling the hydroxylamine of formula XXII with an acid (Z=OH) or acid derivative (e.g. Z=Cl) of formula XXXII (Y is a carboxylic acid derived functional group, e.g. CO$_2$Et, CN) using conventional amide bond forming techniques, as described above.

Alternatively an acyl chloride of formula XXXII may be reacted with the hydroxylamine of formula XXII in the presence of a tertiary amine, such as triethylamine or N-ethyldiisopropylamine in a suitable solvent such as dichloromethane at from about 10° C. to about room temperature.

Cyclocondensation of the compounds of formula XXXIII, according to the methods described in synthesis V, may provide the compound of formula XXXIV.

In a further variation, the compound of formula XXXIV may be formed in a "one-pot" procedure, by coupling the hydroxylamine of formula XXII with the acid derivative of formula XXXII, and cyclising the resultant intermediate, according to the methods described above. Compounds of formula XXXVI may be prepared by reaction of the compounds of formula XXXIV, with an alkylating agent of formula XXXV (where P is a protecting group preferably benzyl, and L is a leaving group, such as halo, and preferably chloro). This reaction may be performed in a suitable solvent such as 2-methylpyrrolidine, in the presence of an excess of base, such as sodium hydride, additionally in the presence of a catalyst, such as tetra-n-butylammonium bromide, at elevated temperature (e.g. 60° C.).

Compounds of formula XXXVII may be prepared by functional group transformations, form compounds of formula XXXVI, using standard methodology. For example, the methylamide (Y'=CONHMe) may be prepared from the corresponding ethyl ester of formula XXXVI, by treatment with methylamine in a solvent such as tetrahydrofuran, in a sealed vessel at elevated temperature (e.g. 100° C.).

Synthesis IX

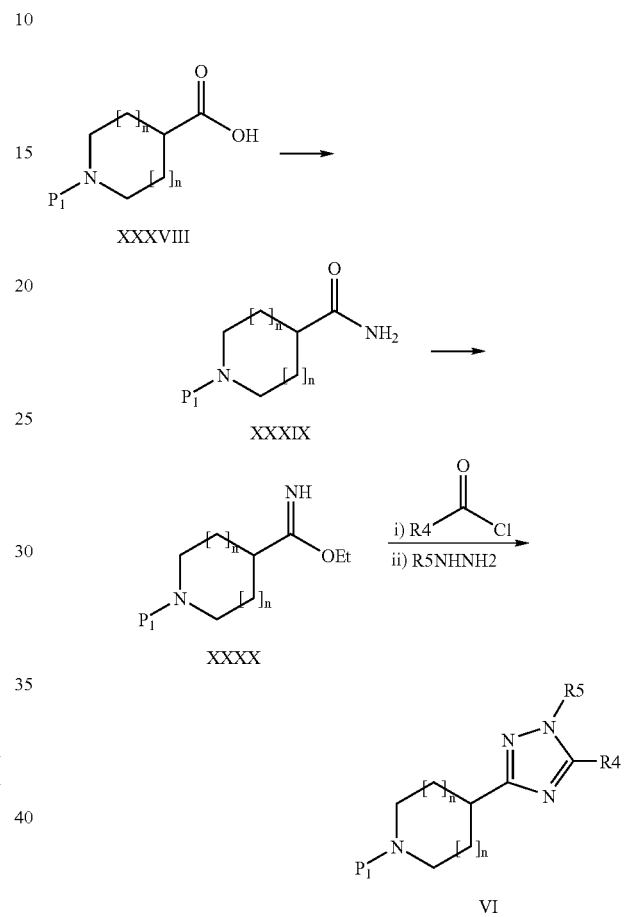

Preparation of the compound of formula XXXIX from the protected amino acid of formula XXXVIII (where P is a suitable protecting group, preferably Boc), may be achieved for example, by reaction with ethyl chloroformate, in the presence of a tertiary amine, such as triethylamine, in a suitable solvent such as dichloromethane, followed by addition of aqueous ammonia, at room temperature. The compounds of formula XXXX, may be prepared by alkylation of the compounds of formula XXXIX, using an excess of suitable alkylating agent, such as triethyloxonium hexafluorophosphate, in a solvent such as dichloromethane at room temperature. Compounds of formula VI may be prepared by reaction of the compounds of formula XXXX with an acylating agent, typically an acyl chloride (R4COCl), in the presence of a tertiary amine, such as triethylamine, in a suitable solvent such as toluene, at room temperature for about an hour. Reaction of the resultant intermediate with an appropriate hydrazine (R5NHNH$_2$) for between 5 and 18 hours at room temperature may provide the compound of formula VI.

Synthesis X

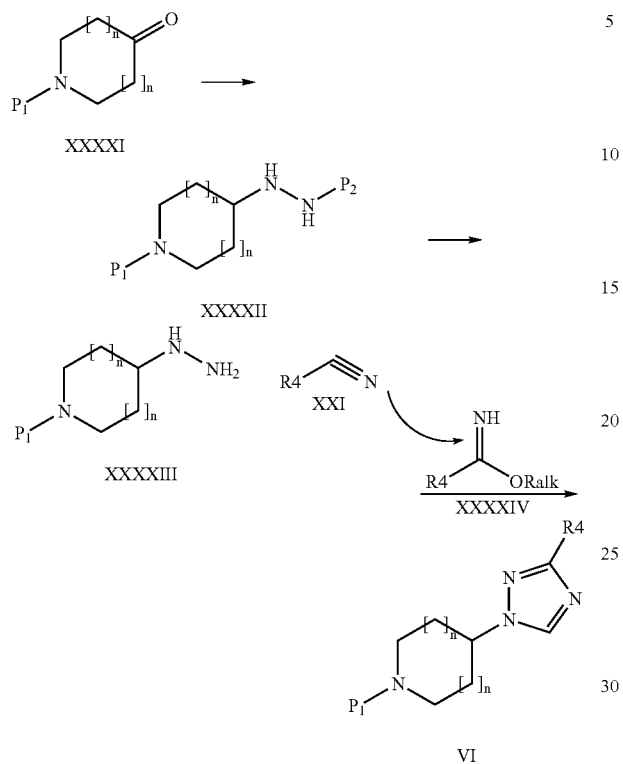

Compounds of formula XXXXII may be prepared by the reductive alkylation of the protected carbonyl compound of formula XXXXI (P is typically benzyl), with a protected hydrazine (P2NHNH$_2$), where P2 is preferably Boc, according to the methods described above. Subsequent removal of the nitrogen protecting group using standard methodology, such as protonolysis using trifluoroacetic acid in dichloromethane, according to the methods previously described, may provide the compound of formula XXXXIII.

Compounds of formula XXXXIV may be prepared from the nitrile compound of formula XXI, by initial protonolysis using hydrochloric acid, in a suitable solvent such as diethyl ether, and treatment of the resultant intermediate with an alcohol, preferably methanol, at room temperature.

Alternatively, the imidate of formula XXXXIV may be prepared from the corresponding bromo compound, by treatment, for example, with an excess of 1,1,3,3-tetramethylguanidine and acetone cyanohydrin in a solvent such as acetonitrile, at room temperature.

Compounds of formula VI, may be prepared by coupling the hydrazine of formula XXXXIII, with the imidate of formula XXXXIV, in a suitable solvent such as dichloromethane or methanol, and cyclising the resultant intermediate in the presence of an appropriate orthoester, typically triethylorthoacetate or triethylorthoformate, at reflux temperature.

Alternatively, the compounds of formula VI may be prepared from the compounds of formula XXXXIII in a "one-pot" procedure, by deprotection of the nitrogen group, P2, coupling the product with the imidate of formula XXXXIV, and then cyclising the intermediate, according to the methods described above.

Compounds of formula VI may also be prepared according to one of the plethora of methods currently available. For example, the method of Lin et Al (J. Org. Chem. 44; 23; 1979; 4160), provides 1,2,4-triazoles from compounds of formula XXXIX by reaction with N,N-dimethylformamide dimethylacetal, and the appropriate hydrazine. Alternatively, treatment of the compound of formula XXXIX with Lawesson's reagent, followed by reaction of the resulting thioamide intermediate with an appropriate hydrazide according to the method of Bull et al. (WO 9732873) may also provide compounds of formula VI.

In a further variation, nitrogen protected 4-piperidinamines (e.g. 1-benzyl-4-piperidinamine), may be treated with N,N-dimethylformamide azine (J.A.C.S. 1995; 117; 5951), to provide compounds of formula VI. The reaction may be performed in a suitable solvent, such as toluene in the presence of an acid catalyst, such as p-toluenesulphonic acid, at room temperature for about 24 hours.

Preparation 1

Methyl 3-amino-3-phenylpropanoate hydrochloride

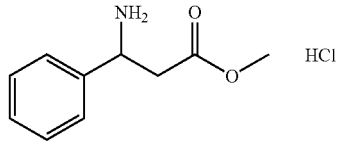

3-Phenyl-β-alanine (13.0 g, 78.8 mmol) was dissolved in methanolic hydrochloric acid (200 ml, 2.25M). The reaction was heated under reflux for 18 hours, then the cooled mixture was concentrated under reduced pressure to afford the title compound as a yellow oil, 16.9 g.

$^1$H-NMR (400 MHz, CD$_3$OD): δ [ppm] 3.00–3.19 (2H, m), 3.72 (3H, s), 4.74 (1H, t), 7.48 (5H, s)

Preparation 2

Methyl 3-[(cyclobutylcarbonyl)amino]-3-phenylpropanoate

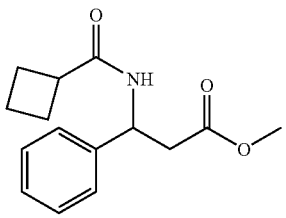

Cyclobutanecarbonyl chloride (6.91 ml, 86.7 mmol) was added dropwise to a solution of the title compound of preparation 1 (16.9 g, 78.8 mmol) and triethylamine (24.2 ml, 173.4 mmol) in dichloromethane (200 ml) at 0° C. The reaction mixture was stirred for 56 hours at room temperature after which time the mixture was washed with water then brine, dried (MgSO$_4$), filtered and the solvent removed under reduced pressure to afford the title compound as a yellow oil, 20.8 g.

¹H-NMR (400 MHz, CDCl₃): δ [ppm] 2.00–2.10 (2H, m), 2.10–2.35 (4H, m), 2.80–3.00 (2H, m), 3.03 (1H, m), 3.62 (3H, s), 5.42 (1H, m), 6.50 (1H, d), 7.25–7.35 (5H, m)

LRMS: m/z 262 (MH⁺)

Preparation 3

N-(3-Oxo-1-phenylpropyl)cyclobutanecarboxamide

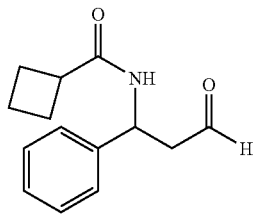

Diisobutylaluminium hydride (42.1 ml of a 1.0M solution in dichloromethane, 42.1 mmol) was added dropwise to a solution of the title compound of preparation 2 (5.0 g, 19.1 mmol) in dichloromethane (100 ml) at −78° C. The reaction mixture was stirred at this temperature for an hour, then methanol (5 ml) pre-cooled to −78° C. was added. The mixture was warmed to room temperature and washed with 2M hydrochloric acid, water, brine, dried (MgSO₄), filtered and the solvent evaporated under reduced pressure to afford the title compound as a yellow oil, 3.3 g.

¹H-NMR (400 MHz, CDCl₃): δ [ppm] 1.81–2.35 (6H, m), 2.90–3.10 (3H, m), 5.50 (1H, m), 6.00 (1H, br d), 7.23–7.39 (5H, m), 9.75 (1H, m)

LRMS: m/z 232 (MH⁺)

Preparation 4

Methyl(3S)-3-amino-3-phenylpropanoate

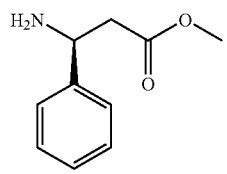

A solution of tert-butyl (3S)-3-amino-3-phenylpropanoate (5.04 g, 22.9 mmol) in 2.25M methanolic hydrochloric acid (100 ml) was heated under reflux for 2 hours. The mixture was cooled to room temperature, basified with saturated sodium carbonate solution to pH 8 and the phases separated. The aqueous layer was extracted with dichloromethane (4×), the combined organic solutions were washed with brine, dried (MgSO₄), filtered and evaporated under reduced pressure to afford the title compound 3.97 g.

¹H-NMR (400 MHz, CDCl₃): δ [ppm] 1.70 (2H, s), 2.66 (2H, d), 3.68 (3H, s), 4.43 (1H, t), 7.25–7.40 (5H, m)

LRMS: m/z 180.3 (MH⁺).

Preparation 5

Methyl(3S)-3-[(tert-butoxycarbonyl)amino]-3-phenylpropanoate

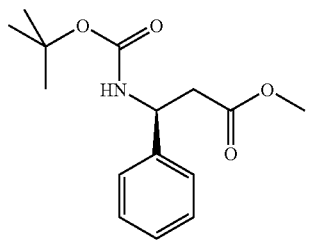

The title compound from preparation 4 (5.38 g, 30 mmol) and di-tert-butyl dicarbonate (8.72 g, 40 mmol) in tetrahydrofuran (50 ml) and 2N sodium hydroxide solution (25 ml) were stirred at room temperature for 2 hours. The reaction mixture was diluted with ethyl acetate, the layers separated and the aqueous phase extracted with ethyl acetate (2×). The combined organic solutions were washed with water, brine, dried (MgSO₄), filtered and evaporated under reduced pressure to afford the title compound as a white solid, 8.39 g.

¹H NMR (400 MHz, CDCl₃): δ [ppm] 1.41 (9H, s), 2.84 (2H, m), 3.61 (3H, s), 5.10 (1H, bs), 5.41 (1H, bs), 7.22–7.36 (5H, m)

LRMS: m/z 279.7 (MH⁺)

Preparation 6

Methyl(3S)-3-[(cyclobutylcarbonyl)amino]-3-phenylpropanoate

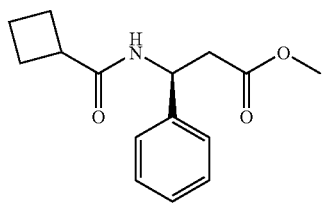

Obtained from the title compound of preparation 4 and cyclobutanecarbonyl chloride as a brown solid in 82% yield using a similar procedure to that in preparation 2.

¹H-NMR (300 MHz, CDCl₃): δ [ppm] 1.81–2.06 (2H, m), 2.10–2.40 (5H, m), 2.82–3.08 (2H, m), 3.62 (3H, s), 5.42 (1H, m), 6.42 (1H, d), 7.22–7.38 (5H, m)

Preparation 7 tert-Butyl (1S)-3-oxo-1-phenylpropylcarbamate

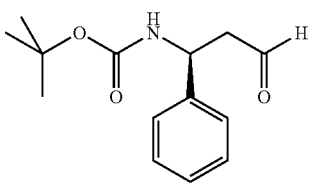

Diisobutylaluminium hydride (1M in dichloromethane, 60 ml, 60 mmol) was cooled to −78° C. and added dropwise to a solution of the title compound from preparation 5 (8.39 g, 30 mmol) in dichloromethane (150 ml) at −78° C. The reaction was stirred for 90 minutes, then methanol (pre-cooled to −78° C.) (40 ml) was added. The mixture was allowed to warm to room temperature and poured into 2M hydrochloric acid (200 ml). The layers were separated and the aqueous phase extracted with dichloromethane (2×). The combined organic layers were dried (MgSO$_4$), filtered and evaporated under reduced pressure to afford the title compound as a white solid, 6.72 g.

$^1$H NMR (400 MHz, CDCl$_3$): δ [ppm] 1.42 (9H, s), 2.86–3.00 (2H, m), 5.06 (1H, bs), 5.20 (1H, bs), 7.22–7.38 (5H, m), 9.75 (1H, s)

LRMS: m/z 250.1 (MH$^+$)

Preparation 8

N-[(1S)$_3$-Oxo-1-phenylpropyl]cyclobutanecarboxamide

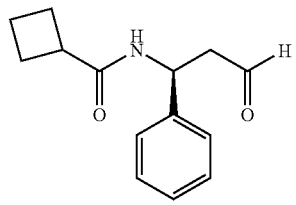

Obtained from the title compound of preparation 6 as a brown oil in 82% yield using a similar procedure to that in preparation 7.

$^1$H-NMR (300 MHz, CDCl$_3$): δ [ppm] 1.81–2.35 (6H, m), 2.90–3.10 (3H, m), 5.53 (1H, m), 5.98 (1H, br d), 7.23–7.39 (5H, m), 9.78 (1H, m)

Preparation 9 tert-Butyl (E)-3=(3-fluorophenyl)-2-propenoate

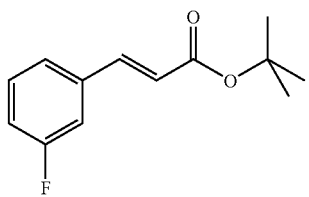

To a solution of 3-fluorobenzaldehyde (10.0 g, 80 mmol) in tetrahydrofuran (350 ml) was added tert-butyl-2-(triphenylphosphoranylidene)acetate (27.6 g, 73 mmol) in 1 g portions over 30 minutes. Upon the final addition, the mixture was heated under reflux for 10 minutes. The solvent was removed under reduced pressure and the solid residue was triturated with pentane (×2). The pentane extracts were combined and evaporated under reduced pressure. The residue was purified by filtration though a plug of silica gel using diethyl ether:hexane (1:2) as eluant to afford the title compound as a colourless oil, 16.2 g.

$^1$H NMR (400 MHz, CDCl$_3$): δ [ppm] 1.52 (9H, s), 6.32–639 (1H, d), 7.00–7.06 (1H, m), 7.16–7.21 (1H, m), 7.26–7.29 (1H, m), 7.29–7.37 (1H, m), 7.48–7.55 (1H, d)

Preparation 10 tert-Butyl (3S)-3-{benzyl[(1R)-1-phenylethyl]amino}-3-(3-fluorophenyl)propanoate

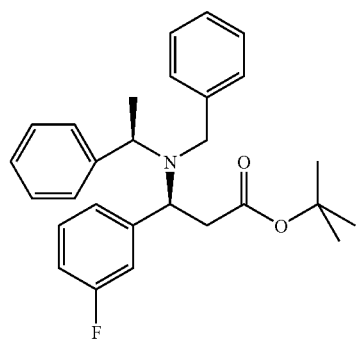

To a solution of (1R)-N-benzyl-1-phenyl-1-ethanamine (23.1 g, 109 mmol) in tetrahydrofuran (100 ml) at −10° C. was added n-butyl lithium (66 ml of a 1.6M solution in hexane, 105 mmol) dropwise. The purple solution was stirred for 15 minutes, cooled to −78° C. and a solution of the title compound of preparation 9 (18.6 g, 84 mmol) in tetrahydrofuran (100 ml) added dropwise. After stirring for 30 minutes the mixture was quenched with saturated ammonium chloride solution (100 ml) and stirred to room temperature. The mixture was extracted with diethyl ether (×2) and the combined organic layers were dried (MgSO$_4$), filtered and evaporated under reduced pressure. The residue was dissolved in diethyl ether and washed with 1 M citric acid (×2) then water, dried (MgSO$_4$), filtered and evaporated under reduced pressure. The pale yellow oily residue was purified by column chromatography on silica gel using a gradient elution of diethyl ether hexane (0:100 to 5:95) to afford the title compound as a colourless oil, 23.0 g.

$^1$H NMR (400 MHz, CDCl$_3$): δ [ppm] 1.19–1.32 (3H, m), 1.23 (9H, s), 2.42–2.52 (2H, m), 3.68 (2H, s), 3.90–4.00 (1H, m), 4.354.42 (1H, m), 6.89–6.97 (1H, m), 7.10–7.35 (11H, m), 7.35–7.42 (2H, m)

LRMS: m/z 434.5 (MH$^+$)

Preparation 11

Methyl(3S)-3-amino-3-(3-fluorophenyl)propanoate

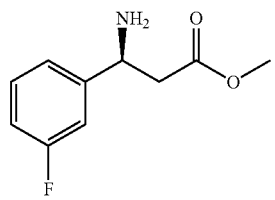

A mixture of the title compound of preparation 10 (23.0 g, 53 mmol), ammonium formate (33.5 g, 531 mmol) and 20% palladium hydroxide on carbon (12.5 g) were heated under reflux in ethanol for 30 minutes (500 ml). The reaction was cooled and filtered through Arbocel® and the filtrate evaporated under reduced pressure. The residue (16.3 g, 68 mmol) was heated under reflux for 1 hour in methanolic hydrochloric acid (100 ml, 2.25M). The mixture was evaporated under reduced pressure and the resulting solid triturated with ethyl acetate to afford the title compound as a white solid, 4.40 g.

$^1$H NMR (400 MHz, CD$_3$OD): δ [ppm] 3.00–3.16 (2H, m), 3.71 (3H, s), 4.74–4.81 (1H, m), 7.13–7.23 (1H, m), 7.24–7.34 (2H, m), 7.44–7.53 (1H, m)

LRMS: m/z 198.2 (MH$^+$)

Preparation 12

Methyl(3S)-3-[(tert-butoxycarbonyl)amino]-3-(3-fluorophenyl)propanoate

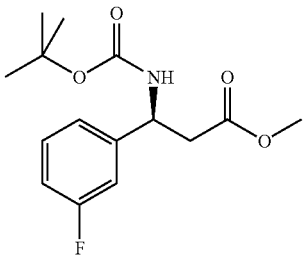

To a suspension of the title compound of preparation 11 (3.81 g, 16.3 mmol) in tetrahydrofuran (50 ml) was added di-tert-butyl dicarbonate (4.26 g, 19.5 mmol) and 2M aqueous sodium hydroxide (20 ml). The mixture was stirred for 16 hours at room temperature. The mixture was diluted with water and extracted with diethyl ether (×3), the combined organic solutions were dried (MgSO$_4$), filtered and evaporated under reduced pressure. The residue was purified by recrystallisation from hexane to afford the title compound as a white solid, 4.10 g.

$^1$H NMR (400 MHz, CHCl$_3$): δ [ppm] 1.40 (9H, s), 2.76–2.89 (2H, m), 3.63 (3H, m), 5.01–5.13 (1H, m), 5.42–5.65 (1H, bs), 6.90–6.97 (1H, m), 6.97–7.02 (1H, m), 7.03–7.10 (1H, m), 7.26–7.32 (1H, m)

Preparation 13

1-(tert-Butoxycarbonyl)-3-azetidinecarboxylic acid

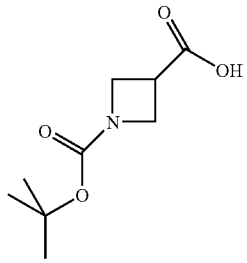

Di-tert-butyl dicarbonate (3.02 g, 13.8 mmol) was added to a suspension of 3-azetidine carboxylic acid (1.00 g, 10.0 mmol) and potassium carbonate (1.80 g, 13.0 mmol) in water (18 ml) and dioxane (18 ml) at 0° C. and allowed to warm to room temperature. The reaction was stirred for 15 hours and concentrated under reduced pressure. The residue was acidified to pH 4 by the addition of 1M citric acid solution and extracted with dichloromethane (×3). The combined organic solutions were washed with water and brine, dried (MgSO$_4$), filtered and evaporated under reduced pressure to afford the title compound as a white solid, 2.10 g.

$^1$H NMR (400 MHz, CDCl$_3$): δ [ppm] 1.44 (9H, s), 3.38 (1H, m), 4.14 (4H, d)

Preparation 14

1-Acetyl-3-azetidinecarboxylic acid

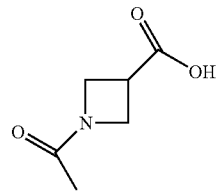

3-Azetidine carboxylic acid (2.25 g, 22.2 mmol) and acetic anhydride (80 ml) were heated gently until all of the acid had dissolved. The reaction was stirred at room temperature for 18 hours and then the acetic anhydride was removed under reduced pressure. Water was added and evaporated under reduced pressure. The residue was dissolved in hot ethyl acetate and filtered whilst hot and the filtrate was evaporated under reduced pressure to afford the title compound as a white solid, 1.54 g.

$^1$H NMR (400 MHz, CD$_3$OD): δ [ppm] 1.84 (3H, s), 3.37–3.50 (1H, m), 4.004.09 (1H, m), 4.124.18 (1H, m), 4.234.41 (2H, m)

LRMS: m/z 142.1 (MH$^+$)

Preparation 15

1-[(tert-Butoxycarbonyl)amino]cyclopentanecarboxylic acid

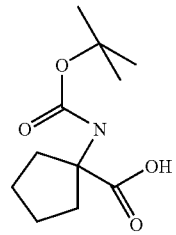

1-Aminocyclopentanecarboxylic acid (1.00 g, 7.74 mmol), di-tert-butyl dicarbonate (3.85 g, 17.6 mmol) and potassium carbonate (2.28 g, 16.5 mmol) were stirred together for 16 hours at room temperature in dioxane (20 ml) and water (20 ml). The solvents were removed under reduced pressure and the residue acidified with 1M citric acid solution and extracted with dichloromethane (×3). The organic solutions were dried (MgSO$_4$), filtered and evaporated under reduced pressure to yield an oil which crystallized on standing, this was triturated with hexane to afford the title compound as a white solid, 1.26 g.

$^1$H NMR (400 MHz, CDCl$_3$): δ [ppm] 1.4 (9H, s), 1.74–1.81 (4H, m), 1.85–1.97 (2H, m), 2.20–2.32 (2H, m).

Preparation 16

4-(Methoxymethylene)tetrahydro-2H-pyran

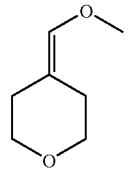

Tetrahydro-4H-pyran-4-one (5.00 g, 50 mmol) was dissolved in tetrahydrofuran (250 ml) and cooled in an ice-water bath. To this solution was added n-butyl lithium (24 ml of a 2.5M solution in hexane, 60 mmol) and the reaction mixture was then allowed to warm to room temperature and stirred for 1 hour. This was then cooled to 0° C. and a solution of (methoxymethyl)triphenyl phosphonium chloride (25.6 g, 75 mmol) in tetrahydrofuran (10 ml) was added and the reaction stirred for 30 minutes. The reaction mixture was then concentrated under reduced pressure and the residue triturated with diethyl ether (10×), decanting the supernatant each time. The combined supernatants were then evaporated under reduced pressure. The residue was purified by column chromatography on silica gel using an elution gradient of pentane:ethyl acetate (95:5 to 90:10) to provide the title compound, 1.80 g.

$^1$H NMR (300 MHz, CDCl$_3$): δ [ppm] 2.05 (2H, t), 2.30 (2H, t), 3.50 (3H, s), 3.60 (4H, m), 5.80 (1H, s).

LRMS: m/z 146 (MNH$_4^+$)

Preparation 17

Tetrahydro-2H-pyran-4-carboxylic acid

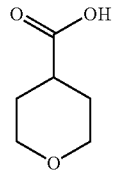

To a stirred solution of the title compound of preparation 16 (1.80 g, 14.0 mmol) in acetone (30 ml) was added 1 M hydrochloric acid (1 ml) at room temperature and the mixture stirred for 3 hours. The solution was then diluted with additional acetone and Jones' reagent added until the solution became permanently brown. The reaction mixture was then evaporated under reduced pressure and the residue purified by column chromatography on silica gel using ethyl acetate:pentane (75:25) as eluant to afford the title compound as a white solid, 1.18 g.

$^1$H NMR (400 MHz, CDCl$_3$): δ [Ppm] 1.85 (4H, m), 2.55 (1H, m), 3.45 (2H, m), 3.99 (2H, m), 11.10 (1H, bs)

LRMS: m/z 129 (M–H$^-$)

Preparation 18

1-Hydroxycyclobutanecarboxylic acid

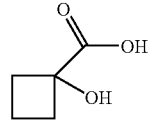

n-Butyllithium (96 ml of a 2.5M solution in hexane, 240 mmol) was added dropwise to a tetrahydrofuran (400 ml) solution of diisopropylamine (34 ml, 240 mmol) at −78° C. The reaction was warmed to 0° C. and a solution of cyclopentanecarboxylic acid (6.64 g, 66 mmol) in tetrahydrofuran (100 ml) was added dropwise. The reaction was allowed to warm to room temperature and stirred for 6 hours. The reaction was cooled to 10° C. and oxygen bubbled through for 15 minutes and stirred for 1 hour, 10% aqueous sodium sulphite was then added in one portion and the reaction warmed to room temperature. The reaction was diluted with water (200 ml) and extracted with ether (5×). The combined organic solutions were dried (MgSO$_4$), filtered and evaporated under reduced pressure to afford the title compound as a white solid, 1.16 g.

$^1$H NMR (300 MHz, CDCl$_3$): δ[ppm] 1.98 (2H, m), 2.34 (2H, m), 2.56 (2H, m), 6.35 (1H, bs)

LRMS: m/z 231 (2M–H$^-$)

Preparation 19

1-Methoxycyclobutanecarboxylic acid

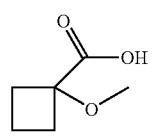

Sodium hydride (60% dispersion in oil, 1.20 g, 30 mmol) was added in one portion to a tetrahydrofuran (100 ml) solution of the title compound of preparation 18 (1.16 g, 10 mmol) and iodomethane (1.86 ml, 30 mmol) at 0° C. The reaction was allowed to warm to room temperature and stirred for 5 days. The solvent was removed under reduced pressure and 2M hydrochloric acid (100 ml) added. The aqueous mixture was extracted with diethyl ether (3×) and the combined organic solutions dried (MgSO$_4$), filtered and evaporated under reduced pressure to afford a clear oil. The oil was purified by column chromatography on silica gel using dichloromethane:methanol:acetic acid (90:10:1) as eluant to afford the title compound as an orange solid, 1.11 g.

$^1$H NMR (300 MHz, CDCl$_3$): є[ppm] 1.98 (2H, m), 2.28 (2H, m), 2.54 (2H, m), 3.38 (3H, s)

Preparation 20

1-(2,2,2-Trifluoroacetyl)-4-piperidinecarboxylic acid

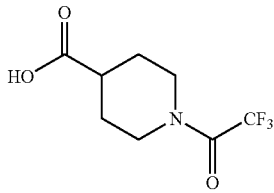

Trifluoroacetic anhydride (32.5 g, 155 mmol) was added dropwise to a suspension of 4-piperidinecarboxylic acid (16.7 g, 130 mmol) in dichloromethane (900 ml) at 0° C. and stirred for 12 hours. The reaction mixture was washed with water and brine, dried (MgSO$_4$), filtered and evaporated under reduced pressure to afford the title compound as a white solid, 10.0 g.

$^1$H NMR (300 MHz, CDCl$_3$): δ[ppm] 1.80 (2H, m), 2.05 (2H, m), 2.65 (1H, m), 2.80 (1H, m), 3.10 (1H, m), 3.30 (1H, m), 3.95 (1H, m), 4.30 (1H, m)

LRMS: m/z 224 (M−H$^-$)

Preparation 21

2,2,2-Trifluoro-1-[4-(3-methyl-1,2,4-oxadiazol-5-yl)-1-piperidinyl]-1-ethanone

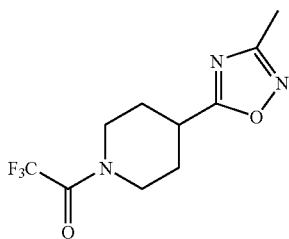

The title compound from preparation 20 (1.00 g, 4.44 mmol) was added to a solution of N-hydroxy-acetamidine (362 mg, 4.88 mmol) [Chem. Ber., (1884), 17, 2746] and 1-(3-dimethyl aminopropyl)-3-ethylcarbodiimide hydrochloride (1.02 g, 5.33 mmol) in dichloromethane (20 ml) and the reaction stirred at room temperature for 18 hours. The mixture was then washed with water and brine, dried (MgSO$_4$), filtered and evaporated under reduced pressure to afford a clear oil. This intermediate was dissolved in toluene (30 ml) and heated under reflux with continuous removal of water for 18 hours. The cooled solution was evaporated under reduced pressure and the residue purified by column chromatography on silica gel using ethyl acetate:hexane (50:50) as eluant to afford the title compound as an oil, 580 mg.

$^1$H-NMR (300 MHz, CDCl$_3$): δ [ppm] 1.88–2.05 (2H, m), 2.20 (2H, m), 2.40 (3H, s), 3.13–3.48 (3H, m), 4.01 (1H, d), 4.37 (1H, m)

Preparation 22

2,2,2-Trifluoro-1-[4-(3-phenyl-1,2,4-oxadiazol-5-yl)-1-piperidinyl]-1-ethanone

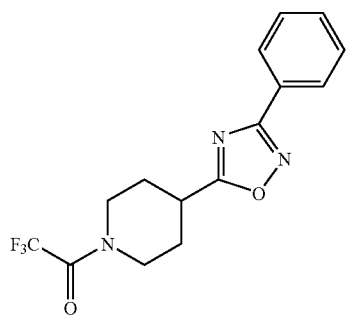

Obtained from the title compound of preparation 20 and N-hydroxybenzenecarboximidamide [Tetrahedron, (1997), 53(5), 1787–1796] as a brown oil in 82% yield using a similar procedure to that in preparation 21.

$^1$H-NMR (300 MHz, CDCl$_3$): δ [ppm] 2.04 (2H, m), 2.26 (2H, m), 3.20–3.51 (3H, m), 4.08 (1H, m), 4.20 (1H, m), 7.49 (3H, m), 8.09 (2H, m)

LRMS: m/z 343 (MNH$_4^+$)

Preparation 23

1-{4-[({Amino(4-methoxyphenyl)methylidene]amino}oxy)carbonyl]-1-piperidinyl}2,2,2-trifluoro-1-ethanone

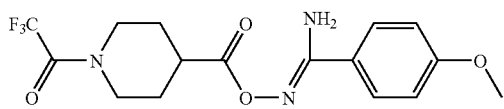

N-Methylmorpholine (0.32 ml, 2.92 mmol), 4-dimethylaminopyridine (81 mg, 0.66 mmol) and 1-(3-dimethylaminopropyl)-3-ethylcarbodiimide hydrochloride (306 mg, 1.59 mmol) were added to a suspension the title compound from preparation 20 (299 mg, 1.33 mmol) and N-hydroxy-4-methoxybenzamidine [Chem. Ber., (1889), 22, 2791] (268 mg, 1.33 mmol) in dichloromethane (20 ml), and the reaction stirred at room temperature for 40 minutes. The reaction mixture was washed with 1M citric acid solution, saturated aqueous sodium bicarbonate solution, water and brine, dried (MgSO$_4$), filtered and evaporated under reduced pressure to afford the title compound as a yellow foam, 320 mg.

$^1$H-NMR (300 MHz, CDCl$_3$): δ [ppm] 1.94 (2H, m), 2.11 (2H, m), 2.88 (1H, m), 3.16 (1H, m), 3.35 (1H, m), 3.61 (3H, s), 4.02 (1H, m), 4.37 (1H, m), 4.99 (2H, s), 6.94 (2H, d), 7.64 (2H, d)

LRMS: m/z 391 (MNH$_4^+$)

Preparation 24

2,2,2-Trifluoro-1-[4-{3-(4-methoxyphenyl)-1,2,4-oxadiazol-5-yl}-1-piperidinyl]-1-ethanone

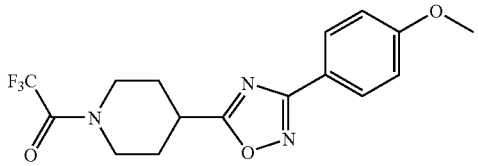

A solution of the title compound of preparation 23 (317 mg, 0.85 mmol) in toluene (65 ml) was heated under reflux with continuous removal of water for 18 hours, and the cooled mixture concentrated under reduced pressure. The residue was purified by column chromatography on silica gel, using an elution gradient of pentane:dichloromethane:methanol:0.88 ammonia (50:50:0:0 to 0:98:1:0.3) to afford the title compound, as a clear oil, 197 mg.

$^1$H-NMR (300 MHz, CDCl$_3$): δ [ppm] 1.98–2.15 (2H, m), 2.26 (2H, m), 3.22–3.52 (3H, m), 3.88 (3H, s), 4.06 (1H, m), 4.39 (1H, m), 7.00 (2H, d), 8.01 (2H, d)

LRMS: m/z 356 (MH$^+$)

Preparation 25

2,2,2-Trifluoro-1-[4-(3-Benzyl-1,2,4-oxadiazol-5-yl)-1-piperidinyl]-1-ethanone

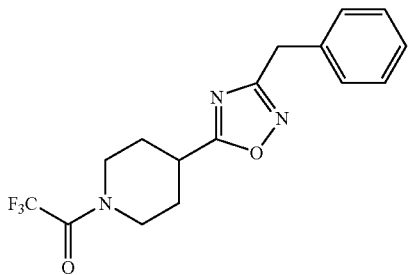

Obtained from the title compounds of preparations 20 and 56 as an oil in 11% yield using a similar procedure to that in preparation 21.

$^1$H-NMR (300 MHz, CDCl$_3$): δ [ppm] 1.81–2.02 (2H, m), 2.18 (2H, m), 3.09–3.42 (3H, m), 3.944.08 (3H, m), 4.36 (1H, m), 7.31 (5H, m)

LRMS: m/z 357 (MH$^+$)

Preparation 26

1-(tert-Butyl)-4-ethyl-1,4-piperidinecarboxylate

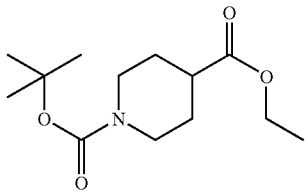

1 M Sodium hydroxide solution (50 ml, 50.0 mmol) was added to a solution of ethyl 4-piperidinecarboxylate (10.0 g, 63.6 mmol) and di-tert-butyl dicarbonate (16.7 g, 76.3 mmol) in dioxane (50 ml). The reaction mixture was stirred at room temperature for 3 hours, the solvent was evaporated under reduced pressure and the residue acidified with 2M hydrochloric acid. The aqueous solution was extracted with ethyl acetate (×3), the combined organic extracts were washed with brine, dried (MgSO$_4$), filtered and evaporated under reduced pressure to afford the title compound as a colourless oil, 16.7 g.

$^1$H-NMR (300 MHz, CDCl$_3$): δ [ppm] 1.23 (3H, t), 1.47 (9H, s), 1.58–1.71 (2H, m), 1.83 (2H, m), 2.45 (1H, m), 2.78–2.88 (2H, m), 4.09 (2H, m), 4.15 (2H, q)

LRMS: m/z 258 (MH$^+$)

Preparation 27 tert-Butyl 4-(hydrazinocarbonyl)-1-piperidinecarboxylate

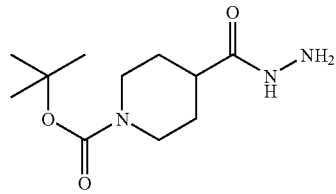

Hydrazine hydrate (5 ml) was added to a solution of the title compound of preparation 26 (4.96 g, 19.3 mmol) in methanol (50 ml) and the reaction heated under reflux for 48 hours. The cooled mixture was evaporated under reduced pressure, and the residue purified by column chromatography on silica gel using ethyl acetate:methanol (95:5) as eluant to afford the title compound as a white crystalline solid, 3.72 g.

$^1$H-NMR (300 MHz, CDCl$_3$): δ [ppm] 1.40–1.58 (9H, bs), 1.60–1.85 (4H, m), 2.20–2.33 (1H, m), 2.62–2.85 (2H, m), 4.15 (2H, m)

LRMS: m/z 243 (MH$^+$)

Preparation 28 tert-Butyl 4-[amino(hydroxyimino)methyl]-1-piperidinecarboxylate

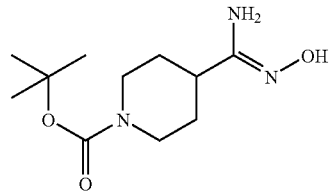

A mixture of tert-butyl 4-cyano-1-piperidinecarboxylate (2.69 g, 12.8 mmol), hydroxylamine hydrochloride (4.45 g, 64 mmol) and sodium carbonate (6.78 g, 64 mmol) in water (40 ml) and methanol (40 ml) was heated under reflux for 5 hours. The cooled mixture was concentrated under reduced pressure and the remaining aqueous solution extracted with ethyl acetate (3×). The combined organic extracts were washed with water and brine, dried (MgSO$_4$), filtered and evaporated under reduced pressure to afford the title compound as a white solid, 2.60 g.

¹H-NMR (300 MHz, CDCl₃): δ [ppm] 1.38–1.62 (11H, m), 1.80 (2H, m), 2.26 (2H, m), 2.76 (2H, m), 4.16 (2H, m), 4.58 (2H, s)

Preparation 29 tert-Butyl 4-{amino[(benzoyloxy)imino]methyl}-1-piperidinecarboxylate

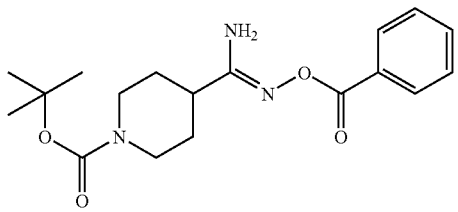

N-methylmorpholine (1.08 ml, 9.86 mmol), benzoic acid (1.10 g, 9.04 mmol), 4-dimethylaminopyridine (502 mg, 4.11 mmol) and 1-(3-dimethylaminopropyl)-3-ethylcarbodiimide hydrochloride (1.89 g, 9.86 mmol) were added to a solution of the title compound of preparation 28 (2.009, 8.22 mmol) in dichloromethane (100 ml), and the reaction stirred at room temperature for 16 hours. The mixture was washed with 1M citric acid solution, saturated aqueous sodium bicarbonate solution, water and brine, dried (MgSO₄), filtered and evaporated under reduced pressure to afford the title compound as a white foam, 1.84 g.

¹H-NMR (300 MHz, CDCl₃): ε [ppm] 1.46 (9H, s), 1.57–1.72 (2H, m), 1.94 (2H, m), 2.60 (1H, m), 2.78 (2H, m), 4.23 (2H, m), 4.80 (2H, s), 7.46 (2H, m), 7.58 (1H, m), 8.02 (2H, d)

Preparation 30 tert-Butyl 4-(amino{[(2-phenylacetyl)oxy]imino}methyl)-1-piperidinecarboxylate

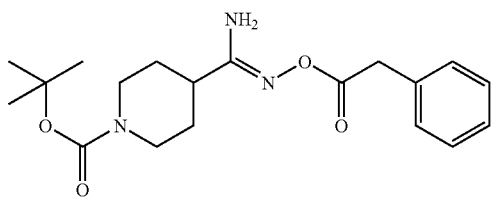

Obtained from the title compound of preparation 28 and phenylacetic acid as a white foam in 69% yield using a similar procedure to that in preparation 29.

¹H-NMR (300 MHz, CDCl₃) δ [ppm] 1.45 (9H, s), 1.55 (2H, m), 1.82 (2H, m), 2.44 (1H, m), 2.72 (2H, m), 3.78 (2H, s), 4.19 (2H, m), 4.51 (2H, s), 7.31 (5H, m)

Preparation 31 tert-Butyl 4-(3-methyl-1,2,4-oxadiazol-5-yl)-1-piperidinecarboxylate

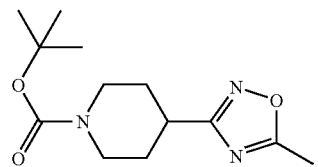

Glacial acetic acid (0.67 ml, 11.7 mmol), 1-(3-dimethyl aminopropyl)-3-ethylcarbodiimide hydrochloride (2.46 g, 12.8 mmol), 4-dimethylaminopyridine (635 mg, 5.54 mmol) and N-methylmorpholine (1.41 ml, 12.8 mmol) were added to a solution of the title compound of preparation 28 (2.60 g, 10.7 mmol) in dichloromethane (100 ml) and the reaction stirred at room temperature for one hour. The reaction was washed with 1M citric acid solution, aqueous saturated sodium bicarbonate solution, water, dried (MgSO₄), filtered and evaporated under reduced pressure to give a yellow oil. A solution of this product in toluene (30 ml) was heated under reflux for 24 hours, then cooled. The solution was evaporated under reduced pressure and the residue purified by column chromatography on silica gel, using ethyl acetate: pentane (50:50) as eluant to afford the title compound as a clear oil, 1.10 g.

¹H-NMR (300 MHz, CDCl₃): δ [ppm] 1.47 (9H, s), 1.66–1.81 (2H, m), 1.98 (2H, m), 2.58 (3H, s), 2.92 (3H, m), 4.12 (2H, m)

LRMS: m/z 268 (MH)⁺

Preparations 32 to 33

The compounds of the following tabulated preparations:

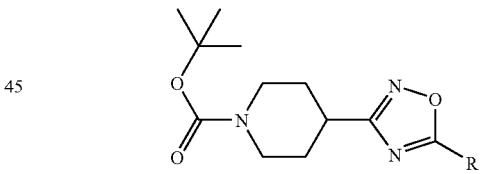

were prepared from the corresponding amidoxime esters using similar methods to that described in preparation 24.

| Preparation | R | Data |
|---|---|---|
| 32[1] | *-phenyl | ¹H-NMR(300MHz, CDCl₃): δ[ppm] 1.49(9H, s), 1.80–1.96(2H, m), 2.07 (2H, m), 2.92–3.10(3H, m), 4.18(2H, m), 7.46–7.61(3H, m), 8.16(2H, d) LRMS: m/z 330(MH)⁺ |
| 33[1] | *-CH₂-phenyl | ¹H-NMR(300MHz, CDCl₃): δ[ppm] 1.46(9H, s), 1.68–1.83(2H, m), 2.00 (2H, m), 2.94(3H, m), 4.14(2H, m), 4.20(2H, s), 7.18–7.38(5H, m) LRMS: m/z 344(MH)⁺ |

[1]= isolated without column chromatography

Preparation 34 tert-Butyl-4-(5-methyl-1,3,4-oxadiazol-2-yl)-1-piperidinecarboxylate

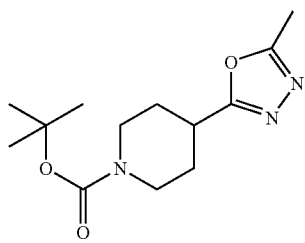

Ethyl acetimidate hydrochloride (2.35 g, 119.0 mmol) was added to a solution of the title compound of preparation 27 (1.83 g, 7.60 mmol) in ethanol (30 ml). The reaction mixture was heated under reflux for 18 hours and then cooled, filtered and the filtrate evaporated under reduced pressure. The residue was purified by column chromatography on silica gel using an elution gradient of dichloromethane:methanol:0.88 ammonia (99:1:0.1 to 95:5:0.0.5) to afford the title compound as a clear oil (1.62 g).

$^1$H-NMR (300 MHz, CDCl$_3$): δ [ppm] 1.45 (9H, s), 1.70–1.85 (3H, m), 2.04 (2H, m), 2.50 (3H, s), 2.92–3.06 (2H, m), 4.08 (2H, m)

LRMS: m/z 290 (MH$^+$)

Preparation 35 tert-Butyl 4-(5-phenyl-1,3,4-oxadiazol-2-yl)-1-piperidinecarboxylate

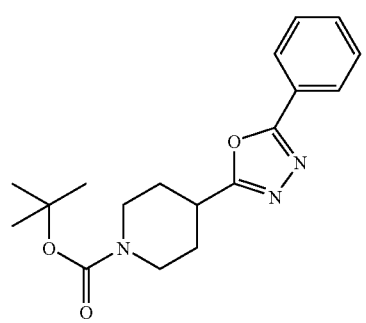

Obtained from the title compound of preparation 27 and ethylbenzimidate hydrochloride as a white solid in 69% yield using a similar procedure to that in preparation 34.

LRMS: m/z 330 (MH$^+$)

Preparation 36 tert-Butyl 4-(5-Benzyl-1,3,4-oxadiazol-2-yl)-1-piperidinecarboxylate

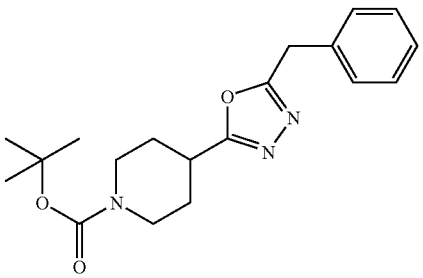

Obtained from the five compound of preparation 27 and ethyl 2-phenylacetimidate as an oil in 99% yield using a similar procedure to that in preparation 34.

$^1$H-NMR (300 MHz, CDCl$_3$): δ [ppm] 1.45 (9H, s), 1.68–1.82 (2H, m), 2.00 (2H, m), 2.84–3.06 (3H, m), 4.01–4.19 (4H, m), 7.22–7.40 (5H, m)

Preparation 37

4-(3-Phenyl-1,2,4-oxadiazol-5-yl)-piperidine

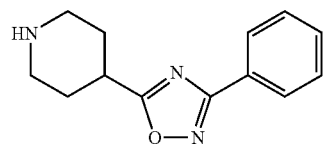

A mixture of the title compound of preparation 22, (520 mg, 1.60 mmol), and sodium hydroxide (96 mg, 2.40 mmol) in ethanol (10 ml) was stirred at room temperature for 2 hours. The reaction was evaporated under reduced pressure and the residue triturated with ethyl acetate and dichloromethane. The suspension was filtered, and the filtrate evaporated under reduced pressure to afford the title compound as a white solid, 340 mg.

$^1$H-NMR (300 MHz, CD$_3$OD): δ [ppm] 1.78–1.92 (3H, m), 2.13 (2H, m), 2.77 (2H, t), 3.02–3.35 (3H, m), 7.48 (3H, m), 8.04 (2H, m)

LRMS: m/z 230 (MH$^+$)

Preparation 38

4-{3-(4-Methoxyphenyl)-1,2,4-oxadiazol-5-yl}piperidine

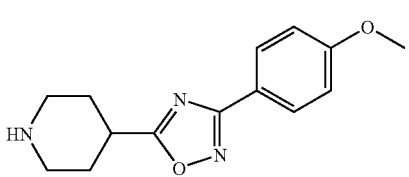

Obtained from the title compound of preparation 24 in quantitative yield using a similar procedure to that in preparation 37, except the product was isolated without trituration.

LRMS: m/z 260 (MH+)

Preparation 39

4-(3-Benzyl-1,2,4-oxadiazol-yl)piperidine

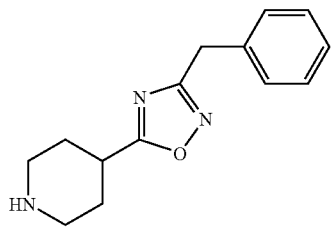

Obtained from the title compound of preparation 25 as an oil in 99% yield using a similar procedure to that in preparation 37.

¹H NMR (300 MHz, CDCl₃): ε [ppm] 1.80 (2H, m), 2.05 (2H, m), 2.75 (2H, m), 3.05 (1H, m), 3.15 (2H, m), 4.05 (2H, s), 7.35 (5H, m)

LRMS: m/z 244 (MH+)

Preparation 40

4-(5-Methyl-1,2,4-oxadiazol-3-yl)piperidine hydrochloride

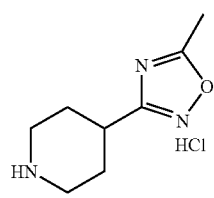

Hydrogen chloride gas was bubbled through an ice-cold solution of the title compound of preparation 31 (1.10 g, 4.12 mmol) in dichloromethane (30 ml) for 30 minutes. The reaction mixture was evaporated under reduced pressure and the resulting solid triturated with ether. The solid was filtered and dried to afford the title compound as a white solid, 670 mg.

¹H-NMR (300 MHz, CD₃OD): δ [ppm] 1.95–2.08 (2H, m), 2.25 (2H, m), 2.58 (3H, s), 3.19 (3H, m), 3.44 (2H, m)

LRMS: m/z 168 (MH+)

Preparations 41 to 44

The compounds of the following tabulated preparations:

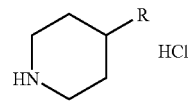

were prepared from the corresponding tert-butyl piperidinecarboxylates, using similar methods to that described in preparation 40.

| Preparation | R | Data |
|---|---|---|
| 1 | ![](*-N=... 5-phenyl-1,2,4-oxadiazol-3-yl) | ¹H-NMR(300MHz, CD₃OD): δ[ppm] 2.03–2.19(2H, m), 2.35(2H, m), 3.15–3.29(4H, m), 3.52(2H, m), 7.55–7.71 (3H, m), 8.14(2H, m) LRMS: m/z 230(MH+) |
| 2 | ![](*-3-benzyl-1,2,4-oxadiazol-5-yl) | ¹H-NMR(300MHz, CD₃OD): δ[ppm] 1.92–2.10(2H, m), 2.28(2H, m), 3.09–3.30(3H, m), 3.44(3H, m), 4.24(2H, s), 7.22–7.39(5H, m) LRMS: m/z 244(MH+) |
| 3 | ![](*-5-methyl-1,3,4-oxadiazol-2-yl) | LRMS: m/z 168(MH+) |
| 4 | ![](*-5-benzyl-1,3,4-oxadiazol-2-yl) | ¹H-NMR(300MHz, CD₃OD): 1.87–2.17(3H, m), 2.34(1H, m), 3.01–3.23(2H, m), 3.31–3.50(4H, m), 3.64(1H, m), 4.25(1H, s), 7.29(5H, m) |

Preparation 45

4-(5-Phenyl-1,3,4-oxadiazol-2-yl)piperidine

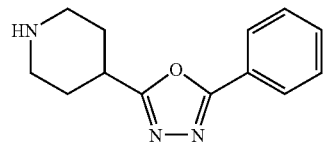

The title compound was prepared by a similar method to preparation 40 from the title compound of preparation 35. The crude product was basified with 0.88 ammonia and purified by column chromatography on silica gel using a solvent gradient of dichloromethane:methanol:0.88 ammonia (95:5:1 to 90:10:1) to afford the title compound as an oil, 300 mg.

¹H-NMR (300 MHz, CDCl₃): δ [ppm] 1.66–1.95 (3H, m), 2.47 (2H, d), 2.78 (2H, t), 3.02–3.24 (3H, m), 7.43 (3H, m), 8.00 (2H, m)

LRMS: m/z 230 (MH+)

Preparation 46

2-(3-Aminophenyl)acetonitrile

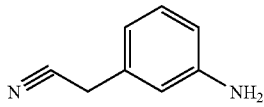

3-Nitrophenylacetonitrile (6.87 g, 42 mmol) and tin(II) chloride dihydrate (50 g, 220 mmol) in ethyl acetate (125 ml) were stirred at room temperature for 72 hours. The reaction was diluted with ethyl acetate and saturated aqueous sodium bicarbonate solution was added. The resulting precipitate was filtered off and the filtrate extracted with ethyl acetate (3×). The combined organic solutions were dried (MgSO$_4$), filtered and evaporated under reduced pressure to afford the title compound as a pale yellow oil, 5.33 g.

$^1$H NMR (400 MHz, CDCl$_3$): δ [ppm] 3.59 (2H, s), 3.78 (2H, bs), 6.576.63 (3H, m), 7.09–7.15 (1H, m)

LRMS: m/z 132 (MH$^+$)

Preparation 47

N-[4-(Cyanomethyl)phenyl]methanesulphonamide

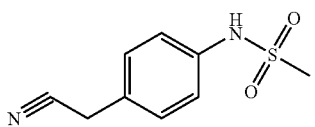

Methanesulphonyl chloride (3.22 ml, 41.6 mmol) was added dropwise to a solution of 4-aminobenzylcyanide (5.00 g, 37.8 mmol) and triethylamine (5.79 ml, 41.6 mmol) in dichloromethane (30 ml). The reaction mixture was stirred for 1 hour and then poured onto water, the organic layer was separated, dried (MgSO$_4$), filtered and the solvent removed under reduced pressure to afford the title compound as a pale orange solid, 6.50 g.

$^1$H NMR (400 MHz, CDCl$_3$): δ [ppm] 3.05 (3H, s), 3.79 (2H, s), 6.60 (1H, s), 7.21 (2H, d), 7.35 (2H, d)

LRMS: m/z 228 (MNH$_4^+$)

Preparations 48 to 49

The compounds of the following tabulated preparations:

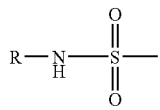

were prepared from the corresponding anilines, using similar methods to that described in preparation 47

| PREP-ARA-TION | R | YIELD | DATA |
|---|---|---|---|
| 48 | 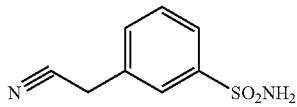 | 88% | $^1$H NMR(400MHz, CDCl$_3$): δ[ppm] 3.08(3H, s), 3.99(2H, s), 6.30(1H, s), 7.31(3H, m), 7.55(1H, dd) LRMS: m/z 228(MNH$_4^+$) |
| 49 | 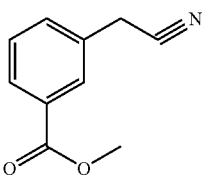 | 84% | $^1$H NMR(400MHz, CDCl$_3$): δ[ppm] 3.10(3H, s), 3.71(2H, s), 7.10–7.18(1H, m), 7.21 (1H, s), 7.32–7.40(3H, m) LRMS: m/z 228.2(MNH$_4^+$) |

Preparation 50

3-(Cyanomethyl)benzenesulfonamide

A solution of the title compound of preparation 46 (5.00 g, 37.8 mmol) in concentrated hydrochloric acid (13 ml) and glacial acetic acid (38 ml) was cooled to 0° C. and sodium nitrite (2.80 g, 40.5 mmol) in water (4 ml) was added dropwise. Once the addition was complete a suspension of copper(I)chloride (1.50 g, 15.0 mmol) and sulphur dioxide (10.0 g) in glacial acetic acid (30 ml) was added and the reaction stirred for 1 hour at 0° C. The reaction was poured onto ice and the yellow solid collected by filtration, dissolved in 0.88 ammonia (30 ml) and stirred for 1 hour. The title compound was collected by filtration as a yellow solid and dried under vacuum, 5.80 g.

$^1$H NMR (300 MHz, DMSOd$_6$): δ [ppm] 4.18 (2H, s), 7.34 (2H, br s), 7.58 (2H, m), 7.78 (2H, m)

LRMS: m/z 214 (MNH$_4^+$)

Preparation 51

Methyl-3-(cyanomethyl)benzoate 1,1,3,3-Tetramethylguanidine (3.21 ml, 25.6 mmol) was added dropwise to a solution of methyl 3-bromomethylbenzoate (2.80 g, 12.2 mmol) and acetone cyanohydrin (1.59 ml, 18.3 mmol) in acetonitrile (40 ml) at room temperature. The reaction was stirred for 3 days and the solvent then removed under reduced pressure. The resulting brown oil was purified by column chromatography on silica gel using ethyl acetate:pentane (50:50) as eluant to afford the title compound as a clear oil, 1.80 g.

$^1$H NMR (300 MHz, CDCl$_3$): δ [ppm] 3.79 (2H, s), 3.93 (3H, s), 7.48 (1H, dd), 7.58 (1H, d), 8.02 (2H, m)

LRMS: m/z 198 (MNa$^+$)

Preparation 52

3-(Cyanomethyl)benzoic acid

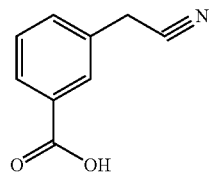

Sodium hydroxide (822 mg, 20.6 mmol) was added in one portion to a solution of the title compound of preparation 51 (1.80 g, 10.3 mmol) in tetrahydrofuran (6 ml) and water (2 ml) at room temperature. The reaction was stirred for 5 hours and then poured onto 2M hydrochloric acid (20 ml) and the aqueous extracted with dichloromethane (3×). The combined organic extracts were dried (MgSO$_4$), filtered and the solvent evaporated under reduced pressure to give the title compound as a white solid, 1.45 g.

$^1$H NMR (300 MHz, CDCl$_3$): δ [ppm] 3.79 (2H, s), 7.48 (1H, dd), 7.61 (1H, d), 8.03 (2H, m)

LRMS: m/z 160 (M−H$^-$)

Preparation 53

Methyl-4-(cyanomethyl)benzoate

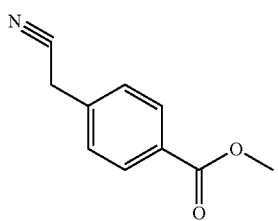

Obtained from methyl 4-bromomethyl)benzoate as a yellow solid in 77% yield using a similar procedure to that in preparation 51.

$^1$H NMR (400 MHz, CDCl$_3$): δ [ppm] 3.80 (2H, s), 3.93 (3H, s), 7.20 (2H, d), 8.17 (2H, d)

Preparation 54

4-(Cyanomethyl)benzoic acid

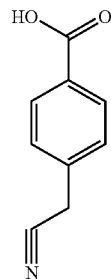

Obtained from the title compound of preparation 53 as a yellow solid in 97% yield using a similar procedure to that in preparation 52.

$^1$H NMR (400 MHz, CD$_3$OD): δ [ppm] 3.98 (2H, s), 7.49 (2H, d), 8.02 (2H, d)

LRMS: m/z 160.0 (MH$^-$)

Preparation 55

4-(Cyanomethyl)benzamide

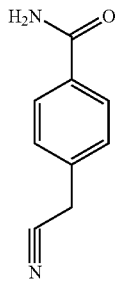

The title compound of preparation 54 (9.66 g, 60 mmol), was dissolved in dichloromethane (250 ml) and cooled to 0° C. Oxalyl chloride (5.34 ml, 61 mmol), was added followed by the dropwise addition of N,N-dimethylformamide (0.25 ml). The reaction was stirred at room temperature for 2 hours and then evaporated under reduced pressure to afford a yellow solid. This residue was dissolved in tetrahydrofuran (100 ml) and 0.88 ammonia (5 ml) added dropwise. After stirring for a further 10 minutes the resulting precipitate was filtered off to afford the title compound as a white solid, 6.74 g.

$^1$H NMR (400 MHz, CD$_3$OD): δ [ppm] 3.97 (2H, s), 7.48 (2H, d), 7.89 (2H, d)

LRMS: m/z 161.1 (MH$^+$)

Preparation 56

N-Hydroxy-2-phenylethanimidamide

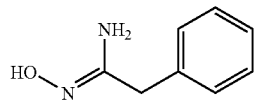

Phenyl acetonitrile (20 g, 170 mmol), hydroxylamine hydrochloride (60 g, 850 mmol) and sodium carbonate (71 g, 850 mmol) were heated under reflux in methanol (300 ml) and water (300 ml) for 5 hours. The reaction mixture was cooled to room temperature, filtered and the filtrate was evaporated and extracted with dichloromethane (3×). The combined organic solutions were washed with water and brine, dried (MgSO$_4$), filtered and concentrated under reduced pressure to give the title compound as a white solid, 15.5 g.

$^1$H NMR (300 MHz, CDCl$_3$): δ [ppm] 3.70 (2H, s), 7.30 (5H, m)

LRMS: m/z 151 (MH$^+$)

Preparations 57 to 63

The compounds of the following tabulated preparations:

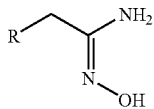

were prepared from the corresponding commercial nitrites, using similar methods to that described in preparation 56.

| PREP-ARA-TION | R | YIELD | DATA |
|---|---|---|---|
| 57 | 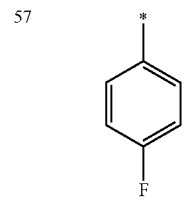 | 90% | $^1$H NMR(300MHz, CDCl$_3$): δ[ppm] 3.43(2H, s), 4.47(2H, s), 7.01(2H, m), 7.24(2H, m) 8.14(1H, s) LRMS: m/z 169.0(MH$^+$) |
| 58 | 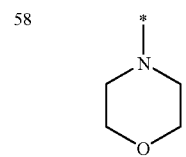 | 48% | $^1$H NMR(300MHz, DMSOd$_6$): δ[ppm] 2.30(4H, m), 2.80(2H, s), 3.55(4H, m), 5.2(2H, bs), 8.95(1H, s) |
| 59 | 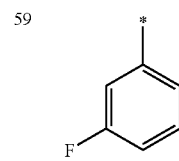 | 91% | $^1$H NMR(400MHz, CDCl$_3$): δ[ppm] 1.60(1H, s), 3.46(2H, s), 4.56(2H, s), 6.80–7.18(3H, m) LRMS: m/z 187.2(MH$^+$) |
| 60 | 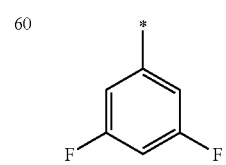 | 61% | $^1$H NMR(400MHz, CDCl$_3$): δ[ppm] 1.60(1H, s), 3.42(2H, s), 4.46(2H, s), 6.80(2H, m), 7.10–7.30(1H, m) LRMS: m/z 187.3(MH$^+$) |
| 61 | 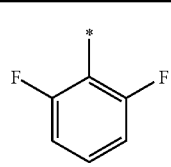 | 58% | $^1$H NMR(400MHz, CDCl$_3$): δ[ppm] 1.66(1H, s), 3.54(2H, s), 4.60(2H, s), 6.90(2H, m), 7.10(1H, m) LRMS: m/z 187.2(MH$^+$) |
| 62 | 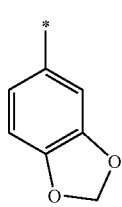 | 36% | $^1$H NMR(400MHz, DMSOd$_6$): δ[ppm] 3.12(2H, s), 5.32(2H, s), 5.94(2H, s), 6.71(1H, d), 6.75–6.85(2H, m), 8.85(1H, s) LRMS: m/z 195.0(MH$^+$) |
| 63 | 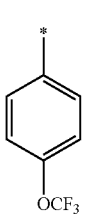 | 68% | $^1$H NMR(400MHz, CD$_3$OD): δ[ppm] 3.40(2H, s), 7.20(2H, m), 7.40(2H, m) LRMS: m/z 235.1(MH$^+$) |

Preparation 64

2-[4-(Aminosulphonyl)phenyl]-N-hydroxyethanimidamide

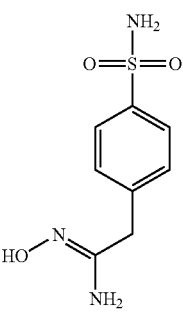

Obtained from 4-(cyanomethyl)benzenesulphonamide [J. Med. Chem., (1965), 8, 548] and hydroxylamine hydrochloride as a solid in 7% yield using a similar procedure to that in preparation 56.

$^1$H NMR (400 MHz, CD$_3$OD): δ [ppm] 3.42 (2H, s), 3.60 (1H, s), 7.46 (2H, m), 7.81 (2H, d)

LRMS: m/z 230 (MH$^+$)

Preparation 65

2-[3-(Aminosulphonyl)phenyl]-N-hydroxyethanimidamide

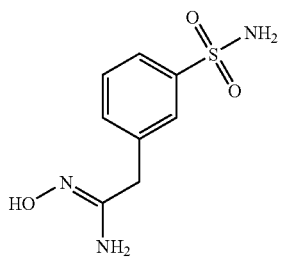

Obtained from the title compound of preparation 50 and hydroxylamine hydrochloride as a solid in 52% yield using a similar procedure to that in preparation 56.

$^1$H NMR (300 MHz, DMSOd$_6$): δ [ppm] 5.43 (2H, s), 7.21 (2H, s), 7.45 (2H, m), 7.62 (1H, m), 7.71 (1H, s), 8.95 (1H, s)

LRMS: m/z 230 (MH$^+$)

Preparation 66

N-Hydroxy-2-{3-[(methylsulphonyl)amino]phenyl}ethanimidamide

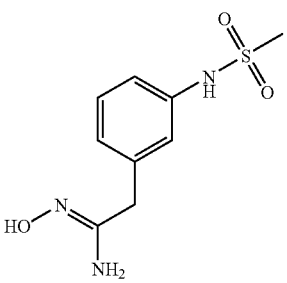

Obtained from the title compound of preparation 49 and hydroxylamine hydrochloride as a solid in 21% yield using a similar procedure to that in preparation 56.

$^1$H NMR (400 MHz, CD$_3$OD): δ [ppm] 2.93 (3H, s), 3.38 (2H, s), 7.03–7.12 (2H, m), 7.19 (1H, s), 7.30 (1H, m)

LRMS: m/z 243.9 (MH$^+$)

Preparation 67

2-(1-Benzofuran-5-yl)-N'-hydroxyethanimidamide

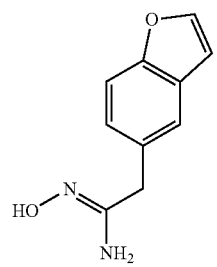

Obtained from 2-(1-benzofuran-5-yl)acetonitrile [Chim. Ther. (1972), 7(4), 337] and hydroxylamine hydrochloride as a solid in 31% yield using a similar procedure to that in preparation 56.

$^1$H NMR (400 MHz, CD$_3$OD): δ [ppm] 3.50 (2H, s), 6.80 (1H, d), 7.25 (1H, d), 7.40 (1H, d), 7.50 (1H, s), 7.70 (1H, s)

LRMS: m/z 191.2 (MH$^+$)

Preparation 68

2-(4-Acetyl-1-piperazinyl)acetonitrile

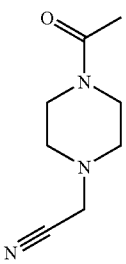

Chloroacetonitrile (14.7 ml, 234 mmol) was added slowly to a well stirred suspension of sodium carbonate (32 g, 300 mmol) and acetylpiperazine (30 g, 230 mmol) in toluene (200 ml). The mixture was heated under reflux for 3 hours. The reaction was cooled, filtered and the filtrate evaporated under reduced pressure. The resulting solid was recrystallised from ethyl acetate to afford the title compound as a yellow solid, 18.6 g.

$^1$H NMR (400 MHz, CDCl$_3$): δ [ppm] 2.09 (3H, s), 2.58 (4H, m), 3.51 (4H, m), 3.67 (2H, m)

Preparation 69

2-(4-Acetyl-1-piperazinyl)-N'-hydroxyethanimidamide

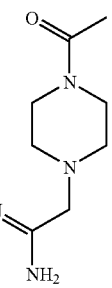

Sodium methoxide (6.6 g, 67 mmol) was added to the title compound of preparation 68 (18.6 g, 111 mmol) and hydroxylamine hydrochloride (8.5 g, 122 mmol) in methanol (200 ml). The mixture was heated under reflux for 15 hours. The reaction was cooled to room temperature and filtered. The filtrate was evaporated under reduced pressure to afford the title compound as a white solid, 23.8 g.

$^1$H NMR (400 MHz, CD$_3$OD): δ [ppm] 2.07 (3H, s), 2.43 (4H, m), 2.95 (2H, s), 3.59 (4H, m)

LRMS: m/z 223 (MNa$^+$)

Preparation 70 tert-Butyl 4-{3-[4-(trifluoromethoxy)benzyl]-1,2,4-oxadiazol-5-yl}-1-piperidinecarboxylate

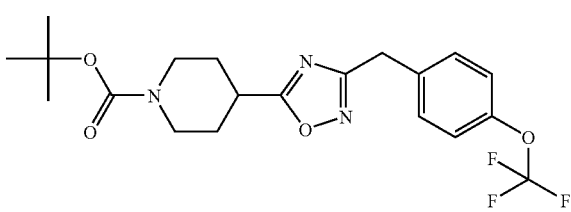

1-(tert-Butoxycarbonyl)-4-piperidinecarboxylic acid (250 mg, 1.09 mmol) in dichloromethane (5 ml) was treated with diisopropylethylamine (0.28 ml, 2.70 mmol). Bis(tetramethylene)fluoroformamidinium hexafluorophosphate (413 mg, 1.31 mmol) in dichloromethane (5 ml) was added and the solution stirred at room temperature for 1 hour. The title compound of preparation 63 (307 mg, 1.31 mmol) and diisopropylethylamine (0.23 ml, 1.09 mmol) in dichloromethane (2 ml) were added, the resulting solution was stirred at room temperature for 16 hours, then heated to 50° C. to concentrate the solution. Dioxane (10 ml) was added and the solution heated to 120° C. for 3 hours. The reaction was cooled to room temperature, diluted with ethyl acetate, washed with saturated aqueous sodium bicarbonate solution and 1M citric acid solution. The combined organic solutions were dried (MgSO$_4$), filtered and evaporated under reduced pressure. The residue was purified by column chromatography on silica gel, using ethyl acetate: pentane (25:75) as eluant to afford the title compound as an oil, 306 mg.

$^1$H NMR (400 MHz, CDCl$_3$): δ [ppm] 1.41 (9H, s), 1.80 (2H, m), 2.02 (2H, m), 2.94 (2H, m), 3.12 (1H, m), 4.08 (2H, s), 4.16 (2H, m), 7.15 (2H, d), 7.35 (2H, d)

LRMS: m/z 427.4 (MH$^+$)

Preparation 71 tert-Butyl 4-[3-(1-benzofuran-5-ylmethyl)-1,2,4-oxadiazol-5-yl]-1-piperidinecarboxylate

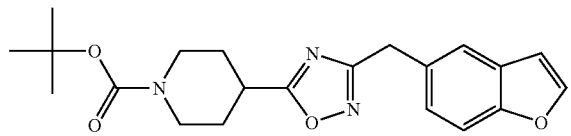

Obtained from the title compound of preparation 67 as a clear oil in 43% yield using a similar procedure to that in preparation 70.

$^1$H NMR (400 MHz, CDCl$_3$): δ [ppm] 1.41 (9H, s), 1.86 (2H, m), 2.04 (2H, m), 2.95 (2H, m), 3.05 (1H, m), 4.05 (2H, bm), 4.10 (2H, s), 7.10–7.50 (5H, m)

LRMS: m/z 383.4 (MH$^+$)

Preparation 72 tert-Butyl 4-[3-(4-chlorobenzyl)-1,2,4-oxadiazol-5-yl]-1-piperidinecarboxylate

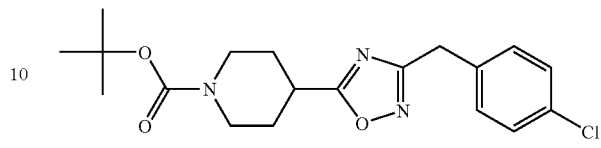

Obtained from (4-chlorophenyl)acetamidoxime [Bioorg. Med. Chem. Lett. (1996), 6(7), 833] as a clear oil in 63% yield using a similar procedure to that in preparation 70.

$^1$H NMR (400 MHz, CDCl$_3$): δ [ppm] 1.45 (9H, s), 1.84 (2H, m), 2.02 (2H, m), 2.95 (2H, m), 3.05 (1H, m), 4.02 (2H, s), 4.16 (2H, m), 7.25 (4H, m)

LRMS: m/z 395.1 (MNH$_4^+$)

Preparation 73 tert-Butyl 4-(3-isobutyl-1,2,4-oxadiazol-5-yl)-1-piperidinecarboxylate

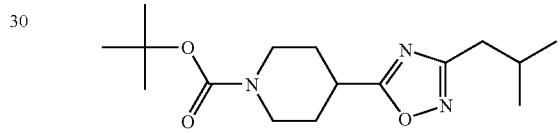

Isovaleronitrile (14.1 g, 170 mmol) and hydroxylamine hydrochloride (60 g, 850 mmol) were heated under reflux in methanol (300 ml) and water (300 ml) for 5 hours. The reaction mixture was cooled to room temperature, solid sodium carbonate added cautiously and the mixture filtered. The filtrate was concentrated under reduced pressure and extracted with dichloromethane (3×). The combined organic solutions were washed with water and brine, dried (MgSO$_4$), filtered and concentrated under reduced pressure to give a white solid, 15.5 g. In a separate flask 1-(tert-butoxycarbonyl)$_4$-piperidinecarboxylic acid (250 mg, 1.09 mmol) in dichloromethane (5 ml) was treated with diisopropylethylamine (0.28 ml, 2.70 mmol). Bis(tetramethylene)fluoroformamidinium hexafluorophosphate (413 mg, 1.31 mmol) in dichloromethane (5 ml) was added to the solution and stirred at room temperature for 1 hour. A portion of the intermediate white solid (150 mg, 1.31 mmol) and diisopropylethylamine (0.23 ml, 1.09 mmol) in dichloromethane (2 ml) were added, the resulting solution was stirred at room temperature for 16 hours, then heated to 50° C. to concentrate the solution. Dioxane (10 ml) was added and the solution heated to 120° C. for 3 hours. The reaction was cooled to room temperature, diluted with ethyl acetate, washed with saturated aqueous sodium bicarbonate solution and 1M citric acid solution. The combined organic solutions were dried (MgSO$_4$), filtered and evaporated under reduced pressure. The residue was purified by column chromatography on silica gel, using ethyl acetate: pentane (25:75) as eluant to afford the title compound as an oil, 209 mg.

$^1$H NMR (400 MHz, CDCl$_3$): δ [ppm] 0.91 (6H, d), 1.25 (9H, s), 1.84 (2H, m), 2.05 (3H, m), 2.54 (2H, d), 2.98 (2H, m), 3.05 (1H, m), 4.07 (2H, m)

LRMS: m/z 309.9 (MH$^+$)

Preparation 74 tert-Butyl 4-{3-[2,5-difluorobenzyl]-1,2,4-oxadiazol-5-yl}1-piperidinecarboxylate

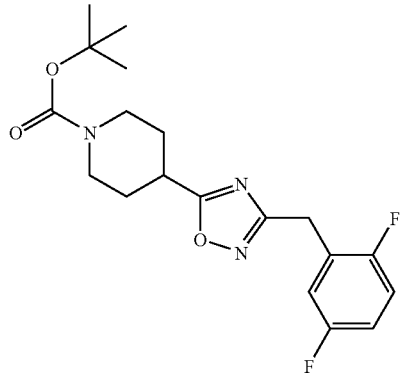

Obtained from the title compound of preparation 59 as a clear oil in 34% yield using a similar procedure to that in preparation 70.

$^1$H NMR (400 MHz, CDCl$_3$): δ [ppm] 1.45 (9H, s), 1.76–1.84 (2H, m), 2.02 (2H, m), 2.94 (2H, m), 3.06 (1H, m), 4.06–4.12 (4H, m), 6.90–7.06 (3H, m)

LRMS: m/z 380.7 (MH$^+$)

Preparation 75 tert-Butyl 4-{3-[3,5-difluorobenzyl]-1,2,4-oxadiazol-5-yl}1-piperidinecarboxylate

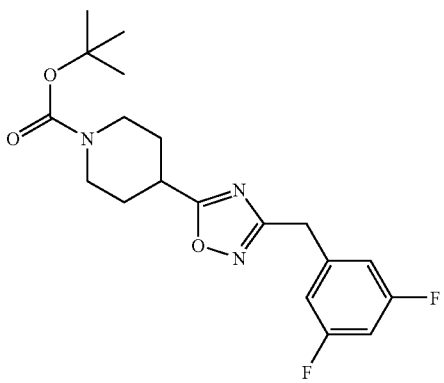

Obtained from the title compound of preparation 60 as a clear oil in 24% yield using a similar procedure to that in preparation 70.

$^1$H NMR (400 MHz, CDCl$_3$): δ [ppm] 1.44 (9H, s), 1.75–1.84 (2H, m), 2.03 (2H, m), 2.96 (2H, t), 3.06 (1H, m), 4.00 (2H, s), 4.06 (2H, m), 6.70 (1H, m), 6.82 (2H, m)

LRMS: m/z 380.0 (MH$^+$)

Preparation 76 tert-Butyl 4-{3-[2,6-difluorobenzyl]-1,2,4-oxadiazol-5-yl}1-piperidinecarboxylate

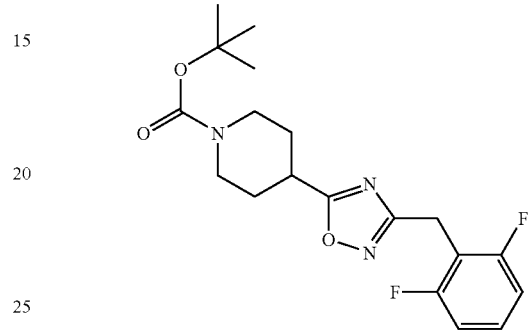

Obtained from the tide compound of preparation 61 as a clear oil in 39% yield using a similar procedure to that in preparation 70.

$^1$H NMR (400 MHz, CDCl$_3$): δ [ppm] 1.47 (9H, s), 1.76–1.84 (2H, m), 2.02 (2H, m), 2.94 (2H, m), 3.06 (1H, m), 4.00–4.14 (4H, m), 6.94 (2H, m), 7.23 (1H, m)

LRMS: m/z 380.0 (MH$^+$)

Preparation 77 tert-Butyl 4-{3-[4-methylbenzyl]-1,2,4-oxadiazol-5-yl}-1-piperidinecarboxylate

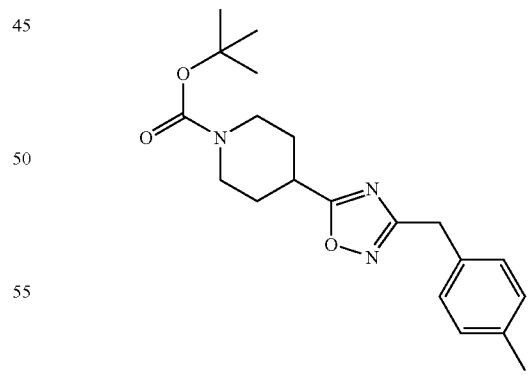

Obtained from 4-methylbenzylcyanide as an oil in 60% yield using a similar procedure to that in preparation 73.

$^1$H NMR (400 MHz, CDCl$_3$): δ [ppm] 1.45 (9H, s), 1.76–1.84 (2H, m), 2.02 (2H, m), 2.34 (3H, s), 2.93 (2H, t), 3.05 (1H, m), 4.00 (2H, s), 4.05 (2H, m), 7.11 (2H, d), 7.20 (2H, d)

LRMS: m/z 358.1 (MH$^+$)

Preparation 78 tert-Butyl 4-{3-[4-trifluoromethylbenzyl]-1,2,4-oxadiazol-5-yl}1-piperidinecarboxylate

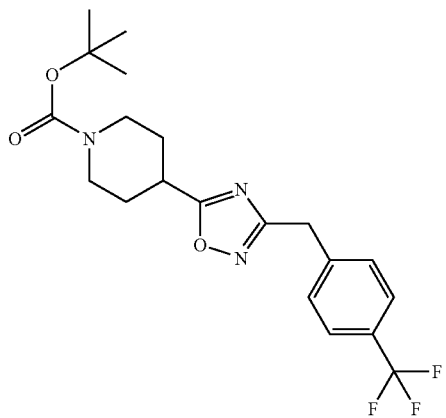

Obtained from (4-trifluoromethylphenyl)acetamidoxime [Bioorg. Med. Chem. Lett. (1996), 6(7), 833] as a clear oil in 49% yield using a similar procedure to that in preparation 70.

$^1$H NMR (400 MHz, CDCl$_3$): δ [ppm] 1.44 (9H, s), 1.72–1.86 (2H, m), 2.03 (2H, m), 2.92 (2H, t), 3.03 (1H, m), 4.00–4.12 (4H, m), 7.43 (2H, d), 7.58 (2H, d)

LRMS: m/z 411.8 (MH$^+$)

Preparation 79 tert-Butyl 4-{3-[1,3-benzodioxol-5-ylmethyl]-1,2,4-oxadiazol-5-yl}-1-piperidinecarboxylate

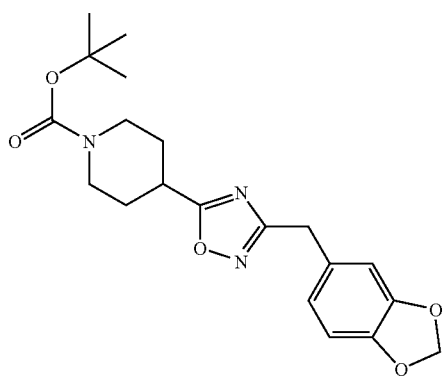

Obtained from the title compound of preparation 62 as a clear oil in 73% yield using a similar procedure to that in preparation 70.

$^1$H NMR (400 MHz, CDCl$_3$): δ [ppm] 1.45 (9H, s), 1.70–1.84 (4H, m), 2.03 (2H, m), 2.93 (2H, t), 3.03 (1H, m), 3.95 (2H, s), 4.05 (2H, m), 6.704.82 (3H, m)

Preparation 80 tert-Butyl (1S)-3-[4-(3-benzyl-1,2,4-oxadiazol-5-yl)-1-piperidinyl]-1-phenylpropylcarbamate

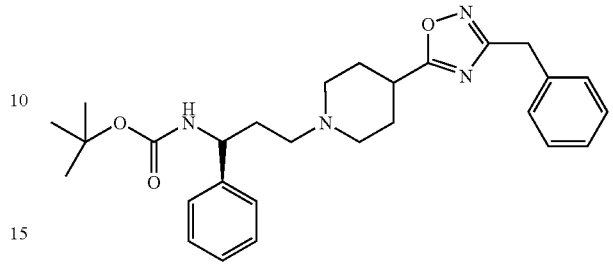

Sodium triacetoxyborohydride (1.28 g, 6.02 mmol) was added to a solution of the title compounds of preparation 7 (1.00 g, 4.01 mmol) and preparation 39 (1.07 g, 4.41 mmol) in dichloromethane/acetic acid (40 ml, 10% solution). The reaction mixture was stirred for 30 minutes after which time the solution was basified using saturated sodium carbonate and the product was extracted with dichloromethane (×3). The combined organic extracts were dried (MgSO$_4$), filtered and the solvent evaporated under reduced pressure to give a brown oil. This was purified by column chromatography on silica gel using dichloromethane:methanol:0.88 ammonia (95:5:0.5) as eluant to afford the title compound as an oil, 1.04 g.

$^1$H NMR (400 MHz, CDCl$_3$): δ[ppm] 1.40 (9H, bs), 1.90–2.10 (7H, m), 2.30 (2H, m), 2.85 (2H, m), 2.98 (1H, m), 4.15 (2H, s), 4.80 (1H, bs), 6.50 (1H, bs), 7.30 (10H, m)

LRMS: m/z 477 (MH$^+$)

Preparation 81

(1S)-3-[4-(3-Benzyl-1,2,4-oxadiazol-5-yl)-1-piperidinyl]-1-phenylpropylamine

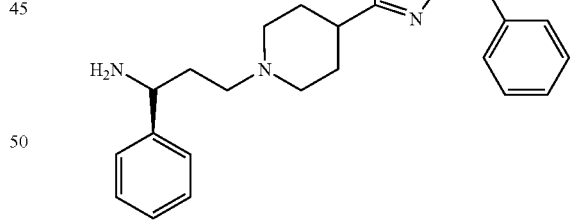

To a stirred solution of the title compound of preparation 80 (560 mg, 1.17 mmol) in dichloromethane (10 ml) at 0° C. was added trifluoroacetic acid (5 ml). The reaction was allowed to warm to room temperature and stirred for 90 minutes. The mixture was then concentrated, basified with saturated sodium carbonate and extracted with dichloromethane (3×). The combined organic solutions were washed with brine, dried (MgSO$_4$), filtered and concentrated to give the title compound as a yellow oil, 314 mg.

$^1$H NMR (400 MHz, CDCl$_3$): δ [ppm] 1.90 (2H, m), 2.05 (4H, m), 2.40 (4H, m), 2.85 (2H, m), 2.95 (1H, m), 3.99 (3H, m), 4.05 (2H, s), 7.30 (10H, m)

LRMS: m/z 377 (MH$^+$)

Preparation 82 tert-Butyl-4-(3-{4-[(methylsulphonyl)amino]benzyl}1,2,4-oxadiazol-5-yl)-1-piperidinecarboxylate

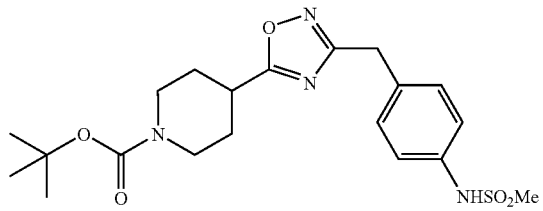

The title compound of preparation 47 (10.0 g, 47 mmol), hydroxylamine hydrochloride (16.5 g, 238 mmol) and sodium carbonate (25 g, 238 mmol) were heated under reflux in methanol (200 ml) and water (200 ml) for 5 hours. The reaction mixture was cooled to room temperature, filtered and the filtrate was evaporated and extracted with dichloromethane (3×). The combined organic solutions were washed with water and brine, dried ($MgSO_4$), filtered and concentrated under reduced pressure to give a white solid, 8.0 g. A portion of this amidoxime (5.00 g, 20.6 mmol), 1-(tert-butoxycarbonyl)-4-piperidine carboxylic acid (5.18 g, 22.6 mmol) and 1-(3-dimethylaminopropyl)-3-ethyl-carbodiimide hydrochloride (4.71 g, 24.6 mmol) were stirred in dichloromethane (100 ml) for 2 hours. The solvent was removed under reduced pressure and the brown oil dissolved in dioxane (50 ml) and heated under reflux for 5 hours. The solvent was removed under reduced pressure and the residue dissolved in ethyl acetate (200 ml) washed with water and brine, dried ($MgSO_4$), filtered and concentrated under reduced pressure. The tide compound was purified by column chromatography on silica gel using dichloromethane:methanol:0.88 ammonia (95:5:0.5) as eluant to afford the title compound as a yellow foam, 3.40 g.

$^1$H NMR (300 MHz, $CDCl_3$): δ [ppm] 1.41 (9H, s), 1.78 (2H, m), 2.01 (2H, m), 2.83–3.05 (5H, m), 4.03–4.19 (5H, m), 6.40 (1H, m), 7.18 (2H, d), 7.31 (2H, d)

LRMS: m/z 459 ($MNa^+$)

Preparation 83

N-(4-{[5-(4-Piperidinyl)-1,2,4-oxadiazol-3-yl]methyl}phenyl)methanesulphonamide hydrochloride

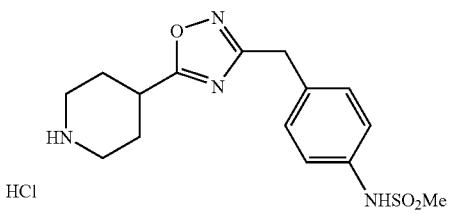

The title compound of preparation 82 (3.20 g, 7.33 mmol) was dissolved in methanolic hydrochloric acid (100 ml, 2.5M) and stirred at room temperature for 2 hours. The solvent was removed under reduced pressure to afford the title compound as a white solid, 2.50 g.

$^1$H NMR (300 MHz, $D_2O$): δ [ppm] 1.85 (2H, dd), 2.21 (2H, d), 2.98 (3H, s), 3.05 (2H, dd), 3.38 (4H, m), 4.00 (2H, s), 7.18 (2H, d), 7.24 (2H, d)

LRMS: m/z 337 ($MH^+$)

Preparation 84

2,2,2-Trifluoro-1-{4-[3-(4-fluorobenzyl)-1,2,4-oxadiazol-5-yl]-1-piperidinyl}-1-ethanone

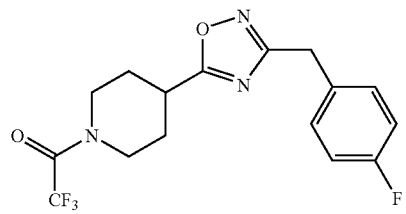

Obtained from the title compounds of preparations 20 and 57 as an oil in 15% yield using a similar procedure to that in preparation 21.

$^1$H NMR (400 MHz, $CDCl_3$): δ [ppm] 1.80 (2H, m), 2.20 (2H, m), 3.15–3.40 (3H, m), 4.00 (2H, s), 7.00 (2H, m), 7.30 (2H, m)

Preparation 85

4-[3-(4-Fluorobenzyl)-1,2,4-oxadiazol-5-yl]piperidine

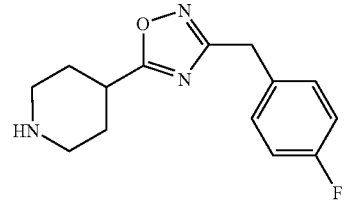

Obtained from the title compound of preparation 84 as an oil in 75% yield using a similar procedure to that in preparation 37.

$^1$H NMR (400 MHz, $CDCl_3$): δ [ppm] 1.80 (2H, m), 2.10 (2H, dd), 2.80 (2H, m), 3.05 (1H, m), 3.20 (2H, m), 4.00 (2H, s), 7.00 (2H, m), 7.25 (2H, m)

LRMS: m/z 262 ($MH^+$)

Preparation 86 tert-Butyl 3-(3-benzyl-1,2,4-oxadiazol-5-yl)-1-azetidinecarboxylate

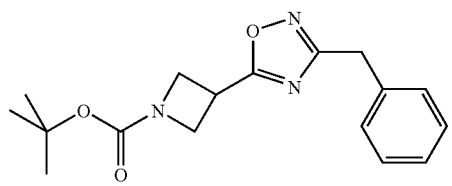

Obtained from the title compounds of preparations 13 and 56 as an oil in 72% yield using a similar procedure to that in preparation 21.

¹H NMR (400 MHz, CDCl₃): δ [ppm] 1.45 (9H, s), 3.95 (1H, m), 4.08 (2H, s), 4.20 (2H, m), 4.30 (2H, t), 7.25 (1H, m), 7.35 (4H, m)
LRMS: m/z 338 (MNa⁺)

Preparation 87

5(3-Azetidinyl)-3-benzyl-1,2,4-oxadiazole

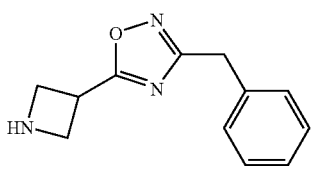

Obtained from the title compound of preparation 86 as an oil in 72% yield using a similar procedure to that in preparation 81.
¹H NMR (400 MHz, CDCl₃): δ [ppm] 3.92 (2H, m), 4.06 (4H, m), 4.13 (1H, m), 7.25 (1H, m), 7.35 (4H, m)
LRMS: m/z 216 (MH⁺)

Preparation 88 tert-Butyl (1S)-3-[4-(3-{4-[(methylsulphonyl)amino]benzyl}1,2,4-oxadiazol-5-yl)-1-piperidinyl]-1-phenylpropylcarbamate

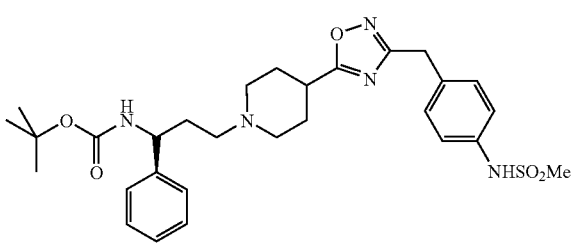

Sodium triacetoxyborohydride (1.28 g, 6.02 mmol) was added to a solution of the title compounds of preparation 7 (1.00 g, 4.01 mmol) and preparation 83 (1.65 g, 4.41 mmol) in dichloromethane/acetic acid (40 ml, 10% solution). The reaction mixture was stirred for 30 minutes after which time the solution was basified using saturated sodium carbonate and the product was extracted with dichloromethane (×3). The combined organic extracts were dried (MgSO₄), filtered and the solvent evaporated under reduced pressure to give a brown oil. This was purified by column chromatography on silica gel using dichloromethane:methanol:0.88 ammonia (95:5:0.5) as eluant to afford the title compound as a white foam, 1.30 g.

¹H NMR (300 MHz, CDCl₃): δ [ppm] 1.41 (9H, s), 1.80–2.19 (10H, m), 2.30 (2H, m), 2.80–3.01 (5H, m), 4.02 (2H, s), 4.75 (1H, bs), 6.38 (1H, bs), 7.15–7.40 (9H, m)
LRMS: m/z 570 (MH⁺)

Preparation 89 tert-Butyl (1S)-3-{4-[3-(4-fluorobenzyl)-1,2,4-oxadiazol-5-yl]-1-piperidinyl}1-phenylpropylcarbamate

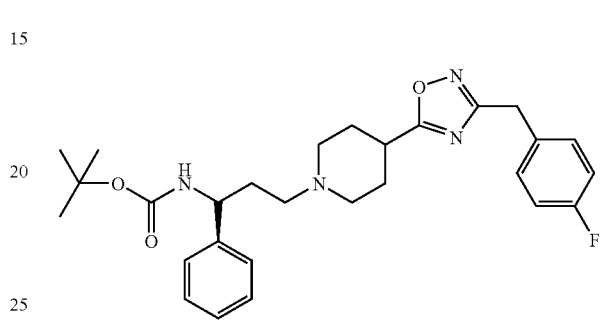

Obtained from the title compounds of preparations 7 and 85 as an oil in 81% yield using a similar procedure to that in preparation 80.
¹H NMR (400 MHz, CDCl₃): δ [ppm] 1.30 (9H, bs), 1.70 (1H, m), 1.80–2.00 (4H, m), 2.20 (2H, m), 2.80 (2H, m), 2.90 (1H, m), 3.95 (2H, s), 4.70 (1H, bs), 6.60 (1H, bs), 6.90 (2H, m), 7.10 (1H, m), 7.15–7.25 (8H, m)
LRMS: m/z 495 (MH⁺)

Preparation 90 tert-Butyl (1S)-3-[3-(3-benzyl-1,2,4-oxadiazol-5-yl)-1-azetidinyl]-1-phenylpropylcarbamate

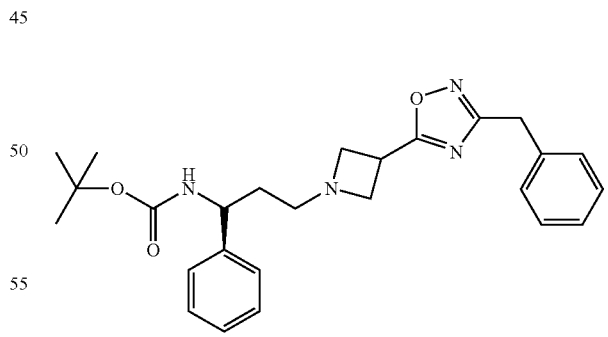

Obtained from the title compounds of preparations 7 and 87 as an oil in 64% yield using a similar procedure to that in preparation 80.
¹H NMR (400 MHz, CDCl₃): δ [ppm] 1.40 (9H, bs), 1.79 (2H, m), 2.45 (2H, m), 3.31 (2H, m), 3.67 (2H, m), 3.84 (1H, m), 4.05 (2H, m), 4.3–4.5 (1H, m), 5.62 (1H, bs), 7.25 (3H, m), 7.35 (7H, m)
LRMS: m/z 449 (MH⁺)

Preparation 91

N-{4-[(5-{1-[(3S)-3-Amino-3-phenylpropyl]-4-piperidinyl}-1,2,4-oxadiazol-3-yl)methyl]phenyl}methanesulfonamide hydrochloride

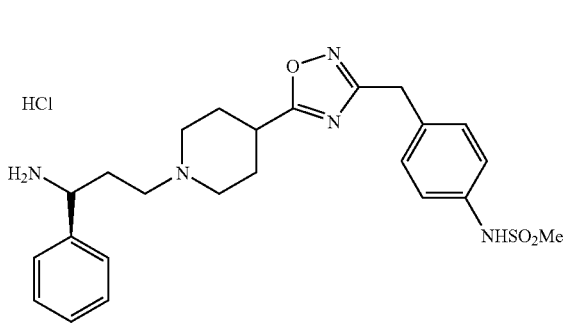

The title compound of preparation 88 (1.20 g, 2.10 mmol) was dissolved in methanolic hydrochloric acid (30 ml, 2.5M) and stirred at room temperature for 2 hours. The solvent was removed under reduced pressure to afford the title compound as a white solid, 1.04 g.

$^1$H NMR (300 MHz, D$_2$O): δ [ppm] 1.95 (2H, m), 2.23 (2H, m), 2.40 (2H, m), 2.71 (1H, m), 2.91–3.10 (6H, m), 3.25 (1H, m), 3.48 (2H, m), 4.03 (2H, s), 4.38 (1H, t), 7.15 (2H, d), 7.23 (2H, d), 7.40 (5H, m)

LRMS: m/z 470 (MH$^+$)

Preparation 92

(1S)-3-{4-[3-(4-Fluorobenzyl)-1,2,4-oxadiazol-5-yl]-1-piperidinyl}1-phenylpropylamine

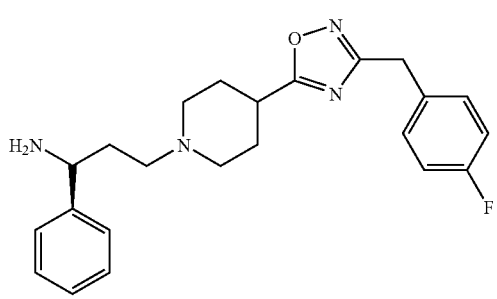

Obtained from the title compound of preparation 89 as an oil in 81% yield using a similar procedure to that in preparation 81.

$^1$H NMR (400 MHz, CDCl$_3$): δ [ppm] 1.90 (4H, m), 2.05 (4H, m), 2.40 (2H, m), 2.50 (2H, bs), 2.85 (2H, m), 2.98 (1H, m), 4.00 (3H, m), 7.00 (2H, m), 7.30 (7H, m)

LRMS: m/z 395 (MH$^+$)

Preparation 93

(1S)-3-[3-(3-Benzyl-1,2,4-oxadiazol-5-yl)-1-azetidinyl]-1-phenyl-1-propanamine

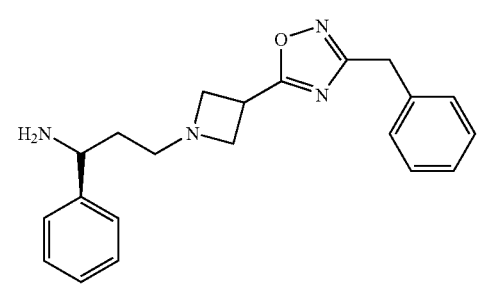

Obtained from the title compound of preparation 90 as an oil in 92% yield using a similar procedure to that in preparation 81.

$^1$H NMR (3/400 MHz, CDCl$_3$): δ [ppm] 1.60 (2H, m), 2.51 (2H, m), 3.53 (2H, t), 3.68 (2H, m), 3.87 (1H, m), 3.98 (1H, m), 4.06 (3H, m), 4.35–4.55 (1H, m), 7.2–7.36 (10H, m)

LRMS: m/z 349 (MH$^+$)

Preparation 94

Ethyl 3-({[1-amino-2-phenylethylidene]amino}oxy)-3-oxopropanoate

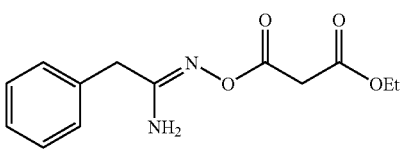

A solution of ethyl malonyl chloride (3.30 ml, 24 mmol) in dichloromethane (5 ml) was added dropwise to a stirred solution of the title compound of preparation 56 (3.34 g, 22 mmol) and diisopropylethylamine (4.27 ml, 24 mmol) in dichloromethane (45 ml) at 10° C. The reaction mixture was stirred and warmed to room temperature over 1 hour, then washed with brine, evaporated under reduced pressure and purified by column chromatography on silica gel using dichloromethane:methanol (97:3) as eluant to afford the title compound as a foam, 1.15 g.

$^1$H NMR (300 MHz, CDCl$_3$): δ [ppm] 1.25 (3H, t), 3.48 (2H, s), 3.57 (2H, s), 4.19 (2H, q), 4.84 (2H, bs), 7.26 (5H, m)

LRMS: m/z 265 (MH$^+$)

Preparation 95

3-({[1-Amino-2-phenylethylidene]amino}oxy)-3-oxopropanenitrile

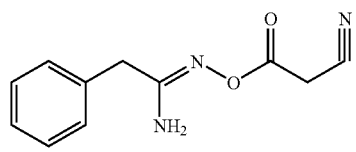

To a stirred solution of the title compound of preparation 56 (12.3 g, 82 mmol) in dichloromethane (100 ml) was added cyanoacetic acid (6.97 g, 82 mmol) and 3-ethyl-1-(3-dimethylaminopropyl)-carbodiimide hydrochloride (15.7 g, 82 mmol). The reaction mixture was stirred for 96 hours at room temperature, then partitioned between dichloromethane and water. The organic layer was separated, washed with brine, dried (MgSO$_4$), filtered and evaporated under reduced pressure. The resulting solid was triturated with ether to afford the title compound as a pale yellow solid, 1.71 g.

$^1$H NMR (300 MHz, CDCl$_3$+DMSOd$_6$): δ [ppm] 3.47 (2H, s), 3.59, (2H, s), 5.16 (2H, bs), 7.25 (5H, m)

LRMS: m/z 218 (MH$^+$)

Preparation 96

3-({[1-Amino-2-(4-fluorophenyl)ethylidene]amino}oxy)-3-oxopropanenitrile

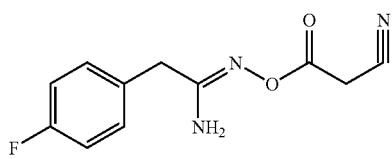

Obtained from the title compound of preparation 57 as an orange solid in 28% yield using a similar procedure to that in preparation 95.

$^1$H NMR (300 MHz, CDCl$_3$): δ [ppm] 3.38 (2H, s), 3.57 (2H, s), 5.40 (2H, s), 6.88 (2H, m), 7.17 (2H, m)

LRMS: m/z 236.1 (MH$^+$)

Preparation 97

Ethyl 2-(3-benzyl-1,2,4-oxadiazol-5-yl)acetate

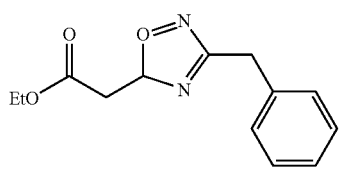

A solution of the title compound of preparation 94 (8.09 g, 30 mmol) in dioxane (110 ml) was heated under reflux for 4 hours. The solvent was evaporated under reduced pressure and the residual oil purified by column chromatography on silica gel using dichloromethane:methanol (95:5) as eluant, to afford the title compound as an oil, 4.85 g.

$^1$H NMR (300 MHz, CDCl$_3$): δ [ppm] 1.24 (3H, t), 3.95 (2H, s), 4.08 (2H, s), 4.22 (2H, q), 7.26 (5H, m)

LRMS: m/z 247 (MH$^+$)

Preparation 98

Ethyl 2-[5-(4-fluorobenzyl)-1,2,4-oxadiazol-3-yl]acetate

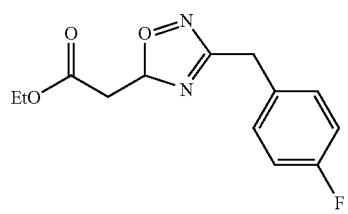

A solution of ethyl malonyl chloride (15 ml, 110 mmol) in dichloromethane (50 ml) was added dropwise to a stirred suspension of the title compound of preparation 57 (16.0 g, 100 mmol) and diisopropylethylamine (20 ml, 110 mmol) in dichloromethane (150 ml) with ice-bath cooling. The reactants were stirred at ambient temperature overnight then washed with water and concentrated to a gum.

This gum was dissolved in dioxane (150 ml) and heated under reflux for 12 hours. Pre-adsorption silica was added to the cooled solution which was concentrated and purified by column chromatography on silica gel using dichloromethane:methanol (95:5) as eluant to provide the title compound as an oil, 22.8 g.

$^1$H NMR (300 MHz, CDCl$_3$): δ [ppm] 1.26 (3H, t), 3.93 (2H, s), 4.07 (2H, s), 4.22 (2H, q), 7.00 (2H, m), 7.28 (2H, m)

LRMS: m/z 265.0 (MH$^+$)

Preparation 99

2-(3-Benzyl-1,2,4-oxadiazol-5-yl)acetonitrile

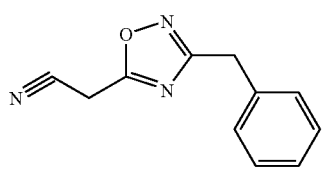

Obtained from the title compound of preparation 95 as an oil in residual dioxane using a similar procedure to that in preparation 97.

$^1$H NMR (300 MHz, CDCl$_3$): δ [ppm] 3.70 (dioxan), 3.99 (2H, s), 4.11 (2H, s), 7.32 (5H, m)

Preparation 100

2-[3-(4-Fluorobenzyl)-1,2,4-oxadiazol-5-yl]acetonitrile

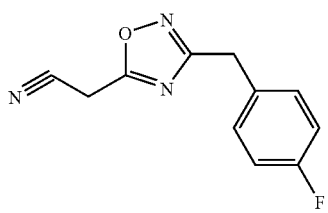

Obtained from the title compound of preparation 96 as an oil in 59% yield using a similar procedure to that in preparation 97.

¹H NMR (300 MHz, CDCl₃): δ [ppm] 4.02 (2H, s), 4.08 (2H, s), 7.03 (2H, m), 7.28 (2H, m)

Preparation 101

Ethyl 1-benzyl-4-(3-benzyl-1,2,4-oxadiazol-5-yl)₄-piperidinecarboxylate

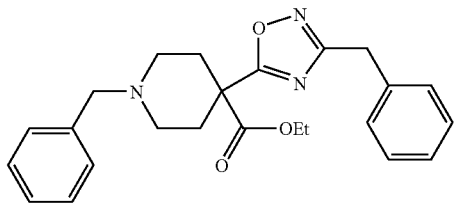

A solution of the title compound of preparation 97 (4.85 g, 19.7 mmol) in 1-methylpyrrolidin-2-one (10 ml) was added to a stirred suspension of sodium hydride (60% dispersion in mineral oil, 2.40 g, 60 mmol) in 1-methylpyrrolidin-2-one (30 ml). The reaction mixture was stirred for 45 minutes at room temperature before bis-(2-chloroethyl)benzylamine hydrochloride (5.00 g, 18.6 mmol) and tetra-n-butylammonium bromide (0.509, 1.5 mmol) were added. The reaction mixture was stirred for 24 hours at 60° C., then cooled and partitioned between ethyl acetate and water. The layers were separated and the organic phase washed with brine (3×). The organic extract was separated, pre-adsorbed on silica gel and purified by column chromatography on silica gel using dichloromethane:methanol (95:5) as eluant to provide the title compound as an oil, 4.76 g.

¹H NMR (300 MHz, CDCl₃): δ [ppm] 1.16 (3H, t), 2.32 (8H, m), 3.42 (2H, s), 4.08 (2H, s), 4.17 (2H, q), 7.26 (10H, m)

LRMS: m/z 406 (MH⁺)

Preparation 102

Ethyl 1-benzyl-4-(3-benzyl-1,2,4-oxadiazol-5-yl)-4-piperidinecarboxylate

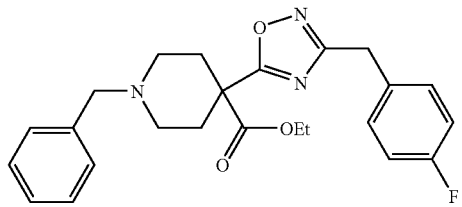

Obtained from the title compound of preparation 98 as an oil in 22% yield using a similar procedure to that in preparation 101.

¹H NMR (300 MHz, CDCl₃): δ [ppm] 1.18 (3H, t), 2.32 (6H, m), 2.58 (2H, m), 3.41 (2H, s), 4.06 (2H, s), 4.15 (2H, q), 7.00 (2H, m), 7.28 (7H, m)

LRMS: m/z 424.1 (MH⁺)

Preparation 103

1-Benzyl-4-(3-benzyl-1,2,4-oxadiazol-5-yl)-4-piperidinecarbonitrile

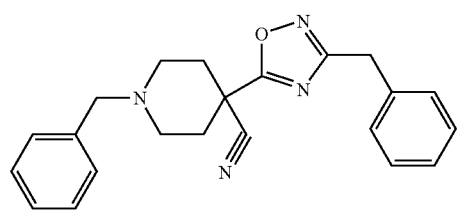

Obtained from the title compound of preparation 99 as an oil in 10% yield using a similar procedure to that in preparation 101.

¹H NMR (300 MHz, CDCl₃): δ [ppm] 2.26 (4H, m), 2.49 (2H, m), 2.92 (2H, m), 3.56 (2H, s), 4.08 (2H, s), 7.26 (10H, m)

LRMS: m/z 359 (MH⁺)

Preparation 104

1-Benzyl-4-[3-(4-fluorobenzyl)-1,2,4-oxadiazol-5-yl]-4-piperidinecarbonitrile

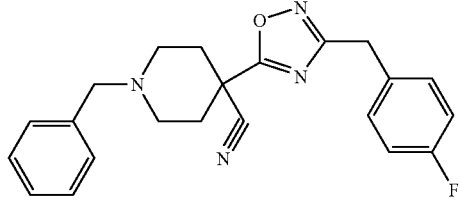

Obtained from the title compound of preparation 100 as an oil in 22% yield using a similar procedure to that in preparation 101.

¹H NMR (300 MHz, CDCl₃): δ [ppm] 2.24 (4H, m), 2.49 (2H, m), 2.92 (2H, m), 3.57 (2H, s), 4.04 (2H, s), 6.88 (2H, t), 7.25 (7H, m)

LRMS: m/z 377.3 (MH⁺)

Preparation 105

Ethyl 1-benzyl-4-[3-(4-fluorobenzyl)-1,2,4-oxadiazol-5-yl]-4-piperidinecarboxylate

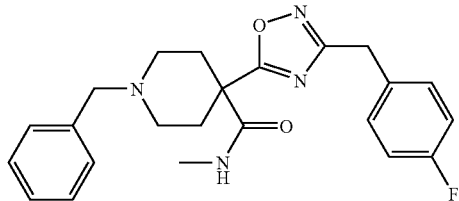

A solution of the title compound of preparation 102 (1.50 g, 3.50 mmol) and methylamine (20 ml of a 2M solution in tetrahydrofuran, 40 mmol) in ethanol (20 ml) was stirred in an autoclave at 100° C. for 5 hours. The solution was cooled, concentrated under reduced pressure and purified by column chromatography on silica gel using dichloromethane:methanol (95:5) as eluant, to provide the title compound as an oil, 295 mg.

¹H NMR (300 MHz, CDCl₃): δ [ppm] 2.07 (2H, m), 2.36 (4H, m), 2.73 (5H, m), 3.40 (2H, s), 4.06 (2H, s), 5.88 (1H, s), 7.00 (2H, m), 7.26 (7H, m)

LRMS: m/z 409.1 (MH⁺)

Preparation 106

Ethyl 4-(3-benzyl-1,2,4-oxadiazol-5-yl)-4-piperidinecarboxylate

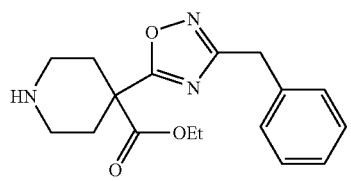

A solution of 1-chloroethylchloroformate (0.28 ml, 2.6 mmol) in dichloromethane (1 ml) was added to a solution of the title compound of preparation 101 (820 mg, 2 mmol) in dichloromethane (9 ml) at 0° C. The reaction mixture was stirred for 3 hours at room temperature, then the solvent evaporated and the residual oil dissolved in methanol (10 ml). The solution was heated under reflux for 1 hour. The solution was cooled, pre-adsorbed on silica gel, concentrated under reduced pressure and chromatographed on silica gel using dichloromethane:methanol:0.88 ammonia (95:5:0.5) as eluant, to provide the title compound as an oil 195 mg.

¹H NMR (300 MHz, CDCl₃): δ [ppm] 1.18 (3H, t), 2.57 (4H, m), 3.06 (2H, m), 3.24 (2H, m), 3.46 (1H, s), 4.06 (2H, s), 4.18 (2H, q), 7.27 (5H, m)

LRMS: m/z 316 (MH⁺)

Preparation 107

4-(3-Benzyl-1,2,4-oxadiazol-5-yl)-4-piperidinecarbonitrile

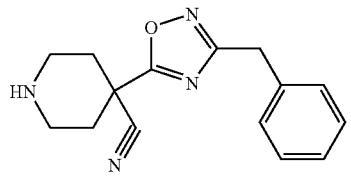

Obtained from the title compound of preparation 103 as an oil in 59% yield using a similar procedure to that in preparation 106.

¹H NMR (300 MHz, CDCl₃): δ [ppm] 2.34 (4H, m), 3.21 (4H, m), 4.08 (2H, s), 7.26 (5H, m)

LRMS: m/z 269 (MH⁺)

Preparation 108

4-[3-(4-Fluorobenzyl)-1,2,4-oxadiazol-5-yl]-4-piperidinecarbonitrile

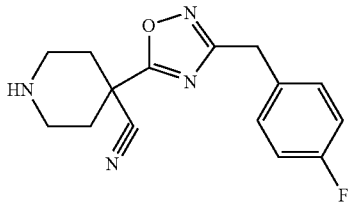

Obtained from the title compound of preparation 104 as an oil in 44% yield using a similar procedure to that in preparation 106.

¹H NMR (300 MHz, CDCl₃): δ [ppm] 2.50 (4H, m), 3.26 (2H, m), 3.42 (2H, m), 4.06 (2H, s), 7.02 (2H, m), 7.27 (2H, m)

LRMS: m/z 287.2 (MH⁺)

Preparation 109

4-[3-(4-Fluorobenzyl)-1,2,4-oxadiazol-5-yl]-N-methyl-4-piperidinecarboxamide

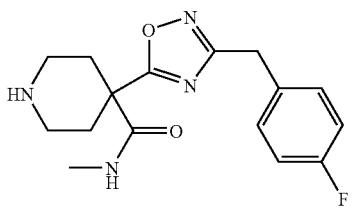

Obtained from the title compound of preparation 105 as an oil in 68% yield using a similar procedure to that in preparation 106.

¹H NMR (300 MHz, CDCl₃): δ [ppm] 2.21 (2H, m), 2.36 (2H, m), 2.62 (2H, m), 2.74 (3H, d), 3.03 (2H, m), 4.04 (2H, s), 5.88 (1H, s), 7.00 (2H, m), 7.26 (2H, m)

LRMS: m/z 319.1 (MH⁺)

Preparation 110 tert-Butyl (1S)-3-{4-cyano-4-[3-(4-fluorobenzyl)-1,2,4-oxadiazol-5-yl]-1-piperidinyl}-1-phenylpropyl-carbamate

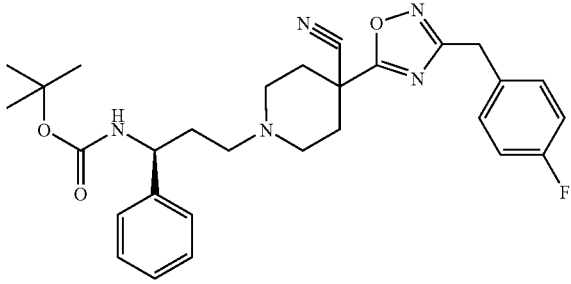

Obtained from the title compounds of preparations 7 and 108 as an oil in 54% yield using a similar procedure to that in preparation 80.

$^1$H NMR (300 MHz, CDCl$_3$): δ [ppm] 1.28 (9H, s), 1.94 (2H, m), 2.38 (8H, m), 2.90 (2H, m), 4.06 (2H, s), 4.78 (1H, s), 5.85 (1H, s), 7.02 (2H, m), 7.27 (7H, m)

LRMS: m/z 520.3 (MH$^+$)

Preparation 111

1-[(3S)-3-Amino-3-phenylpropyl]-4-[3-(4-fluorobenzyl)-1,2,4-oxadiazol-5-yl]-4-piperidinecarbonitrile

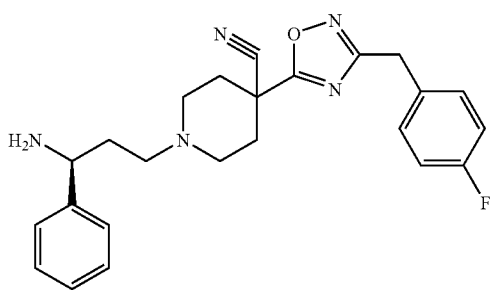

Obtained from the title compound of preparation 110 as an oil in 68% yield using a similar procedure to that in preparation 81.

$^1$H NMR (300 MHz, CDCl$_3$): δ [ppm] 1.85 (1H, m), 2.00 (1H, m), 2.38 (8H, m), 2.85 (1H, m), 3.02 (1H, m), 4.04 (3H, m), 7.02 (2H, m), 7.27 (7H, m)

LRMS: m/z 420.2 (MH$^+$)

Preparation 112

Benzyl 1-[(3S)-3{(tert-butoxycarbonyl)amino}-3-phenylpropyl]-4-piperidine carboxylate

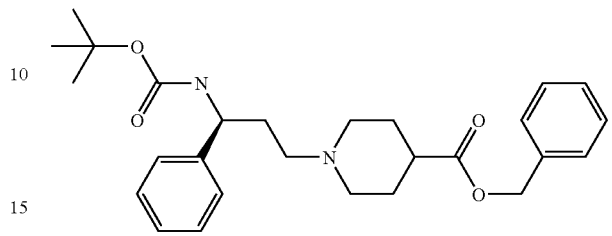

Obtained from the title compound of preparation 7 and benzyl 4-piperidinecarboxylate as an oil in 67% yield using a similar procedure to that in preparation 80.

$^1$H NMR (400 MHz, CDCl$_3$): δ [ppm] 1.33 (9H, s), 1.60–2.12 (11H, m), 2.64–3.00 (2H, m), 4.75 (1H, s), 5.10 (2H, s), 6.55 (1H, s), 7.10–7.45 (10H, m)

LRMS: m/z 453.3 (MH$^+$)

Preparation 113

Benzyl 1-[(3S)-3-amino-3-phenylpropyl]-4-piperidine carboxylate

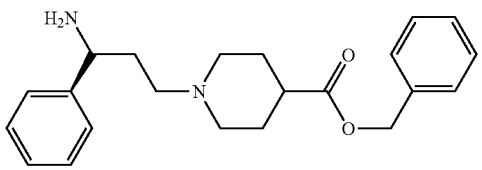

Obtained from the title compound of preparation 112 as an oil in 88% yield using a similar procedure to that in preparation 81.

$^1$H NMR (400 MHz, CDCl$_3$): δ [ppm] 1.60–2.05 (10H, m), 2.25–2.44 (3H, m), 2.86 (2H, m), 3.97 (1H, m), 5.14 (2H, s), 7.23–7.43 (10H, m)

LRMS: m/z 353.3 (MH$^+$)

Preparation 114

Benzyl 1-{(3S)-3-[(cyclobutylcarbonyl)amino]-3-phenylpropyl}-4-piperidine carboxylate

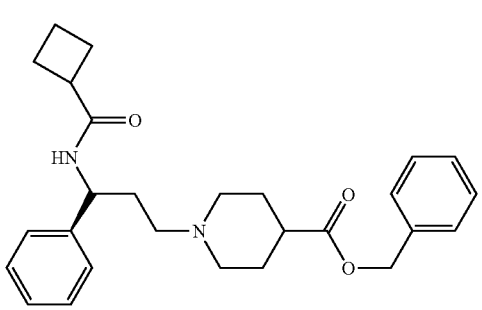

A solution of the title compound of preparation 113 (10.3 g, 29.2 mmol) in dichloromethane (200 ml) was treated with diisopropylethylamine (5.72 ml, 32.1 mmol) and cyclobutanecarbonylchloride (3.66 ml, 32.1 mmol). The mixture was stirred at room temperature under nitrogen for 18 hours then diluted with sodium carbonate solution and extracted with dichloromethane (2×). The combined organic extracts were washed with brine, dried (MgSO$_4$), filtered and evaporated under reduced pressure. The residue was purified by column chromatography on silica gel using dichloromethane:methanol (99:1) as eluant to afford the title compound, 4.63 g.

$^1$H NMR (400 MHz, CDCl$_3$): δ [ppm] 1.77–2.45 (16H, m), 2.80 (1H, m), 2.98–3.18 (2H, m), 5.11–5.26 (3H, m), 5.14 (2H, s), 7.18–7.45 (10H, m)

LRMS: m/z 435.3 (MH$^+$)

Preparation 115

1-{(3S)-3[(Cyclobutylcarbonyl)amino]-3-phenylpropyl}-piperidinecarboxylic acid

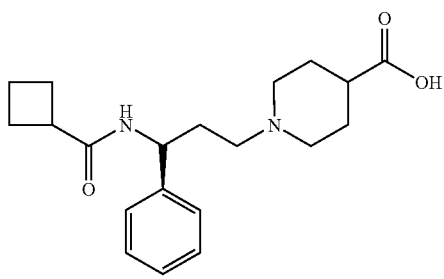

A solution the title compound of preparation 114 (7.63 g, 17.6 mmol) in ethanol (300 ml) was hydrogenated at 1 atmosphere for 12 hours at room temperature using 10% palladium on carbon as a catalyst (700 mg). The catalyst was removed by filtration through a glass-fibre filter, then the solvent was evaporated under reduced pressure to give the title compound as a white crystalline solid, 6.04 g.

$^1$H NMR (400 MHz, CD$_3$OD): δ [ppm] 1.16 (1H, m), 1.75–2.40 (13H, m), 2.75–3.05 (4H, m), 3.12 (1H, m), 3.23–3.45 (3H, m), 4.94 (1H, m), 7.23–7.46 (5H, m)

LRMS: m/z 345.0 (MH$^+$)

Preparation 116

1-Benzyl-4-(4H-1,2,4-triazol-4-yl)piperidine

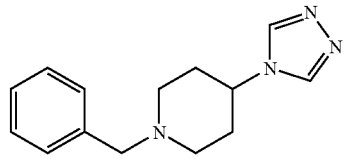

1-Benzyl-4-piperidinamine (617 mg, 3.25 mmol) was added to a solution of N'-[(E)-(dimethylamino)methylidene]-N,N-dimethylhydrazonoformamide (550 mg, 3.90 mmol) [J. Am. Chem. Soc, (1995), 117(22), 5951] and p-toluenesulphonic acid (62 mg, 0.33 mmol) in toluene (30 ml). The reaction mixture was stirred for 24 hours at room temperature and the solvent evaporated under reduced pressure. The residue was purified by column chromatography on silica gel using dichloromethane:methanol:0.88 ammonia (95:5:0.5) as eluant to afford the title compound as a white solid, 560 mg.

$^1$H-NMR (300 MHz, CDCl$_3$): δ [ppm] 1.92–2.21 (6H, m), 3.03 (2H, d), 3.55 (2H, s), 4.04 (1H, m), 7.13–7.36 (5H, m), 8.21 (2H, s)

Preparation 117

1-Benzyl-4-(3,5-dimethyl-4H-1,2,4-triazol-4-yl)piperidine

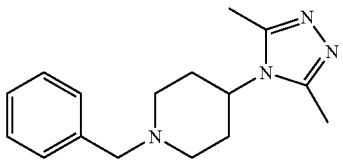

Lawessons reagent (11.69 g, 28.9 mmol) was added to a solution of N-(1-benzyl-4-piperidinyl)acetamide (6.1 g, 26.3 mmol) [J. Med. Chem, (1996), 39(19), 3769] in tetrahydrofuran (100 ml). The reaction mixture was stirred at room temperature for 18 hours, and then evaporated under reduced pressure. The residue was purified by column chromatography on silica gel using dichloromethane:methanol:0.88 ammonia (93:7:0.3) as eluant, to give a yellow oil, 2.8 g.

Acetylhydrazide (919 mg, 12.4 mmol) was added to a solution of the intermediate thioamide and mercuric oxide (2.44 g, 11.3 mmol) in butanol (50 ml). The reaction mixture was heated under reflux for 24 hours and then cooled and filtered through Arbocel®. The filtrate was evaporated under reduced pressure and the crude product was purified by column chromatography on silica gel using dichloromethane:methanol:0.88 ammonia (95:5:0.5) as eluant, to afford the title compound, 1.80 g.

LRMS: m/z 271 (MH$^+$)

Preparations 118 to 119

The compounds of the following tabulated preparations:

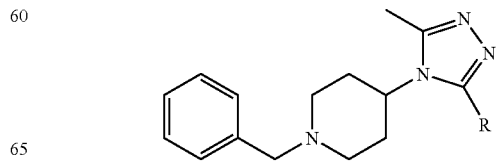

were prepared from the corresponding hydrazides, using similar methods to that described in preparation 117.

| PREPA-RATION | R | YIELD | DATA |
|---|---|---|---|
| 118 | *–CH2–C6H5 | 38% | $^1$H NMR(300MHz, CDCl$_3$): δ[ppm] 1.78(2H, t), 1.95(1H, dd), 2.00(1H, dd), 2.08(2H, m), 2.50(3H, s), 2.81(2H, d), 3.41(2H, s), 3.78(1H, m), 4.18(2H, s), 7.15–7.39(10H, m) LRMS: m/z 348(MH$^+$) |
| 119 | *–C6H5 | 29% | $^1$H NMR(300MHz, CDCl$_3$): δ[ppm] 1.78(2H, d), 1.95(2H, t), 2.20(2H, m), 2.63(3H, s), 2.93(2H, d), 3.48(2H, s), 4.18(1H, m), 7.20(5H, m), 7.40(4H, m), 7.75(1H, d) LRMS: m/z 333(MH$^+$) |

Preparation 120

4-(3-Methyl-5-phenyl-4H-1,2,4-triazol-4-yl)piperidine

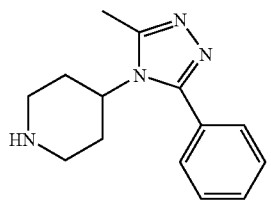

The title compound of preparation 119 (1.00 g, 3.00 mmol) was dissolved in ethanol (30 ml) and 20% w/w palladium hydroxide on carbon (500 mg) and ammonium formate (0.95 g, 15.0 mmol) added. The reaction was heated under reflux for 1 hour, cooled and filtered through a plug of Arbocel®. The filtrate was concentrated under reduced pressure and the crude product was purified by column chromatography on silica gel using dichloromethane:methanol:0.88 ammonia (80:20:1) as eluant to afford the title compound as a pale yellow oil, 400 mg.

$^1$H NMR (300 MHz, CDCl$_3$): δ [ppm] 1.78 (2H, d), 2.10 (1H, dd), 2.18 (1H, dd), 2.60 (2H, m), 2.63 (3H, s), 3.20 (2H, d), 4.10 (1H, m), 7.50 (5H, m)

LRMS: m/z 243 (MH$^+$)

Preparation 121

4-(3-Benzyl-5-methyl-4H-1,2,4-triazol-4-yl)piperidine

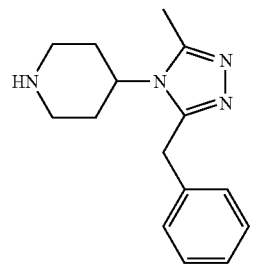

Obtained from the title compound of preparation 118 as an oil in 66% yield using a similar procedure to that in preparation 120.

$^1$H NMR (400 MHz, CDCl$_3$): δ [ppm] 1.20–1.23 (1H, m), 1.35–1.41 (1H, m), 1.80–2.00 (4H, m), 2.38–2.48 (1H, m), 2.51 (2H, s), 3.02–3.10 (1H, m), 3.46 (3H, m), 3.60–3.72 (1H, m), 4.20 (1H, s), 7.15–7.35 (5H, m)

LRMS: m/z 257.2 (MH$^+$)

Preparation 122

1-Benzyl-N-[(E)-(dimethylamino)methylidene]4-piperidinecarboxamide

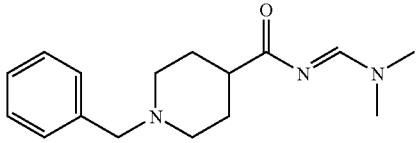

A mixture of N-benzyl-4-piperidinecarboxamide (2.49 g, 11.4 mmol) [J.A.C.S. (1977), 99(6), 1858] and dimethylformamide dimethylacetal (10 ml) was heated to 170° C., allowing continuous removal of solvent, and the mixture stirred for 10 minutes. The reaction was then cooled to 120° C. and stirred for 90 minutes, followed by a further 18 hours at room temperature. The resulting crystals were filtered off and washed with pentane to afford the title compound as a white crystalline solid, 1.75 g.

$^1$H-NMR (300 MHz, CDCl$_3$): δ [ppm]1.55 (2H, m), 1.75 (2H, d), 1.93 (2H, t), 2.16 (1H, m), 2.74 (2H, d), 2.94 (3H, s), 3.08 (3H, s), 3.40 (2H, s), 7.20–7.32 (5H, m), 8.33 (1H, s)

LRMS: m/z 274 (MH$^+$)

Preparation 123

1-Benzyl-4(1-methyl-1H-1,2,4-triazol-5-yl)piperidine

Preparation 124

1-Benzyl-4-(1-methyl-1H-1,2,4-triazol-3-yl)piperidine

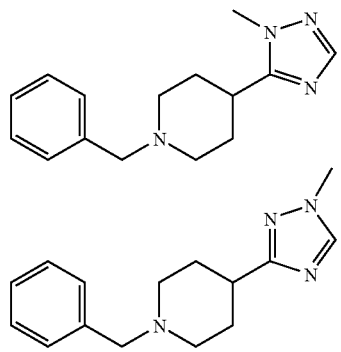

The title compound from preparation 122 (1.89 g, 6.91 mmol) was added to a solution of methyl hydrazine (0.4 ml, 7.60 mmol) in acetic acid (20 ml). The reaction mixture was heated to 92° C. for 4 hours and the solvent was evaporated under reduced pressure. The residue was basified using sodium hydrogen carbonate and the product extracted with ethyl acetate (×4). The combined organic extracts were washed with brine, dried (MgSO$_4$), filtered and evaporated under reduced pressure to afford the title compounds as an oil, 2.74 g.

$^1$H-NMR (300 MHz, CDCl$_3$): δ [ppm] 1.81–2.26 (6H, m), 2.88–3.06 (3H, m), 3.50–3.65 (2H, d), 3.85 (2H, d), 7.21–7.40 (5H, m), 7.79–7.92 (2H, 2xs)

LRMS: m/z 274 (MH$^+$)

Preparation 125 tert-Butyl 4-(aminocarbonyl)-1-piperidinecarboxylate

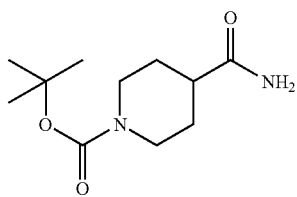

Ethyl chloroformate (4.6 ml, 48.3 mmol) was added slowly to a solution of 1-(tert-butoxycarbonyl)$_4$-piperidinecarboxylic acid (10 g, 43.6 mmol) in dichloromethane (100 ml) stirred at 0° C. Triethylamine (7.6 ml, 52.3 mmol) was added with stirring over two minutes. 0.88 Ammonia solution (40 ml) was added and the mixture allowed to warm to room temperature with stirring. The mixture was washed with water, 1M citric acid solution and brine, dried (MgSO$_4$), filtered and evaporated under reduced pressure gave the title compound as white solid, 8.94 g.

$^1$H NMR (300 MHz, CDCl$_3$): δ [ppm] 1.43 (9H, m), 1.64 (2H, m), 1.83 (2H, m), 2.30 (1H, m), 2.78 (2H, t), 4.16 (2H, d), 5.4 (2H, bs)

LRMS: m/z 251 (MNa$^+$)

Preparation 126 tert-Butyl 4-[ethoxy(imino)methyl]-1-piperidinecarboxylate

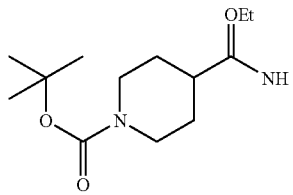

A solution of the title compound of preparation 125 (2.80 g, 12.2 mmol) in dichloromethane (30 ml) was added slowly to triethyloxonium hexafluorophosphate (3.30 g, 13.3 mmol) in dichloromethane (20 ml) at room temperature and the resultant mixture stirred at room temperature overnight. The mixture was basified with sodium hydrogen carbonate solution and then extracted with dichloromethane (×2). The combined organic solutions were dried (MgSO$_4$), filtered and evaporated under reduced pressure to afford the title compound as a thick yellow oil, 2.90 g.

$^1$H NMR (400 MHz, CDCl$_3$): δ [ppm] 1.26 (3H, m), 1.43 (9H, s), 1.64 (2H, d), 2.31 (1H, m), 2.75 (4H, m), 4.10 (4H, m)

LRMS: m/z 257 (MH$^+$)

Preparation 127 tert-Butyl-4-(5-benzyl-1H-1,2,4-triazol-3-yl)-1-piperidinecarboxylate

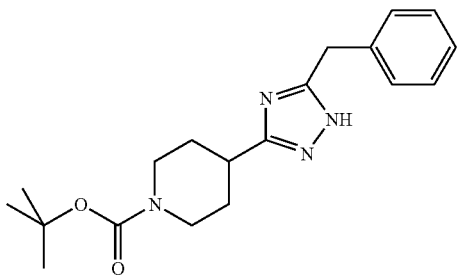

Phenylacetyl chloride (2.26 ml, 17.0 mmol) was added to a solution of the title compound of preparation 126 (4.00 g, 15.6 mmol) and triethylamine (2.5 ml, 1.60 mmol) in toluene (26 ml) and stirred at room temperature for 90 minutes. Hydrazine hydrate (0.91 ml, 19.0 mmol) was added and the reaction mixture stirred at room temperature for 15 hours. The mixture was acidified by addition of 1M citric acid solution and extracted with ethyl acetate (×3). The combined organic solutions were washed with brine, dried (MgSO$_4$), filtered and evaporated under reduced pressure. The residue was purified by column chromatography on silica gel using dichloromethane:methanol (99:1) as eluant to afford the title compound, 1.70 g.

¹H NMR (400 MHz, CDCl₃): δ [ppm] 1.34 (9H, s), 1.75 (2H, m), 2.00 (2H, d), 2.90 (3H, m), 4.12 (4H, m), 7.30 (5H, m)

LRMS: m/z 343 (MH⁺)

Preparation 128 tert-Butyl 4-(5-benzyl-1-methyl-1H-1,2,4-triazol-3-yl)-1-piperidinecarboxylate

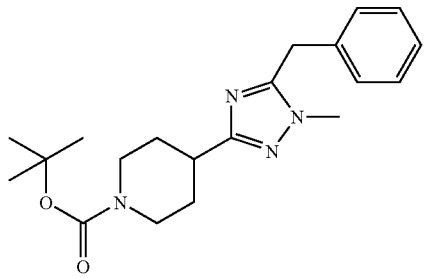

A solution of the title compound of preparation 126 (2.90 g, 11.3 mmol) and triethylamine (1.7 ml, 12.3 mmol) in toluene (20 ml) was treated with phenylacetyl chloride (1.6 ml, 12.1 mmol) and stirred at room temperature for 1 hour. Methyl hydrazine (0.66 ml, 12.5 mmol) was added dropwise and the mixture stirred at room temperature for 5 hours. The mixture was acidified by addition of 1M citric acid solution and extracted with ethyl acetate (×3). The combined organic solutions were washed with brine, dried (MgSO₄), filtered and concentrated under reduced pressure to give a yellow oil. Purification of this residue by column chromatography on silica gel using dichloromethane: methanol (99:1) as eluant afforded the title compound, 1.10 g.

¹H NMR (400 MHz, CDCl₃): δ [ppm] 1.41 (9H, s), 1.72–1.85 (2H, m), 2.00 (2H, m), 2.83 (3H, m), 3.62 (3H, s), 4.10 (2H, s), 4.15 (2H, m), 7.15 (2H, d), 7.24–7.35 (3H, m)

LRMS: m/z 357 (MH⁺)

Preparation 129

4-(5-Benzyl-1H-1,2,4-triazol-3-yl)piperidine trifluoroacetate

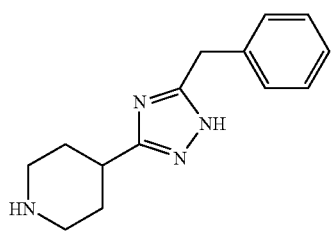

A solution of the title compound of preparation 127 (530 mg, 1.50 mmol) in dichloromethane (5 ml) at 0° C. was treated with trifluoroacetic acid (1 ml) and stirred at room temperature for 3 hours. The mixture was concentrated under reduced pressure, toluene (20 ml) added and removed under reduced pressure to afford the title compound as a yellow oil, 1.09 g.

¹H NMR (400 MHz, CD₃OD): δ [ppm] 2.03 (2H, m), 2.25 (2H, m), 3.20 (3H, m), 3.50 (2H, m), 4.20 (2H, m), 7.30 (5H, m)

LRMS: m/z 243 (MH⁺)

Preparation 130

4-(5-Benzyl-1-methyl-1H-1,2,4-triazol-3-yl)-1-piperidine

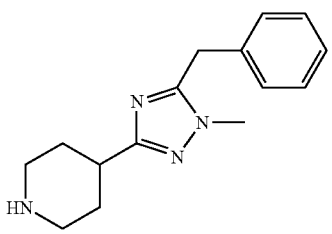

Obtained from the title compound of preparation 128 as an oil in 46% yield using a similar procedure to that in preparation 81.

¹H NMR (400 MHz, CDCl₃): δ [ppm] 1.72–1.85 (2H, m), 2.05 (2H, m), 2.76 (2H, t), 2.83 (1H, m), 3.17 (2H, m), 3.60 (3H, s), 4.05 (2H, s), 7.15 (2H, d), 7.21–7.35 (3H, m)

LRMS: m/z 258 (MH⁺)

Preparation 131

Benzyl 4-[2-(tert-butoxycarbonyl)hydrazino]-1-piperidinecarboxylate

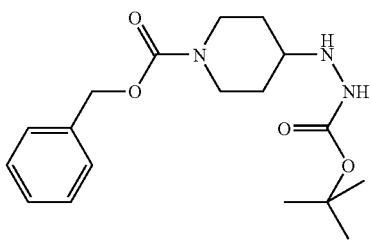

Benzyl 4-oxo-1-piperidinecarboxylate (10.0 g, 42.9 mmol), tert-butyl-1-hydrazinecarboxylate (5.70 g, 42.9 mmol) and sodium triacetoxyborohydride (13.6 g, 64.1 mmol) were stirred together for 4 hours at room temperature in dichloromethane/acetic acid (40 ml, 10% solution). The solvents were evaporated under reduced pressure. The residue was basified with saturated sodium carbonate solution and extracted with ethyl acetate. The combined organic solutions were dried (MgSO₄), filtered and evaporated under reduced pressure to yield the title compound as a colourless gum, 14.2 g.

¹H NMR (400 MHz, CDCl₃): δ [ppm] 1.23–1.39 (2H, m), 1.45 (9H, s), 1.71–1.87 (2H, m), 2.89–3.08 (3H, m), 3.61–3.69 (1H, m), 3.87–3.97 (1H, m), 3.97–4.10 (2H, m), 5.68–5.81 (1H, bs), 5.94–6.06 (1H, bs), 7.26–7.39 (5H, m)

LRMS: m/z 350.0 (MH⁺)

Preparation 132

Benzyl 4-hydrazino-1-piperidinecarboxylate

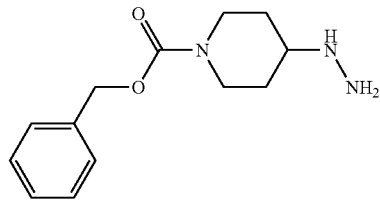

The title compound of preparation 131 (1.00 g, 37.8 mmol) in dichloromethane (250 ml) was stirred at 0° C. while trifluoroacetic acid (30 ml, 390 mmol) was added. The mixture was stirred for 16 hours and allowed to warm to room temperature. The solvents were removed under reduced pressure. The residue was basified with saturated sodium carbonate solution and extracted with dichloromethane (×4). The combined organic solutions were dried (MgSO$_4$), filtered and evaporated under reduced pressure. The residue was purified by column chromatography on silica gel using an eluant of dichloromethane:methanol:0.88 ammonia (95:5:0.5) to afford the title compound as a colourless gum, 4.25 g.

$^1$H NMR (400 MHz, CDCl$_3$): δ [ppm] 1.23–1.35 (2H, m), 1.81–1.94 (2H, m), 2.61–2.71 (1H, m), 2.86–3.00 (2H, m), 4.00–4.24 (2H, m), 5.11 (2H, s), 7.26–7.37 (5H, m)

LRMS: m/z 250.1 (MH$^+$)

Preparation 133

Benzyl 4-(3-benzyl-1H-1,2,4-triazol-1-yl)-1-piperidinecarboxylate

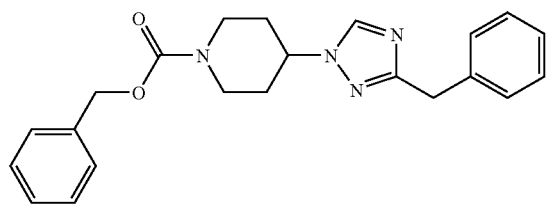

Phenylacetimidate (2.0 g, 10.8 mmol) and the title compound OT preparation 132 (3.1 g, 10.8 mmol) were stirred in dichloromethane (100 ml) at room temperature for 1 hour. The solvent was removed under reduced pressure and the residue was heated under reflux for 2 hours in triethyl orthoformate (50 ml). The solvent was removed under reduced pressure. The residue was dissolved in ethyl acetate and washed with water (×2). The organic layer was dried (MgSO$_4$), filtered and evaporated under reduced pressure to give an oil which quickly crystallised on standing. The residue was purified by recrystallization from ethyl acetate to afford the title compound as a white solid, 1.73 g.

$^1$H NMR (400 MHz, CD$_3$OD): δ [ppm] 1.87–2.00 (2H, m), 2.03–2.16 (2H, m), 2.94–3.15 (2H, m), 4.00 (2H, s), 4.20–4.29 (2H, m), 4.40–4.50 (1H, m), 5.13 (2H, s), 7.13–7.19 (1H, m), 7.19–7.40 (9H, m)

LRMS: m/z 377.2 (MH$^+$)

Preparation 134

4-(3-Benzyl-1H-1,2,4-triazol-1-yl)piperidine

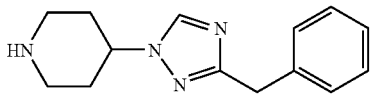

Obtained from the title compound of preparation 133 as an oil in 88% yield using a similar procedure to that in preparation 120.

$^1$H NMR (400 MHz, CDCl$_3$): δ [ppm] 1.68–1.94 (2H, m), 2.10–2.20 (2H, m), 2.71–2.81 (2H, m), 3.20–3.29 (2H, m), 4.06 (2H, s), 4.16–4.26 (1H, m), 7.16–7.23 (1H, m), 7.23–7.35 (4H, m), 7.97 (1H, s)

Preparation 135

Methyl 4-(2-imino-2-methoxyethyl)benzoate

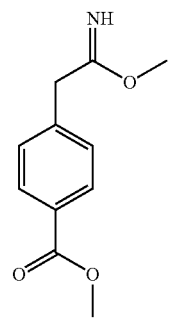

To a solution of methyl 4-(bromomethyl)benzoate (5.00 g, 21.8 mmol) and acetone cyanohydrin (3 ml, 32.7 mmol) stirring at room temperature in acetonitrile (200 ml) was added 1,1,3,3-tetramethylguanidine (5.8 ml, 45.8 mmol) and the mixture stirred for 16 hours. The solvent was removed under reduced pressure. The residue was triturated with diethyl ether (×3), filtered and the filtrate evaporated under reduced pressure. The residue was purified by filtering through a pad of silica, eluting with diethyl ether to afford a colorless oil, 4.0 g. The oil was dissolved in 200 ml of diethyl ether and gaseous hydrogen chloride was bubbled though the solution until saturated while stirring at 0° C. Methanol (1.5 ml, 37.2 mmol) was added and the mixture stirred for 1 hour. The solvents were removed under reduced pressure and the residue was basified using saturated sodium carbonate solution and extracted with dichloromethane (×3). The combined organic solutions were dried (MgSO$_4$), filtered and evaporated under reduced pressure to afford the title compound as a colourless oil, 4.20 g.

$^1$H NMR (400 MHz, CDCl$_3$): δ [ppm] 3.60 (2H, s), 3.74 (3H, s), 3.92 (3H, s), 7.26–7.32 (2H, d), 8.00–8.06 (2H, d)

LRMS: m/z 208.1 (MH$^+$)

Preparation 136

Sodium 4-{[1-(1-{(3S)-3-[(tert-butoxycarbonyl)amino]-3-phenylpropyl}-4-piperidinyl)-1H-1,2,4-triazol-3-yl]methyl}benzoate

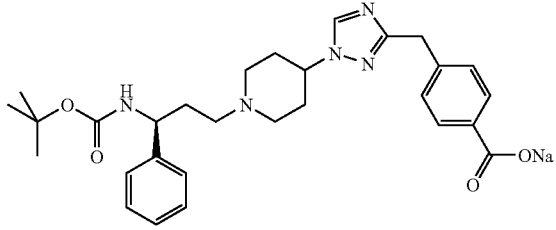

The title compound of preparation 132 (3.50 g, 14.04 mmol) and the title compound of preparation 135 (2.90 g, 14.04 mmol) were stirred together for 1 hour at room temperature methanol (50 ml). The solvent was removed under reduced pressure. The residue was dissolved in triethylorthoformate (50 ml) and heated under reflux for 3 hours. The solvent was removed under reduced pressure and the residue purified by column chromatography on silica gel using an eluant of dichloromethane:methanol:0.88 ammonia (95:5:0.5). The residue (4.00 g, 9.18 mmol), ammonium formate (4.00 g, 82.49 mmol) and 20% w/w palladium hydroxide on carbon (400 mg) were heated under reflux for 30 minutes in ethanol (100 ml). The mixture was filtered through Arbocel® and the filtrate evaporated under reduced pressure.

The residue (2.50 g, 8.32 mmol), the title compound of preparation 7 (2.00 g, 8.32 mmol) and sodium triacetoxyborohydride (2.50 g, 12.48 mmol) were stirred at room temperature for 1 hour in dichloromethane:acetic acid (30 ml, 10%). The solvents were evaporated under reduced pressure and the residue was basified with saturated sodium carbonate solution and extracted with dichloromethane (×3). The combined organic solutions were dried (MgSO$_4$), filtered and evaporated under reduced pressure. The residue was purified by column chromatography on silica gel using dichloromethane:methanol:0.88 ammonia (98:2:0.25) as eluant to give a foam, 2.50 g. The residue (1.00 g, 1.87 mmol) and sodium hydroxide (150 mg, 3.74 mmol) was stirred for 2 hours at 50° C. in a mixture of dioxane:water (5:1). The solvents were removed under reduced pressure to afford a white solid, 993 mg.

LRMS: m/z 520.1 (MH$^+$)

Preparation 137

N-{4-[(1-{1-[1-(Benzyloxy)vinyl]-4-piperidinyl}-1H-1,2,4-triazol-3-yl)methyl]phenyl}methanesulphonamide

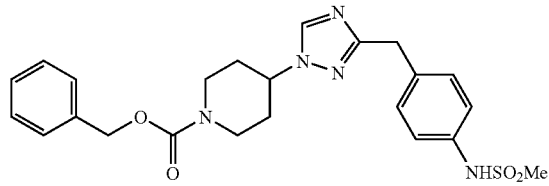

The title compound of preparation 131 (1.90 g, 9.04 mmol) was stirred at room temperature in diethyl ether methanol (100 ml, 4:1) while hydrogen chloride gas was bubbled through the solution until saturated. The mixture was stirred for 16 hours and the solvents were removed under reduced pressure. The residue was basified with saturated sodium carbonate solution and extracted with dichloromethane (×3). The combined organic solutions were dried (MgSO$_4$), filtered and evaporated under reduced pressure.

In a separate flask the title compound of preparation 47 (1.00 g, 4.76 mmol) was dissolved in 20 ml of diethyl ether and gaseous hydrogen chloride was bubbled though the solution until saturated while stirring at 0° C. Methanol (1.5 ml, 37.2 mmol) was added and the mixture stirred for 1 hour. The solvents were removed under reduced pressure and the residue was basified using saturated sodium carbonate solution and extracted with dichloromethane (×3). The combined organic solutions were dried (MgSO$_4$), filtered and evaporated under reduced pressure. The crude hydrazine (595 mg, 2.46 mmol) and the intermediate amidoxime (600 mg, 2.41 mmol) were stirred together at room temperature for 3 hours in 40 ml of methanol. The solvent was removed under reduced pressure. The residue was dissolved in triethyl orthoacetate (30 ml) and heated under reflux for 30 minutes. The solvent was removed under reduced pressure. The residue was purified by column chromatography on silica gel using dichloromethane:methanol:0.88 ammonia (95:5:0.5) as eluant to afford the title compound as a foam, 560 mg.

$^1$H NMR (400 MHz, CD$_3$OD): δ [ppm] 1.68–2.00 (2H, m), 2.05–2.15 (2H, m), 2.90 (3H, s), 2.97–3.11 (2H, m), 3.99 (2H, s), 4.21–4.31 (2H, m), 4.40 4.50 (1H, m), 5.15 (2H, s), 7.11–7.16 (2H, d), 7.16–7.26 (2H, d), 7.30–7.39 (4H, m), 8.35 (1H, s)

LRMS: m/z 492.1 (MNH$_4^+$)

Preparation 138 tert-Butyl-(1S)-3-[4-(3-{4-[(methylsulphonyl)amino]benzyl}-1H-1,2,4-triazol-1-yl)-1-piperidinyl]-1-phenylpropylcarbamate

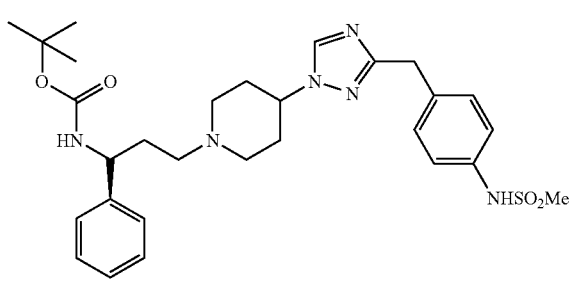

The title compound of preparation 137 (500 mg, 1.06 mmol), ammonium formate (500 mg, 7.93 mmol) and 20% w/w palladium hydroxide on carbon (50 mg) were heated under reflux in ethanol (20 ml) until gas evolution ceased. The mixture was filtered through Arbocel® and the filtrate evaporated under reduced pressure. The residue was purified by column chromatography on silica gel using gradient elution of dichloromethane:methanol:0.88 ammonia (90:10:1 to 80:20:4). The residue (300 mg, 0.89 mmol) and the title compound of preparation 7 (222 mg, 0.88 mmol) and sodium triacetoxyborohydride (285 mg, 1.34 mmol) were stirred together at room temperature for 30 minutes in a mixture of dichloromethane:acetic acid (30 ml, 10%). The solvents were removed under reduced pressure and the residue was basified with saturated sodium carbonate solution and extracted with ethyl acetate (3×). The combined organic solutions were dried (MgSO₄), filtered and evaporated under reduced pressure to afford the title compound as a white solid, 407 mg.

¹H NMR (400 MHz, CDCl₃): δ [ppm] 1.31–1.48 (9H, m), 1.48–1.60 (2H, m), 1.77–1.90 (1H, m), 1.90–2.23 (4H, m), 2.26–2.44 (2H, m), 2.95 (3H, s), 3.02–3.10 (1H, m), 3.66–3.74 (1H, m), 4.03 (2H, s), 4.06–4.16 (1H, m), 4.74–5.02 (2H, m), 6.16–6.26 (1H, m), 6.35–6.44 (1H, m), 7.10–7.15 (2H, d), 7.19–7.37 (7H, m), 7.00 (1H, s)

Preparation 139

Benzyl 4-(3-benzyl-5-methyl-1H-1,2,4-triazol-1-yl)-1-piperidinecarboxylate

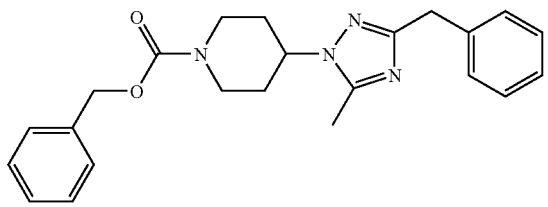

Hydrogen chloride gas was bubbled through a solution of the title compound of preparation 131 (3.00 g, 8.59 mmol) in methanol (50 ml), at 0° C., for 1 hour. The solvent was removed under reduced pressure and the residue dissolved in dichloromethane (50 ml) and triethylamine (2.51 ml, 18.00 mmol) and phenylacetimidate hydrochloride (1.59 g, 8.59 mmol) added. The reaction was stirred at room temperature for 1 hour and the solvent removed under reduced pressure, the residue was dissolved in triethyl orthoacetate (20 ml) and heated under reflux for 12 hours. The reaction was cooled, the solvent removed under reduced pressure and the resulting brown oil was purified by column chromatography on silica gel using dichloromethane:methanol:0.88 ammonia (95:5:0.5) as eluant to afford the title compound as a pale yellow oil, 2.20 g.

¹H NMR (300 MHz, CDCl₃): δ [ppm] 1.83 (2H, d), 2.08 (1H, dd), 2.20 (1H, dd), 2.40 (3H, s), 2.85 (2H, m), 3.95 (2H, s), 4.10 (1H, m), 4.38 (2H, m), 5.18 (2H, m), 7.05–7.39 (10H, m)

LRMS: m/z 391 (MH⁺)

Preparation 140

4-(3-Benzyl-5-methyl-1H-1,2,4-triazol-1-yl)piperidine

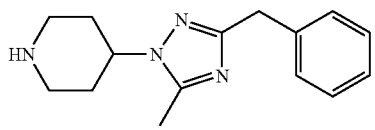

Obtained from the title compound of preparation 139 as an oil in 100% yield using a similar procedure to that in preparation 120.

¹H NMR (300 MHz, CDCl₃): δ [ppm] 2.03–2.38 (4H, m), 2.41 (3H, s), 3.01 (2H, m), 3.43 (2H, m), 4.01 (2H, s), 4.23 (1H, m), 7.18 (5H, m), 8.43 (1H, s)

LRMS: m/z 257 (MH⁺)

Preparation 141 tert-Butyl (1S)-3-[4-(3-benzyl-5-methyl-1H-1,2,4-triazol-yl)-1-piperidinyl-1-phenylpropylcarbamate

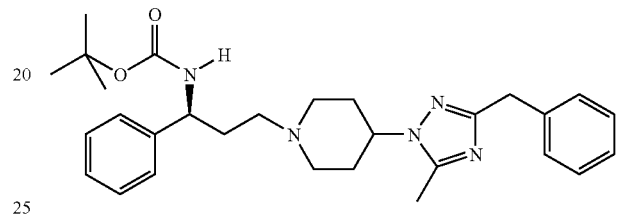

Obtained from the title compounds of preparations 7 and 140 as an oil in 59% yield using a similar procedure to that in preparation 80.

¹H NMR (400 MHz, CDCl₃): δ [ppm] 1.41 (9H, s), 1.85 (4H, m), 2.05 (4H, m), 2.38 (4H, m), 2.41 (3H, s), 2.98 (1H, d), 3.14 (1H, d), 4.00 (2H, s), 4.81 (1H, s), 7.28 (10H, m)

LRMS: m/z 491 (MH⁺)

Preparation 142

(1S)-3-[4-(3-Benzyl-5-methyl-1H-1,2,4-triazol-1-yl)-1-piperidinyl]-1-phenyl-1-propanamine

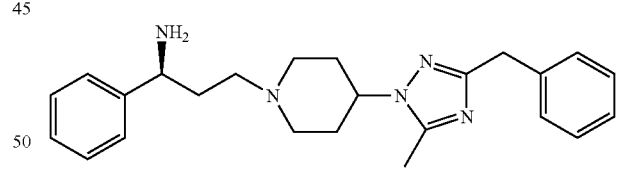

The title compound of preparation 141 (1.70 g, 3.50 mmol) was dissolved in methanolic hydrochloric acid (30 ml, 2.5M) and stirred at room temperature for 2 hours. The solvent was removed under reduced pressure and saturated sodium carbonate added. The aqueous was extracted with dichloromethane (3×), the combined organic solutions were dried (MgSO₄), filtered and the solvent removed under reduced pressure to afford the title compound as a clear oil, 1.40 g.

¹H NMR (300 MHz, CDCl₃): δ [ppm] 1.68–1.91 (6H, m), 1.98–2.18 (3H, m), 2.21 (2H, m), 2.38 (4H, m), 3.13 (2H, m), 3.89–4.03 (4H, m), 7.18–7.41 (10H, m)

LRMS: m/z 390 (MH⁺)

Preparation 143

N-{(1S)-3-[4-(3-Benzyl-5-methyl-1H-1,2,4-triazol-1-yl)-1-piperidinyl]-1-phenylpropyl}-3-azetidinecarboxamide

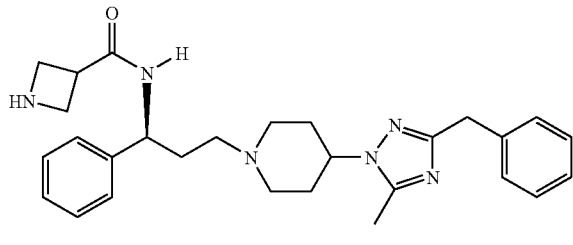

1-(3-Dimethylaminopropyl)-3-ethyl-carbodiimide hydrochloride (177 mg, 0.93 mmol) was added to a stirred solution of the title compound of preparation 13 (186 mg, 0.93 mmol) and the title compound of preparation 142 (300 mg, 0.76 mmol) in dichloromethane (20 ml). After 1 hour trifluoroacetic acid (5 ml) was added and the reaction stirred for 12 hours. The solvent was removed under reduced pressure and the resulting oil was loaded directly onto a column of silica and eluted with dichloromethane:methanol:0.88 ammonia (95:5:0.5) to afford the title compound as a white foam, 200 mg.

$^1$H NMR (300 MHz, CDCl$_3$): δ [ppm] 1.78–2.40 (15H, m), 2.96 (1H, d), 3.12 (1H, d), 3.39 (2H, m), 3.66–4.02 (6H, m), 5.06 (1H, dd), 7.08–7.19 (9H, m), 8.03 (1H, d)

LRMS: m/z 473 (MH$^+$)

Preparation 144

1-Benzyl N-methyl-4-piperidinecarboxamide

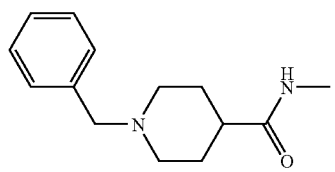

N-Benzyl 4-piperidinecarboxylic acid (5.00 g, 22.8 mmol), 1-(3-dimethylaminopropyl)-3-ethyl-carbodiimide hydrochloride (5.25 g, 27.4 mmol) and 1-hydroxybenzotriazole hydrate (3.84 g, 25.1 mmol) were added to a solution of methylamine (11.4 ml of a 2.0M solution in tetrahydrofuran, 22.8 mmol) in dichloromethane (100 ml). The mixture was stirred for 1 hour at room temperature, then partitioned between dichloromethane and water. The organic layer was separated and washed with brine, dried (MgSO$_4$), filtered and evaporated under reduced pressure to furnish a pale yellow solid, 3.50 g.

$^1$H NMR (300 MHz, CDCl$_3$): δ [ppm] 1.78 (3H, m), 2.05 (3H, m), 2.79 (3H, d), 2.98 (3H, m), 3.50 (2H, s), 7.21 (m, 5H)

LRMS: m/z 233 (MH$^+$)

Preparation 145

1-Benzyl-4-(5-benzyl-4-methyl-4H-1,2,4-triazol-3-yl)piperidine

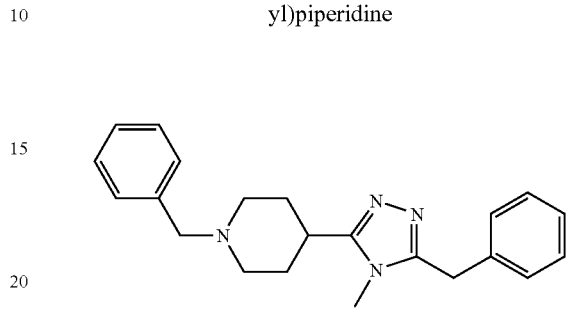

Lawesson's reagent (6.76 g, 16.7 mmol) was added in one portion to a solution of the title compound of preparation 144 (3.50 g, 15.2 mmol) in toluene (100 ml) and the mixture stirred at room temperature overnight. The reaction mixture was filtered through a short plug of silica gel washing with dichloromethane (100 ml) and the solvent removed under reduced pressure to furnish a yellow foam, 5.00 g. The foam was dissolved in n-butanol (100 ml) and mercury(II)oxide (4.81 g, 22.2 mmol) and phenylacetic hydrazide (3.02 g, 20.2 mmol) added. The reaction was heated under reflux for 12 hours, cooled, filtered through a plug of Arbocel® and the solvent removed under reduced pressure. The crude product was purified by column chromatography on silica gel using dichloromethane:methanol:0.88 ammonia (95:5:0.5) as eluant to afford the title compound as a pale yellow oil, 0.85 g.

$^1$H NMR (300 MHz, CDCl$_3$): δ [ppm] 1.60–2.20 (6H, m), 2.80–3.00 (3H, m), 3.28 (3H, s), 3.58 (2H, m), 4.19 (2H, m), 7.19–7.40 (10H, m)

LRMS: m/z 347 (MH$^+$)

Preparation 146

4-(5-Benzyl-4-methyl-4H-1,2,4-triazol-3-yl)piperidine

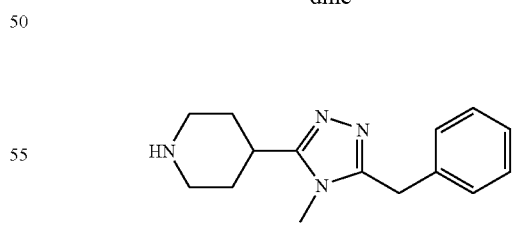

Obtained from the title compound of preparation 145 as an oil in 41% yield using a similar procedure to that in preparation 120.

$^1$H NMR (300 MHz, CDCl$_3$): δ [ppm] 1.95 (4H, m), 2.20–2.60 (4H, br m), 2.80 (3H, m), 3.31 (2H, m), 4.20 (2H, s), 7.10–7.40 (5H, m)

LRMS: m/z 257 (MH$^+$)

Preparation 147

{1-Benzyl-4-[3-(4-fluorobenzyl)-1,2,4-oxadiazol-5-yl]-4-piperidinyl}methanol

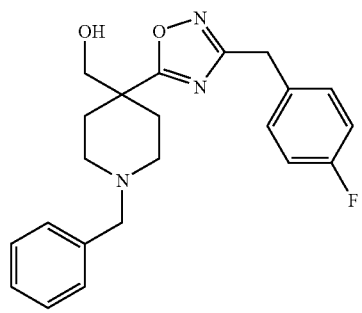

Sodium borohydride (160 mg, 4.20 mmol) was added to a stirred solution of the title compound of preparation 102 (1.35 g, 3.53 mmol) in methanol (15 ml) and the reactants stirred at ambient temperature for 2 hours. The methanol was evaporated under reduced pressure and the residue partitioned between dichloromethane and water. The organic extract was separated, concentrated under reduced pressure and the residue purified by column chromatography on silica gel using dichloromethane:methanol:0.88 ammonia (90:10:1) as eluant, to afford the title compound as an oil, 860 mg.

$^1$H NMR (300 MHz, CDCl$_3$): δ (ppm) 1.79 (2H, m), 2.23 (4H, m), 2.65 (2H, m), 3.46 (2H, s), 3.74 (2H, s), 4.05 (2H, s), 7.02 (2H, m), 7.26 (7H, m)

LRMS m/z 382.4 (MH$^+$)

Preparation 148

1-Benzyl-4-[3-(4-fluorobenzyl)-1,2,4-oxadiazol-yl]-4-(methoxymethyl)piperidine

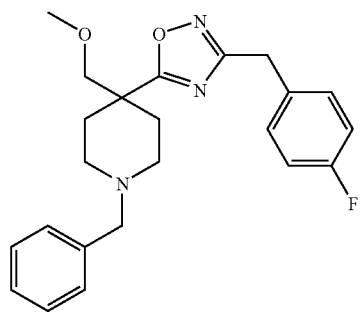

To a stirred solution of the title compound of preparation 147 (495 mg, 1.31 mmol) in dry acetonitrile (8 ml) was added potassium tert-butoxide (184 mg, 1.56 mmol) and methyl tosylate (296 mg, 1.56 mmol) and the solution stirred at ambient temperature for 5 days. The solution was partitioned between ethyl acetate and water. The organic layer was separated, concentrated under reduced pressure and purified by column chromatography on silica gel using methanol:dichloromethane (95:5) as eluant, to afford the title compound as an oil 270 mg.

$^1$H NMR (300 MHz, CDCl$_3$): δ [ppm] 1.82 (2H, m), 2.05 (2H, m), 2.50 (2H, m), 2.70 (2H, m), 3.22 (3H, s), 3.42 (2H, s), 3.52 (2H, s), 4.04 (2H, s), 7.02 (2H, m), 7.26 (7H, m)

LRMS m/z 396.5 (MH$^+$)

Preparation 149

4-[3-(4-Fluorobenzyl)-1,2,4-oxadiazol-5-yl]-4-(methoxymethyl)piperidine

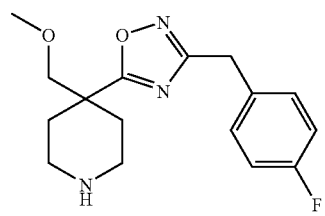

1-Chloroethyl chloroformate (0.96 ml, 0.87 mmol) was added to a solution of the title compound of preparation 148 (265 mg, 0.67 mmol) in dichloromethane (5 ml). The reaction mixture was stirred for 24 hours at ambient temperature, then concentrated under reduced pressure. The residual oil was dissolved in methanol (5 ml) and the reaction mixture heated under reflux for 2 hours. Silica gel was added to the cooled solution, which was concentrated under reduced pressure and purified by column chromatography on silica gel using dichloromethane:methanol:0.88 ammonia (95:5:0.5) as eluant, to afford the title compound as a gum, 160 mg.

$^1$H NMR (300 MHz, CDCl$_3$): δ [ppm] 2.01 (2H, m), 2.39 (2H, m), 2.81 (2H, m), 3.24 (5H, m), 3.53 (2H, s), 4.05 (2H, s), 7.02 (2H, m), 7.26 (2H, m)

LRMS m/z 306 (MH$^+$)

Preparation 150 tert-Butyl (1S)-3-[4-[3-(4-fluorobenzyl)-1,2,4-oxadiazol-5-yl]-4-(methoxymethyl)-1-piperidinyl]-1-phenylpropylcarbamate

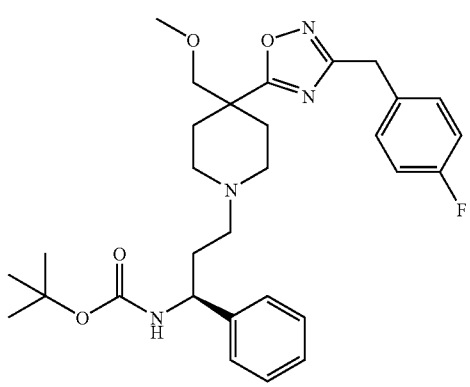

Obtained from the tide compounds of preparations 7 and 149 as an oil in 93% yield using a similar procedure to that in preparation 80.

¹H NMR (300 MHz, CDCl₃): δ [ppm] 1.28 (9H, s), 1.87 (6H, m), 2.28 (4H, m), 2.66 (1H, m), 2.78 (1H, m), 3.22 (3H, s), 3.49 (2H, s), 4.04 (2H, s), 4.77 (1H, m), 6.72 (1H, m), 6.98 (2H, t), 7.25 (7H, m)

LRMS: m/z 539.6 (MH⁺)

Preparation 151

(1S)-3-[4-[3-(4-Fluorobenzyl)-1,2,4-oxadiazol-5-yl]-4-(methoxymethyl)-1-piperidinyl]-1-phenyl-1-propanamine

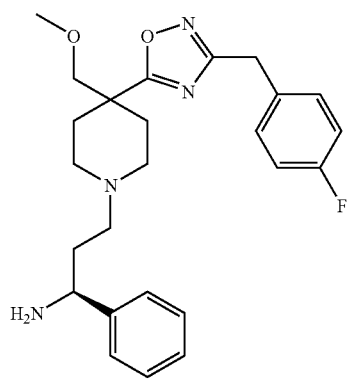

Obtained from the title compound of preparation 150 as an oil in 98% yield using a similar procedure to that in preparation 81.

LRMS: m/z 439.7 (MH⁺)

EXAMPLE 1

N-{(1S)-3-[4-(3-Benzyl-1,2,4-oxadiazol-5-yl)-1-piperidinyl]-1-phenylpropyl}cyclobutanecarboxamide

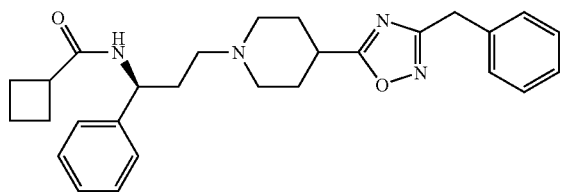

The title compounds of preparation 39 (200 mg, 0.82 mmol) and preparation 8 (285 mg, 1.23 mmol) were stirred together with sodium triacetoxyborohydride (209 mg, 0.98 mmol) in dichloromethane:acetic acid (10 ml, 10%) for 4 hours at room temperature. Saturated aqueous sodium bicarbonate solution was added and the product extracted with dichloromethane (3×). The combined organic layers were washed with water and brine, dried (MgSO₄), filtered and the solvent evaporated under reduced pressure. The product was purified by chromatography on silica gel using ethyl acetate:methanol (95:5) as eluant, then dissolved in diethyl ether saturated with hydrogen chloride gas. Evaporation to dryness provided the title compound as the hydrochloride salt, 60 mg.

Found C, 64.68; H, 7.26; N, 10.51%

C₂₈H₃₄N₄O₂; 1HCl; 1.4H₂O requires C, 64.64; H, 7.32; N, 10.77%

¹H NMR (400 MHz, CDCl₃): δ [ppm] 1.78–2.20 (13H, m), 2.20–2.40 (3H, m), 2.81–2.95 (2H, m), 2.95–3.00 (2H, m), 4.05 (2H, s), 5.10 (1H, m), 7.17–7.25 (2H, m), 7.25–7.35 (7H, m), 7.45–7.55 (1H, m)

LRMS: m/z 459 (MH⁺)

[α]_D: −45.6 (c=0.34, methanol)

EXAMPLE 2

N-{1-Phenyl-3-[4-(4H-1,2,4-triazol-4-yl)-1-piperidinyl]propyl}cyclobutanecarboxamide

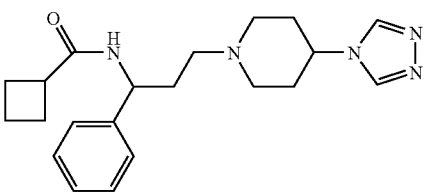

The title compound of preparation 116 (560 mg, 2.31 mmol) was dissolved in ethanol (20 ml) and 20% w/w palladium hydroxide on carbon (500 mg) and ammonium formate (728 mg, 11.5 mmol) added. The reaction was heated under reflux for 1 hour, cooled and filtered through a plug of Arbocel®. The filtrate was concentrated under reduced pressure and the resulting oil and the title compound of preparation 3 were used to prepare the title compound using a similar method to example 1. The reaction mixture was purified by column chromatography on silica gel using dichloromethane:methanol:0.88 ammonia (95:5:0.5) as eluant to afford the title compound as a white foam, 50 mg.

Found C, 66.90; H, 7.92; N, 18.68%

C₂₁H₂₉N₅O; 0.5H₂O; requires C, 66.64; H, 7.95; N, 19.06%

¹H-NMR (300 MHz, CDCl₃): δ [ppm] 1.82–2.45 (17H, m), 2.95–3.12 (3H, m), 4.05 (1H, m), 5.13 (1H, m), 7.21–7.40 (5H, m), 8.21 (2H, m)

LRMS: m/z 368 (MH⁺)

EXAMPLE 3–5

The compounds of the following tabulated examples with the general formula:

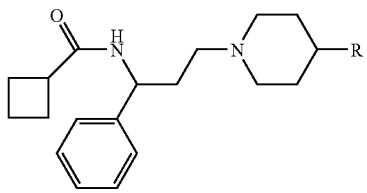

were prepared using a similar method to example 2 from the title compound of preparation 3 and the corresponding benzylamine.

| EXAMPLE | R | YIELD | DATA |
|---|---|---|---|
| 3[1] | *N-{3-[4-(1-Methyl-1H-1,2,4-triazol-5-yl)-1-piperidinyl]-1-phenylpropyl}cyclobutanecarboxamide | 9% | Found C, 52.96; H, 7.16; N, 13.01% $C_{22}H_{31}N_5O$; HCl; 1.1$CH_2Cl_2$; 0.8$H_2O$ requires C, 52.77; H, 6.86; N, 13.32% $^1$H-NMR(400MHz, CDCl$_3$): δ[ppm] 1.75–2.46(16H, m), 2.75(1H, m), 2.95–3.20(3H, m), 3.85(3H, s), 5.12(1H, m), 7.19–7.40(5H, m), 7.60(1H, d), 7.81(1H, s). LRMS: m/z 382(MH$^+$) |
| 4[1] | *N-{3-[4-(1-Methyl-1H-1,2,4-triazol-3-yl)-1-piperidinyl]-1-phenylpropyl}cyclobutanecarboxamide | 10% | Found C, 53.42; H, 7.10; N, 13.57% $C_{22}H_{31}N_5O$; HCl; $CH_2Cl_2$; 0.8$H_2O$ requires C, 53.40; H, 6.94; N, 13.54% $^1$H-NMR(400MHz, CDCl$_3$): δ[ppm] 1.76–2.43(16H, m), 2.79(1H, m), 2.88(1H, d), 3.08(2H, m), 3.83(3H, s), 5.48(1H, m), 7.15–7.35(5H, m), 7.92(1H, s), 8.06(1H, d) LRMS: m/z 382(MH$^+$) |
| 5 | *N-{3-[4-(3,5-Dimethyl-4H-1,2,4-triazol-4-yl)-1-piperidinyl]-1-phenylpropyl}cyclobutanecarboxamide | 4% | $^1$H-NMR(300MHz, CDCl$_3$): δ[ppm] 1.80–2.40(16H, m), 2.50(6H, s), 3.00(1H, t), 3.12(2H, d), 3.83(1H, m), 5.12(1H, m), 6.55(1H, d), 7.23–7.39(5H, m) |

[1] = Product obtained as the hydrochloride salt

EXAMPLE 6

N-{1-Phenyl-3-[4-(3-methyl-1,2,4-oxadiazol-5-yl)-1-piperidinyl]propyl}cyclobutanecarboxamide

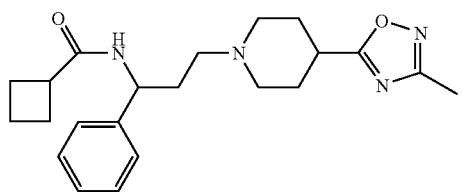

A mixture of the title compound of preparation 21 (566 mg, 2.27 mmol) and sodium hydroxide (136 mg, 3.41 mmol) in ethanol (20 ml) was stirred for 2 hours at room temperature and the solvent evaporated under reduced pressure. This intermediate and the title compound of preparation 3 were then used to prepare the title compound using a similar method to example 1. The reaction mixture was purified by column chromatography on silica gel using dichloromethane:methanol:0.88 ammonia (98:2:0.25). The product was dissolved in methanolic hydrochloric acid (3 ml, 2.5M), and the solvent evaporated under reduced pressure to afford the title compound, 85 mg.

Found C, 62.16; H, 7.53; N, 12.19%

$C_{22}H_{30}N_4O_2$; HCl; 0.6MeOH; requires C, 61.69; H, 7.70; N, 12.73%

$^1$H NMR (300 MHz, CDCl$_3$): δ [ppm] 1.80–2.45 (16H, m), 3.06–3.40 (6H, m), 3.62–3.80 (2H, m), 5.00 (1H, dd), 7.20–7.40 (5H, m)

LRMS: m/z 383 (MH$^+$)

EXAMPLE 7

N-{1-Phenyl-3-[4-(3-phenyl-1,2,4-oxadiazol-5-yl)-1-piperidinyl]propyl}cyclobutanecarboxamide

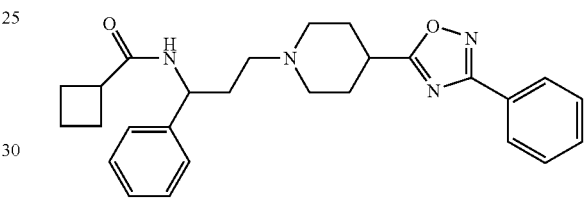

The title compounds of preparations 3 and 37 were used to prepare the title compound using a similar method to example 1. The reaction mixture was purified by column chromatography on silica gel using dichloromethane:methanol:0.88 ammonia (98:2:0.25) as eluant to afford the title compound, 218 mg.

$^1$H NMR (300 MHz, CDCl$_3$): δ [ppm] 1.60 (3H, s), 1.78–2.48 (14H, m), 2.93 (1H, d), 3.04 (2H, m), 5.13 (1H, m), 7.20–7.40 (5H, m), 7.50 (3H, m), 8.09 (2H, m)

LRMS: m/z 445 (MH$^+$)

EXAMPLE 8–15

The compounds of the following tabulated examples with the general formula:

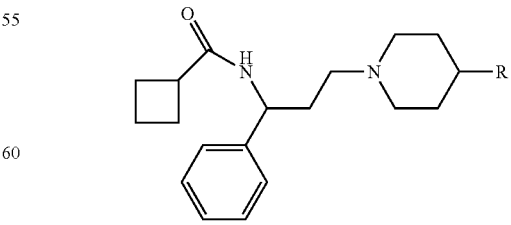

were prepared using a similar method to example 1 from the title compound of preparation 3 and the corresponding amine.

| EXAMPLE | R | YIELD | DATA |
|---|---|---|---|
| 8[1] | 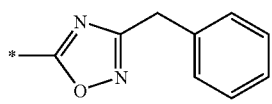<br>N-{3-[4-(3-Benzyl-1,2,4-oxadiazol-5-yl)-1-piperidinyl]-1-phenylpropyl}cyclo-butanecarboxamide | 51% | $^1$H NMR(300MHz, CDCl$_3$): δ [ppm] 1.74–2.42(9H, m), 2.48–3.20(8H, m), 3.17–3.55(2H, m), 3.68(1H, m), 4.06 (2H, d), 4.97(1H, s), 7.20–7.40(10H, m), 8.98(1H, m)<br>LRMS: 459(MH$^+$) |
| 9 | 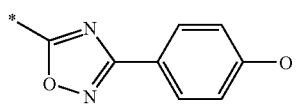<br>N-(3-{4-[3-(4-Methoxy-phenyl)-1,2,4-oxadiazol-5-yl]-1-piperidiny}-1-phenylpropyl}cyclo-butanecarboxamide | 32% | $^1$H NMR(300MHz, CD$_3$OD): δ [ppm] 1.80–2.58(14H, m), 3.04–3.84(4H, m), 3.88(3H, s), 4.96–5.06(1H, m), 7.08 (2H, d), 7.22–7.46(5H, m), 7.98(2H, d)<br>LRMS: m/z 476(MH$^+$) |
| 10 | 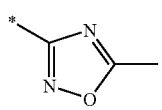<br>N-{3-[4-(5-Methyl-1,2,4-oxadiazol-3-yl)-1-piperidinyl]-1-phenylpropyl}cyclo-butanecarboxamide | 5% | $^1$H NMR(300MHz, CD$_3$OD): δ [ppm] 1.80–2.40(15H, m), 2.58(3H, s), 3.03–3.24(5H, m), 3.89(1H, m), 4.97(1H, m), 7.25–7.40(5H, m)<br>LRMS: m/z 383.3(MH$^+$)<br>Melting point [° C.]: >60 (softens to gum) |
| 11[1] | 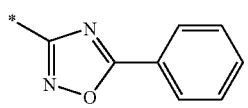<br>N-{1-Phenyl-3-[4-(5-phenyl-1,2,4-oxadiazol-3-yl)-1-piperidinyl]propyl}cyclo-butanecarboxamide | 30% | $^1$H NMR(300MHz, CD$_3$OD): δ [ppm] 1.78–1.92(1H, m), 1.92–2.05(1H, m), 2.05–2.45(11H, m), 3.10–3.55(6H, m), 3.40–3.62(1H, m), 3.62–3.80(1H, m), 7.20–7.45(5H, m), 7.52–7.69(3H, m), 8.05–8.18(2H, m)<br>LRMS: m/z 445.2(MH$^+$) |
| 12[1] | 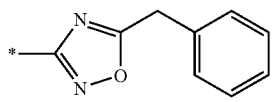<br>N-{3-[4-(5-Benzyl-1,2,4-oxadiazol-3-yl)-1-piperidinyl]-1-phenylpropyl}cyclo-butanecarboxamide | 35% | Found C, 62.23; H, 7.26; N, 10.15%. C$_{28}$H$_{34}$N$_4$O$_2$; 1HCl; 2.5H$_2$O requires C, 62.23; H, 7.46; N, 10.37%.<br>$^1$H NMR(300MHz, CD$_3$OD): δ [ppm] 1.78–2.40(12H, m), 3.04–3.38(6H, m), 3.58–3.75(2H, m), 4.20–4.35(2H, m), 4.92–5.11(1H, m), 7.21–7.45(10H, m)<br>LRMS: m/z 459.2(MH$^+$) |
| 13 | 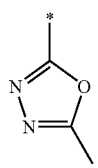<br>N-{3-[4-(5-Methyl-1,3,4-oxadiazol-2-yl)-1-piperidinyl]-1-phenylpropyl}cyclo-butanecarboxamide | 67% | $^1$H NMR(300MHz, CDCl$_3$): δ [ppm] 1.76–2.62(16H, m), 2.53(3H, s), 2.83–3.15(4H, m), 5.18(1H, m), 7.20–7.38(5H, m), 7.52(1H, d)<br>LRMS: m/z 384(MH$^+$) |

-continued

| EXAMPLE | R | YIELD | DATA |
|---|---|---|---|
| 14[1] | 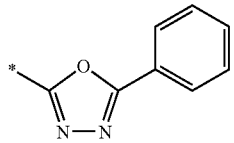 | 95% | ¹H NMR(300MHz, CD$_3$OD): δ [ppm] 1.82–2.34(9H, m), 2.52(2H, d), 3.07–3.83(10H, m), 5.01(1H, m), 7.27–7.42(5H, m), 7.60(3H, m), 8.06(2H, m) LRMS: m/z 445(MH$^+$) |
| | N-{1-Phenyl-3-[4-(5-phenyl-1,3,4-oxadiazol-2-yl)-1-piperidinyl]propyl}cyclobutanecarboxamide | | |
| 15 | 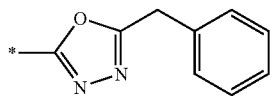 | 8% | ¹H NMR(300MHz, CD$_3$OD): δ [ppm] 1.78–2.38(14H, m), 2.92–3.22(5H, m), 3.56–3.78(3H, m), 4.19–4.25(1H, m), 7.12 7.58(10, m) LRMS: m/z 459.2(MH$^+$) |
| | N-{3-[4-(5-Benzyl-1,3,4-oxadiazol-2-yl)-1-piperidinyl]-1-phenylpropyl}cyclobutanecarboxamide | | |

[1]= Product obtained as the hydrochloride salt

EXAMPLE 16

N-[(1S)-3-[4-(3-Benzyl-1,2,4-oxadiazol-5-yl)-1-piperidinyl]-1-(3-fluorophenyl)propyl]-2-cyclopropylacetamide

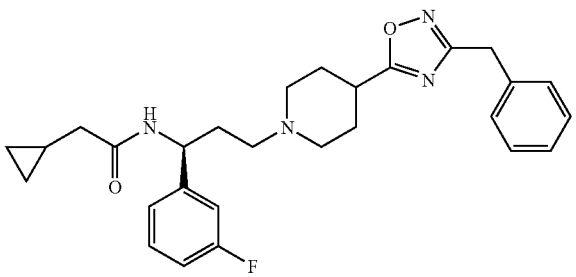

Diisobutylaluminium hydride (42.1 ml of a 1.0M solution in dichloromethane, 42.1 mmol) was added dropwise to a solution of the title compound of preparation 12 (5.7 g, 19.1 mmol) in dichloromethane (100 ml) at −78° C. The reaction mixture was stirred at this temperature for 1 hour, then methanol (5 ml) pre-cooled to −78° C. was added. The mixture was warmed to room temperature and washed with 2M hydrochloric acid, water and brine, dried (MgSO$_4$), filtered and the solvent evaporated under reduced pressure to afford the aldehyde as a yellow oil, 3.3 g. From this oil (485 mg, 1.81 mmol), the title compound of preparation 39 (420 mg, 1.81 mmol) and sodium triacetoxyborohydride (578 mg, 2.73 mmol) were stirred together for 72 hours at room temperature in dichloromethane:acetic acid (30 ml, 10%). The solvents were evaporated under reduced pressure. The residue was dissolved in ethyl acetate and washed with saturated aqueous sodium carbonate solution then water. The organic layer was dried (MgSO$_4$), filtered and evaporated under reduced pressure. The residue (700 mg, 1.42 mmol) was stirred for 1 hour at room temperature in dichloromethane (14 ml) and trifluoroacetic acid (14 ml). The solvents were evaporated under reduced pressure. The residue was basified with saturated aqueous sodium bicarbonate solution and extracted with dichloromethane (3×). The combined organic layers were dried (MgSO$_4$), filtered and evaporated under reduced pressure. The residue was purified by column chromatography on silica gel using dichlorormethane:methanol:0.88 ammonia (97:3:0.3) as eluant A portion of the residue (100 mg, 0.25 mmol), 2-cyclopropylacetic acid (28 mg, 0.28 mmol), 1-hydroxybenzotriazole hydrate (41 mg, 0.3 mmol), 1-(3-dimethylaminopropyl)-3-ethyl-carbodiimide hydrochloride (63 mg, 0.33 mmol) and triethylamine (46 μl, 0.33 mmol) were stirred for 2 hours at room temperature in dichloromethane (20 ml). The solvent was evaporated under reduced pressure. The residue was dissolved in ethyl acetate and washed with water. The organic layer was dried (MgSO$_4$), filtered and evaporated. The residue was purified by column chromatography on silica gel using dichloromethane:methanol:0.88 ammonia (98:2:0.25) as eluant to afford the title compound as an oil, 97 mg.

¹H NMR (400 MHz, CDCl$_3$): δ [ppm] 0.16–0.23 (2H, m), 0.58–0.65 (2H, m), 0.97–1.08 (1H, m), 1.81–1.97 (3H, m), 1.97–2.23 (7H, m), 2.23–2.40 (2H, m), 2.82–2.95 (2H, m), 2.95–3.05 (1H, m), 4.05 (2H, s), 5.08–5.16 (1H, m), 6.89–7.00 (2H, m), 7.00–7.06 (1H, d), 7.23–7.35 (6H, m), 7.63–7.71 (1H, m)

LRMS: m/z 477.3 (MH$^+$)

EXAMPLE 17

N-((1S)-3-{4-[3-(4-Methylbenzyl)-1,2,4-oxadiazol-5-yl]-1-piperidinyl}-1-phenylpropyl)cyclobutanecarboxamide

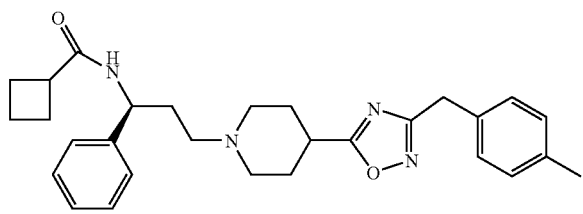

The title compound of preparation 77 (200 mg, 0.56 mmol) in dichloromethane (10 ml) was treated with trifluoroacetic acid (4 ml). The solution was stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (131 mg, 0.51 mmol), the title compound of preparation 8 (130 mg, 0.56 mmol) and sodium triacetoxyborohydride (162 mg, 0.76 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPCL (phenomonex magellenC$_{18}$ (2) aqueous TFA 0.1%:acetonitrile 1:19–19:1) to afford the title compound, 38 mg.

$^1$H NMR (400 MHz, CDCl$_3$): δ [ppm] 1.71–2.60 (16H, m), 2.61–2.82 (1H, m), 2.81–3.25 (4H, m), 3.32–3.83 (2H, m), 4.02 (2H, s), 4.95 (1H, s), 6.75 (1H, m), 7.15–7.47 (9H, m)

LRMS: m/z 473.3 (MH$^+$)

EXAMPLE 18

N-((1S)-3-{4-[3-(4-Trifluoromethylbenzyl)-1,2,4-oxadiazol-5-yl]-1-piperidinyl}-1-phenylpropyl)cyclobutanecarboxamide

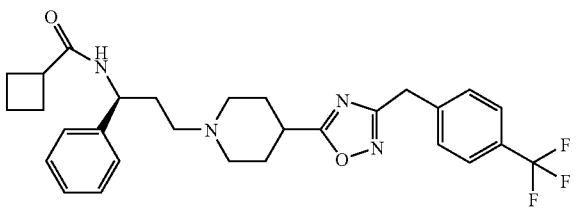

The title compound of preparation 78 (221 mg, 0.54 mmol) in dichloromethane (10 ml) was treated with trifluoroacetic acid (4 ml). The solution was stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (164 mg, 0.53 mmol), the title compound of preparation 8 (134 mg, 0.58 mmol) and sodium triacetoxyborohydride (168 mg, 0.70 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 40 mg.

$^1$H NMR (400 MHz, CDCl$_3$): δ [ppm] 1.46–2.61 (13H, m), 2.61–3.25 (5H, m), 3.45 (1H, m), 3.72 (1H, m), 4.13 (2H, s), 4.95 (1H, m), 6.65 (1H, m), 7.13–7.45 (7H, m), 7.42 (1H, d), 7.58 (1H, d)

LRMS: m/z 527.4 (MH$^+$)

EXAMPLE 19

N-((1S)-3-{4-[3-(1,3-Benzodioxol-5-ylmethyl)-1,2,4-oxadiazol-5-yl]-1-piperidinyl}-1-phenylpropyl)cyclobutanecarboxamide (UK-383290-51)

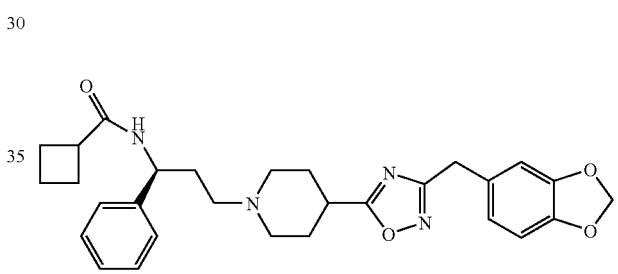

The title compound of preparation 79 (258 mg, 0.67 mmol) in dichloromethane (10 ml) was treated with trifluoroacetic acid (4 ml). The solution was stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (175 mg, 0.44 mmol), the title compound of preparation 8 (113 mg, 0.49 mmol) and sodium triacetoxyborohydride (141 mg, 0.66 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 31 mg.

$^1$H NMR (400 MHz, CDCl$_3$): δ [ppm] 1.74–3.35 (18H, m), 3.46 (1H, m), 3.70 (1H, m), 3.96 (2H, s), 4.90 (1H, m), 4.95 (1H, m), 5.95 (2H, s), 6.65–6.85 (3H, m), 7.25–7.51 (5H, m)

LRMS: m/z 503.4 (MH$^+$)

EXAMPLE 20

N-((1S)-3-{4-[3-(3,5-Difluorobenzyl)-1,2,4-oxadiazol-5-yl]-1-piperidinyl}1-phenylpropyl)cyclobutanecarboxamide

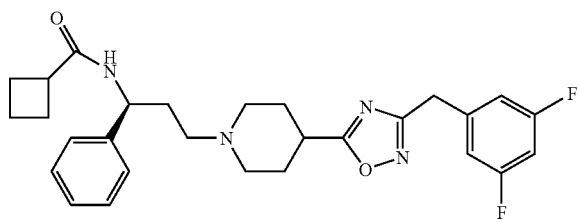

The title compound of preparation 75 (100 mg, 0.26 mmol) in dichloromethane (10 ml) was treated with trifluoroacetic acid (4 ml). The solution was stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (69 mg, 0.25 mmol), the title compound of preparation 8 (63 mg, 0.27 mmol) and sodium triacetoxyborohydride (79 mg, 0.37 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 39 mg.

$^1$H NMR (400 MHz, CDCl$_3$): δ [ppm] 1.74–3.35 (18H, m), 3.45 (1H, m), 3.70 (1H, m), 4.04 (2H, s), 4.93 (1H, m), 6.65–0.91 (3H, m), 7.23–7.45 (6H, m)

LRMS: m/z 495.0 (MH$^+$)

EXAMPLE 21

N-[(1S)-3-[4-(3-Benzyl-1,2,4-oxadiazol-5-yl)-1-piperidinyl]-1-(3-fluorophenyl)propyl]cyclobutanecarboxamide

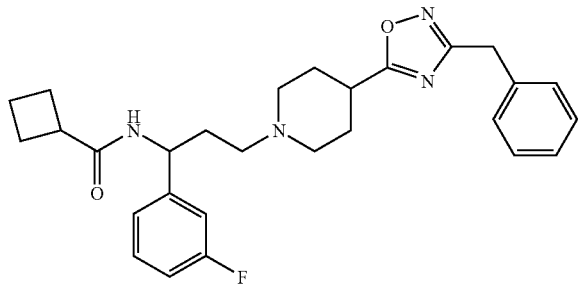

Diisobutylaluminium hydride (42.1 ml of a 1.0M solution in dichloromethane, 42.1 mmol) was added dropwise to a solution of the title compound of preparation 12 (5.7 g, 19.1 mmol) in dichloromethane (100 ml) at −78° C. The reaction mixture was stirred at 78° C. for an hour, then methanol (5 ml) pre-cooled to −78° C. was added. The mixture was warmed to room temperature and washed with 2M hydrochloric acid, water and brine, dried (MgSO$_4$), filtered and the solvent evaporated under reduced pressure to afford the title compound as a yellow oil, 3.3 g. From this oil (485 mg, 1.81 mmol), the title compound of preparation 39 (420 mg, 1.81 mmol) and sodium triacetoxyborohydride (578 mg, 2.73 mmol) were stirred together for 72 hours at room temperature in dichloromethane:acetic acid (30 ml, 10%). The solvents were evaporated under reduced pressure. The residue was dissolved in ethyl acetate and washed with saturated aqueous sodium carbonate solution then water. The organic layer was dried (MgSO$_4$), filtered and evaporated under reduced pressure. The residue (700 mg, 1.42 mmol) was stirred for 1 hour at room temperature in dichloromethane (14 ml) and trifluoroacetic acid (14 ml). The solvents were evaporated under reduced pressure. The residue was basified with saturated aqueous sodium carbonate solution and extracted with dichloromethane (3×). The combined organic layers were dried (MgSO$_4$), filtered and evaporated under reduced pressure. The residue was purified by column chromatography on silica gel using dichloromethane:methanol:0.88 ammonia (97:3:0.3) as eluant A portion of the residue (100 mg, 0.25 mmol), cyclobutanecarboxylic acid (28 mg, 0.28 mmol), 1-hydroxybenzotriazole hydrate (41 mg, 0.3 mmol), 1-(3-dimethylaminopropyl)-3-ethyl-carbodiimide hydrochloride (63 mg, 0.33 mmol) and triethylamine (46 μl, 0.33 mmol) were stirred for 2 hours at room temperature in dichloromethane (20 ml). The solvent was evaporated under reduced pressure. The residue was dissolved in ethyl acetate and washed with water. The organic layer was dried (MgSO$_4$), filtered and evaporated. The residue was purified by column chromatography on silica gel using dichloromethane:methanol:0.88 ammonia (98:2:0.25) as eluant to afford the title compound as a gum which solidified on standing, 108 mg.

Found C, 70.26; H, 7.00; N, 11.66%

C$_{28}$H$_{33}$FN$_4$O$_2$; 0.1H$_2$O requires C, 70.30; H, 7.00; N, 11.71%

$^1$H NMR (400 MHz, CDCl$_3$): δ [ppm] 1.31–2.44 (14H, m), 2.80–3.10 (5H, m), 4.02–4.15 (3H, m), 5.06–5.18 (1H, m), 6.84–7.03 (4H, m), 7.18–7.42 (5H, m), 7.71–7.84 (1H, m)

LRMS: m/z 477.3 (MH$^+$)

EXAMPLE 22

N-{(1S)-3-[4-(3-{4-[(Methylsulfonyl)amino]benzyl}-1,2,4-oxadiazol-5-yl)-1-piperidinyl]-1-phenylpropyl}cyclobutanecarboxamide

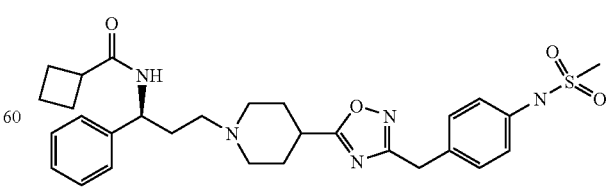

The title compound of preparation 47 (6.50 g, 30.9 mmol), hydroxylamine hydrochloride (10.7 g, 154 mmol) and sodium carbonate (16.3 g, 154 mmol) in methanol (100 ml) and water (100 ml) were heated under reflux for 5 hours. The reaction was cooled, filtered and the methanol evaporated under reduced pressure. The remaining aqueous layer was extracted with dichloromethane (3×) and the combined organic layers were dried (MgSO$_4$), filtered and the solvent evaporated under reduced pressure to furnish a pale orange solid. The solid and carbonyldiimidazole (158 mg, 0.97 mmol) were then added to a solution of carbonyldiimidazole (158 mg, 0.97 mmol) and the title compound of preparation 115 in DMF (2 ml) which had been stirred at room temperature for 1 hour. The reaction was heated at 115° C. for 6 hours cooled to room temperature and the solvent evaporated under reduced pressure. The resulting brown oil was purified by column chromatography on silica gel using dichloromethane:methanol:0.88 ammonia (95:5:0.5) as eluant to afford the title compound as a pale orange oil that was freeze dried from water/acetonitrile to furnish a pale orange foam, 43 mg.

Found C, 62.23; H, 6.82; N, 12.60%
$C_{29}H_{37}N_5SO_4$; 0.3H$_2$O requires C, 62.52; H, 6.80; N, 12.57%
$^1$H NMR (400 MHz, CDCl$_3$): δ [ppm] 1.78–2.40 (18H, m), 2.80–3.05 (7H, m), 4.03 (2H, s), 5.08 (1H, dd), 7.15–7.45 (9H, m)
LRMS: m/z 552 (MH$^+$)
[α]$_D$ –32.6 (c=1.97, MeOH)

EXAMPLE 23

4-{[5-(1-{(3S)-3-[(Cyclobutylcarbonyl)amino]-3-phenylpropyl}-piperidinyl)-1,2,4-oxadiazol-3-yl]methyl}benzamide

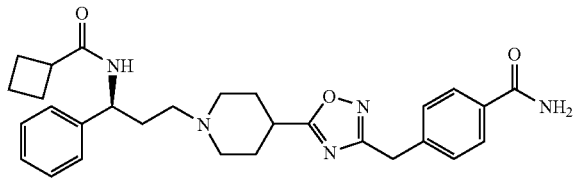

The title compound of preparation 55 (7.00 g, 43.8 mmol), hydroxylamine hydrochloride (15.2 g, 218 mmol) and sodium carbonate (23.1 g, 218 mmol) in methanol (100 ml) and water (100 ml) were heated under reflux for 5 hours. The reaction was cooled, filtered and the methanol evaporated under reduced pressure. The remaining aqueous layer was extracted with dichloromethane (3×) and the combined organic layers were dried (MgSO$_4$), filtered and the solvent evaporated under reduced pressure to furnish a pale orange solid. The solid and carbonyldiimidazole (158 mg, 0.97 mmol) were then added to a solution of carbonyldiimidazole (158 mg, 0.97 mmol) and the title compound of preparation 115 in DMF (2 ml) which had been stirred at room temperature for 1 hour. The reaction was heated at 115° C. for 6 hours allowed to cool to room temperature and the solvent evaporated under reduced pressure. The resulting brown oil was purified by column chromatography on silica gel using dichloromethane:methanol:0.88 ammonia (95:5:0.5) as eluant to afford the title compound as a clear oil that was freeze dried from water/acetonitrile to furnish a white solid, 12 mg.

$^1$H NMR (400 MHz, CDCl$_3$): δ [ppm] 1.78–2.40 (17H, m), 2.80–3.05 (4H, m), 4.03 (2H, s), 5.08 (1H, dd), 5.58 (1H, br s), 6.01 (1H, br s), 7.15–7.30 (5H, m), 7.40 (2H, d), 7.75 (2H, d)
LRMS: m/z 502 (MH$^+$)

EXAMPLE 24

N-((1S)-3-{4-[3-(2,5-Difluorobenzyl)-1,2,4-oxadiazol-5-yl]-1-piperidinyl}-1-phenylpropyl)cyclobutanecarboxamide

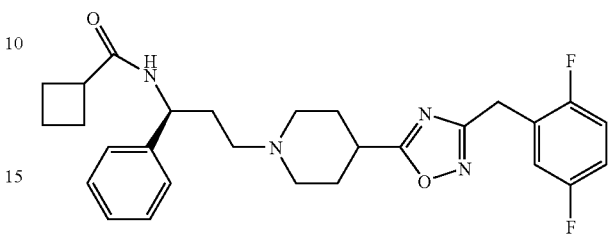

The title compound of preparation 74 (142 mg, 0.37 mmol) in dichloromethane (10 ml) was treated with trifluoroacetic acid (4 ml) and the solution stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (107 mg, 0.38 mmol), the title compound of preparation 8 (97 mg, 0.42 mmol) and sodium triacetoxyborohydride (122 mg, 0.59 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 9 mg.

$^1$H NMR (400 MHz, CDCl$_3$): δ [ppm] 1.43–2.05 (4H, m), 2.05–2.41 (8H, m), 2.50 (1H, bs), 2.66–2.83 (1H, m), 2.85–3.36 (4H, m), 3.45 (1H, m), 3.70 (1H, bs), 4.08 (2H, s), 4.95 (1H, s), 6.70 (1H, bs), 6.93–7.14 (2H, m), 7.27–7.41 (6H, m)
LRMS: m/z 495.1 (MH$^+$)

EXAMPLE 25

N-((1S)-3-{4-[3-(2,6-Difluorobenzyl)-1,2,4-oxadiazol-5-yl]-1-piperidinyl}-1-phenylpropyl)cyclobutanecarboxamide

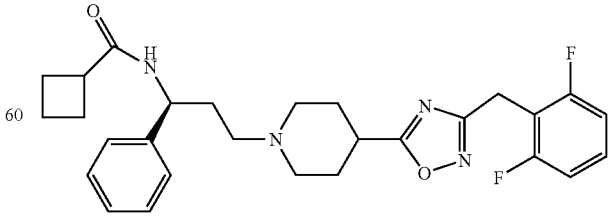

The title compound of preparation 76 (163 mg, 0.43 mmol) in dichloromethane (10 ml) was treated with trifluoroacetic acid (4 ml) and the solution stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (118 mg, 0.42 mmol), the title compound of preparation 8 (107 mg, 0.47 mmol) and sodium triacetoxyborohydride (143 mg, 0.63 mmol) were stirred in dichloromethane:acetic acid (20 ml, 10%) at room temperature for 3 days. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 10 mg.

$^1$H NMR (400 MHz, CDCl$_3$): δ [ppm] 1.33–2.05 (4H, m), 2.05–2.45 (8H, m), 2.41–2.82 (2H, m), 2.86–3.25 (4H, m), 3.35–3.87 (2H, m), 4.15 (2H, s), 4.95 (1H, s), 6.85 (1H, m), 6.95 (2H, m), 7.23–7.45 (6H, m)

LRMS: m/z 495.1 (MH$^+$)

EXAMPLE 26

N-((1S)-1-Phenyl-3-{4-[3-(3-pyridinylmethyl)-1,2,4-oxadiazol-5-yl]-1-piperidinyl}propyl)cyclobutanecarboxamide

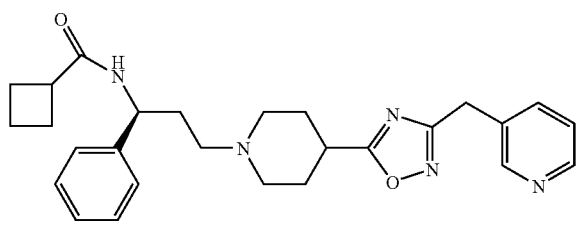

A solution of the title compound of preparation 115 (300 mg, 0.87 mmol) in dichloromethane (20 ml) was treated with diisopropylethylamine (0.36 ml, 2.09 mmol) and bis(tetramethylene)fluoroformamidinium hexafluorophosphate (331 mg, 1.05 mmol). After 1 hour N'-hydroxy-2-(3-pyridinyl)ethanimidamide [WO 9600720] (171 mg, 1.13 mmol) was added and stirring continued for 12 hours. The reaction was diluted with dioxane (30 ml) then heated at 120° C. for 4 hours. The cooled mixture was diluted with dichloromethane (100 ml) and washed with saturated aqueous sodium carbonate solution and brine, dried (MgSO$_4$), filtered and evaporated under reduced pressure. The crude product was purified by column chromatography on silica gel using dichloromethane:methanol:0.88 ammonia (94.5:5:0.5) as eluant. The resultant oil was dissolved in dichloromethane (10 ml), treated with 1M hydrochloric acid in dioxane (4 ml) and evaporated under reduced pressure. Freeze drying from water/acetonitrile gave the title compound as a yellow solid, 191 mg.

Found C, 51.85; H, 7.06; N, 11.02%

C$_{27}$H$_{33}$N$_5$O$_2$; 5H$_2$O; 2HCl requires C, 52.09; H, 7.29; N, 11.25%

$^1$H NMR (400 MHz, DMSOd6): δ [ppm] 1.70 (1H, m), 1.86 (1H, m), 1.92–2.14 (10H, m), 2.91–3.17 (5H, m), 3.28–4.02 (2H and H$_2$O), 4.36 (2H, s), 4.83 (1H, m), 7.22 (1H, m), 7.30 (3H, m), 7.94 (1H, m), 8.24 (1H, d), 8.41 (1H, d), 8.78 (1H, d), 8.88 (1H, s)

LRMS: m/z 460.2 (MH$^+$)

EXAMPLE 27

N-((1S)-1-Phenyl-3-{4-[3-(4-pyridinylmethyl)-1,2,4-oxadiazol-5-yl]-1-piperidinyl}propyl)cyclobutanecarboxamide

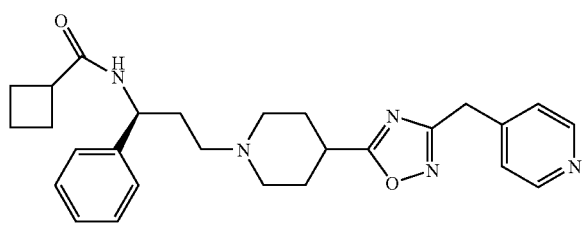

A solution of the title compound of preparation 115 (300 mg, 0.87 mmol) in dichloromethane (20 ml) was treated with diisopropylethylamine (0.36 ml, 2.09 mmol) and bis(tetramethylene)fluoroformamidinium hexafluorophosphate (331 mg, 1.05 mmol). After 1 hour N'-hydroxy-2(4-pyridinyl)ethanimidamide [WO 9600720] (171 mg, 1.13 mmol) was added and stirring continued for 12 hours. The reaction was diluted with dioxane (30 ml) then heated at 120° C. for 4 hours. The cooled mixture was diluted with dichloromethane (100 ml) and washed with saturated aqueous sodium carbonate solution and brine, dried (MgSO$_4$), filtered and evaporated under reduced pressure. The crude product was purified by column chromatography on silica gel using dichloromethane:methanol:0.88 ammonia (94.5:5:0.5) as eluant. Freeze-drying from water/acetonitrile gave the title compound as a yellow foam, 121 mg.

$^1$H NMR (400 MHz, CDCl$_3$): δ [Ppm] 1.75–2.20 (12H, m), 2.20–2.40 (4H, m), 2.80–3.10 (4H, m), 4.05 (2H, s), 5.14 (1H, m), 7.16–7.37 (8H, m), 8.57 (1H, d)

LRMS: m/z 460.2 (MH$^+$)

EXAMPLE 28

N-{(1S)-3-[4-(3-{2-[(Methylsulfonyl)amino]benzyl}-1,2,4-oxadiazol-5-yl)-1-piperidinyl]-1-phenylpropyl}cyclobutanecarboxamide

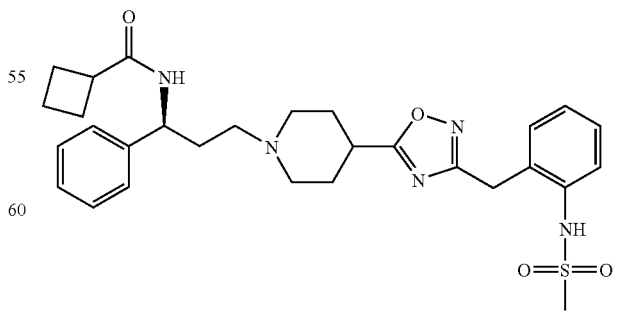

The title compound of preparation 48 (5.60 g, 28.5 mmol), hydroxylamine hydrochloride (9.9 g, 142 mmol) and sodium carbonate (15.1 g, 142 mmol) in methanol (100 ml) and water (100 ml) were heated under reflux for 5 hours. The reaction was cooled, filtered and the methanol evaporated under reduced pressure. The remaining aqueous was extracted with dichloromethane (3×) and the combined organic layers dried (MgSO$_4$), filtered evaporated under reduced pressure to furnish a red solid. The solid and carbonyldiimidazole (158 mg, 0.97 mmol) were then added to a solution of carbonyldiimidazole (158 mg, 0.97 mmol) and the title compound of preparation 115 in DMF (2 ml) which had been stirred at room temperature for 1 hour. The reaction was heated at 115° C. for 6 hours cooled to room temperature and the solvent evaporated under reduced pressure, the resulting brown oil was purified by column chromatography on silica gel using dichloromethane:methanol: 0.88 ammonia (95:5:0.5) as eluant to afford the title compound as a clear oil that was freeze dried from water/acetonitrile to furnish a white solid, 24 mg.

Found C, 62.83; H, 6.84; N, 12.95%

$C_{29}H_{37}N_5SO_4$; 0.1H$_2$O requires C, 62.93; H, 6.77; N, 12.65%

$^1$H NMR (300 MHz, CDCl$_3$): δ [ppm] 1.80–2.40 (17H, m), 2.80–3.05 (4H, m), 3.11 (3H, s), 4.08 (2H, s), 5.05 (1H, dd), 7.15–7.45 (8H, m), 7.60 (1H, d), 9.73 (1H, bs)

LRMS: m/z 552 (MH$^+$)

[α]$_D$ –31.0 (c=1.16, MeOH)

EXAMPLE 29

N-((1S)-1-Phenyl-3-{4-[3-(2-pyridinylmethyl)-1,2,4-oxadiazol-5-yl]-1-piperidinyl}propyl)cyclobutanecarboxamide

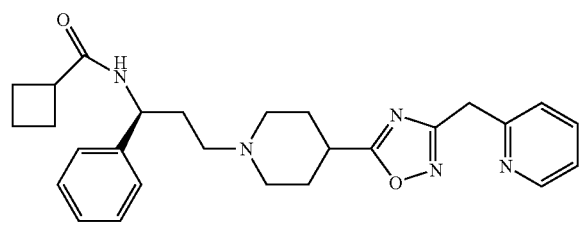

A solution of the title compound of preparation 115 (300 mg, 0.87 mmol) in dichloromethane (20 ml) was treated with diisopropylethylamine (0.36 ml, 2.09 mmol) and bis(tetramethylene)fluoroformamidinium hexafluorophosphate (331 mg, 1.05 mmol). After 1 hour N-hydroxy-2-(2-pyridinyl)ethanimidamide [WO 9600720] (171 mg, 1.13 mmol) was added and stirring continued for 12 hours. The reaction was diluted with dioxane (30 ml) then heated at 120° C. for 4 hours. The cooled mixture was diluted with dichloromethane (100 ml) and washed with saturated aqueous sodium carbonate solution and brine, dried (MgSO$_4$), filtered and evaporated under reduced pressure. The crude product was purified by column chromatography on silica gel using dichloromethane:methanol:0.88 ammonia (94.5:5:0.5) as eluant. The resulting oil was dissolved in dichloromethane (10 ml), treated with 1 M hydrochloric acid in dioxane (4 ml) and evaporated under reduced pressure. Freeze-drying from water/acetonitrile gave the title compound as a green gum, 95 mg.

Found C, 52.25; H, 6.97; N, 11.14%

$C_{27}H_{33}N_5O_2$; 4.9H$_2$O; 2HCl requires C, 52.24; H, 7.27; N, 11.28%

$^1$H NMR (400 MHz, DMSOD6): δ [ppm] 1.72 (1H, m); 1.86 (1H, m); 1.9–2.1 (10H, m); 2.9–3.1 (5H, m); 3.2–4.0 (2H and H$_2$O); 4.45 (2H, s); 4.83 (1H, m); 7.23 (1H, m); 7.30 (3H, m); 7.65 (1H, t); 7.70 (1H, d); 8.15 (1H, t); 8.23 (1H, d); 8.67 (1H, d)

LRMS: m/z 460.2 (MH$^+$)

EXAMPLE 30

N-{(1S)-3-[4-(3-isobutyl-1,2,4-oxadiazol-5-yl)-1-piperidinyl-1-phenylpropyl}cyclobutanecarboxamide

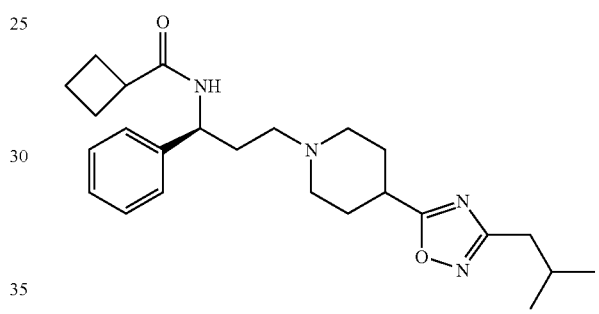

The title compound of preparation 73 (305 mg, 0.98 mmol) in dichloromethane (10 ml) was treated with trifluoroacetic acid (4 ml) and solution stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (161 mg, 0.76 mmol), the title compound of preparation 8 (213 mg, 0.923 mmol) and sodium triacetoxyborohydride (244 mg, 1.15 mmol) were stirred in dichloromethane:acetic acid (20 ml, 10%) at room temperature for 2 weeks. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 52 mg.

$^1$H NMR (400 MHz, CDCl$_3$): δ [ppm] 0.95 (6H, d), 1.80–2.20 (13H, m), 2.22–2.40 (4H, m), 2.60 (2H, d), 2.90 (2H, m), 3.05 (2H, m), 5.10 (1H, m), 7.20 (3H, d), 7.30 (2H, m), 7.50 (1H, d)

LRMS: m/z 425 (MH$^+$)

EXAMPLE 31

N-((1S)-3-{4-[3-(3-Chlorobenzyl)-1,2,4-oxadiazol-5-yl]-1-piperidinyl}-1-phenylpropyl)cyclobutanecarboxamide

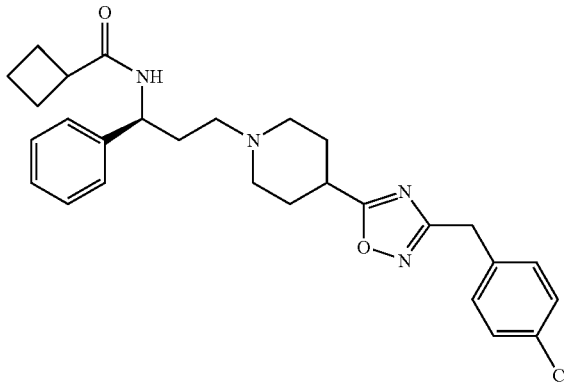

The title compound of preparation 72 (260 mg, 0.68 mmol) in dichloromethane (10 ml) was treated with trifluoroacetic acid (4 ml) and the solution stirred at room temperature for 12 hours. The solvent was evaporated under reduced pressure and the residue was partitioned between saturated aqueous sodium carbonate solution and dichloromethane. The aqueous layer was extracted with dichloromethane (2×). The combined organic layers were dried (MgSO$_4$), filtered and evaporated under reduced pressure. The residue obtained (145 mg, 0.52 mmol), the title compound of preparation 8 (145 mg, 0.62 mmol) and sodium triacetoxyborohydride (166 mg, 0.78 mmol) were stirred in dichloromethane:acetic acid (20 ml, 10%) at room temperature for 2 weeks. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 9 mg.

$^1$H NMR (400 MHz, CDCl$_3$): δ [ppm] 1.82–2.00 (4H, m), 2.00–2.22 (8H, m), 2.25–2.32 (4H, m), 3.00 (4H, m), 4.02 (2H, s), 5.05 (1H, m), 7.20–7.35 (9H, m), 7.38 (1H, d)

LRMS: m/z 494 (MH$^+$)

EXAMPLE 32

N-((1S)-3-{4-[3-(1-Benzofuran-5-ylmethyl)-1,2,4-oxadiazol-5-yl]-1-piperidinyl}1-phenylpropyl)cyclobutanecarboxamide

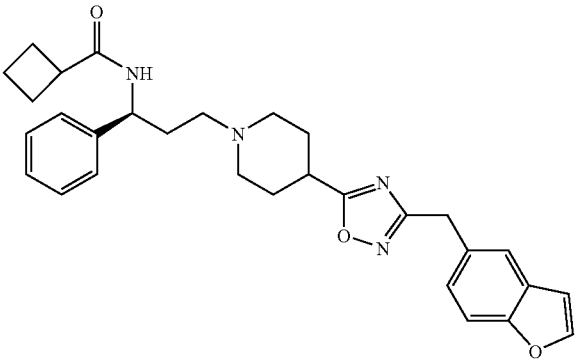

The title compound of preparation 71 (176 mg, 0.45 mmol) in dichloromethane (10 ml) was treated with trifluoroacetic acid (4 ml) and the solution stirred at room temperature for 12 hours. The solvent was evaporated under reduced pressure and the residue was partitioned between saturated aqueous sodium carbonate solution and dichloromethane and the aqueous layer extracted with dichloromethane (2×). The combined organic layers were dried (MgSO$_4$), filtered and evaporated under reduced pressure. The residue obtained (130 mg, 0.45 mmol), the title compound of preparation 8 (127 mg, 0.55 mmol) and sodium triacetoxyborohydride (146 mg, 0.68 mmol) were stirred in dichloromethane:acetic acid (20 ml, 10%) at room temperature for 2 weeks. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 44 mg.

$^1$H NMR (400 MHz, CDCl$_3$): δ [ppm] 1.82–2.00 (5H, m), 2.00 (2H, s), 2.05–2.30 (8H, m), 2.40 (2H, m), 2.90 (2H, m), 3.05 (1H, m), 4.10 (2H, s), 5.05 (1H, m), 5.25 (1H, bs), 6.70 (1H, s), 7.20 (3H, m), 7.30 (2H, m), 7.40 (1H, d), 7.42 (1H, d), 7.58 (2H, d)

LRMS: m/z 499 (MH$^+$)

EXAMPLE 33

N-[(1S)-1-Phenyl-3-(4-{3-[4-(trifluoromethoxy)benzyl-1,2,4-oxadiazol-5-yl}-1-piperidinyl)propyl]cyclobutanecarboxamide

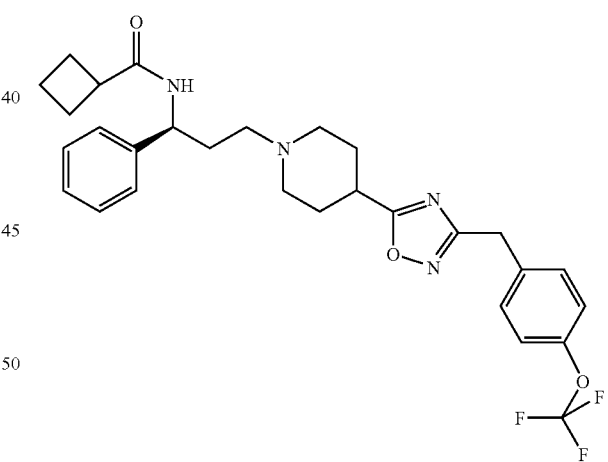

The title compound of preparation 70 (306 mg, 0.71 mmol) in dichloromethane (10 ml) was treated with trifluoroacetic acid (4 ml) and the solution stirred at room temperature for 12 hours. The solvent was evaporated under reduced pressure and the residue was partitioned between saturated aqueous sodium carbonate solution and dichloromethane and the aqueous layer extracted with dichloromethane (2×). The combined organic layers were dried (MgSO$_4$), filtered and evaporated under reduced pressure. The residue obtained (204 mg, 0.62 mmol), the title compound of preparation 8 (173 mg, 0.74 mmol) and sodium triacetoxyborohydride (198 mg, 0.93 mmol) were stirred in dichloromethane:acetic acid (20 ml, 10%) at room temperature for 2 weeks. The reaction mixture was basified with saturated aqueous sodium carbonate solution. The aqueous layer was extracted with dichloromethane (2×) and the combined organic extracts washed with brine, dried (MgSO$_4$), filtered and evaporated under reduced pressure. The residue was purified by preparative HPLC (phenomonex magellenC$_{18}$ (2) aqueous TFA 0.1%:acetonitrile 1:19–19:1) to afford the title compound, 38 mg.

$^1$H NMR (400 MHz, CDCl$_3$): δ [ppm] 1.81–2.30 (14H, m), 2.40 (2H, m), 2.92 (2H, m), 3.05 (2H, m), 4.05 (2H, s), 5.05 (2H, m), 7.18 (2H, d), 7.22 (3H, m), 7.32 (4H, m)

LRMS: m/z 543 (MH$^+$)

EXAMPLE 34

N-{(1S)-3-[4-(3-{3-[(Methylsulfonyl)amino]benzyl}-1,2,4-oxadiazol-5-yl)-1-piperidinyl]-1-phenylpropyl}cyclobutanecarboxamide

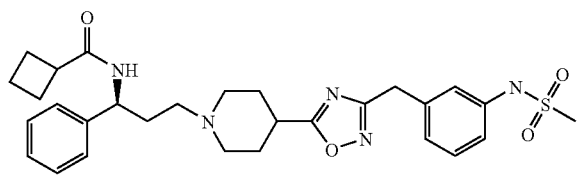

To a solution of the title compound of preparation 66 (220 mg, 0.91 mmol) in dichloromethane (10 ml) was added the title compound of preparation 115 (340 mg, 0.99 mmol), 1-(3-dimethylaminopropyl)-3-ethyl-carbodiimide hydrochloride (210 mg, 1.09 mmol) and triethylamine (1.08 ml, 7.12 mmol). The reaction was stirred at room temperature for 18 hours then water was added and the layers separated. The organic layer was washed with brine, dried (MgSO$_4$) and evaporated under reduced pressure. Toluene (25 ml) was added and the solution was heated under reflux for 5 hours. The reaction mixture was cooled and evaporated under reduced pressure. The crude material was purified by column chromatography on silica gel using dichloromethane:methanol:0.88 ammonia (95:5:0.5) as eluant to afford the title compound as a brown oil. This was freeze dried from water/acetonitrile to give the title compound as a brown foam, 100 mg.

Found C, 62.37; H, 6.92; N, 12.29%

C$_{29}$H$_{37}$H$_5$O$_4$S; 0.4H$_2$O requires C, 62.32; H, 6.82; N, 12.53%

$^1$H NMR (400 MHz, CDCl$_3$): δ [ppm] 1.79–1.99 (5H, m), 2.00–2.19 (8H, m), 2.20–2.40 (4H, m), 2.82–3.09 (7H, m), 3.42 (1H, m), 4.02 (2H, s), 5.09–5.17 (1H, m), 7.10–7.41 (9H, m)

LRMS: m/z 552.1 (MH$^+$)

[α]$_D$ –45.3 (c=2.12, methanol)

EXAMPLE 35

3,3,3-Trifluoro-N-{(1S)-3-[4-(3-{4-[(methylsulfonyl)amino]benzyl}-1,2,4-oxadiazol-5-yl)-1-piperidinyl]-1-phenylpropyl}propanamide

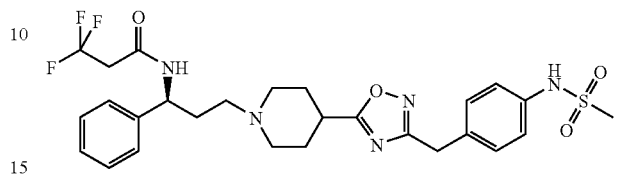

1-(3-Dimethylaminopropyl)-3-ethyl-carbodiimide hydrochloride (49 mg, 0.25 mmol) was added to a stirred solution of 3,3,3-trifluoropropionic acid (29 mg, 0.23 mmol) and the title compound of preparation 91 (100 mg, 0.21 mmol) in dichloromethane (10 ml). After 1 hour the reaction mixture was loaded directly onto a column of silica and eluted with dichloromethane: methanol:0.88 ammonia (95:5:0.5) to afford the title compound as a white foam, 55 mg.

$^1$H NMR (300 MHz, CDCl$_3$): δ [ppm] 1.73–2.35 (12H, m), 2.81–3.18 (8H, m), 4.03 (2H, s), 5.12 (1H, dd), 7.05–7.19 (8H, m), 8.34 (1H, d)

LRMS: m/z 580 (MH$^+$)

EXAMPLE 36

2-Cyclopropyl-N-{(1S)-3-[4-(3-{4-[(methylsulfonyl)amino]benzyl}1,2,4-oxadiazol-5-yl)-1-piperidinyl]-1-phenylpropyl}acetamide 1-(3-Dimethylaminopropyl)-3-ethyl-carbodiimide hydrochloride (49 mg, 0.25 mmol) was added to a stirred solution of cyclopropylacetic acid (24 mg, 0.23 mmol) and the title compound of preparation 91 (100 mg, 0.21 mmol) in dichloromethane (10 ml). After 1 hour the reaction mixture was loaded directly onto a column of silica and eluted with dichloromethane:methanol:0.88 ammonia (95:5:0.5) to afford the title compound as a white foam, 75 mg.

Found C, 62.06; H, 6.83; N, 12.49%

C$_{29}$H$_{37}$N$_5$SO$_4$; 0.5H$_2$O requires C, 62.12; H, 6.83; N, 12.49%

$^1$H NMR (300 MHz, CDCl$_3$): δ [ppm] 0.20 (2H, m), 0.58 (2H, m), 1.01 (1H, m), 1.81–2.00 (3H, m), 2.03–2.19 (7H, m), 2.21–2.43 (2H, m), 2.98 (6H, m), 4.02 (2H, s), 5.11 (1H, dd), 7.09–7.38 (9H, m)

LRMS: m/z 552 (MH$^+$)

[α]$_D$ –90.0 (C=1.00, MeOH)

EXAMPLE 37

N-{(1S)-3-[4-(3-{4-[(Methylsulfonyl)amino]benzyl}-1,2,4-oxadiazol-5-yl)-1-piperidinyl]-1-phenylpropyl}tetrahydro-2H-pyran-4-carboxamide

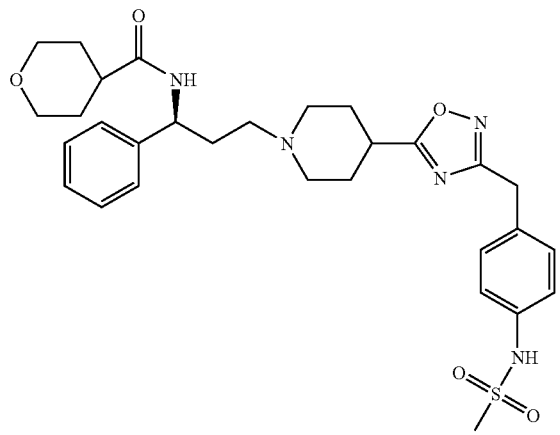

1-(3-Dimethylaminopropyl)-3-ethyl-carbodiimide hydrochloride (49 mg, 0.25 mmol) was added to a stirred solution of the title compound of preparation 17 (30 mg, 0.23 mmol) and the title compound of preparation 91 (100 mg, 0.21 mmol) in dichlorometnane (10 ml). After 1 hour the reaction mixture was loaded directly onto a column of silica and eluted with dichloromethane:methanol:0.88 ammonia (95:5:0.5) to afford the title compound as a white foam, 45 mg.

Found C, 59.39; H, 6.73; N, 11.21%

$C_{30}H_{39}N_5SO_5$; 1.5$H_2O$ requires C, 59.19; H, 6.95; N, 11.50%

$^1$H NMR (300 MHz, CDCl$_3$): δ [ppm] 1.71–2.15 (14H, m), 2.18–2.50 (3H, m), 2.84–3.12 (6H, m), 3.38 (2H, m), 3.89–4.09 (4H, m), 5.09 (1H, dd), 7.09–7.39 (8H, m), 7.81 (1H, d)

LRMS: m/z 582 (MH$^+$)

EXAMPLE 38

1-Acetyl-N-{(1S)-3-[4-(3-{4-[(methylsulfonyl)amino]benzyl}-1,2,4-oxadiazol-5-yl)-1-piperidinyl]-1-phenylpropyl}-3-azetidinecarboxamide

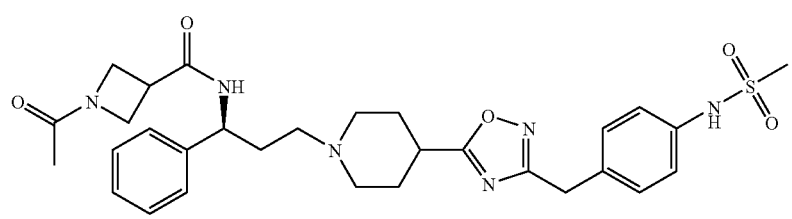

To a solution of the title compound of preparation 91 (100 mg, 0.21 mmol) in dichloromethane (3 ml) was added the title compound of preparation 14 (35 mg, 0.23 mmol) and 1-(3-dimethylaminopropyl)-3-ethyl-carbodiimide hydrochloride (50 mg, 0.25 mmol). The reaction was stirred at room temperature for 1 hour. The crude material was purified by column chromatography on silica gel, using dichloromethane:methanol:0.88 ammonia (90:10:1) as eluant to afford the title compound as a white foam, 102 mg.

Found C, 59.51; H, 6.59; N, 13.71%

$C_{30}H_{38}N_6O_5$; 0.6$H_2O$ requires C, 59.51; H, 6.53; N, 13.88%

$^1$H NMR (400 MHz, CDCl$_3$): δ [ppm] 1.69–2.20 (10H, m), 1.88 (3H, s), 2.25–2.35 (1H, m), 2.38–2.49 (1H, m), 2.81–3.10 (6H, m), 3.18–3.23 (1H, m), 4.05 (2H, s), 4.10–4.20 (3H, m), 4.38–4.45 (1H, m), 5.10–5.19 (1H, m), 7.17–7.38 (8H, m), 8.02–8.10 (0.5H, m), 8.30–8.39 (0.5H, m)

LRMS: m/z 595.2 (MH$^+$)

[α]$_D$: −33.2 (c=1.93, methanol)

EXAMPLE 39

N-{(1S)-3-[4-(3-Benzyl-1,2,4-oxadiazol-5-yl)-1-piperidinyl]-1-phenylpropyl}tetrahydro-2Ht-pyran-4-carboxamide

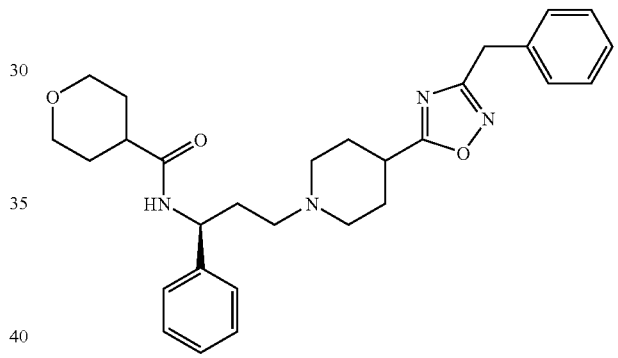

The title compound of preparation 81 (77 mg, 0.20 mmol), the title compound of preparation 17 (26 mg, 0.20 mmol) and 1-(3-dimethylaminopropyl)-3-ethylcarbodiimide hydrochloride (51 mg, 0.26 mmol) were stirred in dichloromethane (10 ml) at room temperature for 2 hours. The reaction mixture was then washed with brine (2×), dried (MgSO$_4$), filtered and concentrated under reduced pressure. The residue was purified by column chromatography on silica gel using dichlormethane:methanol (95:5) as eluant to afford the title compound as a white solid, 57 mg.

Found C, 69.85; H, 7.45; N. 11.11%

$C_{29}H_3N_4O_3$; 1$H_2O$, requires C, 71.30; H, 7.40; N, 11.50%

$^1$H NMR (400 MHz, CDCl$_3$): δ [ppm] 1.80–2.10 (12H, m), 2.20–2.40 (3H, m), 2.90 (2H, m), 3.05 (1H, d), 3.40 (2H, m), 4.00 (2H, m), 4.05 (2H, s), 5.10 (1H, m), 7.20–7.35 (10H, m), 7.90 (1H, d)

LRMS: m/z 489 (MH$^+$)

[α]$_D$ –32 (c=1.0, MeOH)

EXAMPLE 40

1-Acetyl-N-{(1S)-3-[4-(3-benzyl-1,2,4-oxadiazol-5-yl)-1-piperidinyl]-1-phenylpropyl}-3-azetidinecarboxamide

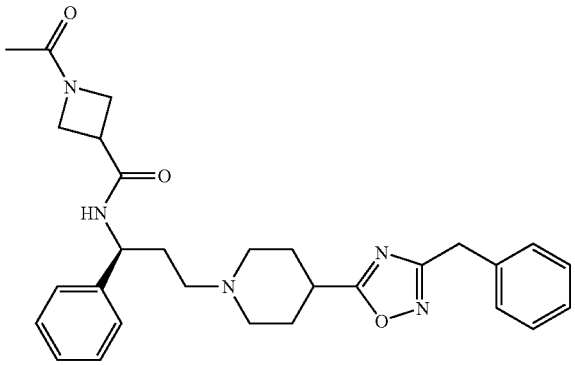

The title compound of preparation 81 (58 mg, 0.15 mmol), the title compound of preparation 14 (33 mg, 0.23 mmol) and 1-(3-dimethylaminopropyl)-3-ethylcarbodiimide hydrochloride (44 mg, 0.23 mmol) were stirred in dichloromethane (10 ml) at room temperature for 2 hours. The reaction mixture was then washed with brine (2×), dried (MgSO$_4$), filtered and concentrated under reduced pressure. The residue was purified by column chromatography on silica gel using dichlormethane:methanol (95:5) as eluant to afford the title compound as a white solid, 23 mg.

Found: C, 66.88; H, 7.25; N, 13.45%

C$_{29}$H$_{35}$N$_5$O$_3$; 1H$_2$O requires C, 69.44; H, 7.03; N, 13.96%

$^1$H NMR (400 MHz, CDCl$_3$): δ [ppm] 1.85 (3H, s), 1.90–2.40 (10H, m), 2.90–3.00 (2H, m), 3.20 (1H, m), 4.05 (2H, s), 4.18 (4H, m), 4.40 (1H, m), 5.15 (1H, m), 7.20–7.35 (10H, m), 8.00–8.15 (1H, dd)

LRMS: m/z 502 (MH$^+$)

[α]$_D$ –42 (c=1.00, MeOH)

EXAMPLE 41

1-(Acetylamino)-N-{(1S)-3-[4-(3-benzyl-1,2,4-oxadiazol-5-yl)-1-piperidinyl]-1-phenylpropyl}cyclopentanecarboxamide

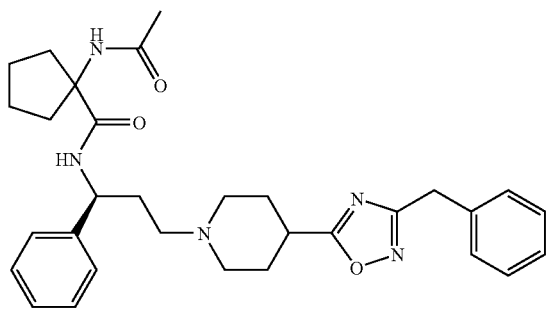

The title compound of preparation 81 (58 mg, 0.15 mmol), 1-(acetylamino)cyclopentanecarboxylic acid [Bull. Soc. Chim. Fr., (1965), 2942] (26 mg, 0.15 mmol) and 1-(3-dimethylaminopropyl)-3-ethylcarbodiimide hydrochloride (38 mg, 0.20 mmol) were stirred in dichloromethane (10 ml) at room temperature for 2 hours. The reaction mixture was then washed with brine (2×), dried (MgSO$_4$), filtered, then concentrated under reduced pressure. The residue was purified by column chromatography on silica gel using dichloromethane:methanol (98:2) as eluant to afford the title compound as a white solid 42 mg.

Found C, 68.37; H, 7.49; N, 12.78%

C$_{31}$H$_{39}$N$_5$O$_3$; 1H$_2$O requires C, 70.30; H, 7.42; N, 13.2%

$^1$H NMR (400 MHz, CDCl$_3$): δ [ppm] 1.90 (3H, s), 1.95–2.10 (14H, m), 2.30–2.35 (4H, m), 2.90 (2H, m), 2.95 (1H, m), 4.02 (2H, s), 5.05 (1H, m), 5.90 (1H, s), 7.20–7.30 (10H, m), 8.15 (1H, d)

LRMS: m/z 530 (MH$^+$)

[α]$_D$ –36 (c 1.0, MeOH)

EXAMPLE 42

N-{(1S)-3-[4-(3-Benzyl-1,2,4-oxadiazol-5-yl)-1-piperidinyl]-1-phenylpropyl}-1-methoxycyclobutanecarboxamide

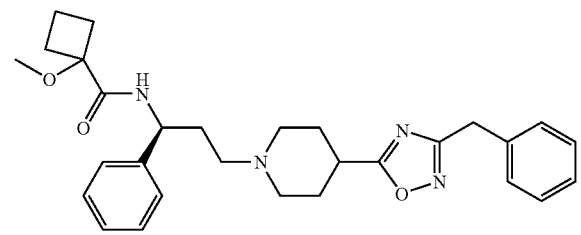

The title compound of preparation 81 (58 mg, 0.15 mmol), the title compound of preparation 19 (20 mg, 0.15 mmol) and 1-(3-dimethylaminopropyl)-3-ethylcarbodiimide hydrochloride (38 mg, 0.20 mmol) were stirred together in dichloromethane (10 ml) at room temperature for 2 hours. The reaction mixture was then washed with brine (2×), dried (MgSO$_4$), filtered and evaporated under reduced pressure. The residue was purified by column chromatography on silica gel using dichloromethane:methanol (99:1) as eluant to afford the title compound as a yellow oil, 31 mg.

$^1$H NMR (400 MHz, CDCl$_3$): δ [ppm] 1.75–2.40 (16H, m), 2.85–2.95 (3H, m), 3.20 (3H, s), 4.05 (2H, s), 5.10 (1H, m), 7.20–7.35 (10H, m), 8.00 (1H, d)

LRMS: m/z 489.2 (MH$^+$)

EXAMPLE 43

3-{[5-(1-{(3S)-3-[(Cyclobutylcarbonyl)amino]-3-phenylpropyl}-4-piperidinyl)-1,2,4-oxadiazol-3-yl]methyl}benzamide

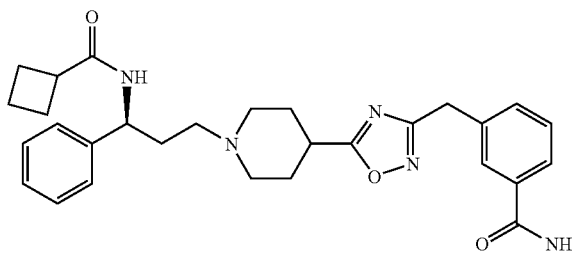

Oxalyl chloride (0.86 ml, 9.90 mmol) was added dropwise to a solution of the title compound of preparation 52 (1.45 g, 9.00 mmol) in dichloromethane (20 ml) and dimethylformamide (3 drops) at 0° C. The reaction was allowed to warm to room temperature and stirred for 12 hours then 0.88 ammonia (1 ml) was added cautiously, the solvent was evaporated under reduced pressure to furnish a yellow solid. The yellow solid was dissolved in methanol (30 ml) and water (30 ml) and hydroxylamine hydrochloride (3.15 g, 45.0 mmol) and sodium carbonate (4.77 g, 45.0 mmol) added. The reaction was heated under reflux for 5 hours, then cooled, filtered and the solvent evaporated under reduced pressure to give a yellow oil. The yellow oil was dissolved in dioxane (10 ml) and the title compound from preparation 115 (344 mg, 1.00 mmol) and 1-(3-dimethylaminopropyl)-3-ethyl-carbodiimide hydrochloride (210 mg, 1.10 mmol) were added and the reaction heated under reflux for 12 hours. The reaction was cooled and the solvent evaporated under reduced pressure. The resulting brown oil was purified by column chromatography on silica gel using dichloromethane:methanol:0.88 ammonia (95:5:0.5) as eluant to afford the title compound as a white foam, 16 mg.

$^1$H NMR (300 MHz, CDCl$_3$): δ [ppm] 1.83–2.41 (16H, m), 2.80–3.09 (5H, m), 4.15 (2H, s), 5.08 (1H, dd), 5.71 (1H, bs), 6.18 (1H, bs), 7.19–7.58 (7H, m), 7.71 (1H, d), 7.80 (1H, s)

LRMS: m/z 502 (MH$^+$)

EXAMPLE 44

Ethyl 4-(3-benzyl-1,2,4-oxadiazol-5-yl)-1-{(3S)-3-[(cyclobutylcarbonyl)amino]-3-phenylpropyl}-4-piperidinecarboxylate

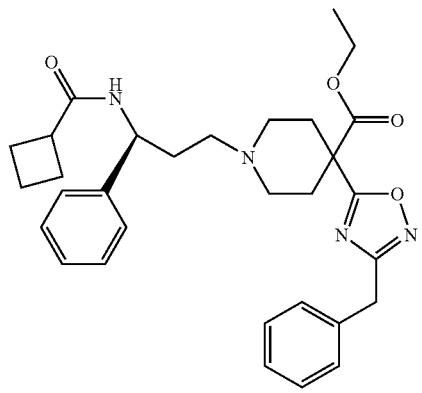

A suspension of the title compound of preparation 106 (195 mg, 0.62 mmol), the title compound of preparation 8 (215 mg, 0.93 mmol) and sodium triacetoxyborohydride (207 mg, 0.93 mmol) were stirred for 18 hours in dichloromethane:acetic acid (10 ml, 10%) at room temperature, then washed with saturated aqueous sodium carbonate solution. The organic extract was separated, pre-adsorbed on silica gel, concentrated and purified by column chromatography on silica gel using ethyl acetate as eluant to afford the title compound as an oil, 170 mg.

$^1$H NMR (300 MHz, CDCl$_3$): δ [ppm] 1.16 (3H, t), 2.18 (19H, m) 3.00 (1H, m), 4.06 (2H, s), 4.15 (2H, q), 5.10 (1H, m), 7.24 (10H, m)

LRMS: m/z 531 (MH$^+$)

EXAMPLE 45

N-{(1S)-3-[4-(3-Benzyl-1,2,4-oxadiazol-5-yl)-4-cyano-1-piperidinyl]-1-phenylpropyl}cyclobutanecarboxamide

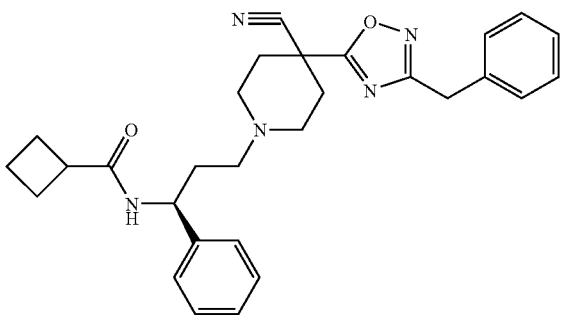

Sodium triacetoxyborohydride (294 mg, 1.32 mmol) was added to a solution of the title compound of preparation 107 (236 mg, 0.88 mmol) and the title compound of preparation 8 (305 mg, 1.32 mmol) in dichloromethane:acetic acid (10 ml, 10%). The reaction mixture was stirred for 18 hours at room temperature, then partitioned between dichloromethane and saturated aqueous sodium carbonate solu tion. The organic extract was separated, concentrated under reduced pressure and purified by column chromatography on silica gel using dichloromethane:methanol (95:5) as eluant to afford the title compound as a foam, 150 mg.

$^1$H NMR (300 MHz, CDCl$_3$): δ [ppm] 1.93 (6H, m), 2.30 (9H, m), 2.93 (4H, m), 4.09 (2H, s), 5.10 (1H, dd), 6.48 (1H, d), 7.26 (10H, m)

LRMS: m/z 484.2 (MH$^+$)

[α]$_D$ –38 (c=1, methanol)

EXAMPLE 46

N-[(1S)-3-(4-{3-[3-(Aminosulfonyl)benzyl]-1,2,4-oxadiazol-5-yl}-1-piperidinyl)-1-phenylpropyl]cyclobutanecarboxamide

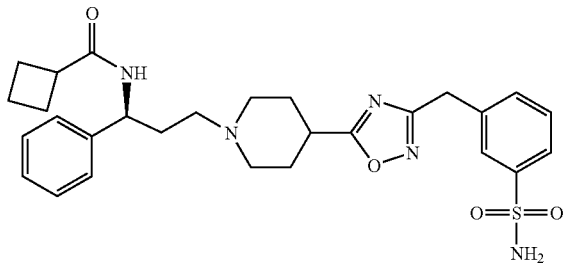

The title compound of preparation 115 (400 mg, 1.16 mmol), the title compound of preparation 65 (320 mg, 1.39 mmol) and 1-(3-dimethylaminopropyl)-3-ethyl-carbodiimide hydrochloride (267 mg, 11.39 mmol) were stirred in dioxane (30 ml) at room temperature for 1 hour. The reaction was then heated under reflux for 12 hours, cooled and the solvent evaporated under reduced pressure. The resulting brown oil was dissolved in ethyl acetate (100 ml) and washed with water, brine, dried (MgSO$_4$), filtered and the solvent evaporated under reduced pressure. The resulting brown oil was purified by column chromatography on silica gel using dichloromethane:methanol:0.88 ammonia (95:5:0.5) as eluant to afford the title compound as a foam, 250 mg.

Found C, 61.33; H, 6.56; N, 12.93%

C$_{28}$H$_{35}$N$_5$SO$_4$; 0.5H$_2$O requires C, 61.52; H, 6.64; N, 12.81%

$^1$H NMR (300 MHz, CDCl$_3$): δ [ppm] 1.78–2.41 (16H, m), 2.80–3.10 (5H, m), 4.18 (2H, s), 4.89 (2H, bs), 5.09 (1H, dd), 7.18–7.40 (5H, m), 7.42 (1H, m), 7.58 (1H, d), 7.81 (1H, d), 7.91 (1H, s)

LRMS: m/z 538 (MH$^+$)

EXAMPLE 47

1-{(3S)-3-[(Cyclobutylcarbonyl)amino]-3-phenylpropyl}-4-[3-(4-fluorobenzyl)-1,2,4-oxadiazol-5-yl]-N-methyl-4-piperidinecarboxamide

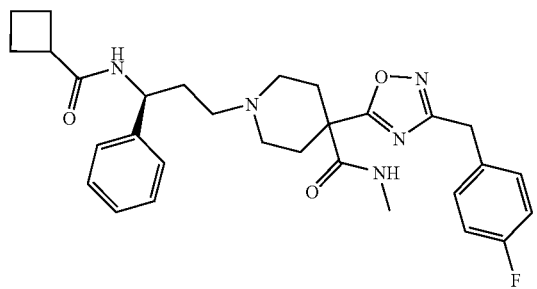

Sodium triacetoxyborohydride (159 mg, 0.71 mmol) was added to a solution of the title compound of preparation 109 (153 mg, 0.48 mmol) and the title compound of preparation 8 (164 mg, 0.71 mmol) in dichloromethane:acetic acid (10 ml, 10%). The reaction mixture was stirred for 18 hours at room temperature, then partitioned between dichloromethane and saturated aqueous sodium carbonate solution. The organic extract was separated, concentrated and purified by column chromatography on silica gel using dichloromethane:methanol (95:5) as eluant to afford the title compound as a foam, 60 mg.

$^1$H NMR (300 MHz, CDCl$_3$): δ [ppm] 1.41–2.53 (18H, m), 2.6–2.9 (4H, m), 3.02 (1H, q), 4.04 (2H, s), 5.12 (1H, dd), 5.88 (1H, s), 7.00 (2H, m), 7.26 (7H, m)

LRMS: m/z 534.5 (MH$^+$)

[α]$_D$ –28 (c=1, methanol)

EXAMPLE 48

N-((1S)-3-{4-[3-(4-Fluorobenzyl)-1,2,4-oxadiazol-yl]-1-piperidinyl}-1-phenylpropyl)tetrahydro-2H-pyran-4-carboxamide

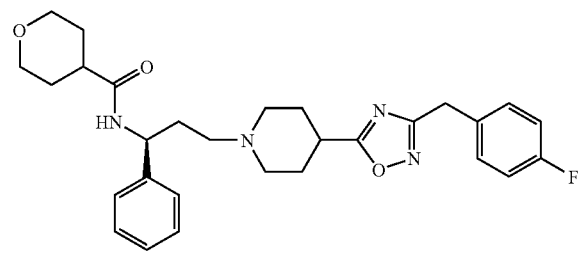

The title compound of preparation 92 (150 mg, 0.38 mmol), the title compound of preparation 17 (59 mg, 0.45 mmol) and 1-(3-dimethylaminopropyl)-3-ethylcarbodiimide hydrochloride (87 mg, 0.45 mmol) were stirred together in dichloromethane (10 ml) at room temperature for 2 hours. The reaction mixture was then washed with brine (2×), dried (MgSO$_4$), filtered and concentrated under reduced pressure. The residue was purified by column chromatography on silica gel using dichloromethane:methanol (98:2) as eluant to afford the title compound as a white solid, 113 mg.

Found C, 67.77; H, 6.99; N, 10.84%

C$_{29}$H$_{35}$N$_4$O$_3$F; 0.5H$_2$O requires C, 67.55; H, 7.04; N, 10.87%

$^1$H NMR (400 MHz, CDCl$_3$): δ [ppm] 1.80–2.10 (11H, m), 2.20–2.40 (4H, m), 2.90 (2H, m), 3.05 (1H, m), 3.40 (2H, t), 3.98 (2H, m), 4.00 (2H, s), 5.10 (1H, m), 7.00 (2H, m), 7.18–7.30 (7H, m), 7.90 (1H, d)

LRMS: m/z 507 (MH$^+$)

[α]$_D$ –30.6 (c=1.0, MeOH)

EXAMPLE 49

3,3,3-Trifluoro-N-((1S)-3-{4-[3-(4-fluorobenzyl)-1,2,4-oxadiazol-5-yl]-1-piperidinyl}-1-phenylpropyl)propanamide

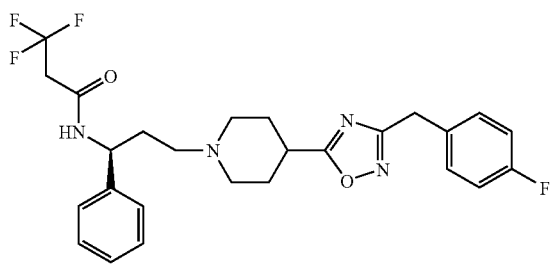

The title compound of preparation 92 (15 mg, 0.38 mmol), 3,3,3-trifluoropropionic acid (58 mg, 0.45 mmol) and 1-(3-dimethylaminopropyl)-3-ethylcarbodiimide hydrochloride (87 mg, 0.45 mmol) were stirred together in dichloromethane (10 ml) at room temperature for 2 hours. The reaction mixture was then washed with brine (2×), dried (MgSO$_4$), filtered and concentrated under reduced pressure. The residue was purified by column chromatography on silica gel using dichloromethane:methanol (95:5) as eluant to afford the title compound as an oil, 100 mg.

$^1$H NMR (400 MHz, CDCl$_3$): δ [ppm] 1.80–2.00 (3H, m), 2.00–2.20 (5H, m), 2.28 (1H, m), 2.40 (1H, m), 2.82–2.99 (2H, m), 3.00 (3H, m), 4.00 (2H, s), 5.18 (1H, dd), 7.00 (2H, m), 7.20–7.35 (7H, m), 8.40 (1H, d).

LRMS: m/z 505 (MH$^+$)

EXAMPLE 50

N-((1S)-3-{4-[3-(4-Morpholinylmethyl)-1,2,4-oxadiazol-5-yl]-1-piperidinyl}-1-phenylpropyl)cyclobutanecarboxamide

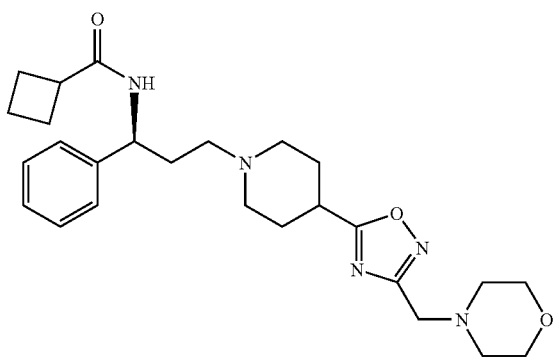

1(3-Dimethylaminopropyl)-3-ethyl-carbodiimide hydrochloride (190 mg, 0.91 mmol) was added to a solution of triethylamine (0.15 ml, 0.93 mmol) and the title compound of preparation 115 (300 mg, 0.91 mmol) in dichloromethane (30 ml) and the mixture stirred for 10 minutes. The title compound of preparation 58 (140 mg, 0.88 mmol) was added and the mixture stirred for 2 hours, then concentrated under reduced pressure. The residue was dissolved in dioxane (30 ml) and heated under reflux for 15 hours. The mixture was concentrated under reduced pressure and the residue taken up in saturated aqueous sodium carbonate solution and extracted with ethyl acetate (3×). The combined organic layers were washed with brine, dried (MgSO$_4$), filtered and evaporated under reduced pressure. The residue was purified by column chromatography on silica gel using dichloromethane:methanol:0.88 ammonia (97:3:0.3) as eluant to afford the title compound as a white foam, 40 mg.

Found C, 64.92; H, 8.05; N, 14.68%

C$_{26}$H$_{37}$N$_5$O$_3$; 0.75H$_2$O, requires C, 64.91; H, 8.07; N, 14.56%

$^1$H NMR (400 MHz, CDCl$_3$): δ [ppm] 1.81–2.42 (16H, m), 2.60 (4H, m), 2.84–3.08 (4H, m), 3.67 (2H, s), 3.75 (4H, m), 5.12 (2H, m), 7.20–7.25 (2H, m), 7.30–7.37 (3H, m)

LRMS: m/z 469 (MH$^+$)

EXAMPLE 51

N-((1S)-3-{4-Cyano-4-[3-(4-fluorobenzyl)-1,2,4-oxadiazol-5-yl]-1-piperidinyl}-1-phenylpropyl)tetrahydro-2H-pyran-4-carboxamide

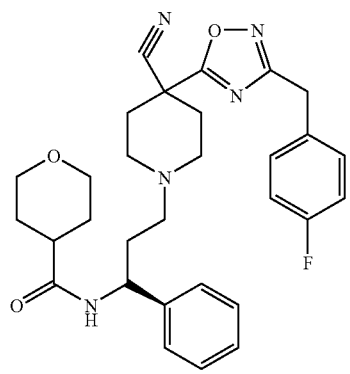

To a stirred solution of the title compound of preparation 111 (68 mg, 0.16 mmol) in dichloromethane (2 ml) was added the title compound of preparation 17 (25 mg, 0.19 mmol) and 1-(3-dimethylaminopropyl)-3-ethyl-carbodiimide (36 mg, 0.19 mmol). The reaction mixture was stirred for 2 hours at room temperature, then partitioned between dichloromethane and water. The organic extract was separated, concentrated under reduced pressure and the residue purified by column chromatography on silica gel using dichloromethane:methanol (90:10) as eluant to afford the title compound as a white foam, 31 mg.

$^1$H NMR (300 MHz, CDCl$_3$+DMSOd6): δ [ppm] 0.85 (1H, m), 1.54 (4H, m), 1.74 (2H, m), 1.98 (2H, m), 2.33 (6H, m), 2.94 (2H, m), 3.38 (2H, m), 3.97 (2H, m), 4.06 (2H, s), 5.09 (1H, dd), 6.73 (1H, d), 7.03 (2H, m), 7.26 (7H, m)

LRMS: m/z 532.6 (MH$^+$)

EXAMPLE 52

N-((1S)-3-{4-Cyano-4-[3-(4-fluorobenzyl)-1,2,4-oxadiazol-5-yl]-1-piperidinyl}-1-phenylpropyl)-2-cyclopropylacetamide

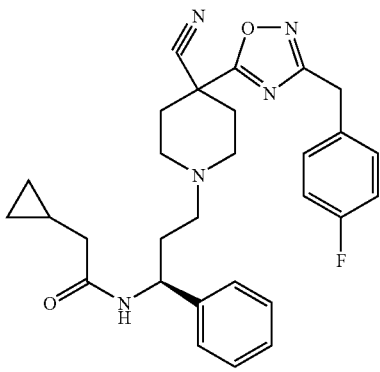

To a stirred solution of the title compound of preparation 111 (68 mg, 0.16 mmol) in dichloromethane (2 ml) was added cyclopropaneacetic acid (19 mg, 0.19 mmol) and 1-(3-dimethylaminopropyl)-3-ethyl-carbodiimide (36 mg, 0.19 mmol). The reaction mixture was stirred for 2 hours at room temperature, then partitioned between dichloromethane and water. The organic extract was separated, concentrated under reduced pressure and the residue purified by column chromatography on silica gel using dichloromethane:methanol (90:10) as eluant to afford the title compound as a white foam, 35 mg.

$^1$H NMR (300 MHz, CDCl$_3$+DMSOd6): δ [ppm] 0.18 (2H, m), 0.59 (2H, m), 0.90 (1H, m), 2.22 (12H, m), 2.90 (2H, m), 4.04 (2H, s), 5.12 (1H, dd), 6.58 (1H, d), 7.02 (2H, m), 7.26 (7H, m)

LRMS: m/z 502.6 (MH$^+$)

EXAMPLE 53

1-Acetyl-N-((1S)-3-{4-cyano-4-[3-(4-fluorobenzyl)-1,2,4-oxadiazol-5-yl]-1-piperidinyl}-1-phenylpropyl)-3-azetidinecarboxamide

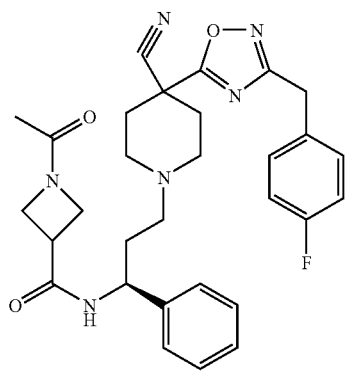

To a stirred solution of the title compound of preparation 111 (68 mg, 0.16 mmol) in dichloromethane (2 ml) was added the title compound of preparation 14 (27 mg, 0.19 mmol) and 1-(3-dimethylaminopropyl)-3-ethyl-carbodiimide (36 mg, 0.19 mmol). The reaction mixture was stirred for 2 hours at room temperature, then partitioned between dichloromethane and water. The organic extract was separated, concentrated under reduced pressure and the residue purified by column chromatography on silica gel using dichloromethane:methanol (90:10) as eluant to afford the title compound as a white foam, 33 mg.

$^1$H NMR (300 MHz, CDCl$_3$+DMSOd6): δ [ppm] 1.23 (2H, m), 1.83 (2H, m), 2.00 (3H, s), 2.38 (7H, m), 2.90 (2H, m), 3.08 (1H, m), 4.04 (2H, s), 4.12 (2H, m), 4.38 (1H, m), 5.12 (1H, dd), 7.02 (2H, m), 7.23 (7H, m)

LRMS: m/z 545.6 (MH$^+$)

EXAMPLE 54

N-((1S)-3-{4-Cyano-4-[3-(4-fluorobenzyl)-1,2,4-oxadiazol-5-yl]-1-piperidinyl}-1-phenylpropyl)-3,3,3-trifluoropropanamide

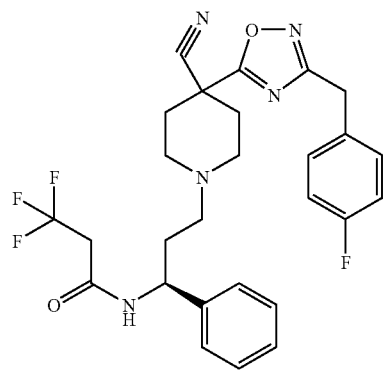

To a stirred solution of the title compound of preparation 111 (68 mg, 0.16 mmol) in dichloromethane (2 ml) was added 3,3,3-trifluoropropionic acid (24 mg, 0.19 mmol) and 1-(3-dimethylaminopropyl-3-ethyl-carbodiimide (36 mg, 0.19 mmol). The reaction mixture was stirred for 2 hours at room temperature, then partitioned between dichloromethane and water. The organic extract was separated, concentrated under reduced pressure and the residue purified by column chromatography on silica gel using dichloromethane:methanol (90:10) as eluant to afford the title compound as a white foam, 39 mg.

$^1$H NMR (300 MHz, CDCl$_3$): δ [ppm] 2.00 (2H, m), 2.38 (8H, m), 2.94 (2H, m), 3.05 (2H, q), 4.06 (2H, s), 5.18 (1H, dd), 7.02 (2H, m), 7.26 (7H, m)

LRMS: m/z 530.6 (MH$^+$)

EXAMPLE 55

N-[(1S)-3-(4-{3-[4-(Aminosulfonyl)benzyl]-1,2,4-oxadiazol-5-yl}-1-piperidinyl)-1-phenylpropyl]cyclobutanecarboxamide

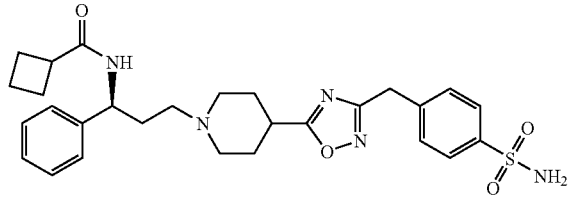

A solution of the title compound of preparation 64 (175 mg, 0.77 mmol), the title compound of preparation 115 (290 mg, 0.85 mmol) and 1-(3-dimethylaminopropyl)-3-ethyl-carbodiimide hydrochloride (176 mg, 0.92 mmol) in dioxane (25 ml) was stirred for 72 hours at room temperature and then heated under reflux for 5 hours. The mixture was cooled and evaporated under reduced pressure. The residue was purified by column chromatography on silica gel using dichloromethane:methanol:0.88 ammonia (95:5:0.5) as eluant to afford the title compound as a white solid, 10 mg.

Found C, 61.78; H, 6.74; N, 12.62%

$C_{27}H_{35}N_5SO_4$; $0.1CH_2Cl_2$ requires C, 61.80; H, 6.50; N, 12.82%

$^1$H NMR (400 MHz, CDCl$_3$): δ [ppm]: 1.18–1.22 (1H, m), 1.78–1.98 (5H, m), 2.00–2.19 (7H, m), 2.20–2.40 (4H, m), 2.82–3.09 (4H, m), 3.42–3.51 (1H, m), 4.10 (2H, m), 5.02–5.19 (2H, m), 7.18–7.28 (5H, m), 7.46 (2H, d), 7.86 (2H, d)

LRMS: m/z 538.5 (MH$^+$)

EXAMPLE 56

N-{(1S)-3-[3-Benzyl-1,2,4-oxadiazol-5-yl)-1-azetidinyl-1-phenylpropyl}tetrahydro-3-furancarboxamide

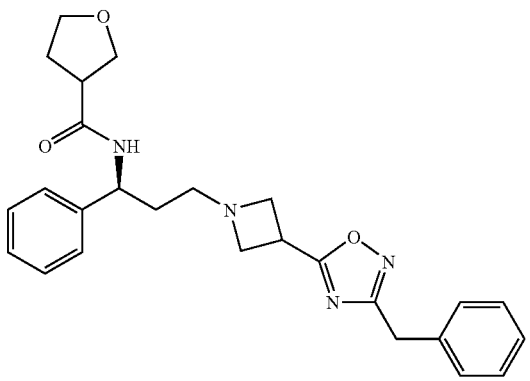

The title compound of preparation 93 (150 mg, 0.43 mmol) was added to a solution of tetrahydro-3-furoic acid (50 μl, 0.50 mmol) and 1-(3-dimethylaminopropyl-3-ethyl-carbodiimide hydrochloride (100 mg, 0.52 mmol) in dichloromethane and stirred for 4 hours. The mixture was basified by the addition of saturated aqueous sodium carbonate solution and extracted with ethyl acetate (3×). The combined organic layers were washed with brine, dried (MgSO$_4$), filtered and evaporated under reduced pressure. The residue was purified by column chromatography on silica gel using dichloromethane:methanol:0.88 ammonia (95:5:0.5) as eluant to afford the title compound as a white foam, 90 mg.

Found C, 68.57; H, 6.86; N, 12.33%

$C_{26}H_{30}N_4O_3$; $0.5H_2O$ requires C, 68.55; H, 6.86; N, 12.30%

$^1$H NMR (400 MHz, CDCl$_3$): δ [ppm] 1.76 (1H, m), 1.84 (1H, m), 2.13 (2H, m), 2.47 (1H, m), 2.52 (1H, m), 2.95 (1H, m), 3.45 (2H, m), 3.63 (2H, m), 3.82 (2H, m), 3.90 (3H, m), 4.11 (2H, s), 5.12 (1H, dd), 7.2–7.36 (10H, m), 7.70 (1H, m)

LRMS: m/z 447 (MH$^+$)

EXAMPLE 57

N-[(1S)-3-(4-{3-[(4-Acetyl-1-piperazinyl)methyl]-1,2,4-oxadiazol-5-yl}-1-piperidinyl)-1-phenylpropyl]cyclobutanecarboxamide

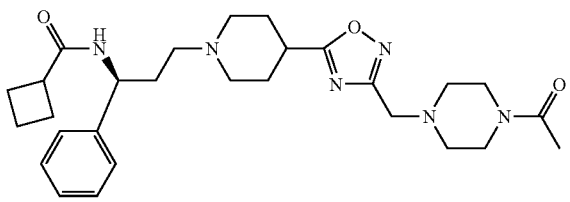

1-(3-Dimethylaminopropyl)-3-ethyl-carbodiimide hydrochloride (305 mg, 1.61 mmol) was added to a solution of triethylamine (0.22 ml, 1.63 mmol) and the title compound of preparation 115 (500 mg, 1.45 mmol) in dichloromethane (25 ml) and stirred for 10 minutes. The title compound of preparation 69 (350 mg, 1.81 mmol) was added and the mixture stirred for 2 hours then the mixture was concentrated under reduced pressure. The residue was dissolved in dioxane (25 ml) and heated under reflux for 15 hours. The mixture was concentrated under reduced pressure and the residue taken up in saturated aqueous sodium carbonate solution and extracted with ethyl acetate (3×). The combined organic layers were washed with brine, dried (MgSO$_4$), filtered and evaporated under reduced pressure. The residue was purified by column chromatography on silica gel using dichloromethane:methanol:0.88 ammonia (97:3:0.3) as eluant to afford the title compound as a white foam, 45 mg.

Found C, 63.49; H. 8.10; N, 15.90%

$C_{28}H_{40}N_6O_3$; $1H_2O$ requires C, 63.85; H, 8.04; N, 15.96%

$^1$H NMR (400 MHz, CDCl$_3$): δ [ppm] 1.8–2.2 (16H, m), 2.2–2.4 (4H, m), 2.54 (4H, m), 2.85–3.05 (4H, m), 3.51 (2H, m), 3.59 (2H, m), 3.62 (1H, s), 5.12 (1H, dd), 7.2–7.35 (2H, m), 7.37 (4H, m)

LRMS: m/z 510 (MH$^+$)

EXAMPLE 58

N-{(1S)-3-[3-Benzyl-1,2,4-oxadiazol-5-yl]-1-azetidinyl]-1-phenylpropyl}tetrahydro-3-furancarboxamide

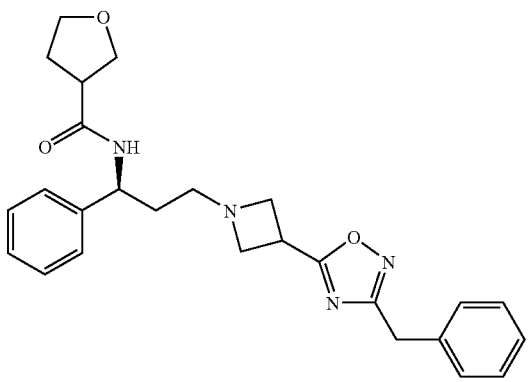

The title compound of preparation 93 (150 mg, 0.43 mmol) was added to a solution of tetrahydro-3-furoic acid (50 µl, 0.52 mmol) and 1-(3-dimethylaminopropyl)$_3$-ethylcarbodiimide hydrochloride (100 mg, 0.52 mmol) in dichloromethane and stirred for 4 hours. The mixture was basified by the addition of saturated aqueous sodium bicarbonate solution and extracted with ethyl acetate (3×). The combined organic layers were washed with brine, dried, (MgSO$_4$), filtered and evaporated under reduced pressure. The residue was purified by column chromatography on silica gel using dichloromethane:methanol:0.88 ammonia (95:5:0.5) as eluant to afford the title compound, 90 mg.

Found C, 68.57; H, 6.86; N, 12.33%

$C_{26}H_{30}N_4O_3$; 0.5H$_2$O requires C, 68.55; H, 6.86; N, 12.30%

$^1$H NMR (400 MHz, CDCl$_3$): δ [ppm] 1.76 (1H, m), 1.84 (1H, m), 2.13 (2H, m), 2.47 (1H, m), 2.52 (1H, m), 2.95 (1H, m), 3.45 (2H, q), 3.63 (2H, q), 3.82 (2H, m), 3.90 (3H, m), 4.11 (2H, s), 5.12 (1H, q), 7.2–7.36 (10H, m), 7.70 (1H, m)

LRMS: m/z 447 (MH$^+$)

EXAMPLE 59

N-{(1S)-3-[4-[3-(4-Fluorobenzyl)-1,2,4-oxadiazol-5-yl]-4-(methoxymethyl)-1-piperidinyl]-1-phenylpropyl}acetamide

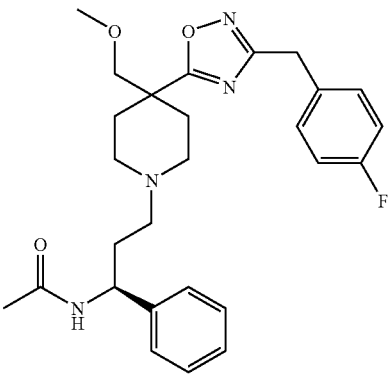

To a stirred solution of the title compound of preparation 151 (88 mg, 0.2 mmol) was added acetyl chloride (16 µl, 0.22 mmol) and triethylamine (31 µl, 0.22 mmol). The reaction mixture was stirred for 2 hours at room temperature, concentrated under reduced pressure and the residue purified by column chromatography on silica gel using dichloromethane:methanol (90:10) as eluant to afford the title compound as a white foam, 45 mg.

$^1$H NMR (300 MHz, CDCl$_3$): δ [ppm] 1.94 (9H, m), 2.31 (4H, m), 2.68 (1H, O m), 2.84 (1H, m), 3.22 (3H, s), 3.52 (2H, s), 4.04 (2H, u), 5.09 (1H, q), 6.99 (2H, t), 7.26 (7H, m), 7.64 (1H, m)

LRMS: m/z 481.3 (MH$^+$)

EXAMPLE 60

N-{3-[4-(3-Methyl-5-phenyl-4H-1,2,4-triazol-4-yl)-1-piperidinyl]-1-phenylpropyl}cyclobutanecarboxamide

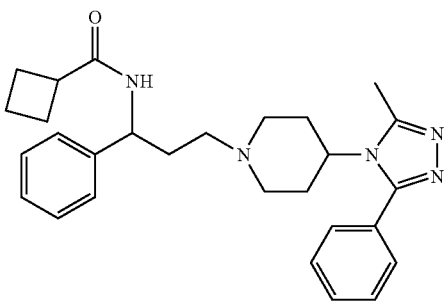

Sodium triacetoxyborohydride (525 mg, 2.47 mmol) was added to a solution of the title compounds of preparation 120 (400 mg, 1.65 mmol) and preparation 3 (419 mg, 1.82 mmol) in dichloromethane/acetic acid (90 ml, 10% solution). The reaction mixture was stirred for 30 minutes after which time the solution was basified using saturated aqueous sodium carbonate solution and the product extracted using dichloromethane (3×). The combined organic extracts were dried (MgSO$_4$), filtered and the solvent evaporated under reduced pressure to give a brown oil. This was purified by column chromatography on silica gel using dichloromethane:methanol:0.88 ammonia (98:2:0.3) as eluant to afford the title compound as a white foam that was freeze dried from water/acetonitrile to afford a white solid, 130 mg.

Found C, 71.54; H, 7.77; N, 14.88%

$C_{28}H_{35}N_5O$; $0.6H_2O$ requires C, 71.80; H, 7.79; N, 14.95%

$^1H$ NMR (400 MHz, $CDCl_3$): δ [ppm] 1.78–2.00 (8H, m), 2.06 (3H, m), 2.18–2.20 (5H, m), 2.61 (3H, s), 2.98 (3H, m), 4.01 (1H, m), 5.09 (1H, dd), 6.58 (1H, d), 7.18–7.30 (5H, m), 7.40–7.48 (5H, m)

LRMS: m/z 458 ($MH^+$)

EXAMPLE 61

N-{(1S)-3-[4-(3-Benzyl-5-methyl-4H-1,2,4-triazol-4-yl)-1-piperidinyl]-1-phenylpropyl}cyclobutanecarboxamide

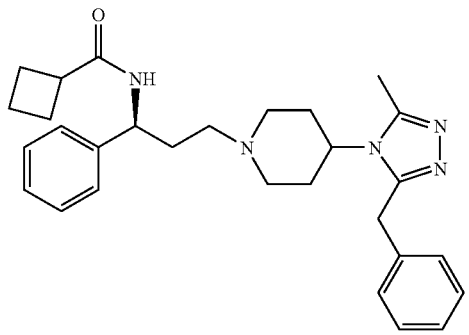

The title compound of preparation 121 (500 mg, 1.95 mmol) and the title compound of preparation 8 (902 mg, 3.91 mmol) were dissolved in dichloromethane (20 ml) and stirred for 5 minutes. Sodium triacetoxyborohydride (620 mg, 2.93 mmol) was then added and the mixture was stirred for a further 2 hours. The mixture was washed with saturated aqueous sodium bicarbonate solution, water and brine, dried ($MgSO_4$), filtered and evaporated under reduced pressure. The residue was purified by column chromatography on silica gel using dichloromethane:methanol:0.88 ammonia (95:5:0.5) as eluant to afford the title compound as a white foam, 330 mg.

Found C, 71.70; H, 8.11; N, 14.35%

$C_{29}H_{37}N_5O$; $0.8H_2O$ requires C, 71.66; H, 8.00; N, 14.41%

$^1H$ NMR (400 MHz, $CDCl_3$): δ [ppm] 1.29–1.42 (2H, m), 1.60–2.09 (9H, m), 2.10–2.18 (2H, m), 2.20–2.31 (3H, m), 2.53 (3H, s), 2.82–3.01 (3H, m), 3.70–3.82 (1H, m), 4.09 (2H, s), 5.00–5.10 (1H, m), 6.50–0.58 (1H, m), 7.17–7.38 (10H, m)

LRMS: m/z 473 ($MH^+$)

$[α]_D$ –34.3 (c=2.00, methanol)

EXAMPLE 62

N-{(1S)-3-[4-(5-Benzyl-4-methyl-4H-1,2,4-triazol-yl)-1-piperidinyl]-1-phenylpropyl}cyclobutanecarboxamide

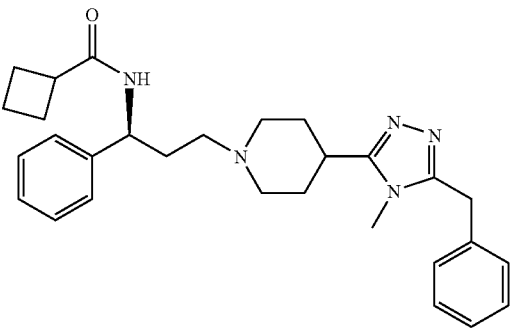

Sodium triacetoxyborohydride (318 mg, 1.50 mmol) was added to a solution of the title compounds of preparation 146 (256 mg, 1.00 mmol) and preparation 8 (231 mg, 1.00 mmol) in dichloromethane:acetic acid (10 ml, 10% solution). The reaction mixture was stirred for 30 minutes after which time the solution was basified using saturated aqueous sodium carbonate solution and the product was extracted using dichloromethane (3×). The combined organic extracts were dried ($MgSO_4$), filtered and the solvent evaporated under reduced pressure to give a brown oil. This was purified by column chromatography on silica gel using dichloromethane:methanol:0.88 ammonia (95:5:0.5) as eluant to afford the title compound as a white foam, 70 mg.

Found C, 71.91; H, 7.78; N, 14.04%

$C_{29}H_{37}N_5O$; $0.8H_2O$ requires C, 71.66; H, 8.00; N, 14.41%

$^1H$ NMR (400 MHz, $CDCl_3$): δ [ppm] 1.78–2.40 (17H, m), 2.59 (1H, m), 2.89–3.17 (3H, m), 3.30 (3H, s), 4.20 (2H, m), 5.18 (1H, dd), 7.16–7.40 (9H, m), 7.63 (1H, d)

LRMS: m/z 472 ($MH^+$)

EXAMPLE 63

N-{(1S)-3-[4-(3-Benzyl-1H-1,2,4-triazol-1-yl)-1-piperidinyl]-1-phenylpropyl}-cyclobutanecarboxamide

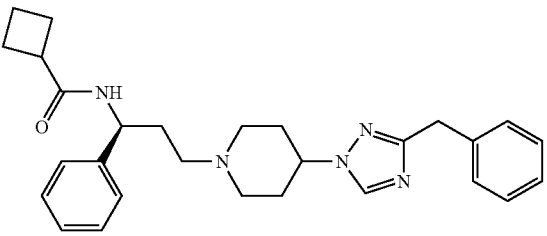

Sodium triacetoxyborohydride (190 mg, 0.92 mmol) was added to a solution of the title compound of preparation 134 (220 mg, 0.61 mmol) and the title compound of preparation 8 (200 mg, 0.82 mmol) in dichloromethane:acetic acid (20 ml, 10% solution) and stirred at room temperature for 15 hours. The mixture was basified by the addition of saturated aqueous sodium carbonate solution and extracted with dichloromethane (3×). The combined organic extracts were washed with brine and dried (MgSO$_4$), filtered and solvent evaporated under reduced pressure. The residue was purified by column chromatography on silica gel using dichloromethane:methanol:0.88 ammonia (97:3:0.3) as eluant This gave a brown oil which was further purified by column chromatography on silica gel using toluene:ethyl acetate:diethylamine (90:10:1) as eluant to afford the title compound as a white solid, 106 mg.

Found C, 72.01; H, 7.81; N, 14.72%

$C_{28}H_{35}N_5O$; 0.5H$_2$O requires C, 72.07; H, 7.78; N, 15.01%

$^1$H NMR (400 MHz, CDCl$_3$): δ [ppm] 1.80–2.40 (17H, m), 3.00 (3H, m), 4.05 (2H, s), 4.10 (1H, m), 5.15 (1H, dd), 7.25–7.35 (10H, m), 8.00 (1H, s)

LRMS: m/z 458 (MH$^+$)

[α]$_D$ −39.6 (c=0.1, methanol)

EXAMPLE 64

N-{(1S)-3-[4-(5-Benzyl-1-methyl-1H-1,2,4-triazol-3-yl)-1-piperidinyl]-1-phenylpropyl}cyclobutanecarboxamide

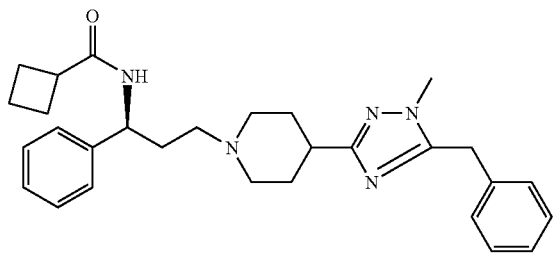

Sodium triacetoxyborohydride (290 mg, 1.40 mmol) was added to a solution of the title compound of preparation 8 (310 mg, 1.34 mmol) and the title compound of preparation 130 (230 mg, 0.93 mmol) in dichloromethane:acetic acid (10 ml, 10% solution) and stirred at room temperature for 15 hours. The reaction mixture was basified by the addition of saturated aqueous sodium bicarbonate solution and extracted with dichloromethane (3×). The combined organic layers were washed with brine, dried (MgSO$_4$), filtered and concentrated under reduced pressure. The residue was purified by column chromatography on silica gel using toluene: ethyl acetate: diethylamine (80:20:1) as eluant to afford the title compound, 210 mg.

Found C, 70.94; H, 8.05; N, 14.28%

$C_{29}H_{37}N_5O$; H$_2$O requires C, 71.13; H, 8.03; N, 14.30%

$^1$H NMR (400 MHz, CDCl$_3$): δ [ppm] 1.71–2.42 (16H, m), 2.70 (1H, m), 2.80 (1H, d), 3.10 (2H, m), 3.61 (3H, s), 4.16 (2H, s), 5.10 (1H, m), 7.15–7.35 (10H, m), 8.05 (1H, bs)

LRMS: m/z 473 (MH$^+$)

[α]$_D$ −42 (c=0.1, methanol)

EXAMPLE 65

N-{3-[4-(5-Benzyl-1H-1,2,4-triazol-3-yl)-1-piperidinyl]-1-phenylpropyl}cyclobutanecarboxamide

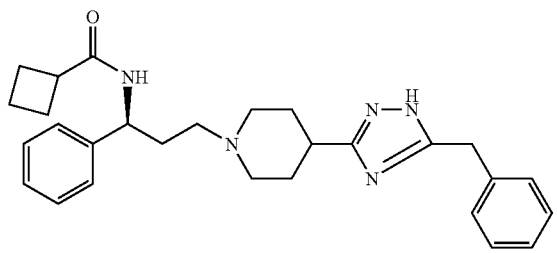

Sodium triacetoxyborohydride (490 mg, 2.32 mmol) was added to a solution of the title compound of preparation 129 (1.09 g, 1.55 mmol) and the title compound of preparation 8 (717 mg, 3.01 mmol) in dichloromethane (20 ml) and stirred at room temperature for 15 hours. The mixture was basified by the addition of saturated aqueous sodium bicarbonate solution and extracted with dichloromethane (3×). The combined organic layers were dried (MgSO$_4$), filtered and the solvent evaporated under reduced pressure. The residue was purified by column chromatography on silica gel using dichloromethane:methanol:0.88 ammonia (190:10:1) giving impure material which was further purified by preparative HPLC (phenomonex magellenC$_8$ (2) aqueous TFA 0.1%:acetonitrile 1:19–19:1) and freeze dried from acetonitrile:water to afford the title compound as a white foam, 75 mg.

Found: C, 53.65; H, 5.48; N, 9.51%

$C_{28}H_{35}N_5O$; 2CF$_3$CO$_2$H, 1.5; H$_2$O requires C, 53.93; H, 5.66; N, 9.83%

$^1$H NMR (400 MHz, CDCl$_3$): δ [ppm] 1.77–2.00 (2H, m), 2.12–2.41 (9H, m), 2.85–2.95 (2H, m), 3.0–3.2 (4H, m), 3.40 (2H, m), 3.60 (2H, d), 4.20 (2H, m), 5.00 (1H, m), 6.40 (1H, d), 7.23–7.44 (10H, m)

LRMS: m/z 459 (MH$^+$)

EXAMPLE 66

N-{(1S)-3-[4-(3-{4-[(methylsulfonyl)amino]benzyl}-1H-1,2,4-triazol-1-yl)-1-piperidinyl]-1-phenylpropyl}tetrahydro-2H-pyran-4-carboxamide

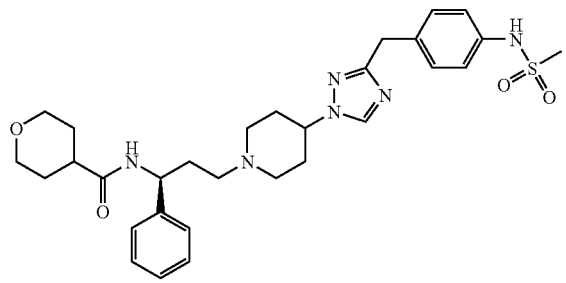

The title compound of preparation 138 (135 mg, 0.24 mmol) was stirred for 1 hour at 37° C. in a mixture of trifluoroacetic acid:dichloromethane (4 ml, 10:1). The solvents were evaporated under reduced pressure and the residue basified with saturated aqueous sodium bicarbonate solution and extracted with dichloromethane (6×). The combined organic layers were dried (MgSO₄), filtered and evaporated under reduced pressure. The residue (90 mg, 0.19 mmol), the title compound of preparation 17 (25 mg, 0.19 mmol), 1-hydroxybenzotriazole hydrate (29 mg, 0.21 mmol) and 1-(3-dimethylaminopropyl)-3-ethyl-carbodiimide hydrochloride (44 mg, 0.23 mmol) were stirred together for 3 hours at room temperature in dichloromethane (5 ml). The reaction mixture was diluted with dichloromethane and washed with saturated aqueous sodium carbonate solution, then water. The organic layer was dried (MgSO₄), filtered and evaporated under reduced pressure. Trituration with diethyl ether yielded a solid which was recrystallized from ethanol/isopropyl alcohol to afford the title compound as a crystalline solid, 60 mg.

Found C, 61.30; H, 6.89; N, 14.27%

$C_{30}H_{40}N_6O_4S$; 0.4$H_2O$ requires C, 61.29; H, 6.99; N, 14.29%

$^1$H NMR (400 MHz, CD₃OD): δ [ppm] 1.60–1.84 (4H, m), 1.90–2.03 (2H, m), 2.03–2.26 (6H, m), 2.32–2.44 (2H, m), 2.44–2.55 (1H, m), 2.89 (3H, s), 2.98–3.08 (2H, m), 3.39–3.50 (2H, m), 3.90–4.00 (2H, m), 4.08 (2H, s), 4.19–4.29 (1H, m), 4.94–5.00 (1H, m), 7.13–7.18 (2H, d), 7.19–7.26 (3H, d), 7.26–7.35 (4H, m), 8.37 (1H, s)

LRMS: m/z 581.2 (MH⁺)

Melting point [° C.]: 210–211

EXAMPLE 67

2-Cyclopropyl-N-{(1S)-3-[4-(3-{4-(methylsulfonyl)amino]benzyl}-1H-1,2,4-triazol-1-yl)-1-piperidinyl]-1-phenylpropyl}acetamide

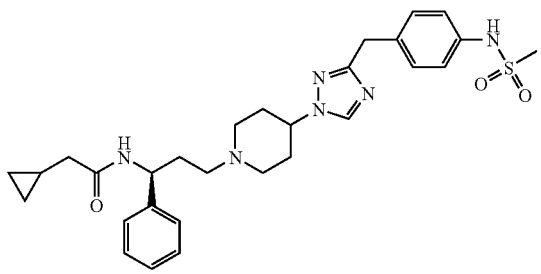

The title compound was prepared using a procedure similar to that described in example 66 from the title compound of preparation 138 and 2-cyclopropylacetic acid in a 35% yield and was recrystallised from isopropyl alcohol/ethyl acetate.

Found C, 62.45; H, 6.95; N, 15.02%

$C_{29}H_{38}N_6O_3S$; 0.4$H_2O$ requires C, 62.43; H, 7.0; N, 15.06%

$^1$H NMR (400 MHz, CD₃OD): δ [ppm] 0.16–0.20 (2H, m), 0.48–0.52 (2H, m), 1.00–1.08 (1H, m), 1.94–2.03 (2H, m), 2.03–2.26 (8H, m), 2.32–2.47 (2H, m), 2.90 (3H, s), 3.00–3.08 (2H, m), 4.00 (2H, s), 4.18–4.27 (1H, m), 4.94–5.00 (1H, m), 7.13–7.20 (2H, d), 7.20–7.26 (3H, m), 7.26–7.35 (4H, m), 8.35 (1H, d)

LRMS: m/z 551.2 (MH⁺)

Melting point [° C.]: 185–186

EXAMPLE 68

3,3,3-Trifluoro-N-{(1S)-3-[4-(3-{4-[(methylsulfonyl)amino]benzyl}-1H-1,2,4-triazol-1-yl)-1-piperidinyl]-1-phenylpropyl)propanamide

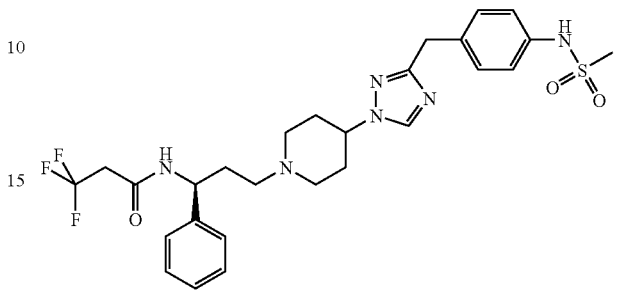

The title compound was prepared using a procedure similar to that described in example 66 from the title compound of preparation 138 and 3,3,3-trifluoropropionic acid in a 35% yield and was recrystallised from ethyl acetate.

Found C, 55.88; H, 5.95; N, 14.67%

$C_{27}H_{33}F_3N_6O_3S$ requires C, 56.04; H. 5.75; N, 14.52%

$^1$H NMR (400 MHz, CD₃OD): δ [ppm] 1.95–2.03 (2H, m), 2.03–2.21 (6H, m), 2.34–2.44 (3H, m), 2.90 (3H, s), 2.97–3.05 (2H, m), 3.10–3.24 (2H, m), 3.29 (1H, S), 4.00 (2H, s), 4.20–4.27 (1H, m), 4.95–5.02 (1H, m), 7.13–7.16 (2H, d), 7.20–7.26 (3H, m), 7.32–7.35 (4H, m), 8.37 (1H, s)

LRMS: m/z 579.1 (MH⁺)

Melting point [° C.]: 162–163

EXAMPLE 69

N-(1S)-{3-[4-(3-Benzyl-1-methyl-1H-1,2,4-triazol-5-yl)-1-piperidinyl]-1-phenylpropyl}cyclobutanecarboxamide

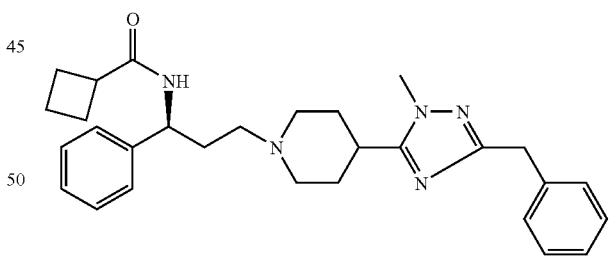

Methyl iodide (0.41 ml, 6.42 mmol) was added to a suspension of the title compound of preparation 127 (1.00 g, 2.90 mmol) and potassium carbonate (480 mg, 3.51 mmol) in acetonitrile (20 ml) and the mixture stirred at room temperature for 15 hours. The mixture was concentrated under reduced pressure and the residue taken up in water (100 ml) and extracted with dichloromethane (×3). The combined organic layers were washed with brine, dried (MgSO₄), filtered and concentrated under reduced pressure. The residue was purified by column chromatography on silica gel, using dichloromethane: methanol (98:2) as eluant to afford a whits solid. Trifluoroacetic acid (2 ml) was added to a solution of the white solid in dichloromethane (10 ml)

at 0° C. and the mixture was allowed to warm to room temperature for 15 hours. The mixture was evaporated under reduced pressure and the residue taken up in saturated aqueous sodium carbonate solution and extracted with dichloromethane (×3). The combined organic layers were washed with brine, dried (MgSO$_4$), filtered and the filtrate evaporated under reduced pressure to afford a pale yellow oil. Sodium triacetoxyborohydride (420 mg, 2 mmol) was added to a solution of piperidine, acetic acid (0.10 ml, 5.70 mmol) and the title compound of preparation 8 (310 mg, 1.32 mmol) in dichloromethane (15 ml) and stirred at room temperature for 15 hours. The mixture was treated with 2M hydrochloric acid (1 ml). The mixture was basified by the addition of saturated aqueous sodium bicarbonate solution and extracted with dichloromethane (3×). The combined organic layers were dried (MgSO4), filtered and solvent evaporated under reduced pressure. The residue was purified by column chromatography on silica gel using dichloromethane: methanol:0.88 ammonia (92:8:1) as eluant giving crude material which was further purified by HPCL (phenomonex Lunac C$_8$ and phenomonex Magellen C$_{18}$ (2) using an eluant of ammonium acetate solution and acetonitrile) and freeze-dried from water/acetonitrile to afford the title compound as a white foam, 40 mg.

Found C, 71.11; H, 7.99; N, 14.18%.

$C_{29}H_{37}N_5O$; 1H$_2$O requires C, 71.13; H, 8.03; N, 14.30%

$^1$H NMR (400 MHz, CDCl$_3$): δ [ppm] 1.74–1.42 (16H, m), 2.63–2.72 (1H, m), 2.90–2.98 (1H, m), 3.00–3.16 (2H, m), 3.75 (3H, s), 4.02 (2H, s), 5.12 (1H, m), 7.15–7.37 (10H, m), 7.72 (1H, d)

LRMS: m/z 473 (MH$^+$)

EXAMPLE 70

4-{[1-(1-{(3S)-3-Phenyl-3-[(3,3,3-trifluoropropanoyl)amino]propyl}-4-piperidinyl)-1H-1,2,4-triazol-3-yl]methyl}benzamide

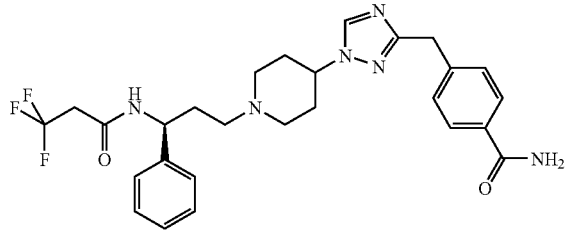

The title compound of preparation 136 (700 mg, 1.35 mmol), cyanuric chloride (125 mg, 0.67 mmol) and triethylamine (0.23 ml, 1.35 mmol) were stirred together at room temperature for 1 hour in acetone (30 ml). The solvent was evaporated under reduced pressure and the residue dissolved in tetrahydrofuran (10 ml) and 0.88 ammonia (10 ml) added. The solvents were evaporated under reduced pressure and the residue purified by column chromatography on silica gel using dichloromethane:methanol:0.88 ammonia (95:5:0.5) as eluant to afford a solid, 280 mg. The solid (280 mg, 0.54 mmol) was stirred for 2 hours at room temperature in a 10 ml mixture of trifluoroacetic acid:dichloromethane (1:1). The solvents were evaporated under reduced pressure and the residue basified with saturated aqueous sodium carbonate solution and extracted with dichloromethane (×6). The combined organic layers were dried (MgSO$_4$), filtered and evaporated under reduced pressure. The residue (70 mg, 0.17 mmol), 3,3,3-trifluoropropanoic acid (21 mg, 0.17 mmol), 1-(3-dimethylaminopropyl)-3-ethyl-carbodiimide hydrochloride (35 mg, 0.18 mmol) and triethylamine (28 µl, 0.20 mmol) were stirred together for 16 hours at room temperature in dichloromethane (5 ml). The solvent was evaporated under reduced pressure and the residue dissolved in ethyl acetate and washed with saturated aqueous sodium carbonate solution, then water. The organic layer was dried (MgSO$_4$), filtered and evaporated under reduced pressure. The residue was recrystallized from ethyl acetate/hexane to afford the title compound as a crystalline solid, 21 mg.

Found C, 60.14; H, 6.07; N, 15.44%

$C_{27}H_{29}F_3N_6O_2$; 0.6H$_2$O requires C, 60.12; H, 6.02; N, 15.58%

$^1$H NMR (400 MHz, CDCl$_3$): δ [ppm] 1.82–1.92 (1H, m), 1.92–2.26 (7H, m), 2.26–2.37 (1H, m), 2.37–2.47 (1H, m), 2.92–3.01 (1H, m), 3.01–3.16 (3H, m), 4.10 (3H, s), 5.13–5.21 (1H, m), 5.40–5.70 (1H, bs), 5.90–6.20 (1H, bs), 7.20–7.29 (3H, m), 7.29–7.37 (2H, m), 7.37–7.45 (2H, d), 7.71–7.79 (2H, d), 7.97 (1H, s), 8.03–8.10 (1H, m)

LRMS: m/z 529.3 (MH$^+$)

EXAMPLE 71

N-{(1S)-3-[4-(3-Benzyl-5-methyl-1H-1,2,4-triazol-1-yl)-1-piperidinyl]-1-phenylpropyl}tetrahydro-2H-pyran-4-carboxamide

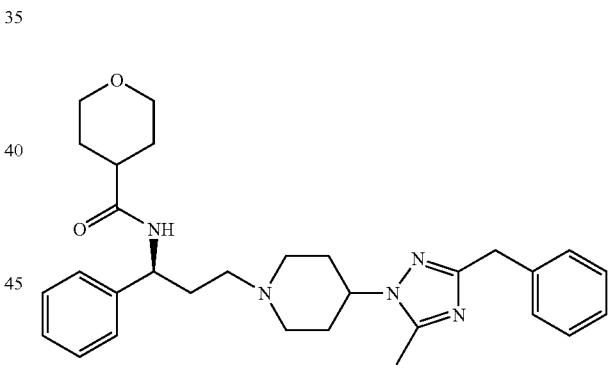

1-(3-Dimethylaminopropyl)-3-ethyl-carbodiimide hydrochloride (59 mg, 0.31 mmol) was added to a stirred solution of the title compound of preparation 17 (40 mg, 0.31 mmol) and the title compound of preparation 142 (100 mg, 0.25 mmol) in dichloromethane (10 ml). After 1 hour the reaction mixture was loaded directly onto a column of silica and eluted with dichloromethane:methanol:0.88 ammonia (95:5:0.5) to afford the title compound as a white foam, 98 mg.

Found C, 69.01; H, 7.63; N, 13.27%

$C_{30}H_{39}N_5O_2$; 1.1H$_2$O requires C, 69.10; H, 7.96; N, 13.43%

$^1$H NMR (300 MHz, CDCl$_3$): δ [ppm] 1.76–2.08 (13H, m), 2.10–2.51 (6H, m), 2.99 (1H, d), 3.20 (1H, d), 3.49 (2H, m), 3.82–4.17 (5H, m), 5.18 (1H, dd), 7.12–7.36 (9H, m), 8.20 (1H, d)

LRMS: m/z 503 (MH$^+$)

EXAMPLE 72

N-{(1S)-3-[4-(3-Benzyl-5-methyl-1H-1,2,4-triazol-1-yl)-1-piperidinyl]-1-phenylpropyl}tetrahydro-3-furancarboxamide

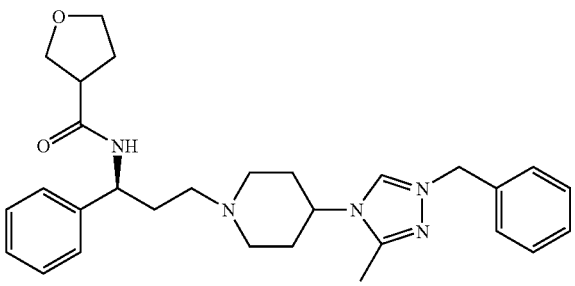

1(3-Dimethylaminopropyl)-3-ethyl-carbodiimide hydrochloride (59 mg, 0.31 mmol) was added to a stirred solution of tetrahydro-3-furoic acid (36 mg, 0.31 mmol) and the title compound of preparation 142 (100 mg, 0.25 mmol) in dichloromethane (10 ml). After 1 hour the reaction mixture was loaded directly onto a column of silica and eluted with dichloromethane:methanol:0.88 ammonia (95:5:0.5) to afford the title compound as a white foam, 107 mg.

Found C, 67.51; H, 7.44; N, 13.40%

$C_{29}H_{37}N_5O_2$; $1H_2O$; $0.15CH_2Cl_2$ requires C, 67.54; H, 7.64; N, 13.51%

$^1$H NMR (300 MHz, CDCl$_3$): δ [ppm] 1.80–1.99 (3H, m), 2.00–2.41 (14H, m), 3.00 (2H, m), 3.18 (1H, m), 3.80 (1H, m), 3.98 (5H, m), 5.17 (1H, m), 7.18–7.35 (9H, m), 8.82 (1H, d)

LRMS: m/z 488 (MH$^+$)

EXAMPLE 73

1-Amino-N-{(1S)-3-[4-(3-benzyl-5-methyl-1H-1,2,4-triazol-1-yl)-1-piperidinyl]-1-phenylpropyl}cyclopentanecarboxamide

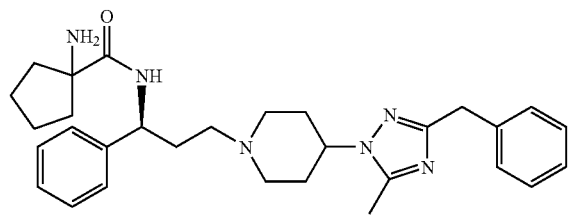

1-(3-Dimethylaminopropyl)-3-ethyl-carbodiimide hydrochloride (118 mg, 0.62 mmol) was added to a stirred solution of the title compound of preparation 15 (141 mg, 0.62 mmol) and the title compound of preparation 142 (200 mg, 0.50 mmol) in dichloromethane (20 ml). After 1 hour trifluoroacetic acid (5 ml) was added and the reaction stirred for 12 hours. The solvent was evaporated under reduced pressure and the resulting oil was loaded directly onto a column of silica and eluted with dichloromethane:methanol:0.88 ammonia (95:5:0.5) to afford the title compound as a white foam, 170 mg.

Found C, 70.24; H, 8.05; N, 16.35%

$C_{30}H_{40}N_6O$; $0.6H_2O$ requires C, 70.45; H, 8.12; N, 16.43%

$^1$H NMR (300 MHz, CDCl$_3$): δ [ppm] 1.40 (4H, m), 1.62–2.09 (10H, m), 2.1–2.41 (9H, m), 2.98 (1H, d), 3.10 (1H, d), 3.98 (3H, m), 5.10 (1H, dd), 7.06–7.38 (10H, m), 8.95 (1H, d)

LRMS: m/z 501 (MH$^+$)

EXAMPLE 74

N-{(1S)-3-[4-(3-Benzyl-1H-1,2,4-triazol-1-yl)-1-piperidinyl]-1-phenylpropyl}tetrahydro-3-furancarboxamide

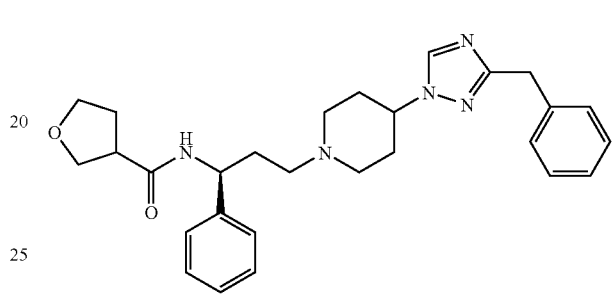

The title compound of preparation 134 (1.17 g, 4.83 mmol), the title compound of preparation 7 (1.20 g, 4.83 mmol) and sodium triacetoxyborohydride (1.53 g, 7.24 mmol) were stirred together for 30 minutes at room temperature in dichloromethane:acetic acid (30 ml, 10%). The solvents were evaporated under reduced pressure and the residue basified with saturated aqueous sodium carbonate solution and extracted with dichloromethane (3×). The combined organic layers were dried (MgSO$_4$), filtered and evaporated under reduced pressure. The residue (2.3 g, 4.83 mmol) was stirred for 16 hours in a mixture of dichloromethane:trifluoroacetic acid (30 ml, 5:1). The solvents were evaporated under reduced pressure and the residue basified with saturated aqueous sodium carbonate solution and extracted with dichloromethane (3×). The combined organic layers were dried (MgSO$_4$), filtered and evaporated under reduced pressure. A portion of the residue (200 mg, 0.53 mmol), tetrahydro-3-furancarboxylic acid (65 mg, 0.65 mmol) and 1-(3-dimethylaminopropyl)-3-ethyl-carbodiimide hydrochloride (125 mg, 0.65 mmol) were stirred together for 1 hour at room temperature in dichloromethane (5 ml). The solvent was evaporated under reduced pressure. The residue was dissolved in ethyl acetate and washed with saturated aqueous sodium carbonate solution, then water. The organic layer was dried (MgSO$_4$), filtered and evaporated under reduced pressure. The residue was purified by column chromatography on silica gel using dichloromethane:methanol:0.88 ammonia (95:5:0.5) as eluant to afford the title compound as a gum, 183 mg.

Found C, 69.42; H, 7.53; N. 14.46%

$C_{28}H_{35}N_5O_2$; $0.6H_2O$ requires C, 69.36; H. 7.55; N, 14.49%

$^1$H NMR (400 MHz, CDCl$_3$): δ [ppm] 1.84–1.94 (1H, m), 2.00–2.23 (9H, m), 2.23–2.32 (1H, m), 2.32–2.44 (1H, m), 2.89–3.02 (2H, m), 3.02–3.11 (1H, m), 3.74–3.82 (1H, m), 3.90–3.97 (3H, m), 4.06 (2H, s), 4.06–4.16 (1H, m), 5.08–5.16 (1H, m), 7.16–7.37 (10H, m), 7.37–7.48 (1H, m), 7.97–8.00 (1H, m)

LRMS: m/z 475 (MH$^+$)

EXAMPLE 75

N-{(1S)-3-[4-(3-Benzyl-1H-1,2,4-triazol-1-yl)-1-piperidinyl]-1-phenylpropyl}tetrahydro-2H-pyran-4-carboxamide

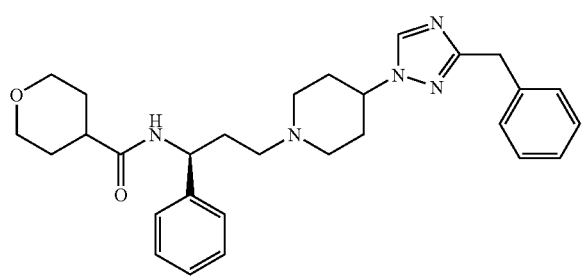

The title compound was obtained using a method similar to that described for example 74 from title compounds of preparations 134, 7 and 17 in 67% yield.

Found C, 69.72; H. 7.67; N, 14.11%

$C_{29}H_{37}N_5O_2$; $0.6H_2O$ requires C, 69.88; H, 7.72; N, 14.05%

$^1$H NMR (400 MHz, CDCl$_3$): δ [ppm] 1.78–1.92 (5H, m), 2.00–2.21 (7H, m), 2.24–2.32 (1H, m), 2.32–2.45 (2H, m), 2.95–3.06 (1H, m), 3.06–3.16 (1H, m), 3.39–3.48 (2H, m), 4.00–4.06 (4H, m), 4.06–4.19 (1H, m), 5.10–5.18 (1H, m), 7.16–7.35 (10H, m), 7.55–7.61 (1H, m), 8.00 (1H, s).

LRMS: m/z 388.4 (MH$^+$)

EXAMPLE 76

1-Amino-N-{(1S)-3-[4-(3-benzyl-1H-1,2,4-triazol-1-yl)-1-piperidinyl]-1-phenylpropyl}cyclopentanecarboxamide

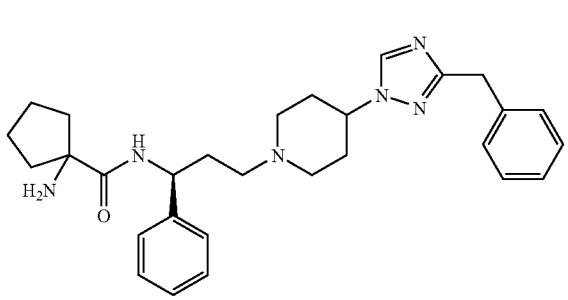

The title compound of preparation 134 (1.17 g, 4.83 mmol), the title compound of preparation 7 (1.20 g, 4.83 mmol) and sodium triacetoxyborohydride (1.53 g, 7.24 mmol) were stirred together for 30 minutes at room temperature in dichloromethane:acetic acid (30 ml, 10%). The solvents were evaporated under reduced pressure and the residue basified with saturated aqueous sodium carbonate solution and extracted with dichloromethane (3x). The combined organic layers were dried (MgSO$_4$), filtered and evaporated under reduced pressure. The residue (2.3 g, 4.83 mmol) was stirred for 16 hours in a mixture of dichloromethane:trifluoroacetic acid (30 ml, 5:1). The solvents were evaporated under reduced pressure and the residue basified with saturated aqueous sodium carbonate solution and extracted with dichloromethane (3x). The combined organic layers were dried (MgSO$_4$), filtered and evaporated under reduced pressure. A portion of the residue (200 mg, 0.53 mmol), the title compound of preparation 15 (121 mg, 0.53 mmol) and 1-(3-dimethylaminopropyl)-3-ethyl-carbodiimide hydrochloride (125 mg, 0.65 mmol) were stirred together for 1 hour at room temperature in dichloromethane (5 ml) and then trifluoroacetic acid (5 ml) was added and the reaction stirred for 12 hours. The solvent was evaporated under reduced pressure. The residue was dissolved in ethyl acetate and washed with saturated aqueous sodium carbonate solution, then water. The organic layer was dried (MgSO$_4$), filtered and evaporated under reduced pressure. The residue was purified by column chromatography on silica gel using dichloromethane:methanol:0.88 ammonia (95:5:0.5) as eluant to afford the title compound as a gum, 58 mg.

Found C, 69.89; H, 7.96; N, 16.94%

$C_{29}H_{38}N_6O$; $0.6H_2O$ requires C, 70.02; H. 7.94; N, 16.89%

$^1$H NMR (400 MHz, CDCl$_3$): δ [ppm] 1.27–1.53 (4H, m), 1.68–1.90 (4H, m), 1.90–2.40 (12H, m), 2.94–3.06 (2H, m), 4.03–4.15 (1H, m), 4.05 (2H, s), 5.03–5.11 (1H, m), 7.16–7.35 (10H, m), 7.97 (1H, s), 8.61–8.69 (1H, m)

LRMS: m/z 488 (MH$^+$)

EXAMPLE 77

1-Acetyl-N{(1S)-3-[4-(3-benzyl-1H-1,2,4-triazol-1-yl)-1-piperidinyl]-1-phenylpropyl}-3-azetidinecarboxamide

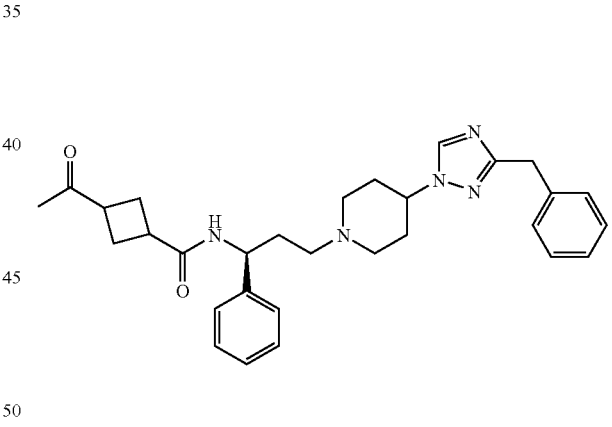

The title compound was obtained using a method similar to that described for example 74 from title compounds of preparations 134, 7 and 14 in 48% yield.

Found C, 67.53; H, 7.51; N, 16.66%

$C_{29}H_{36}N_6O_2$; $0.7H_2O$ requires C, 67.86; H, 7.34; N, 16.37%

$^1$H NMR (400 MHz, CDCl$_3$): δ [ppm] 1.80–2.26 (8H, m), 1.84 (3H, s), 2.26–2.35 (1H, m), 2.35–2.45 (1H, m), 2.94–3.11 (2H, m), 3.18–3.29 (1H, m), 4.03–4.26 (4H, m), 4.06 (2H, s), 4.32–4.44 (1H, m), 5.10–5.27 (1H, m), 7.16–7.35 (10H, m), 7.60–7.65 and 7.77–7.83 (1H, m), 8.00 (1H, s)

LRMS: m/z 501.6 (MH$^+$)

EXAMPLE 78

N-{(1S)-3-[4-(3-Benzyl-1H-1,2,4-triazol-1-yl)-1-piperidinyl]-1-phenylpropyl}-1-propionyl-3-azetidinecarboxamide

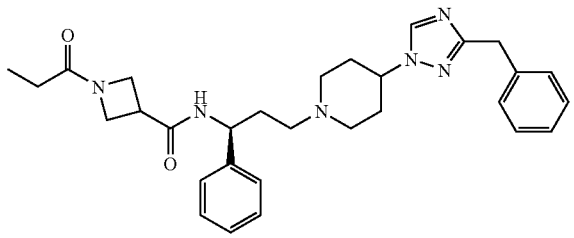

The title compound of preparation 134 (1.17 g, 4.83 mmol), the title compound of preparation 7 (1.20 g, 4.83 mmol) and sodium triacetoxyborohydride (1.53 g, 7.24 mmol) were stirred together for 30 minutes at room temperature in dichloromethane:acetic acid (30 ml, 10%). The solvents were evaporated under reduced pressure and the residue basified with saturated aqueous sodium carbonate solution and extracted with dichloromethane (3×). The combined organic layers were dried (MgSO$_4$), filtered and evaporated under reduced pressure. The residue (2.3 g, 4.83 mmol) was stirred for 16 hours in a mixture of dichloromethane:trifluoroacetic acid (30 ml, 5:1). The solvents were evaporated under reduced pressure and the residue basified with saturated aqueous sodium carbonate solution and extracted with dichloromethane (3×). The combined organic layers were dried (MgSO$_4$), filtered and evaporated under reduced pressure. A portion of the residue (200 mg, 0.53 mmol), the title compound of preparation 13 (106 mg, 0.53 mmol) and 1-(3-dimethylaminopropyl)-3-ethyl-carbodiimide hydrochloride (125 mg, 0.65 mmol) were stirred together for 1 hour at room temperature in dichloromethane (5 ml) and then trifluoroacetic acid (5 ml) was added and the reaction stirred for 12 hours. The solvent was evaporated under reduced pressure. The residue was dissolved in ethyl acetate and washed with saturated aqueous sodium carbonate solution, then water. The organic layer was dried (MgSO$_4$), filtered and evaporated under reduced pressure to furnish an oil. To a solution of this oil (100 mg, 0.22 mmol) and triethylamine (36 μl, 0.26 mmol) was added propionyl chloride (20 μl, 0.24 mmol) with stirring at room temperature. The solvent was evaporated under reduced pressure. The residue was dissolved in ethyl acetate and washed with saturated aqueous sodium carbonate solution, then water. The organics were dried (MgSO$_4$), filtered and evaporated under reduced pressure. The residue was purified by column chromatography on silica gel using dichloromethane:methanol:0.88 ammonia (98:2:0.25) as eluant to afford the title compound as a gum, 41 mg.

Found C, 66.89; H, 7.66; N, 15.75%

$C_{30}H_{38}N_6O_2$; 1H$_2$O; 0.06CH$_2$Cl$_2$ requires C, 67.14; H, 7.52; N, 15.63%

$^1$H NMR (400 MHz, CDCl$_3$): δ [ppm] 1.06–1.13 (3H, t), 1.74–2.47 (12H, m), 2.94–3.13 (2H, m), 3.19–3.32 (1H, m), 4.03–4.26 (4H, m), 4.05 (2H, s), 4.32–4.42 (1H, m), 5.11–5.16 (1H, m), 7.18–7.37 (10H, m), 7.55–7.60 and 7.74–7.80 (1H, m), 8.02 (1H, s)

LRMS: m/z 515.3 (MH$^+$)

EXAMPLE 79

1-Acetyl-N-{(1S)-3-[4-(3-benzyl-5-methyl-1H-1,2,4-triazol-1-yl)-1-piperidinyl]-1-phenylpropyl}3-azetidinecarboxamide

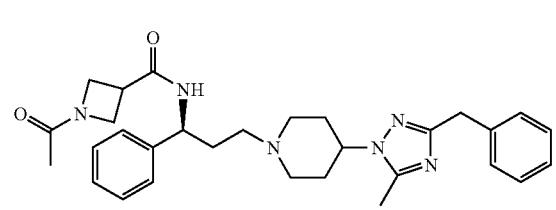

1-(3-Dimethylaminopropyl)-3-ethyl-carbodiimide hydrochloride (96 mg, 0.50 mmol) was added to a stirred solution acetic acid (28 μl, 0.50 mmol) and the title compound of preparation 143 (200 mg, 0.42 mmol) in dichloromethane (10 ml). After 1 hour the reaction mixture was loaded directly onto a column of silica with dichloromethane:methanol:0.88 ammonia (95:5:0.5) as eluant to afford the title compound as a white foam, 102 mg.

Found C, 67.74; H, 7.44; N, 16.03%

$C_{30}H_{38}N_6O_2$; 1H$_2$O requires C, 67.64; H, 7.57; N, 15.78%

$^1$H NMR (300 MHz, CDCl$_3$): δ [ppm] 1.76–2.50 (18H, m), 3.00 (1H, m), 3.18 (1H, dd), 3.30 (1H, ddd), 3.98 (3H, m), 4.18 (2H, m), 4.38 (1H, m), 5.16 (1H, dd), 7.08–7.40 (9H, m), 8.26 (0.5H, d), 8.44 (0.5H, dd)

LRMS: m/z 515 (MH$^+$)

The following compounds have been prepared using methods similar to those described above:

N-{(1S)-3-[4-(3-(4-Fluorobenzyl)-1H-1,2,4-triazol-1-yl)-1-piperidinyl]-phenylpropyl}1-propionyl-3-azetidinecarboxamide

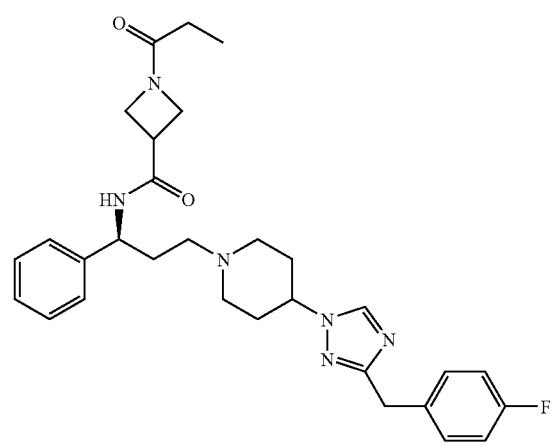

177

1-Acetyl-N-{(1S)-3-[4-(3-(4-fluorobenzyl)-1H-1,2,4-triazol-1-yl]-1-piperidinyl]-1-phenylpropyl}-3-azetidinecarboxamide

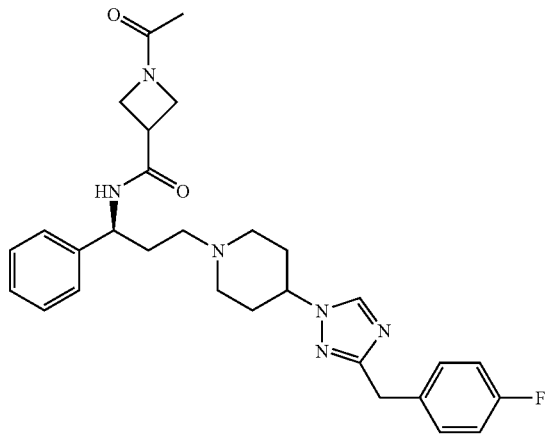

2-Methoxy-N-{(1S)-3-[4(3-(4-fluorobenzyl)-1H-1,2,4-triazol-1-yl]-1-piperidinyl]-1-phenylpropyl}acetamide

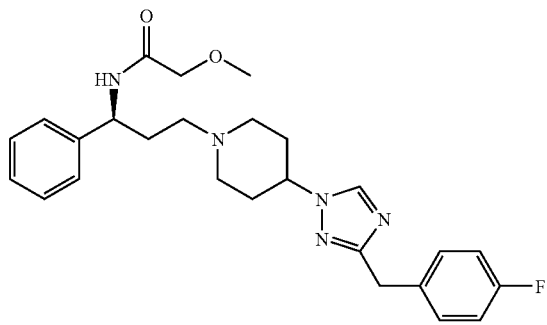

3-Methoxy-N-{(1S)-3-[4-(3-(4-fluorobenzyl)-1H-1,2,4-triazol-1-yl)-1-piperidinyl]-1-phenylpropyl}propanamide

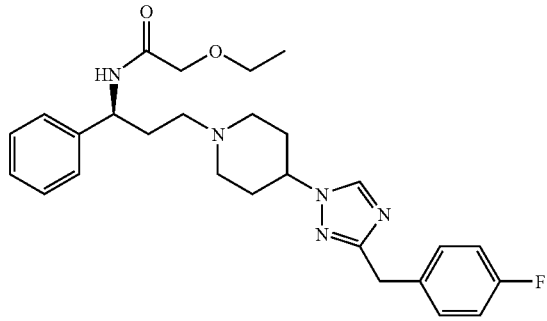

178

The invention claimed is:

1. A compound of the formula

[Region α]–[Region β]–[Region γ]–[Region δ]

or a pharmaceutically acceptable salt thereof, wherein [Region α] is a moiety of the formula

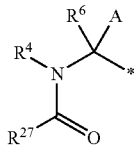

wherein the symbol '*' indicates the point of attachment of [Region α] to [Region β];

$R^4$ is H or $C_1$–$C_2$ alkyl;

$R^6$ is H, $C_1$–$C_2$ alkyl, $C_1$–$C_2$ alkoxy, —CN, —OH, or —CONH$_2$;

A is phenyl optionally substituted by up, to 4 substituents independently selected from fluoro, chloro, —CO$_2$R$^4$, —OH, —CN, —CONR$^4_a$R$^4_b$, —NR$^4_a$R$^4_b$, —NR$^4_a$COR$^4_b$, —NR$^4_a$CO$_2$R$^4_b$, —NR$^4_a$S(O)$_p$R$^4_b$, —S(O)$_p$NR$^4_a$R$^4_b$, $C_1$–$C_4$ alkyl, $C_1$–$C_4$ alkoxy, $C_1$–$C_2$ alkoxycarbonyl, $C_1$–$C_2$ alkylcarbonyl and $C_1$–$C_2$ alkylcarbonyloxy, said $C_1$–$C_4$ alkyl and $C_1$–$C_4$ alkoxy being optionally substituted by up to 3 substituents independently selected from fluoro and chloro;

p is 0, 1 or 2;

$R^4_a$ and $R^4_b$ are each independently H or $C_1$–$C_2$ alkyl;

$R^{27}$ is:

(i) $C_1$–$C_6$ alkyl, $C_2$–$C_6$ alkenyl or $C_2$–$C_6$ alkynyl, each optionally substituted by up to 3 substituents $R^{28}$; or (ii) —(CH$_2$)$_n$—(C$_3$–C$_7$ cycloalkyl), wherein (a) said $C_3$–$C_7$ cycloalkyl is optionally substituted by up to 3 substituents $R^{28}$; and (b) n is 0, 1 or 2, wherein:

(1) where n is 0, the α-carbon of said $C_3$–$C_7$ cycloalkyl is optionally substituted by one substituent selected from $C_1$–$C_4$ alkyl and phenyl, wherein said $C_1$–$C_4$ alkyl and phenyl are optionally substituted by 1 or 2 substituents selected from —CH$_3$, —OCH$_3$, —OH and —NH$_2$; and (2) where n is 1 or 2, the resulting methylene or ethylene is optionally substituted by 1 substituent selected from fluoro, —NH$_2$, —N(CH$_3$)$_2$, —OH, —OCH$_3$, $C_1$–$C_4$ alkyl and phenyl, wherein said $C_1$–$C_4$ alkyl and phenyl are optionally substituted by 1 or 2 substituents selected from —CH$_3$, —OCH$_3$, —OH and —NH$_2$; or (iii), phenyl, furyl, tetrahydrofuranyl, tetrahydropyranyl, oxetanyl), thienyl, pyrrolyl, pyrrolidinyl, oxazolyl, isoxazolyl thiazolyl, isothiazolyl, imidazolyl, pyrazolyl, oxadiazolyl, thiadiazolyl, triazolyl, pyridyl, pyrazinyl, pyridazinyl, piperazinyl, pyrimidinyl, pyranyl, -azetidinyl, morpholinyl, parathiazinyl, indolyl, indolinyl, benzofuranyl 2,3-dihydrobenzofuranyl, benzothienyl, 1H-indazolyl, benzimidazolyl, benzoxazolyl, benzisoxazolyl, benzthiazolyl, quinolinyl, isoquinolinyl, phthalazinyl, quinazolinyl or quinoxalinyl, each optionally substituted:

(a) on any one or more carbon atoms by up to 3 substituents $R^{28}$; or (b) on any one or more nitrogen atoms that is not a point of attachment of said heterocyclic moiety by up to 3 substituents $R^{13}{}_b$; or (c) on any sulphur atom that is not a point of attachment of said heterocyclic moiety by up to 2 oxygen atoms;

$R^{28}$ is phenyl, fluoro, chloro, oxo, —OH, $C_1$–$C_2$ alkyl, $C_1$–$C_3$ alkoxy, —$CO_2R^{29}$, —$CO(C_1$–$C_4)$alkyl, —$SO_2(C_1$–$C_4)$alkyl, —$CONR^{29}R^{30}$, —$NR^{29}R^{30}$, —$NR^{29}COR^{30}$, —$NR^{29}CO_2R^{30}$, —$NR^{29}S(O)_pR^{30}$ or —$SO_2NR^{29}R^{30}$;

$R^{29}$ and $R^{30}$ are each independently H or $C_1$–$C_4$ alkyl optionally substituted by up to 3 substituents selected from fluoro and chloro;

$R^{13}{}_b$ is H, $C_1$–$C_4$ alkyl, $C_2$–$C_4$ alkenyl, $C_1$–$C_2$ alkoxy, $C_3$–$C_7$ cycloalkyl, —$CO(C_1$–$C_4)$alkyl, —$SO_2(C_1$–$C_4)$alkyl or phenyl, wherein said $C_1$–$C_4$ alkyl, $C_2$–$C_4$ alkenyl, $C_1$–$C_2$alkoxy, $C_3$–$C_7$cycloalkyl and phenyl are optionally substituted by up to 2 substituents $R^{11}$;

$R^{11}$ is fluoro, chloro, —$CO_2R^4$, —OH, —CN, —$CONR^4{}_aR^4{}_b$, —$NR^4{}_aR^4{}_b$, —$NR^4{}_aCOR^4{}_b$, —$NR^4{}_aCO_2R^4{}_b$, —$NR^4{}_aS(O)_pR^4{}_b$, —$S(O)_pNR^4{}_aR^4{}_b$, $C_1$–$C_4$ alkyl including dimethyl, $C_1$–$C_4$ alkoxy, $C_1$–$C_2$ alkoxycarbonyl, $C_1$–$C_2$ alkylcarbonyl or $C_1$–$C_2$ alkylcarbonyloxy, wherein said $C_1$–$C_4$ alkyl and $C_1$–$C_4$ alkoxy are each optionally substituted by up to 3; substituents independently selected from fluoro and chloro;

[Region β] is an alkyl bridging element of partial formula

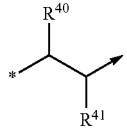

wherein the symbol '*' indicates the point of attachment of [Region β] to [Region α] and the symbol '→' indicates the point of attachment of [Region β] to [Region γ];

$R^{40}$ and $R^{41}$ are both H, $C_1$–$C_2$ alkyl including dimethyl, —OH, or $C_1$–$C_3$ alkoxy;

[Region γ] is piperidine being linked to [Region δ] through the ring nitrogen atom and each being linked to [Region δ] through any ring carbon atom, wherein said, piperidine is optionally substituted on a ring carbon atom by one substituent selected from $C_1$–$C_4$ alkyl including dimethyl, $C_3$–$C_6$ cycloalkyl, $C_1$–$C_4$ alkoxy, $(C_1$–$C_2)$ alkoxy$(C_1$–$C_2)$alkyl, —$CF_3$, —$CO_2R^4$, oxo, —OH, —CN, —$CONR^4{}_aR^4{}_b$, —$NR^4{}_aR^4{}_b$, —$NR^4{}_aCOR^4{}_b$, —$NR^4{}_aCO_2R^4{}_b$, —$NR^4{}_aS(O)_pR^4{}_b$, —$S(O)_pNR^4{}_aR^4{}_b$, $(C_1$–$C_2)$alkyloxycarbonyl, $(C_1$–$C_2)$alkylcarbonyl, $(C_1$–$C_2)$alkylcarbonyloxy and optionally substituted on the ring nitrogen atom by substituent $R^{46}$;

$R^{46}$ is H, $C_1$–$C_4$ alkyl or O, wherein said $C_1$–$C_4$ alkyl is optionally substituted by 1 substituent selected from $C_1$–$C_2$ alkoxy and —$CO_2R^4$;

[$R_{egion}$ δ] is a (substituted)-heterocyclyl moiety selected from the group consisting of:

(i) a heterocyclyl moiety of partial Formula (5.3.0):

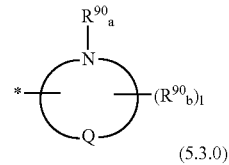

(5.3.0)

wherein the symbol '*' indicates the point of attachment of partial Formula (5.3.0) to [$R_{egion}$ γ] and wherein Q is N, O or S; and wherein partial Formula (5.3.0) is:

is a member of the group consisting of triazoyl and oxadiazolyl, $R^{90}{}_a$ and $R^{90}{}_b$ are each a member independently selected from the group consisting of hydrogen, —$(C_1$-$C_2)$ alkylcarbonyl, —$(C_1$-$C_4)$alkyl, —$(CH_2)_n$-$(C_3$-$C_7)$cycloalkyl, —$(C_2$-$C_3)$alkenyl —$(CH_2)_n$-(phenyl), and —$(CH_2)_n$-($HET_1$), where n is an integer independently selected from 0, 1, and 2; wherein said $(C_1$-$C_4)$alkyl, alkenyl, cycloalkyl, phenyl, and $HET_1$ groups are independently substituted with 0 to 3 substituents $R^{91}$, where:

j is 0, 1 or 2;

$HET_1$ is a heterocyclyl group selected from thienyl, oxazolyl, isoxazolyl, thiazolyl, isothiazolyl, pyrazolyl, oxadiazolyl, thiadiazolyl, triazolyl, pyridyl, pyrazinyl, pyridazinyl, pyrimidinyl, parathiazinyl, and morpholinyl, where:

$R^{91}$ is selected from —F, —Cl, —$CO_2R^4$, -oxo, —OH, —C—N, —$CONR^{93}R^{94}$, —$NR^{93}R^{94}$, $C(=O)(C_1$-$C_4)$ alkyl, —$NR^{93}C(=O)R^{94}$, —$NR^{93}C(=O)OR^{94}$, —$NR^{93}S(=O)R^{94}$, —$S(=O)NR^{93}R^{94}$, $(C_1$-$C_4)$alkyl, and $(C_1$-$C_4)$alkoxy, wherein said alkyl and alkoxy are each independently substituted with 0 to 3 substituents independently selected from F, Cl, $(C_1$-$C_2)$alkoxycarbonyl, $(C_1$-$C_2)$alkylcarbonyl, and $(C_1$-$C_2)$alkylcarbonyloxy;

$R^{93}$ and $R^{94}$ are each a member independently selected from H and $(C_1$-$C_2)$alkyl; and (ii) a heterocyclyl moiety of partial Formula

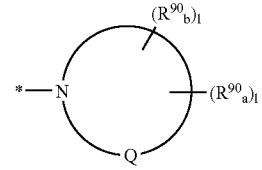

wherein Q is N, O or S.

2. A compound according to claim 1, wherein $R^6$ is H.

3. A compound according to claim 1, wherein A is phenyl.

4. A compound according to claim 1, wherein $R^{27}$ is methyl, ethyl, isopropyl, tert-butyl or alkyl, each optionally substituted by one substituent selected from fluoro, chloro, —OH, —$CF_3$, methyl, methoxy, —CN, —$NH_2$, —NH($CH_3$), —$N(CH_3)_2$, —$NHCOCH_3$, and —$N(CH_3)COCH_3$.

5. A compound according to claim 1, wherein $R^{27}$ is substituted or unsubstituted cyclopropyl, cyclobutyl, cyclopentyl, cyclohexyl, cyclopropylmethyl, cyclobutylethyl, cyclopentylpropylmethyl or cyclopentylmethyl.

6. A compound according to claim 1, wherein $R^{27}$ is tetrahydropyranyl, oxetanyl, azetidinyl or tetrahydrofuranyl, each optionally substituted by up to three substituents $R^{28}$.

7. A compound according to claim 1, wherein [Region β] is unsubstituted ethylene.

8. A compound according to claim 1, wherein $R^{46}$ is absent.

9. A compound according to claim 1, wherein the heterocycle constituting [Region γ] is unsubstituted on any ring carbon atom.

10. A compound according to claim 1, wherein [Region δ] is selected from:

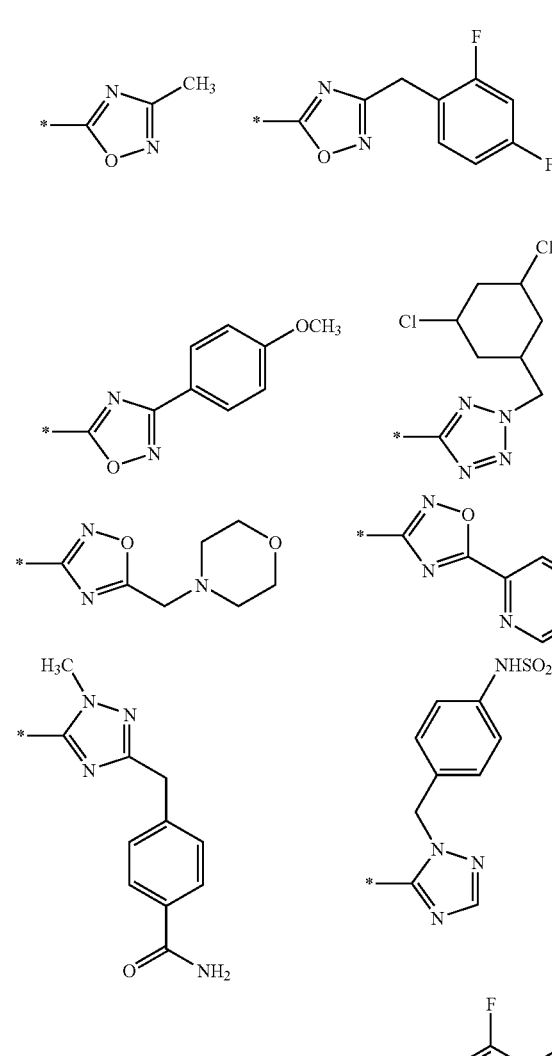

-continued

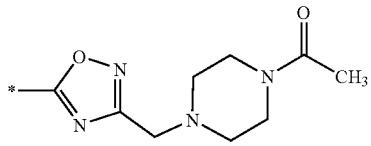

wherein the symbol '*' indicates the point of attachment to [Region γ].

11. A compound according to claim 1, wherein [Region δ] is selected from:

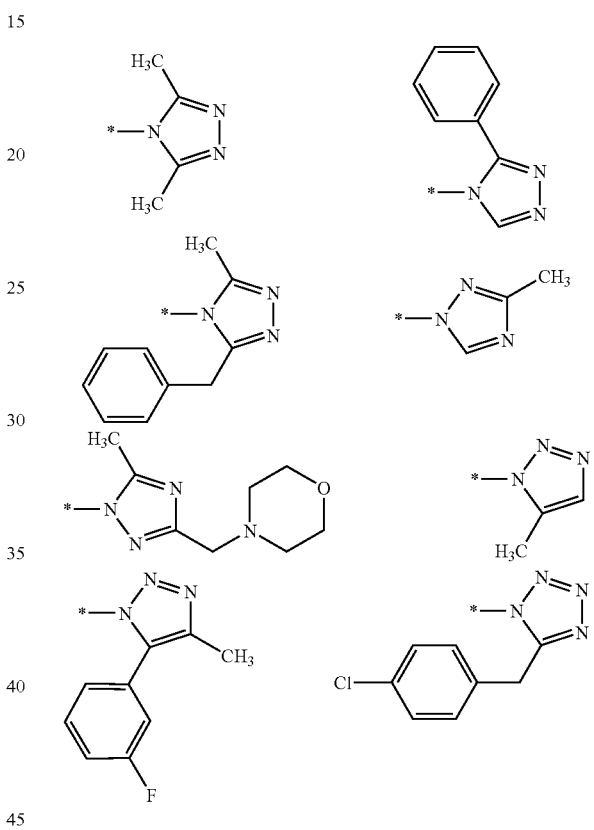

wherein the symbol '*' indicates the point of attachment to Region γ.

12. A compound according to claim 1, which is selected from:
- N-{(1S)-3-[4-(3-Benzyl-1,2,4-oxadiazol-5-yl)-1-piperidinyl]-1-phenylpropyl}cyclobutanecarboxamide;
- N-{1-Phenyl-3-[4-(4H-1,2,4-triazol-4-yl)-1-piperidinyl]-1-phenylpropyl}cyclobutanecarboxamide;
- N-{3-[4-(1-Methyl-1H-1,2,4-triazol-5-yl)-1-piperidinyl]-1-phenylpropyl}cyclobutanecarboxamide;
- N-{3-[4-(1-Methyl-1H-1,2,4-triazol-3-yl)-1-piperidinyl]-1-phenylpropyl}cyclobutanecarboxamide;
- N-{3-[4-(3,5-Dimethyl-4H-1,2,4-triazol-4-yl)-1-piperidinyl]-1-phenylpropyl}cyclobutanecarboxamide;
- N-{1-Phenyl-3-[4-(3-methyl-1,2,4-oxadiazol-5-yl)-1-piperidinyl]propyl}cyclobutanecarboxamide;
- N-{1-Phenyl-3-[4-(3-phenyl-1,2,4-oxadiazol-5-yl)-1-piperidinyl]propyl}cyclobutanecarboxamide;
- N-{3-[4-(3-Benzyl-1,2,4-oxadiazol-5-yl)-1-piperidinyl]-1-phenylpropyl}cyclobutanecarboxamide;

N-(3-{4-[3-(4-Methoxyphenyl)-1,2,4-oxadiazol-5-yl]-1-piperidinyl}-1-phenylpropyl)cyclobutanecarboxamide;
N-{3-[4-(5-Methyl-1,2,4-oxadiazol-3-yl)-1-piperidinyl]-1-phenylpropyl}cyclobutanecarboxamide,
N-{1-Phenyl-3-[4-(5-phenyl-1,2,4-oxadiazol-3-yl)-1-piperidinyl]propyl}cyclobutanecarboxamide;
N-{3-[4-(5-Benzyl-1,2,4-oxadiazol-3-yl)-1-piperidinyl]-1-phenylpropyl}cyclobutanecarboxamide;
N-{3-[4-(5-Methyl-1,3,4-oxadiazol-2-yl)-1-piperidinyl]-1-phenylpropyl}cyclobutanecarboxamide;
N-{1-Phenyl-3-[4-(5-phenyl-1,3,4-oxadiazol-2-yl)-1-piperidinyl]propyl}cyclobutanecarboxamide;
N-{3-[4-(5-Benzyl-1,3,4-oxadiazol-2-yl)-1-piperidinyl]-1-phenylpropyl}cyclobutanecarboxamide;
N-[(1S)-3-[4-(3-Benzyl-1,2,4-oxadiazol-5-yl)-1-piperidinyl]-1-(3-fluorophenyl)propyl]-2-cyclopropylacetamide;
N-((1S)-3-{4-[3-(4-Methylbenzyl)-1,2,4-oxadiazol-5-yl]-1-piperidinyl}-1-phenylpropyl)cyclobutanecarboxamide;
N-((1S)-3-{4-[3-(4-Trifluoromethylbenzyl)-1,2,4-oxadiazol-5-yl]-1-piperidinyl}-1-phenylpropyl)cyclobutanecarboxamide;
N-((1S)-3-{4-[3-(1,3-Benzodioxol-5-ylmethyl)-1,2,4-oxadiazol-5-yl]-1-piperidinyl}-1-phenylpropyl)cyclobutanecarboxamide;
N-((1S)-3-{4-[3-(3,5-Difluorobenzyl)-1,2,4-oxadiazol-5-yl]-1-piperidinyl}-1-phenylpropyl)cyclobutanecarboxamide;
N-[(1S)-3-[4-(3-Benzyl-1,2,4-oxadiazol-5-yl)-1-piperidinyl]-1-(3-fluorophenyl)propyl]cyclobutanecarboxamide;
N-{(1S)-3-[4-(3-{4-[(Methylsulfonyl)amino]benzyl}-1,2,4-oxadiazol-5-yl)-1-piperidinyl]-1-phenylpropyl)cyclobutanecarboxamide;
4-{[5-(1-{(3S)-3-[(Cyclobutylcarbonyl)amino]-3-phenylpropyl}-4-piperidinyl)-1,2,4-oxadiazol-3-yl]methyl}benzamide;
N-((1S)-3-{4-[3-(2,5-Difluorobenzyl)-1,2,4-oxadiazol-5-yl]-1-piperidinyl}-1-phenylpropyl)cyclobutanecarboxamide;
N-((1S)-3-{4-[3-(2,6-Difluorobenzyl)-1,2,4-oxadiazol-5-yl]-1-piperidinyl}-1-phenylpropyl)cyclobutanecarboxamide;
N-((1S)-1-Phenyl-3-{4-[3-(3-pyridinylmethyl)-1,2,4-oxadiazol-5-yl]-1-piperidinyl]propyl)cyclobutanecarboxamide;
N-((1S)-1-Phenyl-3-{4-[3-(4-pyridinylmethyl)-1,2,4-oxadiazol-5-yl]-1-piperidinyl}propyl)cyclobutanecarboxamide;
N-{(1S)-3-[4-(3-{2-[(Methylsulfonyl)amino]benzyl}-1,2,4-oxadiazol-5-yl)-1-piperidinyl]-1-phenylpropyl}cyclobutanecarboxamide;
N-((1S)-1-Phenyl-3-{4-[3-(2-pyridinylmethyl)-1,2,4-oxadiazol-5-yl]-1-piperidinyl}propyl)cyclobutanecarboxamide;
N-(1S)-3-[4-(3-Isobutyl-1,2,4-oxadiazol-5-yl)-1-piperidinyl]-1-phenylpropyl}cyclobutanecarboxamide;
N-((1S)-3-{4-[3-(3-Chlorobenzyl)-1,2,4-oxadiazol-5-yl]-1-piperidinyl}-1-phenylpropyl)cyclobutanecarboxamide;
N-((1S)-3-{4-[3-(1-Benzofuran-5-ylmethyl)-1,2,4-oxadiazol-5-yl]-1-piperidinyl}-1-phenylpropyl)cyclobutanecarboxamide;
N-[(1S)-1-Phenyl-3-(4-{3-[4-(trifluoromethoxy)benzyl]-1,2,4-oxadiazol-5-yl}-1-piperidinyl)propyl]cyclobutanecarboxamide;
N-{(1S)-3-[4-(3-{3-[(Methylsulfonyl)amino]benzyl}-1,2,4-oxadiazol-5-yl)-1-piperidinyl]-1-phenylpropyl}cyclobutanecarboxamide;
3,3,3-Trifluoro-N-{(1S)-3-[4-(3-{4-[(methylsulfonyl)amino]benzyl}-1,2,4-oxadiazol-5-yl)-1-piperidinyl]-1-phenylpropyl}propanamide;
2-Cyclopropyl-N-{(1S)-3-[4-(3-{4-[(methylsulfonyl)amino]benzyl}-1,2,4-oxadiazol-5-yl)-1-piperidinyl]-1-phenylpropyl}acetamide;
N-{(1S)-3-[4-(3-{4-[(Methylsulfonyl)amino]benzyl}-1,2,4-oxadiazol-5-yl)-1-piperidinyl]-1-phenylpropyl}tetrahydro-2H-pyran-4-carboxamide;
1-Acetyl-N-{(1S)-3-[4-(3-{4-[(methylsulfonyl)amino]benzyl}-1,2,4-oxadiazol-5-yl)-1-piperidinyl]-1-phenylpropyl}-3-azetidinecarboxamide;
N-{(1S)-3-[4-(3-Benzyl-1,2,4-oxadiazol-5-yl)-1-piperidinyl]-1-phenylpropyl}tetrahydro-2H-pyran-4-carboxamide;
1-Acetyl-N-{(1S)-3-[4-(3-benzyl-1,2,4-oxadiazol-5-yl)-1-piperidinyl]-1-phenylpropyl}-3-azetidinecarboxamide;
1-(Acetylamino)-N-{(1S)-3-[4-(3-benzyl-1,2,4-oxadiazol-5-yl)-1-piperidinyl]-1-phenylpropyl}cyclopentanecarboxamide;
N-{(1S)-3-[4-(3-Benzyl-1,2,4-oxadiazol-5-yl)-1-piperidinyl]-1-phenylpropyl}-1-methoxycyclobutanecarboxamide;
3-{[5-(1-(3S)-3-[(Cyclobutylcarbonyl)amino]-3-phenylpropyl}4-piperidinyl)-1,2,4-oxadiazol-3-yl]methyl}benzamide;
Ethyl 4-(3-benzyl-1,2,4-oxadiazol-5-yl)-1-((3S)-3-[(cyclobutylcarbonyl)amino]-3-phenylpropyl}-4-piperidinecarboxylate;
N-{(1S)-3-[4-(3-Benzyl-1,2,4-oxadiazol-5-yl)$_4$-cyano-1-piperidinyl]-1-phenylpropyl}cyclobutanecarboxamide;
N-[(1S)-3-[4-3-[3-(Aminosulfonyl)benzyl]-1,2,4-oxadiazol-5-yl}-1-piperidinyl)-1-phenylpropyl]cyclobutanecarboxamide;
1-{(3S)-3-[(Cyclobutylcarbonyl)amino]-3-phenylpropyl}-4-[3-(4-fluorobenzyl)-1,2,4-oxadiazol-5-yl]-N-methyl-4-piperidinecarboxamide;
N-((1S)-3-{4-[3-(4-Fluorobenzyl)-1,2,4-oxadiazol-5-yl]-1-piperidinyl}-1-phenylpropyl)tetrahydro-2H-pyran-4-carboxamide;
3,3,3-Trifluoro-N-((1S)-3-{4-[3-(4-fluorobenzyl)-1,2,4-oxadiazol-5-yl]-1-piperidinyl}-1-phenylpropyl)propanamide;
N-((1S)-3-{4-[3-(4-Morpholinylmethyl)-1,2,4-oxadiazol-5-yl]-1-piperidinyl}-1-phenylpropyl)cyclobutanecarboxamide;
N-((1S)-3-{4-Cyano-4-[3-(4-fluorobenzyl)-1,2,4-oxadiazol-5-yl]-1-piperidinyl}-1-phenylpropyl)tetrahydro-2H-pyran-4-carboxamide;
N-((1S)-3-{4-Cyano-4-[3-(4-fluorobenzyl)-1,2,4-oxadiazol-5-yl]-1-piperidinyl}-1-phenylpropyl)-2-cyclopropylacetamide;
1-Acetyl-N-((1S)-3-{4-cyano-4-[3-(4-fluorobenzyl)-1,2,4-oxadiazol-5-yl]-1-piperidinyl}-1-phenylpropyl)-3-azetidinecarboxamide;
N-((1S)-3-{4-Cyano-4-[3-(4-fluorobenzyl)-1,2,4-oxadiazol-5-yl]-1-piperidinyl}-1-phenylpropyl)-3,3,3-trifluoropropanamide;
N-[(1S)-3-(4-{3-[4-(Aminosulfonyl)benzyl]-1,2,4-oxadiazol-5-yl}1—piperidinyl)-1-phenylpropyl]cyclobutanecarboxamide;
N-{(1S)-3-[3-Benzyl-1,2,4-oxadiazol-5-yl)-1-azetidinyl]-1-phenylpropyl}tetrahydro-3-furancarboxamide;

N-[(1S)-3-(4-{3-[(4-Acetyl-1-piperazinyl)methyl]-1,2,4-oxadiazol-5-yl}-1-piperidinyl)-1-phenylpropyl]cyclobutanecarboxamide;

N-{(1S)-3-[3-Benzyl-1,2,4-oxadiazol-5-yl)-1-azetidinyl]-1-phenylpropyl}tetrahydro-3-furancarboxamide;

N-{(1S)-3-[4-[3-(4-Fluorobenzyl)-1,2,4-oxadiazol-5-yl] 4-(methoxymethyl)-1-piperidinyl]-1-phenylpropyl}acetamide;

N-{3-[4-(3-Methyl-5-phenyl-4H-1,2,4-triazol-4-yl)-1-piperidinyl]-1-phenylpropyl}cyclobutanecarboxamide;

N-{(1S)-3-[4-(3-Benzyl-5-methyl-4H-1,2,4-triazol-4-yl)-1-piperidinyl]-1-phenylpropyl}cyclobutanecarboxamide;

N-{(1S)-3-[4-(5-Benzyl-4-methyl-4H-1,2,4-triazol-3-yl)-1-piperidinyl]-1-phenylpropyl}cyclobutanecarboxamide;

N-{(1S)-3-[4-(3-Benzyl-1H-1,2,4-triazol-1-yl)-1-piperidinyl]-1-phenylpropyl)-cyclobutanecarboxamide;

N-{(1S)-3-[4-(5-Benzyl-1-methyl-1H-1,2,4-triazol-3-yl)-1-piperidinyl]-1-phenylpropyl}cyclobutanecarboxamide;

N-{3-[4-(5-Benzyl-1H-1,2,4-triazol-3-yl)-1-piperidinyl]-1-phenylpropyl}cyclobutanecarboxamide;

N-{(1S)-3-[4-(3-{4-[(methylsulfonyl)amino]benzyl}-1H-1,2,4-triazol-1-yl)-1-piperidinyl]-1-phenylpropyl}tetrahydro-2H-pyran-4-carboxamide;

2-Cyclopropyl-N-{(1S)-3-[4-(3-{4-[(methylsulfonyl)amino]benzyl}-1H-1,2,4-triazol-1-yl)-1-piperidinyl]-1-phenylpropyl}acetamide;

3,3,3-Trifluoro-N-{(1S)-3-[4-(3-{4-[(methylsulfonyl)amino]benzyl}-1H-1,2,4-triazol-1-yl)-1-piperidinyl]-1-phenylpropyl}propanamide;

N-(1S)-{3-[4-(3-Benzyl-1-methyl-1H-1,2,4-triazol-5-yl)-1-piperidinyl]-1-phenylpropyl}cyclobutanecarboxamide;

4-{[1-(1-{(3S)-3-Phenyl-3-[(3,3,3-trifluoropropanoyl)amino]propyl}4-piperidinyl)-1H-1,2,4-triazol-3-yl]methyl}benzamide;

N-(1S)-3-[4-(3-Benzyl-5-methyl-1H-1,2,4-triazol-1-yl)-1-piperidinyl]-1-phenylpropyl}tetrahydro-2H-pyran-4-carboxamide;

N-{(1S)-3-[4-(3-Benzyl-5-methyl-1H-1,2,4-triazol-1-yl)-1-piperidinyl]-1-phenylpropyl}tetrahydro-3-furancarboxamide;

1-Amino-N-{(1S)-3-[4-(3-benzyl-5-methyl-1H-1,2,4-triazol-1-yl)-1-piperidinyl]-1-phenylpropyl}cyclopentanecarboxamide;

N-{(1S)-3-[4-(3-Benzyl-1H-1,2,4-triazol-1-yl)-1-piperidinyl]-1-phenylpropyl}tetrahydro-3-furancarboxamide;

N-{(1S)-3-[4-(3-Benzyl-1H-1,2,4-triazol-1-yl)-1-piperidinyl]-1-phenylpropyl}tetrahydro-2H-pyran-4-carboxamide;

1-Amino-N-{(1S)-3-[4-(3-benzyl-1H-1,2,4-triazol-1-yl)-1-piperidinyl]-1-phenylpropyl}cyclopentanecarboxamide;

1-Acetyl-N-{(1S)-3-[4-(3-benzyl-1H-1,2,4-triazol-1-yl)-1-piperidinyl]-1-phenylpropyl}-3-azetidinecarboxamide;

N-{(1S)-3-[4-(3-Benzyl-1H-1,2,4-triazol-1-yl)-1-piperidinyl]-1-phenylpropyl}-1-propionyl-3-azetidinecarboxamide;

1-Acetyl-N-{(1S)-3-[4-(3-benzyl-5-methyl-1H-1,2,4-triazol-1-yl)-1-piperidinyl]-1-phenylpropyl}-3-azetidinecarboxamide;

N-{(1S)-3-[4-(3-(4-Fluorobenzyl)-1H-1,2,4-triazol-1-yl)-1-piperidinyl]-1-phenylpropyl}-1-propionyl-3-azetidinecarboxamide;

1-Acetyl-N-{(1S)-3-[4-(3-(4-fluorobenzyl)-1H-1,2,4-triazol-1-yl)-1-piperidinyl]-1-phenylpropyl}-3-azetidinecarboxamide;

2-Methoxy-N-{(1S)-3-[4-(3-(4-fluorobenzyl)-1H-1,2,4-triazol-1-yl)-1-piperidinyl]-1-phenylpropyl}acetamide; and 3-Methoxy-N-{(1S)-3-[4-(3-(4-fluorobenzyl)-1H-1,2,4-triazol-1-yl)-1-piperidinyl]-1-phenylpropyl}propanamide;

and the pharmaceutically acceptable salts thereof.

13. A pharmaceutical composition comprising a compound of claim 1 together with a pharmaceutically acceptable excipient, diluent or carrier.

\* \* \* \* \*